US008951522B2

(12) United States Patent
Demopulos et al.

(10) Patent No.: US 8,951,522 B2
(45) Date of Patent: Feb. 10, 2015

(54) METHODS FOR TREATING CONDITIONS ASSOCIATED WITH MASP-2 DEPENDENT COMPLEMENT ACTIVATION

(75) Inventors: Gregory A. Demopulos, Seattle, WA (US); Thomas Dudler, Bellevue, WA (US); Hans-Wilhelm Schwaeble, Mountsorrel (GB)

(73) Assignees: University of Leicester, Leicester (GB); Omeros Corporation, Seattle, WA (US)

( * ) Notice: Subject to any disclaimer, the term of this patent is extended or adjusted under 35 U.S.C. 154(b) by 0 days.

(21) Appl. No.: 13/441,827

(22) Filed: Apr. 6, 2012

(65) Prior Publication Data

US 2012/0258095 A1 Oct. 11, 2012

Related U.S. Application Data

(60) Provisional application No. 61/473,698, filed on Apr. 8, 2011.

(51) Int. Cl.
*A61K 39/395* (2006.01)
*C07K 16/40* (2006.01)
*A61K 39/00* (2006.01)

(52) U.S. Cl.
CPC ........... *C07K 16/40* (2013.01); *A61K 2039/505* (2013.01); *C07K 2317/54* (2013.01); *C07K 2317/76* (2013.01); *C07K 2317/92* (2013.01); *C07K 2317/94* (2013.01)
USPC .................................................... 424/145.1

(58) Field of Classification Search
None
See application file for complete search history.

(56) References Cited

U.S. PATENT DOCUMENTS

| | | | |
|---|---|---|---|
| 4,331,647 A | 5/1982 | Goldenberg | |
| 4,394,370 A | 7/1983 | Jefferies | |
| 4,526,909 A | 7/1985 | Urist | |
| 4,563,489 A | 1/1986 | Urist | |
| 4,816,567 A | 3/1989 | Cabilly et al. | |
| 4,946,778 A | 8/1990 | Ladner et al. | |
| 4,975,527 A | 12/1990 | Koezuka et al. | |
| 5,211,657 A | 5/1993 | Yamada et al. | |
| 5,223,409 A | 6/1993 | Ladner et al. | |
| 5,403,484 A | 4/1995 | Ladner et al. | |
| 5,552,157 A | 9/1996 | Yagi et al. | |
| 5,565,213 A | 10/1996 | Nakamori | |
| 5,567,434 A | 10/1996 | Szoka, Jr. | |
| 5,571,698 A | 11/1996 | Ladner et al. | |
| 5,610,288 A | 3/1997 | Rubenstein | |
| 5,693,762 A | 12/1997 | Queen et al. | |
| 5,718,709 A | 2/1998 | Considine et al. | |
| 5,738,868 A | 4/1998 | Shinkarenko | |
| 5,739,119 A | 4/1998 | Galli et al. | |
| 5,741,516 A | 4/1998 | Webb et al. | |
| 5,759,829 A | 6/1998 | Shewmaker et al. | |
| 5,789,573 A | 8/1998 | Baker et al. | |
| 5,795,587 A | 8/1998 | Gao et al. | |
| 5,801,154 A | 9/1998 | Baracchini et al. | |
| 6,075,181 A * | 6/2000 | Kucherlapati et al. | 800/25 |
| 6,235,494 B1 | 5/2001 | Hugli | |
| 6,297,024 B1 | 10/2001 | Hugli et al. | |
| 6,407,213 B1 | 6/2002 | Carter et al. | |
| 6,420,432 B2 | 7/2002 | Demopulos et al. | |
| 6,645,168 B2 | 11/2003 | Demopulos et al. | |
| 6,649,592 B1 | 11/2003 | Larson | |
| 7,919,094 B2 | 4/2011 | Schwaeble et al. | |
| 2002/0019369 A1 | 2/2002 | Li et al. | |
| 2003/0049260 A1 | 3/2003 | Bell | |
| 2003/0091995 A1 | 5/2003 | Buechler et al. | |
| 2004/0038297 A1 | 2/2004 | Jensenius et al. | |
| 2004/0072809 A1 | 4/2004 | Demopulos et al. | |
| 2004/0259771 A1 | 12/2004 | Stahl et al. | |
| 2005/0191298 A1 | 9/2005 | Bell et al. | |
| 2006/0002937 A1 | 1/2006 | Schwaeble et al. | |
| 2006/0240476 A1 | 10/2006 | Soejima et al. | |
| 2007/0009528 A1 | 1/2007 | Larsen et al. | |
| 2007/0015703 A1 | 1/2007 | Wagner et al. | |
| 2007/0172483 A1 | 7/2007 | Schwaeble et al. | |
| 2011/0002931 A1 | 1/2011 | Tamburini | |
| 2011/0020337 A1 | 1/2011 | Schwaeble et al. | |

FOREIGN PATENT DOCUMENTS

EP   0 321 201    6/1989
JP   7-238100    12/1995
(Continued)

OTHER PUBLICATIONS

Jacquet et al. (J Immunol 2013; 190:3721-3731).*
Woodruff, T.M., et al., "A potent human C5a receptor antagonist protects against disease pathology in a rat model of inflammatory bowel disease," *J Immunol* 171:5514-5520 (2003).
Mulligan, M.S., et al., "Requirement and role of C5a in acute lung inflammatory injury in rats," *J Clin Invest* 98:503-512 (1996).
Goodfellow, R.M., et al., "Local therapy with soluble complement receptor 1 (sCR1) suppresses inflammation in rat mono-articular arthritis," *Clin Exp Immunol* 110:45-52 (1997).
Seelen, M.A., et al., "Autoantibodies against mannose-binding lectin in systemis lupus erythematosus," *Clin Exp Immunol* 134:335-343 (2003).
Xiao, F., et al., "Complement-mediated lung injury and neutrophil retention after ischemia-reperfusion," *J Appl Physiol* 82(5):1459-1465 (1997).

(Continued)

*Primary Examiner* — Zachary Skelding
(74) *Attorney, Agent, or Firm* — Tineka J. Quinton; Marcia S. Kelbon

(57) ABSTRACT

In one aspect, the invention provides methods of inhibiting the effects of MASP-2-dependent complement activation in a living subject. The methods comprise the step of administering, to a subject in need thereof, an amount of a MASP-2 inhibitory agent effective to inhibit MASP-2-dependent complement activation. In some embodiments, the MASP-2 inhibitory agent inhibits cellular injury associated with MASP-2-mediated alternative complement pathway activation, while leaving the classical (C1q-dependent) pathway component of the immune system intact. In another aspect, the invention provides compositions for inhibiting the effects of lectin-dependent complement activation, comprising a therapeutically effective amount of a MASP-2 inhibitory agent and a pharmaceutically acceptable carrier.

14 Claims, 52 Drawing Sheets

(56) References Cited

FOREIGN PATENT DOCUMENTS

| WO | WO 88/04300 | 6/1988 |
|----|----|----|
| WO | WO 91/11465 | 8/1991 |
| WO | WO 95/23161 | 8/1995 |
| WO | WO00/35483 | 6/2000 |
| WO | WO 01/07067 A2 | 2/2001 |
| WO | WO 02/06460 A2 | 1/2002 |
| WO | WO 03/063799 A2 | 8/2003 |
| WO | WO 03/081206 A2 | 10/2003 |
| WO | WO 2004/009664 A2 | 1/2004 |
| WO | WO 2004/050907 A2 | 6/2004 |
| WO | WO 2004/075837 A2 | 9/2004 |
| WO | WO 2004/106384 A1 | 12/2004 |
| WO | WO 2005/074607 A2 | 8/2005 |
| WO | WO 2005/120222 A2 | 12/2005 |
| WO | WO 2005/123128 A2 | 12/2005 |
| WO | WO 2005/123776 A1 | 12/2005 |
| WO | WO2011/047346 | 4/2011 |
| WO | WO 2011057158 A1 * | 5/2011 |

OTHER PUBLICATIONS

Kitano, A., et al., "New Treatment of Ulcerative Colitis with K-76," *Dis Colon Rectum* 35:560-567 (1992).

Takahashi, K., et al., "Mannose-binding lectin and its associated proteases (MASP) mediate coagulation and its deficiency is a risk factor in developing complications from infection, including disseminated intravascular coagulation," *Immunobiology* 216:96-102 (2011).

Tamano, M., et al., "Complement Activation in Cisplatin Nephrology," *Nephron* 81:442-443 (1999).

Fuke, Y., et al., "The role of complement activation, detected by urinary C5b-9 and urinary factor H, in the excretion of urinary albumin in cisplatin nephropathy," *Clin Nephrol* 71(2):110-117 (2009).

Racz, M. J., et al., "A comparison of short- and long-term outcomes after off-pump and on-pump coronary artery bypass graft surgery with sternotomy," *J Am Coll Cardiol* 43(4):557-64 (2004).

Fiane, A.E., et al., "Mechanism of complement activation and its role in the inflammatory response after thoracoabdominal aortic aneurysm repair," *Circulation* 108:849-856 (2003).

Ardehali, A., et al., "Modified reperfusion and ischemia-reperfusion injury in human lung transplantation," *J Thoracic Cardiovasc Surg* 126(6):1929-1934 (2003).

Beinrohr, L., et al., "C1, MBL-MASPs and C1-inhibitor: novel approaches fr targeting complement-mediated inflammation," *Trends in Molecular Medicine* 14(12):511-521 (2008).

Chen, C., et al., "Stoichiornetry of Complexes between Mannose-binding Protein and its Associated Serine Proteases," *The Journal of Biological Chemistry* 276(28):25894-25902 (2001).

Feinberg, H., et al,, "Crystal structure of the CUB1-EGF-CUB2 region of mannose-binding protein associated serine protease-2" *The EMBO Journal* 22(10):2348-2359 (2003).

Lynch, N.J., et al., "L-Ficolin Specifically Binds to Lipoteichoic Acid, a Cell Wall Constituent of Gram-Positive Bacteria, and Activates the Lectin Pathway of Complement," *The Journal of Immunology* 172:1198-1202 (2004).

Stover, C.M., et al., "Two Constituents of the Initiation Complex of the Mannan-Binding Lectin Activation Pathway of Complement Are Encoded by a Single Structural Gene," *The Journal of Immunology* 162:3481-3490 (1999).

Stover, C.M., et al,, "The rat and mouse homologues of MASP-2 and Map19, components of the lectin activation pathway of complement," *J Immunol* 163(12):6848-6859 (1999).

Thiel, S., et al., "A second serine protease associated with mannan-binding lectin that activates complement," *Nature* 386:506-510 (1997).

Thiel., S., et al., "Interaction of C1q and Marman-Binding Lectin (MBL) with C1r, C1s, MBL-Associated Serine Proteases 1 and 2, and the MBL Associated Protein MAp19," *The Journal of Immunology* 165:878-887 (2000).

Vorup-Jensen, T., et al., "Distinct Pathways of Mannan-Binding Lectin (MBL)- and C1 Complex Autoactivation Revealed by Reconstitution of MBL with Recombinant MBL-Associated Serine Protease-2," *The Journal of Immunology* 165:2093-2100 (2000).

Daha, M.R., et al., "Relative Resistance of the F-42-Stabilized Classical Pathway C3 Convertase to Inactivation by C4-Binding Protein," *The Journal of Immunology* 125(5):2051-2054 (1980).

Thielens, N.M., et al., "Interaction Properties of Human Mannan-Binding Lectin (MBL)-Associated Serine proteases-1 and -2, MBL-Associated Protein 19, and MBL," *The Journal of Immunology* 166:5068-5077 (2001).

Huber-Lang, M.S., et al,, "Complement-Induced impairment of Innate Immunity During Sepsis," *The Journal of Immunology* 169:3223-3231 (2002).

Matsushita, M., et al., "Cutting Edge: Complement-Activatting Complex of Fieolin and Mannose-Binding Lectin-Associated Serine Protease," *The Journal of Immunology* 164:2281-2284 (2000).

Rodrigues, M.L., et al., "Engineering Fab' Fragments for Efficient F(ab)$_2$ Formation in *Escherichia coli* and for Improved In Vivo Stability," *The Journal of Immunology* 151(12):6954-6961 (1993).

Pruitt, S.K., et al,, "The Effect of Soluble Complement Receptor Type 1 on Hyperacute Rejection of Porcine Xenografts," *Transplantation* 57(3):363-370 (1994).

Ohsawa, I, et al., "Cryoprecipitate of Patients with Cryoglobulinemic Glomerulonephritis Contains Molecules of the Lectin Complement Pathway," *Clinical Immunology* 101(1):59-66 (2001).

Endo, M., et al., "Regulation of in situ complement activation via the lectin pathway in patients with IgA nephropathy," *Clinical Nephrology* 55(3):185-191 (2001).

Lachmann, P.J., et al., "Initiation of Complement Activation," *Springer Semin Immunoptathol* 7:143-162 (1984).

Riedemann, N.C., et al., "Complement in Ischemia Reperfusion Injury," *American Journal of Pathology* 162(2):363-367 (2003).

Matsushita, M. et al., "Activation of the Lectin Complement Pathway by H-Ficolin (Hakata Antigen)," *The Journal of Immunology* 168:3502-3506 (2002).

Stengaard-Pedersen, K., et al., "Inherited Deficiency of Mannan-Binding Lectin-Associated Serine Protease 2," *The New Englad Journal of Medicine* 349(6):554-560 (2003).

Takahashi, M,, et al., "A truncated form of mannose-binding leetin-associated serine protease (MASP)-2 expressed by alternative polyadenylation is a component of the lectin complement pathway," *International Immunology* 11(5):859-863 (1999).

Ambrus, G., et al., "Natural Substrates and Inhibitors of Mannan-Binding Lectin-Associated Serine Protease-1 and -2: A Study on Recombinant Catalytic Fragments," *The Journal of Immunology* 170:1374-1382 (2003).

Moller-Kristensen, M., et al., "Levels of mannan-binding lectin-associated serine protease-2 in healthy individuals," *Journal of Immunological Methods* 282:159-167 (2003).

Petersen, S.V., et al., "Control of the Classical and MBL Pathway of Complement Activation," *Mol. Immunol* 37(14):803-811 (2000).

Dahl, M.R., et al., "MASP-3 and Its Association with Distinct Complexes of the Mannan-Binding Lectin Complement Activation Pathway," *Immunity* 15:127-135 (2001).

Petersen, S.V., et al., "An assay for the mannan-binding lectin pathway of complement activation," *Journal of Immunological Methods* 257:107-116 (2001).

Endo, M., et al., "Complement Activation Through the Lectin Pathway in Patients with Henoch-Schonlein Purpura Nephritis," *American Journal of Kidney Diseases* 35(3):401-407 (2000).

Collard, C.D., et al., "Complement Activation after Oxidative Stress: Role of the Lectin Complement Pathway," *American Journal of Pathology* 156(5):1549-1556 (2000).

Lu, J., et al., "Collectins and ficolins: sugar pattern recognition molecules of the mammalian innate immune system," *Biochimica et Biophysica Acta* 1572:387-400 (2002).

Jordan, J.E., et al., "Inhibition of Mannose-Binding Lectin Reduces Postischemic Myocardial Reperfusion Injury," *Circulation* 104:1413-1418 (2001).

Maynard, Y., et al., "Characterization of a Mannose and N-Acetylglucosamine-specific Lectin Present in Rat Hepatocytes," *The Journal of Biological Chemistry* 257(7):3788-3794 (1982).

(56) References Cited

OTHER PUBLICATIONS

Lee, R.T., et al., "Multivalent Ligand Binding by Serum Mannose-Binding Protein," *Archives of Biochemistry and Biophysics* 299(1):129-136 (1992).
Collard, C.D., et al.,"Endothelial Oxidative Stress Activates the Lectin Complement Pathway," *American Journal of Pathology* 159(3):1045-1054 (2001).
Ji, Y.H., et al., "Activation of the C4 and C3 Components of Complement by a Proteinase in Serum Bactericidal Factor, Ra Reactive Factor," *The Journal of Immunology* 150(2):571-578 (1993).
Kilpatrick., D.C., "Mannan-binding lectin: clinical significance and applications," *Biochimica et Biophysica Acta* 1572:401-413 (2002).
Weis, W.I., et al., "Structure of a C-type mannose-binding protein complexed with an oligosaccharide," *Nature* 360:127-134 (1992).
Stevens, J.H., et al., "Effects of Anti-C5a Antibodies on the Adult Respiratory Distress Syndrome in Septic Primates," *J. Clin. Invest.* 77:1812-1816 (1986).
Haeney, M.R., "The role of the complement cascade in sepsis," *Journal of Antimicrobial Chemotherapy* 41(Suppl. A):41-46 (1998).
Hack, C.E., et al., "Elevated Plasma Levels of the Anaphylatoxins C3a and C4a are Associated with a Fatal Outcome in Sepsis," *The American Journal of Medicine* 86:20-26 (1989).
Joiner, K.A., et al. "Complement and Bacteria: Chemistry and Biology in Host Defence," *Ann. Rev. Immunol.* 2:461-491 (1984).
Bone, R.C., "The Pathogenesis of Sepsis," *Annals of Internal Medicine* 115:457-469 (1991).
Czermak, B.J., et al., "Protective effects of C5a blockage in sepsis," *Nature Medicine* 5(7):788-792 (1999).
Hangen, D.H., et al., "Complement Levels in Septic Primates Treated with Anti-C5a Antibodies," *Journal of Surgical Research* 46:195-199 (1989).
Nakae, H., et al., "Chronological Changes in the Complement System in Sepsis," *Surg Today* 26:225-229 (1996).
Pangburn, M.K., et al., "Formation of the Initial C3 Convertase of the Alternative Complement Pathway: Acquisition of C3b-like Activities by Spontaneous Hydrolysis of the Putative Thioester in Native C3," *J. Exp. Med.* 154:856-867 (1981).
Wallis, R., et al., "Localization of the Serine Protease-binding Sites in the Collagen-like Domain of Mannose-binding Protein," *The Journal of Biological Chemistry* 279(14):14065-14073 (2004).
Wallis, R., et al., "Interaction of Mannose-binding Protein with Associated Serine Proteases: Effects of Naturally Occurring Mutations," *The Journal of Biological Chemistry* 275(40):30962-30969 (2000).
Sim, R.B., et al., "Innate immunity: Serine proteseases of the complement system," *Biochem Soc Trans* 25(5):545-550 (2000).
Petersen, S.V., et al., "Generation of Antibodies Towards MASP-1 and MASP-2 Using Bascterial Expression Systems," *Molecular Immunology* 35(6-7):409 (1998) (meeting abstract).
Bengtson, A., et al., "Anaphylatoxin Formation in Sepsis," *Arch Surg* 123:645-649 (1988).
Cech, T.R., et al., "Biological Catalysis by RNA," *Ann. Rev. Biochem.* 55:599-629 (1986).
Coremans, I.E.M., et al., "Changes in Antibodies to C1q Predict Renal Relapses in Sytemic Lupus Erythematosus," *American Journal of Kidney Diseases* 26(4):595-601 (1995).
Bone, R.C., et al., "Definitions for sepsis and organ failure," *Critical Care Medicine* 20(6):724-726 (1992).
Couser, W,G., et al., "The Effects pf Soluble Recombinant Complement Receptor 1 on Complement-Mediated Experimental Glomerulonephritis," *J. Am. Soc. Nephrol.* 5(11):1888-1894 (1995).
Bartlow, B.G., et al., "Nonimmunoglobulin C3 activating factor in membranoproliferative glomerulonephritis," *Kidney International* 15:294-302 (1979).
Clackson, T., et al., "Making antibody fragments using phage display libraries," *Nature* 352:624-628 (1991).
Alexopoulos, E., et al., "The pathogenetic significance of C5b-9 in IgA nephropathy," *Nephrol Dial Transplant* 10:1166-1172 (1995).
Bird, R.E., et al., "Single-Chain Antigen-Binding Proteins," *Science* 242:423-426 (1988).

Climie, S., et al., "Chemical synthesis of the thymidylate synthase gene," *Proc. Natl. Acad. Sci.* 87:633-637 (1990).
Cecic, I., et al., "Mediators of peripheral blood neutrophilia induced by photodynamic therapy of solid tumors," *Cancer Letters* 183:43-51 (2002).
Carter, P., et al., "Humanization of an anti-p185$^{HER2}$ antibody for human cancer therapy," *Proc. Natl. Acad. Sci.* 89:4285-4289 (1992).
Altschul, S.F., et al., "Gapped BLAST and PSI-BLAST: a new generation of protein database search programs," *Nucleic Acids Research* 25(17):3389-3402 (1997).
Johnson, L,V., et al., "Complement Activation and Inflammatory Processes in Drusen Formation and Age Related Macular Degeneration," *Exp. Eye Res.* 73:887-896 (2001).
Makino, K., et al., "A Microcapsule Self-Regulating Delivery System for Insulin," *Journal of Controlled Release* 12:235-239 (1990).
Lee, V.H.L., "Protease Inhibitors and Penetration Enhancers as Approaches to Modify Peptide Absorption," *Journal of Controlled Release* 13:213-223 (1990).
Jolliffe, L.K., et al., "Humanized Antibodies: Enhancing Therapeutic Utility Through Antibody Engineering," *Intern. Rev. Immunol* 10:241-250 (1993).
Jackson, D.Y., et al., "Potent α4β1 Peptide Antagonists as Potential Anti-Inflammatory Agents," *J. Med. Chem.* 40:3359-3368 (1997).
Hori, R., et al., "Enhanced Bioavailability of Subcutaneously Injected Insulin Coadministered with Collagen in Rats and Humans," *Pharmaceutical Research* 6(9):813-816 (1989).
Horvath, L., et al., "High levels of antibodies against C1q are associated with disease activity and nephritis but not with other organ manifestations in SLE patients," *Clinical and Experimental Rheumatology* 19:667-672 (2001).
Hageman, G.S., et al,, "An Integrated Hypothesis That Considers Drusen as Biomarkers of Immune-Mediated Processes at the RPE-Bruch's Membrane Interface in Aging and Age-Related Macular Degeneration," *Progress in Retinal and Eye Research* 20(6):705-732 (2001).
Fujita, T., "Evolution of the lectin-complement pathway and its role in innate immunity," *Nature* 2:346-353 (2002).
Flugelman, M.Y., et al., "Low Level In Vivo Gene Transfer Into the Arterial Wall Through a Perforated Balloon Catheter," *Circulation* 85:1110-1117 (1992).
Dickneite, G., "Influence of C1-Inhibitor on Inflammation, Edema and Shock," *Behring Inst. Mitt.* 93:299-305 (1993).
Daha, M.R., et al., "C3 Nephritic Factor (C3NeF): Stabilization of Fluid Phase and Cell-Bound Alternative Pathway Convertase," *The Journal of Immunology* 116(1):1-7 (1976).
Smith, D.B., et al., "Single-step purification of polypeptides expressed in *Escherichia coli* as fusions with glutathione S-transferase," *Gene* 67:31-40 (1988).
Greenspan, N.S., et al., "Idiotypes: structure and immunogenicity," *FASEB J.* 7:437-444 (1993).
De Boer, A.G., et al., "Rectal Absorption Enhancement of Peptide Drugs," *Journal of Controlled Release* 13:241-246 (1990).
Hochuli, E., et al., "New Metal Chelate Adsorbent Selective for Proteins and Peptides Containing Neighbouring Histidine Residues," *Journal of Chromatography* 411:177-184 (1987).
Fuertges, R., et al., "The Clinical Efficacy of Poly(ethylene glycol)-Modified Proteins," *The Journal of Controlled Release* 11:139-148 (1990).
Brenchley, P.E., et al., "Urinary C3dg and C5b-9 indicate active immune disease in human membranes nephropathy," *Kidney International* 41:933-937 (1992).
Salant, D.J., et al,, "Heymann nephritis: Mechanisms of renal injury," *Kidney International* 35:976-984 (1989).
Platt, J.L., et al., "Transplantation of discordant xenografts: a review of progress," *Immunology Today* 11(12):450-456 (1990).
Riechmann, L., et al., "Reshaping human antibodies for therapy," *Nature* 332:323-327 (1988).
Singer, I.I., et al., "Optimal Humanization of 1B4, an Anti-CD18 Murine Monoclonal Antibody, Is Achieved by Correct Choice of Human V-Region Framework Sequences," *The Journal of Immunology* 150(7):2844-2857 (1993).

(56) References Cited

OTHER PUBLICATIONS

Siegert, C.E.H., et al., "The Relationship between Serum Titers of Autoantibodies to C1q and Age in the General Population and in Patients with Systemic Lupus Erythematosus," *Clinical Immunology and Immunopathology* 67(3):204-209 (1993).
Seeger, W., et al., "Reproduction of Transfusion-Related Acute Lung Injury in an Ex Vivo Lung Model," *Blood* 76(7):1438-1444 (1990).
Schwaeble, W., et al., "The Mannan-Binding Lectin-Associated Serine Proteases (MASPs) and MAp19: Four Components of the Lectin Pathway Activation Complex Encoded by Two Genes," *Immunobiology* 205:455-466 (2002).
Kerjaschki, D., "The pathogenesis of membranous glomerulonephritis: from morphology to molecules," *Virchows Archiv B Cell Pathol* 58:253-271 (1990).
Sandhu, J.S., et al., "Protein Engineering of Antibodies," *Critical Reviews in Biotechnology* 12(5/6):437-462 (1992).
Ravetch, J.V., et al., "Fc Receptors," *Annu. Rev. Immnunol.* 9:457-92 (1991).
Rosenblatt, J., et al., "The Effect of Collagen Fiber Size Distribution on the Release Rate of Proteins from Collagen Matrices by Diffusion," *Journal of Controlled Release* 9:195-203 (1989).
Porter, R.R., "The Hydrolysis of Rabbit γ-Globulin and Antibodies with Crystalline Papain," *Biochem. J.* 73:119-126 (1959).
Merrifield, R.B., "Solid Phase Peptide Synthesis. I. The Synthesis of a Tetrapeptide," *J. Amer. Chem. Soc.* 85:2149-2154 (1963).
Presta, L.G., "Antibody engineering," *Current Opinion in Structural Biology* 2:593-596 (1992).
Lee,V.H.L., "Enzymatic Barriers to Peptide and Protein Absorption," *CRC Critical Reviews in Therapeutic Drug Carrier Systems* 5(2):69-97 (1988).
Weisman, H.F., et al., "Soluble Human Complement Receptor Type 1: In Vivo Inhibitor of Complement Suppressing Post-Isehemic Myocardial Inflammation and Necrosis," *Science* 249:146-151 (1990).
Yamakawa, I., et al., "Sustained Release of Insulin by Double-Layered Implant Using Poly(D,L-Lactic Acid)," *Journal of Pharmaceutical Sciences* 79(6):505-509 (1990).
Walport, M.J., et al., "Complement Deficiency and Autoimmunity," *Annals New York Academy of Sciences* 815:267-281 (1997).
Ohman, E.M., et al., "Early clinical experience with integrelin, and inhibitor of the platelet glycoprotein IIb/IIIa integrin receptor," *European Heart Journal* 16(Supplement L):50-55 (1995).
van der Kollo, L.E., et al., "Complement activation plays a key role in the side-effects of rituximab treatment," *British Journal of Haematology* 115:807-811 (2001).
Pack, P.,et al., "Improved Bivalent Miniantibodies, with Identical Avidity as Whole Antibodies, Produced by High Cell Density Fermentation of *Escherichia coli*," *Bio/Technology* 11:1271-1277 (1993).
Trouw, L.A., et al., "Autoantibodies to complement components," *Molecular Immunology* 38:199-206 (2001).
Zhang, L., et al., "A Discrete Site Modulates Activation of I Domains: Application to Integrin $\alpha_M\beta_2$," T*he Journal of Biological Chemistry* 271(47):29953-29957 (1996).
Zhou, W., et al., "Predominant role for C5b-9 in renal ischemia/reperfusion injury," *The Journal of Clinical Investigation* 105(10):1363-1371 (2000).
Taylor, L.D., et al., "Human immunoglobulin transgenes undergo rearrangement, somatic mutation and class switching in mice that lack endogenous IgM," *International Immunology* 6(4):579-591 (1994).
Takakura,Y. et al., "Control of Pharmaceutical Properties of Soybean Trypsin Inhibitor by Conjugation with Dextran I: Synthsis and Characterization," *Journal of Pharmaceutical Sciences* 78(2):117-121 (1989).
Takakura, Y., et al., "Control of Pharmaceutical Properties of Soybean Trypsin Inhibitor by Conjugation with Dextran II: Biopharmaceutical and Pharmacological Properties," *Journal of Pharmaceutical Sciences* 78(3):219-222 (1989).

Siegert, C. et al., "IgG Autoantibodies Against C1q are correlated with Nephritis, Hypocomplementemia, and dsDNA Antibodies in Systemic Lupus Erythematosus," *The Journal of Rheumatology* 18(2):230-234 (1991).
Shin, H.S., "Chemotactic and Anaphylatoxic Fragment Cleaved from the Fifth Component of Guinea Pig Complement," *Science* 162:361-363 (1968).
Slotman, G., et al., "Interaction of prostaglandins, activated. complement, and granulocytes in clinical sepsis and hypotension," *Surgery* 99(6):744-750 (1986).
Spitzer, R.E., et al., "Short Analytical Review on the origin of C3 Nephritic Factor (Antibody to the Alternative Pathway C3 Convertase): Evidence for the Adam and Eve Concept of Autoantibody Production," *Clinical Immunology and Immunopathology* 64(3):177-183 (1992).
Schumacher, W.A., et al., "The anaphylatoxins C3a and C5a are vasodilators in the canine coronary vasculature in vitro and in vivo," *Agents and Actions* 34(3/4):345-349 (1991).
Scandrett, A.L., et al., "Acute inflammation is the harbinger of glomerulosclerosis in anti-glomerular basement membrane nephritis," *Am. J. Physiol.* 268(37):F258-F265 (1995).
van de Winkel, J.G.J., et al., "Human IgG Fc receptor heterogeneity; molecular aspects and clinical implications," *Immunology Today* 14(5):215-221 (1993).
Vaughan, T.J., et al., "Human antibodies by design," *Nature Biotechnology* 16:535-539 (1998).
Ito, Y., et al., "An Insulin-releasing System that is Responisve to Glucose," *Journal of Controlled Release* 10:195-203 (1989).
Scatchard, G., "The Attractions of Proteins for Small Molecules and Ions," *Annals New York Academy of Sciences* 51:660-672 (1949).
Halbwachs, L., et al., "Nephritic Factor of the Classical Pathway of Complement," *J. Clin. Invest.* 65:1249-1256 (1980).
Green, L.L., et al., "Antigen-specific human monoclonal antibodies from mice engineered with human Ig heavy and light chain YACs," *Nature Genetics* 7:13-21 (1994).
Hammerschmidt, D.E., et al., "Association of Complement Activation and Elevated Plasma-C5a with Adult Respiratory Distress Syndrome," *The Lancet* 315:947-949 (1980).
Glover, G.I., et al., "Synthetic Peptide Inhibitors of Complement Serine Proteases—I. Identification of Functionally Equivalent Protease Inhibitor Sequences in Serpins and Inhibition of C1s and D," *Molecular Immunology* 25(12):1261-1267 (1988).
Fearon, D.T., et al., "Activation of the Properdin Pathway of Complement in Patients with Gram-Negative Bacteremia," *The New England Journal of Medicine* 292(18):937-940 (1975).
Fedor, M.J., et al,, "Substrate sequence effects on "hammerhead" RNA catalytic efficiency," *Proc. Natl. Acad. Sci. USA* 87:1668-1672 (1990).
Duncan, A.R., et al., "The binding site for C1q and IgG," *Nature* 332:738-740 (1988).
Dodds, A.W., et al., "Small-Scale Preparation of Complement Components C3 and C4," *Methods in Enzymology* 223:47-61 (1993).
Ault, B.H., "Factor H and the pathogenesis of renal diseases," *Pediatr Nephrol* 14:1045-1053 (2000).
Haseloff, J. et al., "Simple RNA enzymes with new and highly specific endoribonuclease activities," *Nature* 334:585-591 (1988).
Leventhal, J.R., et al., "Prolongation of Cardiac Xenograft Survival by Depletion of Complement," *Transplantation* 55(4):857-866 (1993).
Johnston, P.S., et al., "Discordant Xenograft Rejection in an Antibody-Free Model," *Transplantation* 54(4):573-576 (1992).
Huber-Lang, M.S., et al., "Protection of innate immunity by C5aR antagonist in septic mice," *FASEB J.* 16:1567-1574 (2002).
Hsueh, W., et al., "The role of the complement system in shock and tissue injury induced by tumour necrosis factor and endotoxin," *Immunology* 70:309-314 (1990).
Khan, T.N., et al., "Role of complement in renal tubular damage," *Histopathology* 26:351-356 (1995).
Matsushita, M., et al., "Activation of the Classical Complement Pathway by Mannose-binding Protein in Association with a Novel C1s-like Serine Protease," *J. Exp. Med.* 176:1497-1502 (1992).
Itakura, K. et al., "Synthesis and Use of Synthetic Oligonucleotides," *Ann. Rev. Biochem.* 53:323-356 (1984).

(56) References Cited

OTHER PUBLICATIONS

Kuntz, I.D., "Structure-Based Strategies for Drug Design and Discovery," *Science* 257:1078-1082 (1992).

Holmskov, U., et al., "Collectins and ficolins: humoral lectins of the innate immune defense," *Annu Rev Immunol* 21:547-78 (2003).

Ikeda, K., et al., "Serum Lectin with Known Structure Activates Complement through the Classical Pathway," *The Journal of Biological Chemistry* 262(16):7451-7454 (1987).

Jansen, J.H., et al., "In situ complement activation in porcine membranoproliferative glomerulonephritis type II," *Kidney International* 53:331-349 (1998).

Jensen, S., et al., "Taming of transposable elements by homology-dependent gene silencing," *Nature Genetics* 21:209-212 (1999).

Laudes, I.J., et al., "Anti-C5a Ameliorates Coagulation/Fibrinolytic Protein Changes in a Rat Model of Sepsis," *The American Journal of Pathology* 160(5):1867-1875 (2002).

Lloyd, B.H., et al., "Determination of optimal sites of antisense oligonucleotide cleavage within $TNF\alpha$ mRNA," *Nucleic Acids Research* 29(17):3664-3673 (2001).

DesJarlais, R.L., et al., "Structure-based design of nonpeptide inhibitors specific for the human immunodeficiency virus 1 protease," *Proc. Natl. Acad. Sci. USA* 87:6644-6648 (1990).

Bae, Y.H., et al., "Insulin Permeation Through Thermo-Sensitive Hydrogels," *Journal of Controlled Release* 9:271-279 (1989).

Asano, M. et al., "In Vivo Characteristics of Low Molecular Weight Copoly(L-Lactic Acid/Glycolic Acid) Formulations with Controlled Release of Lutenizing Hormone-Releasing Hormone Agonist," *Journal of Controlled Release* 9:111-122 (1989).

Martin, G.S., et al., "The Epidemiology of Sepsis in the United States from 1979 Through 2000," *The New England Journal of Medicine* 348(16):1546-1554 (2003).

Morath, S., et al., "Synthetic Lipoteichoic Acid from *Staphylococcus aureus* Is a Potent Stimulus of Cytokine Release," *J. Exp. Med.* 195(12):1635-1640 (2002).

Neth, O., et al., "Mannose-binding Lectin Binds to a Range of Clinically Relevant Microorganisms and Promotes Complement Deposition," *Infection and Immunity* 68(2):688-693 (2000).

Köhler, G., et al., "Continuous cultures of fused cells secreting antibody of predefined specificity," *Nature* 256:495-497 (1975).

Kon, S.P., et al., "Urinary C5b-9 excretion and clinical course in idiopathic human membranous nephropathy," *Kidney International* 48:1953-1958 (1995).

Lehto, T., et al., "Urinary excretion of protectin (CD59), Complement SC5b-9 and cytokines in membranous glomerulonephritis," *Kidney International* 47:1403-1411 (1995).

Levy, M., et al., "H deficiency in two brothers with atypical dense intramembranous deposit disease," *Kidney International* 30:949-956 (1986).

Kuntz, I.D., et al., "A Geometric Approach to Macromolecule-Ligand Interactions," *J. Mol. Biol.* 161:269-288 (1982).

Kuhlman, M., et al., "The Human Mannose-Binding Protein Functions as an Opsonin," *The Journal of Experimental Medicine* 169:1733-1745 (1989).

Marino, I.R., et al., "Hyperacute Rejection of Renal Discordant Xenograft (Pig-to-Rabbit): Model Assessment and Rejection Mechanisms," *Transplantation Proceedings* 22(3):1071-1076 (1990).

Losman, M.J., et al., "Baboon Anti-Idiotype Antibodies Mimic a Carcinoembryonic Antigen Epitope," *Int. J. Cancer* 46:310-314 (1990).

Lonberg, N., et al., "Antigen-specific human antibodies from mice comprising four distinct genetic modifications," *Nature* 368:856-859 (1994).

Mannik, M., et al., "Deposition of Antibodies to the Collagen-Like Region of C1q in Renal Glomeruli of Patients with Proliferative Lupus Glomerulonephritis," *Arthritis & Rheumatism* 40(8):1504-1511 (1997).

Meri, S., et al., "Activation of the Alternative Pathway of Complement by Monoclonal λ Light Chains in Membranoproliferative Glomerulonephritis," *J. Exp. Med.* 175:939-950 (1992).

Marks, J.D., et al., "By-passing Immunization: Human Antibodies from V-gene Libraries Displayed on Phage," *J. Mol. Biol.* 222:581-597 (1991).

Matsushita, M., et al., "A Novel Human Serum Lectin with Collagen- and Fibrinogen-like Domains that Functions as an Opsonin," *The Journal of Biological Chemistry* 271(5):2448-2454 (1996).

Mariani, M., et al., "A New Enzymatic Method to Obtain High-yield $F(ab)_2$ Suitable for Clinical Use from Mouse IgG1," *Molecular Immunology* 28(1/2):69-77 (1991).

Nakae, H., et al., "Serum Complement Levels and Severity of Sepsis," *Research Communications in Chemical Pathology and Pharmacology* 84(2):189-195 (1994).

Miyagawa, S., et al., "Effect of Anticomplement Reagents, K-76 COOH and FUT175, on Discordant Xenograft Survival," *Transplantation Proceeding* 24(2):483-484 (1992).

Morrison, S.L., et al., "Chimeric human antibody molecules: Mouse antigen-binding domains with human constant region domains," *Proc. Natl. Acad. Sci. USA* 81:6851-6855 (1984).

Murayama, O., et al., "Novel Peptide Ligands for Integrin $\alpha 6\beta 1$ Selected from a Phage Display Library," *J. Biochem.* 120:445-451 (1996).

Nisonoff, A., et al., "Separation of Univalent Fragments from the Bivalent Rabbit Antibody Molecule by Reduction of Disulfide Bonds," *Archives of Biochemistry and Biophysics* 89:230-244 (1960).

Niculescu, F., et al., "Rapid Communication: Peristent Complement Activation on Tumor Cells in Breast Cancer," *American Journal of Pathology* 140(5):1039-1043 (1992).

Riedemann, N.C., et al., "Increased C5a receptor expression in sepsis," *The Journal of Clinical Investigation* 110(1):101-108 (2002).

Riedemann, N.C., et al, "Regulation by C5a of Neutrophil Activation during Sepsis," *Immunity* 19:193-202 (2003).

Polotsky, V.Y., et al., "Interactions of Human Mannose-Binding Protein with Lipoteichoic Acids," *Injection and Immunity* 64(1):380-383 (1996).

Pickering, M.C., et al., "Uncontrolled C3 activation causes membranoproliferative glomerulonephritis in mice deficient in complement factor H," *Nature Genetics* 31:424-428 (2002).

Scherr, M., et al., "Rapid determination and quantitation of the accessibility to native RNAs by antisense oligodeoxynucleotides in murine cell extracts," *Nucleic Acids Research* 26(22):5079-5085 (1998).

Vogt, W., "Anaphylatoxins: Possible Roles in Disease," *Complement* 3:177-188 (1986).

Isaacs, J,D., et al., "Therapy with Monoclonal Antibodies: An in Vivo Model for the Assessment of Therapeutic Potential," *The Journal of Immunology* 148(10):3062-3071 (1992).

Brandt, J., et al., "Role of the complement membrane attack complex (C5b-9) in mediating experimental mesangioproliferative glomerulonephritis," *Kidney International* 49:335-343 (1996).

Whitlow, M., et al., "Single-Chain Fv Proteins and their Fusion Proteins," *Methods: A Companion to Methods in Enzymology* 2(2):97-105 (1991).

Larrick, J.W., et al., "PCR Amplification of Antibody Genes," *Methods: A Companion to Methods in Enzymology* 2(2):106-110 (1991).

Jones, P.T., et al., "Replacing the complementarity-determining regions in a human antibody with those from a mouse," *Nature* 321:522-525 (1986).

Ward, E.S., et al., "Genetic Manipulation and Expression of Antibodies," *Monoclonal Antibodies: Principles and Applications* pp. 137-185 (Wiley-Liss, Inc.) (1995).

Edens, R.E., et al., "Heparin is Not Just an Anticoagulant Anymore: Six and One-Half Decades of Studies on the Ability of Heparin to Regulate Complement Activity," *Complement Profiles*, vol. 1, Cruse and Lewis, Jr., eds. (Basel, Karger) pp. 69-120 (1993).

Courtenay-Luck, N.S., "Genetic manipulation of monoclonal antibodies," *Monoclonal Antibodies: Production, engineering and clinical application*, Ritter and Ladyman, eds., (Cambridge University Press) pp. 166-179 (1995).

Kelley, R.F., "Engineering Therapeutic Antibodies," *Protein Engineering: Principles and Practice*, Cleland and Craik, eds., (Wiley-Liss, Inc.) pp. 399-434 (1996).

(56) References Cited

OTHER PUBLICATIONS

Baines, M.G., et al., "Purification of Immunoglobulin G (IgG)," *Methods in Molecular Biology, vol. 10: Immunochemical Protocols*, Manson, ed., (The Humana Press, Inc.) pp. 79-104 (1992).

Matsushita, M., et al., "The role of ficolins in innate immunity," *Immunobiology* 205:490-497 (2002).

Green, J.A., et al., "Production of Polyclonal Antisera," *Methods in Molecular Biology, vol. 10: Immunochemical Protocols*, Manson, Ed., (The Humans Press, Inc.) pp. 1-5 (1992).

Klein, R. J., et al., "Complement factor H polymorphism in age-related macular degeneration," *Science* 308:385-389 (2005).

Haines, J.L., et al., "Complement factor H variant increases the risk of age-related macular degeneration," *Science* 308:419-421 (2005).

Edwards, A.O., et al., "Complement factor H polymorphisms and age-related macular degeneration," *Science* 308:421-424 (2005).

Stover, C.M., et al., "The rat and mouse homologues of MASP-2 and Map19, components of the lectin activation pathway of complement," *J Immunol* 163:6848-6859 (1999).

Isaki, D., et al., "Small mannone-binding lectin-associated protein plays a regulatory role in the lectin complement pathway," *J Immunol* 177:8626-8632 (2006).

de Vries, B., et al., "the mannose-binding lectin-pathway is involved in complement activation in the course of renal ischemia-reperfusion injury," *Am J Pathol* 165(5):1677-1688 (2004).

Nozaki, M., et al., "Drusen complement components C3a and C5a promote choroidal neovascularization," *PNAS* 103(7):2328-2333 (2006).

Bora, P.S., et al., "Role of complement and complement membrane attack complex in laser-indeuced choroidal neovascularaization," *J Immunol* 174:491-497 (2005).

Ambati, J., et al., "Age-related macular degeneration: etiology, pathogenesis, and therapeutic strategies," *Survey of Ophthalmology* 48(3):257-293 (2003).

Takahashi, M., et al., "Essential role of mannose-binding lectin-associated serine protease-1 activation of the complement factor D," *J Exp Med* 207(1):29-37 (2009).

Rintala, E., et al., "Protein C substitution in sepsis-associated purpura fulminans," *Critical Care Medicine* 28(7):2373-2378 (2000).

Kumura, E., et al., "Coagulation disorders following acute head injury," *Acta Neurochirurgica* 85(1-2):23-28 (1987) (Abstract only).

Kuehn, M.H., et al., "Disruption of the complement cascade delays retinal ganglion cell death following retinal ischemia-reperfusion," *Exp Eye Res* 87:89-95 (20080.

Ng, Y.C., et al., "Monoclonal rheumatoid factor-IgG immune complexes," *Arthritis and Rheumatism* 31(1):99-107 (1988).

Pickering, M.C., et al., "Spontaneous hemolytic uremic syndrome triggered by complement factor H lacking surface recognition domains," *J Exp Med* 204(6):1249-1256 (2007).

Tezel, G., et al., "Oxidative stress and the regulation of complement activation in human glaucoma," *Investigative Ophthalmology and Visual Science* 51(10):5071-5082 (2010).

Wilcox, L.A., et al., "Molecular basis of the enhanced susceptibility of the erythrocytes of paroxysmal nonturnal hemoglobinuria to hemolysis in acidified serum," *Blood* 78(3):820-829 (1991).

Zipfel, P.F., et al., "Deletion of complement factor H-related genes CFHR1 and CFHR3 is associated with atypical hemolytic uremic syndrome," *PLoS Genetics* 3(3):387-392 (2007).

Rossi, V., et al., "Substrate specificities of recombinant mannan-binding lectin-associated serine proteases-1 and -2", *J Biol Chem* 276(44):40880-40887 (2001).

Becker, J.U., et al., "Desseminated intravascular coagulation," *eMedicine*, WebMD, Medscape. Sep. 9, 2009, 25 pages. http://emedicine.medscape.com/article/779097-print.Downloaded Oct. 11, 2010.

Harlow, E., et al., "Antibodies: a laboratory manual," Cold springs Harbor Laboratory, Cold Springs Harbor, New York, 1988. pp. 567-569.

Krarup, A., et al., "Simultaneous activation of complement and coagulation by MBL-associated serine protease 2," *PLos ONE* 7(e623):1-8 (2007).

Schwaeble, H-W., et al. "Targeting of mannan-binding lectin-ssociated serine protease-2 confers protection from myocardial and gastrointestinal ischemia/reperfusion injury," *PNAS* 108(18):7523-7528 (2011).

Risitano, A.M., et al., "Achievements and limitations of complement inhibition by eculizumab in paroxysmal nocturnal hemoglobinuria: the role of complement component 3," *Mini-reviews in Medicinal Chemistry* 11:528-535 (2011).

Dmytrijuk, A., et al., "FDA report: Eculizumab (Soliris®) for the treatment of patients with paroxysmal nocturnal hemoglobinuria," *The Oncologist* 13:993-1000 (2008).

Morigi, M., et al., "Alternative pathway activation of complement by shiga toxin promotes exuberant C3a formation that triggers microvascular thrombosis," *J Immunol* 187(1):172-80 (2011).

Kavanagh, D., et al., "Genetics and complement in atypical HUS," *Pediatr Nephrol* 25(12):2431-42 (2010).

Moller-Kristensen, M., et al., "Mannan-binding lectin recognizes structures on ischaemic reperfused mouse kidneys and is implicated in tissue injury," *J Immunol* 61:426-434 (2005).

Farrar, C.A., et al., "Mannan binding lectin associated serine protease-2 (MASP-2) is a critical player in the pathophysiology of renal ischaemia reperfusion (I/R) injury and mediates tissue injury in absence of complement C4," *Molecular Immunology* 46:2832 (2009). (Abstract only).

Hillmen, P., et al., "Effect of eculizumab on hemolysis and transfusion requirements in patients with paroxysmal nocturnal hemoglobinuria," *N Eng J Med* 350:552-9 (2004).

Risitano, A.M., et al., "Complement fraction 3 binding on erythrocytes as additional mechanism of disease in paroxysmal nocturnal hemoglobinuria patients treated by eculizumab," *Blood* 113:4094-4100 (2009).

Teh, C., et al., "M-ficolin is expressed on monocytes and is a lectin binding to N-acetyl-D-glucosamine and mediates monocyte adhesion and phagocytosis of *Escherichia coli*," *Immunology* 101:225-232 (2000).

Hansen, S., et al., "Collectin 11 (CL-11, CL-K1) is a MASP-1/3-associated plasma collectin with microbial-binding acitivity," *J Immunol* 185:6096-6104 (2010).

Jack, D.L., et al., "Mannose-binding lectin enhances phagocytosis and killing of *Neisseria meningitidis* by human macrophages," *J Leukoc Biol* 77:328-336 (2005).

Aoyagi, Y., et al., "Role of L-fficolin_mannose-binding lectin-associated serine protease complexes in the opsonophagocytosis of type III group B streptococci," *J Immunol* 174:418-425 (2005).

Degn. S.E., et al., "Map19, the alternative splice product of the MASP2 gene," *J Immunological Methods* 373(1-2):89-101 (2011).

Schwaeble, W.J., et al., "Does properdin crosslink the cellular and the humoral immune response?" *Immunology Today* 20(1):17-21 (1999).

Risitano, A.M., et al., "Paroxysmal nonturnal hemoglobinuria: pathophysiology, natural history and treatment options in the era of biological agents," *Biologics* 2:205-222 (2008).

Sullivan, M., et al., "Epidemiological approach to identifying genetic predispositions for atypical hemolytic uremic syndrome," *Ann Human Genetics* 74(1):17-26 (2010).

Lee, C-S., et al., "Invasive pneumococcal pneumonia is the major cause of paediatric haemolytic-uraemic syndrome in Taiwan," *Nephrology* 17:48-52 (2012).

Noris, M., et al., "Atypical hemolytic-uremic syndrome," *N Eng J Med* 361:1676-87 (2009).

Noris, M., et al., "Atypical hemolytic-uremic syndrome," *GeneReviews* R.A, Pagon, T.D. Bird, C.R. Dolan, Eds. pp. 1-29. http://www.ncbi.nlm.gov/books/NBK1367/?report=printable downloaded Apr. 5, 2012.

Caprioli, J., et al., "Genetics of HUS: the impact of MCP, CFH, and IF mutations on clinical presentation, response to treatment, and outcome," *Blood* 108(4):1267-1279 (2006).

Noris, M., et al., "Relative role of genetic complement abnormalities in sporadic and familial aHUS and their impact on clinical phenotype," *Clin J Am Soc Nephrol* 5:1844-1859 (2010).

Banerjee, R., et al., "*Streptococcus pneumoniae*-associated hemolytic uremic syndrome among children in North America," *Pediatr Infect Dis J* 30:736-739 (2011).

(56) References Cited

OTHER PUBLICATIONS

Zoja, C., et al., "Shiga toxin-2 triggers endothelial leukocyte adhesion and transmigration via NF-κB dependent up-regulation of IL-8 and MCP-1," *Kidney Int* 62:846-856 (2002).
Zanchi, C., et al., "Fractalkine and CX3CR1 mediate leukocyte capture by endothelium in response to Shia Toxin," *J Immunol* 181:1460-1469 (2008).
Morigi, M., et al., "Verotixin-1-induced up-regulation of adhesive molecues render microvascular endothelial cells thrombogenic at high shear stress," *Blood* 98:1828-1835 (2001).
Guessous, F., et al., "Shiga Toxin 2 and lipopolysaccharide induce human microvascular endothelial cells to release chemokines and factors that stimulate platelet function," *Infection and Immunity* 73(12):8306-8316 (2005).
Hickey, C.A., et al., "Early volume expansion during diarrhea and relative nephroprotection during subsequent hemolytic uremic syndrome," *Arch Pediatr Adelesc Med* 165(10):884-889 (2011).
Benz, K., et al., "Thrombotic microangiopathy: new insights," *Curr Opin Nephrol Hypertens* 19:242-247 (2010).
Corrigan, J.J., Jr., et al., "Hemolytic-uremic syndrome," *Pediatrics in Review* 22(11):365-370 (2001).
Boyd, B., et al., "Verotoxin receptor glycolipid in human renal tissue," *Nephron* 51:207-210 (1989).
Wong, C.S., et al., "The risk of the hemolytic-uremic syndrome after antibiotic treatment of *Escherichia coli* 0157:H7 infections," *N Eng J Med* 342:1930-6 (2000).
George, J. N., "Thrombotic thrombocytopenic purpura," *N Eng J Med* 354:1927-35 (2006).
Tsai, H.-M., "Advances in the pathogenesis, diagnosis, and treatment of thrombotic thrombocytopenic purpura," *J Am Soc Nephrol* 14:1072-1081 (2003).
Smith, K.E., et al., "Antibiotic treatment of *Escherichia coli* O157 infection and the risk of hemolytic uremic syndrome, Minnesota," *Pediatr Infect Dis J* 31(1):37-41 (2012).
George, J.N., "The association of pregnancy with thrombotic thrombocytopenic purpura-hemolytic uremic syndrome," *Curr Opin Hematol* 10(5):339-344 (2003).
Hamasaki, K., et al., "Systemic lupus erythematosus and thrombotic thrombocytopenic purpura: a case report and literature review," *Clin Rheumatol* 22:355-358 (2003).
Azarm, T., et al., "Thrombotic thrombocytopenic purpura associated with clopidogral: a case report and review of the literature," *J Res Med Sci* 16(3):353-357 (2011).
Moake, J.L., "Thrombotic microangiopathies," *N Eng J Med* 347(8):589-600 (2002).
Pelras, S., et al., "Severe transient ADAMTS13 deficiency in pneumococcal-associated hemolytic uremic syndrome," *Pediatr Nephrol* 26:631-635 (2011).
Rock, G.A., et al., "Comparison of plasma exchange with plasma infusion in the treatment of thrombotic thrombocytopenic purpura," *N Engl J Med* 325(6):393-397 (1991).
Tsai, H.-M., "Thrombotic thrombocytopenic purpura: A thrombotic disorder caused by ADAMTS13 deficiency," *Hematol Oncol Clin North Am* 21(4):609-v (2007).
Galbusera, M., et al. "Inherited thrombotic thrombocytopenic purpura," *Haematologica* 94(2):166-170 (2009).
Ruiz-Torres, M.P., et al., "Complement activation: the missing link between ADAMTS-13 deficiency and microvascular thrombosis of thrombotic microangiopathies," *Thromb Haemost* 93:443-52 (2005).
Reti, M., et al., "Complement activation in thrombotic thrombocytopenic purpura," *J Hrombosis Haemostatsis* 10:791-798 (2012).
Peerschke, E.I., et al., "Complement activation on platelets: implications for vascular inflammation and thrombosis," *Mol Immunol* 47(13):2170-2175 (2010).
Forsyth, K.D., et al., "Neutrophil-mediated endothelial injury in haemolytic uraemic syndrome," *The Lancet* 2(8660):411-414 (1989).

George, J.N., et al., "Systemic malignancies as a cuase of enexprected microangiopathic hemolytic anemia and thrombocytopenia," *Oncology* 25(10):908-14 (2011).
Huber-Lang, M., et al., "Generation of C5a in the absence of C3: a new complement activation pathway," *Nat Med* 12(6):682-687 (2006).
Schultz, D.W., et al., "Analysis of the *ARMD1* locus: evidence that a mutation in *HEMICENTIN-1* is associated with age-related macular degeneration in a large family," *Hum Mol Genet* 12(24):3315-3323 (2003).
Mullins, R.F., et al., "Drusen associated with aging and age-related macular degeneration contain proteins common to extracellular deposits associated with atherosclerosis, elastosis, amyloidosis, and dense deposit disease," *FASEB J* 14(7):835-846 (2000).
Johnson, L.V., et al., "A potential for immune complex pathogenesis in drusen formation," *Exp Eye Res* 70:441-449 (2000).
Sakurai, E., et al., "Macrophage depletion inhibits experimental choroidal neovascularization," *Invest Ophthalmol Vis Sci* 44(8):3578-3585 (2003).
Espinosa-Heidmann, D.G., et al., "Macrophage depletion diminishes lesion size and severity in experimental choroidal neovascularization," *Invest Opthalmol Vis Sci* 44(8):3586-3592 (2003).
Stasi, K., et al., "Complement component 1Q (C1Q) upregulation in retina of murine, primate, and human glaucomatous eyes," *Invest Ophthalmol Vis Sci* 47(3):1024-1026 (2006).
Kuehn, M.H., et al., "Retinal synthesis and deposition of compement components induced by ocular hypertension," *Exp Eye Res* 83:620-628 (2006).
Kaufman, R.J., et al., "Improved vectors for stable expression of foreign genes in mammalian cells by use of the untranslated leader sequence from EMC virus," *Nucleic Acids Research* 19(16):4485-4490 (1991).
Kaufman, R.J., et al., "Selection and coamplification of heterologous genes in mammalian cells," *Methods in Enzymology* 185:537-566 (1990).
Shea, K.J., et al., "Molecular imprinting of synthetic network polymers: the De Novo synthesis of macromolecular binding and catalytic sites," *Trands in Polymer Science* 2(5):166-173 (1994).
Coligan, J.E., et al. (Eds.). 1991. Production of Monoclonal Antibodies. *Current Protocols in Immunology*, pp. 2.5.1-2.6.7. vol. 1. John E. Wiley & Sons.
Gal, P., et al., "A true autoactivating enzyme: Structural insight into mannose-binding lectin-associated serine protease activations," *J Biol Chem* 280(9):33435-33444 (2005).
Nicholson, M.L., et al., "A comparison of the results of renal transplantation from non-heart-beating, conventional cadaveric, and living donars," *Kidney International* 58(6):2585-2591 (2000).
Ryan, S.J., et al., "the development of an experimental model of subretinal neovascularization in disciform macular degeneration," *Trans Am Ophthalmol Soc* 77:707-745 (1979).
Tobe, T., et al., "Targeted disruption of the FGF2 gene does not prevent choroidal neovascularization in a murine model," *Am J Pathol* 153(5):1641-46 (1998).
Fong, J.S.C., et al., "Prevention of the localized and generalized Shwartzman reactions by an anticomplementary agent, cobra venom factor," *J Exp Med* 134(3 pt 1):642-655 (1971).
Palanki, M.S.S., et al., "Development of prodrug 4-Chloro-3-(5-methyl-3-{[4-(2-pyrrolidin-1-ylethoxy)phenyl]amino}-1,2,4-benzotriazin-7-yl)phenyl benzoate (TG10081): A topically administered therapeutic candidate in clinical trials for the treatment of age-related macular degeneration," *J Med Chem* 51:1546-1559 (2008).
Takahashi, M., et al., "Mannose-binding lectin (MBL)-associated serine protease (MASP)-1 contributes to activation of the lectin complement pathway," *J Immunol* 180(9):6132-6138 (2008).
Yang, Y., et al., "Complete complement components C4A and C4B deficiencies in human kidney diseases and systemic lupus erythematosus," *J Immunol* 173(4):2803-2814 (2004).
Moller-Kristensen, M., et al., "Cooperation between MASP-1 and MASP-2 in the generation of C3 convertase through the MBL pathway," *Int Immunol* 19(2):141-149 (2007).

(56) References Cited

OTHER PUBLICATIONS

Brown, J.S., et al., "The classical pathway is the dominant complement pathway required for innate immunity to *Streptococcus pneumonia* infection in mice," *Proc Natl Acad Sci USA* 99(26):16969-16974 (2002).

Clark, A., et al., "Evidence for non-traditional activation of complement factor C3 during murine liver regeneration," *Mol Immunol* 45(11):3125-3132 (2008).

Lin, T., et al., "Deficiency of C4 from donor or recipient mouse fails to prevent renal allograft rejection," *Am J Pathol* 168(4):1241-1248 (2006).

Zhang, M., et al., "Natural antibody mediated innate autoimmune response," *Mol Immunol* 44(1-3):103-110 (2007).

Zhang, M., et al., "Activation of the lectin pathway by natural IgM in a model of ischemia/reperfusion injury," *J Immunol* 177(7):4727-4734 (2006).

Clark, B. (Aug. 16, 2010). Antibiotics, HUS, and Gastroenteritis. Retrieved from http://www.foodsafetynews.com/2010/08/antibiotics-hus-and-gastroenteritis/ Retrieved on Apr. 3, 2012.

Ng, E.W.M., et al., "Pegaptanib, a targeted anti-VEGF aptamer for ocular vascular disease," *Nat Rev Drug Discov* 5(2):123-132 (2006).

May, J.E., et al., "Homolysis of sheep erythrocytes in guinea pig srum deficient in the fourth component of complement," *J Immunol* 111(6):1668-1676 (1973).

Levy, E.M., et al., "The effect of acute renal failure on mortality," *JAMA* 275:1489-1494 (1996).

Knappik, A., et al., "Fully synthetic human combinatorial antibody libraries (HuCAL) based on modular consensus frameworks and CDRs randomized with trinucleotides," *J Mol Biol* 296:57-86 (2000).

Eskandari, M.E., et al., "Anti-tumor necrosis factor antibody therapy fails to prevent lethality after cecal ligation and puncture or endotoxemia," *J Immunol* 148(9):2724-2730 (1992).

Boos, L.A., et al., "Murine complement C4 is not required for experimental autoimmune encephalomyelitis," *GLIA* 49:158-160 (2004).

Wichterman, K.A., et al., "Sepsis and septic shock—a review of laboratory models and a proposal," *Journal of Surgical Research* 29:189-201 (1980).

Thadhani, R., et al., "Acute renal failure," *New Engl J Med* 334(22):1448-1460 (1996).

Takahashi, K., et al., "Lack of mannose-binding lectin-A enhances survival in a mouse model of acute septic peritonitis," *Microbes and Infection* 4:773-784 (2002).

Shandelya, S.M., et al., "Evaluation of the role of polymorphocuclear leukocytes on contractile function in myocardial reperfusion injury. Evidence for plasma-mediated leukocyte activation," *Circulation* 87:536-546 (1993).

Polak, L., et al, "Suppression of the haemorrhagic component of the Schwartzmann reaction by anti-complement serum," *Nature* 223:738-739 (1969).

Zhang, J., et al., "Early Complement Activation and Decreased Levels of Glycosylphosphatidylinositol-Anchored Complement Inhibitors in Human and Experimental Diabetic Retinopathy," *Diabetes* 51(12):3499-3504 (2002).

Hansen, T.K., et al., "Association Between Mannose-Binding Lectin and Vascular Complications in Type 1 Diabetes," *Diabetes* 53(6):1570-1576 (2004).

Huang, Z., "Structural Chemistry and Therapeutic Intervention of Protein-Protein Interactions in Immune Response, Human Immunodeficiency Virus Entry, and Apoptosis," *Pharmacology & Therapeutics* 86(3):201-215 (2000).

Khan, A.U., et al., "Ribozymes: A Modern Tool in Medicine," *Journal of Biomedical Science* 10(5):457-467 (2003).

Shoji, Y., et al., "Current Status of Delivery Systems to Improve Target Efficacy of Oligonucleotides," *Current Pharmaceutical Design* 10(7):785-796 (2004).

Rieben, R., et al., "Immunoglobulin M-Enriched Human Intravenous Immunoglobulin Prevents Complement Activation In Vitro and In Vivo in a Rat Model of Acute Inflammation," *Blood* 93(3):942-951 (1999).

Simon, H.U., et al., "IVIG—Mechanisms of Action," *Allergy* 58(7):543-552 (2003).

Harlow, E., et al. Using Antibodies: A Laboratory Manual. Cold Springs Harbor Press, 1999. pp. 44, 45 and 52.

Jack, D.L., et al., "Anti-Microbial Activities of Mannose-Binding Lectin," *Biochemical Society Transactions* 31(Pt 4):753-757 (2003).

Turner, M.W., "Mannose-binding lectin: the pluripotent molecule of the innate immune system," *Immunology Today* 17(11):532-540 (1996).

Walsh, M.C., et al., "Complement activation and tissue injury following myocardial ischemia and reperfusion is dependent on MBL," *Molecular Immunology* 41(2-3):322-323 (2004). (Journal abstract).

Norwood, M.G.A., et al., "Consumption of mannan-binding lectin during abdominal aortic aneurysm repair," *Eur J Endovasc Surg* 31:239-243 (2006).

Fidler, K.J., et al., "Increased incidence and severity of the sustemic inflammatory response syndrome in patients deficient in mannose-binding lectin," *Intensive Care Med* 30:1438-1445 (2004).

Schlapbach, L.J., et al., "Differeential role of the lectin pathway of complement activation in susceptibility to neonatal sepsis," *Clinical Infectious Diseases* 51(2):153-162 (2010).

Garred, P., et al., "Genetic susceptibility to sepsis: A possible role for mannose-binding lectin," *Current Infectious Disease Reports* 6(5):367-373 (2004).

Garred, P., et al., "Association of mannose-binding lectin polymorphisms with sepsis and fatal outcome, in patients with systemic inflammatory response syndrome," *J Infectious Diseases* 188(9):1394-1403 (2003).

Hibberd, M.L., et al., "Variation in the mannose binding lectin (MBL) gene and susceptibility to sepsis," *Sepsis* 4(3):201-207 (2001).

Hjelmesaeth, J., et al., "Early posttansplant serum osteoprotegerin levels predict long-term (8-year) patient survival and cardiovascular death in renal transplant patients," *J Amer Soc Nephrology* 17(6):1746-1754 (2006).

Olesen, H.V., et al., "The mannan-binding lectin pathway and lung disease in systic fibrosis-dysfunction of mannan=binding lectin-associated serine protease 2 (MASP-2) may be a major modifier," *Clinical Immunology* 121:324-331 (2006).

Carlsson, M., et al., "Csystie fibrosis patients heterozygous for *MASP-2* gene mutation have lowered MASP-2 concentrations, without relation to clinical findings," *Molecular Immunology* 40(2-4):208 (2003). (Journal Abstract).

Sorensen, R., et al., "Mannan-binding-lectin-associated serine proteases, characteristics and disease assoications," *Springer Semin Immun* 27:299-319 (2005).

Weimann, A., et al., "Role of MBL, MASP2 and NOD2 polymorphisms in patients with inflammatory blowel disease," *DGKL Congress of Clinical Chemistry and Laboratory Medicine 2004* 42(10):A145 (2004). (Abstract only).

Novovic, S., et al., "Mannan-hinding lectin and mannan-binding lectin-associated serine protease 2 in acute pancreatitis," *Pancreas* 40(7):1097-1102 (2011).

Ali, M., et al., "The deficiency of the lectin pathway functional activity in MASP-2 deficient mice does not effect the survival drom acute polymicrobial septic peritonitis," *Molecular Immunology* 45:4181 (P207) (2008). (Abstract only).

Chrysanthou, E., et al., "The lectin pathway of complement activation in cerebral ischaemia and reperfusion injury," Neuroscience 2011 Presentation Abstact.

Orsini, F., et al., "Mannose-binding lectin as a target for cerebral ischemic injury," *Molecular Immunology* 48(14):1677 (2011), (Abstract only).

Arumugam, T.V., et al., "Neuroprotection in stroke by complement inhibition and immunoglobulin therapy," *Neuroscience* 158(3):1074-1089 (2009).

Ostergaard, J., et al., "Complement activation and diabetic vascular complications," *Clinica Chimica* 361:10-19 (2005).

Rasmussen, H.H., et al., "Toweards a comprehensive database of proteins from the urine of patients with bladder cancer," *Journal of Urology* 155:2113-2119 (1996).

Stover, C., et al, "Functional *MASP2* single nucleotide polymorphism plays no role in psoriasis," *Br Assoc Dermatol* 152:1313-1315 (2005).

(56) References Cited

OTHER PUBLICATIONS

Moller-Kristensen, M., et al., "Burn injury reveals altered phenotype in mannan-binding lectin-deficient mice," *J Invest Dermatol* 127:1524-1531 (2007).
Miller, C., et al., "Molecular defects in the mannose binding lectin pathway in dermatological disease: Case report and literature review," *Clinical and Molecular Allergy* 8:6-14 (2010).
Glovsky, M.M., et al., "Complement determinations in human disease," *Ann Allergy Asthma Immunol* 93:513-523 (2004).
Ammitzboll, C.G., et al., "Levels of lectin pathway proteins in plasma and suynovial fluid of rheumatoid arthritis and osteoarthritis," *Rheumatol Int* Apr. 3, 2011 retrieved from the internet at URL/http/www.springerlink.com.
Farrar, C.A., et al., "Role of complement and neutrophil migration in renal ischaemia/reperfusion injury," *Molecular Immunology* 38:87 (2001). (Abstract only).
Roos, A., et al., "Glomerular activation of the lectin pathway of complement in IgA nephropathy is associated with more severe renal disease," *J Am Soc Nephrol* 17:1724-1734 (2006).
Farrar, C.A., et al., "The role of complement in renal ischaemia/reperfusion injury," *Immunobiology* 98(Suppl.1):101 (1999). (Abstract only).
Ytting, H., et al., "Serum mannan-binding lectin-associated serine protease 2 levels in colorectal cancer: Relation to recurrence and mortality," *Clinical Cancer Research* 11:1441-1446 (2005).
Ytting, H., et al., "Increased acitivity of the mannan-binding lectin complement activation pathway in patients with colorectal cancer," *Scand J Gastroenteral* 39:674-679 (2004).
Verma, A., et al., "Clinical significance of mannose-binding lectin-associated serine protease-2 expression in esophageal squamous cell carcinoma," *Int J Cancer* 118:2930-2935 (2006).
Ytting, H., et al., "The postoperative levels of MASP-2, a marker of survival in primary colorectal cancer," *Proc Am Assoc Cancer Res Annual Meeting* 46:Abstract 1205 (Apr. 2012).
Nielsen, H.J., et al., "Soluble Masp-2 and Timp-1 protein levels as selection marker for adjuvant therapy in colon cancer," *Gstroenterology* 128(4)(Suppl.2):A71 (2005). (Abstract only).
Berger, S.P., et al., "Complement in glomerular injury," *Semin Immunopathol* 29:375-384 (2007).
Wagner, E., et al., "Therapeutic potential of complement modulation," *Nature Reviews* 9:43-56 (2010).
Taylor, C.M., "Enterohaemorrhagic *Escherichia coli* and *Shigella dysenteriae* type 1-induced haemolytic uraemic syndrome," *Pediatr Nephrol* 23:1425-1431 (2008).
Gando, S., et al., "Increased Neutrophil Elastase, Persistent intravascular Coagulation, and Decreased Fibrinolytic Activity in Patients with Postraumatic Acute Respiratory Distress Syndrome," *J Trauma, Injury, Infect, Crit Care* 42(6):1068-1072 (1997).
Preston, F.E., et al., "Disseminated intravascular coagulation as a consequence of cerebral damage," *J Neurology, Neyrosurgery, and Psychiatry* 37:241-248 (1974).
Chen, C.B., and Wallis, R., "Two Mechanisms for Mannose-binding Protein Modulation of the Activity of its Associated Serine Proteases," *J.Biol.Chem.* 279(25):26058-26065 (2004).
Wan, S., et al., "Human Cytokine Responses to Cardiac Transplantation and Coronary Artery Bypass Grafting," *J.Thorac.Cardiovasc. Surg* 111(2):469-477 (1996).
Demers, P., et al., "Coronary Artery Endothelial Dysfunction After Ischemia-reperfusion and Acute Untreated Rejection in a Canine Hetertopic Heart Transplantation Model," *Transplantation* 71(1):26-32 (2001).
Hill, A., et al., "Recent develeopments in the understanding and management of paroxysmal nocturnal haemoglobinuria," *British Journal of Haematology* 137:181-192 (2007).

\* cited by examiner

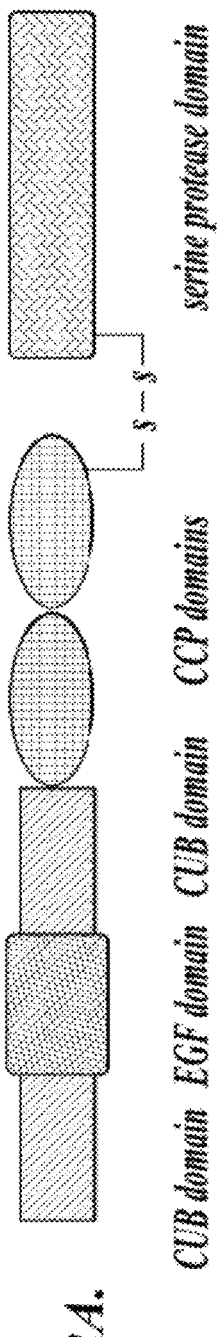
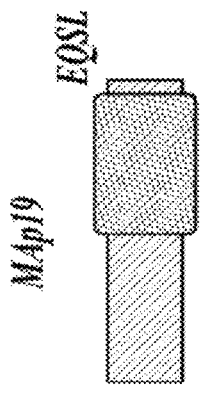
Fig.2A.
Fig.2B.

```
                          SEQUENCE LISTING

<160> NUMBER OF SEQ ID NOS: 65

<210> SEQ ID NO 1
<211> LENGTH: 725
<212> TYPE: DNA
<213> ORGANISM: Homo sapiens
<220> FEATURE:
<221> NAME/KEY: CDS
<222> LOCATION: (27)..(584)

<400> SEQUENCE: 1
ggccaggcca gctggacggg cacacc atg agg ctg ctg acc ctc ctg ggc ctt         53
                               Met Arg Leu Leu Thr Leu Leu Gly Leu
                                 1               5 ctg tgt ggc tcg gtg gcc acc ccc ttg ggc ccg aag tgg cct gaa cct        101
Leu Cys Gly Ser Val Ala Thr Pro Leu Gly Pro Lys Trp Pro Glu Pro
 10                  15                  20                  25 gtg ttc ggg cgc ctg gca tcc ccc ggc ttt cca ggg gag tat gcc aat        149
Val Phe Gly Arg Leu Ala Ser Pro Gly Phe Pro Gly Glu Tyr Ala Asn
                 30                  35                  40 gac cag gag cgg cgc tgg acc ctg act gca ccc ccc ggc tac cgc ctg        197
Asp Gln Glu Arg Arg Trp Thr Leu Thr Ala Pro Pro Gly Tyr Arg Leu
             45                  50                  55 cgc ctc tac ttc acc cac ttc gac ctg gag ctc tcc cac ctc tgc gag        245
Arg Leu Tyr Phe Thr His Phe Asp Leu Glu Leu Ser His Leu Cys Glu
         60                  65                  70 tac gac ttc gtc aag ctg agc tcg ggg gcc aag gtg ctg gcc acg ctg        293
Tyr Asp Phe Val Lys Leu Ser Ser Gly Ala Lys Val Leu Ala Thr Leu
     75                  80                  85 tgc ggg cag gag agc aca gac acg gag cgg gcc cct ggc aag gac act        341
Cys Gly Gln Glu Ser Thr Asp Thr Glu Arg Ala Pro Gly Lys Asp Thr
 90                  95                 100                 105 ttc tac tcg ctg ggc tcc agc ctg gac att acc ttc cgc tcc gac tac        389
Phe Tyr Ser Leu Gly Ser Ser Leu Asp Ile Thr Phe Arg Ser Asp Tyr
                110                 115                 120 tcc aac gag aag ccg ttc acg ggg ttc gag gcc ttc tat gca gcc gag        437
Ser Asn Glu Lys Pro Phe Thr Gly Phe Glu Ala Phe Tyr Ala Ala Glu
            125                 130                 135 gac att gac gag tgc cag gtg gcc ccg gga gag gcg ccc acc tgc gac        485
Asp Ile Asp Glu Cys Gln Val Ala Pro Gly Glu Ala Pro Thr Cys Asp
        140                 145                 150 cac cac tgc cac aac cac ctg ggc ggt ttc tac tgc tcc tgc cgc gca        533
His His Cys His Asn His Leu Gly Gly Phe Tyr Cys Ser Cys Arg Ala
    155                 160                 165 ggc tac gtc ctg cac cgt aac aag cgc acc tgc tca gag cag agc ctc        581
Gly Tyr Val Leu His Arg Asn Lys Arg Thr Cys Ser Glu Gln Ser Leu
170                 175                 180                 185 tag cctcccctgg agctccggcc tgcccagcag gtcagaagcc agagccagcc              634
tgctggcctc agctccgggt tgggctgaga tggctgtgcc ccaactccca ttcacccacc      694
atggacccaa taataaacct ggccccaccc c                                      725

<210> SEQ ID NO 2
<211> LENGTH: 185
<212> TYPE: PRT
<213> ORGANISM: Homo sapiens
```

-continued

<400> SEQUENCE: 2

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185

<210> SEQ ID NO 3
<211> LENGTH: 170
<212> TYPE: PRT
<213> ORGANISM: Homo sapiens

<400> SEQUENCE: 3

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
    130                 135                 140

Leu Gly Gly Phe Tyr Cys Ser Cys Arg Ala Gly Tyr Val Leu His Arg
145                 150                 155                 160

Asn Lys Arg Thr Cys Ser Glu Gln Ser Leu
                165                 170

```
<210> SEQ ID NO 4
<211> LENGTH: 2460
<212> TYPE: DNA
<213> ORGANISM: Homo sapiens
<220> FEATURE:
<221> NAME/KEY: CDS
<222> LOCATION: (22)..(2082)

<400> SEQUENCE: 4
ggccagctgg acgggcacac c atg agg ctg ctg acc ctc ctg ggc ctt ctg        51
                        Met Arg Leu Leu Thr Leu Leu Gly Leu Leu
                         1               5                  10 tgt ggc tcg gtg gcc acc ccc ttg ggc ccg aag tgg cct gaa cct gtg        99
Cys Gly Ser Val Ala Thr Pro Leu Gly Pro Lys Trp Pro Glu Pro Val
                 15                  20                  25 ttc ggg cgc ctg gca tcc ccc ggc ttt cca ggg gag tat gcc aat gac       147
Phe Gly Arg Leu Ala Ser Pro Gly Phe Pro Gly Glu Tyr Ala Asn Asp
             30                  35                  40 cag gag cgg cgc tgg acc ctg act gca ccc ccc ggc tac cgc ctg cgc       195
Gln Glu Arg Arg Trp Thr Leu Thr Ala Pro Pro Gly Tyr Arg Leu Arg
         45                  50                  55 ctc tac ttc acc cac ttc gac ctg gag ctc tcc cac ctc tgc gag tac       243
Leu Tyr Phe Thr His Phe Asp Leu Glu Leu Ser His Leu Cys Glu Tyr
 60                  65                  70 gac ttc gtc aag ctg agc tcg ggg gcc aag gtg ctg gcc acg ctg tgc       291
Asp Phe Val Lys Leu Ser Ser Gly Ala Lys Val Leu Ala Thr Leu Cys
 75                  80                  85                  90 ggg cag gag agc aca gac acg gag cgg gcc cct ggc aag gac act ttc       339
Gly Gln Glu Ser Thr Asp Thr Glu Arg Ala Pro Gly Lys Asp Thr Phe
                 95                 100                 105 tac tcg ctg ggc tcc agc ctg gac att acc ttc cgc tcc gac tac tcc       387
Tyr Ser Leu Gly Ser Ser Leu Asp Ile Thr Phe Arg Ser Asp Tyr Ser
            110                 115                 120 aac gag aag ccg ttc acg ggg ttc gag gcc ttc tat gca gcc gag gac       435
Asn Glu Lys Pro Phe Thr Gly Phe Glu Ala Phe Tyr Ala Ala Glu Asp
        125                 130                 135 att gac gag tgc cag gtg gcc ccg gga gag gcg ccc acc tgc gac cac       483
Ile Asp Glu Cys Gln Val Ala Pro Gly Glu Ala Pro Thr Cys Asp His
    140                 145                 150 cac tgc cac aac cac ctg ggc ggt ttc tac tgc tcc tgc cgc gca ggc       531
His Cys His Asn His Leu Gly Gly Phe Tyr Cys Ser Cys Arg Ala Gly
155                 160                 165                 170 tac gtc ctg cac cgt aac aag cgc acc tgc tca gcc ctg tgc tcc ggc       579
Tyr Val Leu His Arg Asn Lys Arg Thr Cys Ser Ala Leu Cys Ser Gly
                175                 180                 185 cag gtc ttc acc cag agg tct ggg gag ctc agc agc cct gaa tac cca       627
Gln Val Phe Thr Gln Arg Ser Gly Glu Leu Ser Ser Pro Glu Tyr Pro
            190                 195                 200 cgg ccg tat ccc aaa ctc tcc agt tgc act tac agc atc agc ctg gag       675
Arg Pro Tyr Pro Lys Leu Ser Ser Cys Thr Tyr Ser Ile Ser Leu Glu
        205                 210                 215 gag ggg ttc agt gtc att ctg gac ttt gtg gag tcc ttc gat gtg gag       723
Glu Gly Phe Ser Val Ile Leu Asp Phe Val Glu Ser Phe Asp Val Glu
    220                 225                 230 aca cac cct gaa acc ctg tgt ccc tac gac ttt ctc aag att caa aca       771
Thr His Pro Glu Thr Leu Cys Pro Tyr Asp Phe Leu Lys Ile Gln Thr
235                 240                 245                 250 gac aga gaa gaa cat ggc cca ttc tgt ggg aag aca ttg ccc cac agg       819
Asp Arg Glu Glu His Gly Pro Phe Cys Gly Lys Thr Leu Pro His Arg
                255                 260                 265
```

```
att gaa aca aaa agc aac acg gtg acc atc acc ttt gtc aca gat gaa    867
Ile Glu Thr Lys Ser Asn Thr Val Thr Ile Thr Phe Val Thr Asp Glu
        270                 275                 280 tca gga gac cac aca ggc tgg aag atc cac tac acg agc aca gcg cag    915
Ser Gly Asp His Thr Gly Trp Lys Ile His Tyr Thr Ser Thr Ala Gln
    285                 290                 295 cct tgc cct tat ccg atg gcg cca cct aat ggc cac gtt tca cct gtg    963
Pro Cys Pro Tyr Pro Met Ala Pro Pro Asn Gly His Val Ser Pro Val
300                 305                 310 caa gcc aaa tac atc ctg aaa gac agc ttc tcc atc ttt tgc gag act   1011
Gln Ala Lys Tyr Ile Leu Lys Asp Ser Phe Ser Ile Phe Cys Glu Thr
315                 320                 325                 330 ggc tat gag ctt ctg caa ggt cac ttg ccc ctg aaa tcc ttt act gca   1059
Gly Tyr Glu Leu Leu Gln Gly His Leu Pro Leu Lys Ser Phe Thr Ala
        335                 340                 345 gtt tgt cag aaa gat gga tct tgg gac cgg cca atg ccc gcg tgc agc   1107
Val Cys Gln Lys Asp Gly Ser Trp Asp Arg Pro Met Pro Ala Cys Ser
    350                 355                 360 att gtt gac tgt ggc cct cct gat gat cta ccc agt ggc cga gtg gag   1155
Ile Val Asp Cys Gly Pro Pro Asp Asp Leu Pro Ser Gly Arg Val Glu
365                 370                 375 tac atc aca ggt cct gga gtg acc acc tac aaa gct gtg att cag tac   1203
Tyr Ile Thr Gly Pro Gly Val Thr Thr Tyr Lys Ala Val Ile Gln Tyr
380                 385                 390 agc tgt gaa gag acc ttc tac aca atg aaa gtg aat gat ggt aaa tat   1251
Ser Cys Glu Glu Thr Phe Tyr Thr Met Lys Val Asn Asp Gly Lys Tyr
395                 400                 405                 410 gtg tgt gag gct gat gga ttc tgg acg agc tcc aaa gga gaa aaa tca   1299
Val Cys Glu Ala Asp Gly Phe Trp Thr Ser Ser Lys Gly Glu Lys Ser
        415                 420                 425 ctc cca gtc tgt gag cct gtt tgt gga cta tca gcc cgc aca aca gga   1347
Leu Pro Val Cys Glu Pro Val Cys Gly Leu Ser Ala Arg Thr Thr Gly
    430                 435                 440 ggg cgt ata tat gga ggg caa aag gca aaa cct ggt gat ttt cct tgg   1395
Gly Arg Ile Tyr Gly Gly Gln Lys Ala Lys Pro Gly Asp Phe Pro Trp
445                 450                 455 caa gtc ctg ata tta ggt gga acc aca gca gca ggt gca ctt tta tat   1443
Gln Val Leu Ile Leu Gly Gly Thr Thr Ala Ala Gly Ala Leu Leu Tyr
460                 465                 470 gac aac tgg gtc cta aca gct gct cat gcc gtc tat gag caa aaa cat   1491
Asp Asn Trp Val Leu Thr Ala Ala His Ala Val Tyr Glu Gln Lys His
475                 480                 485                 490 gat gca tcc gcc ctg gac att cga atg ggc acc ctg aaa aga cta tca   1539
Asp Ala Ser Ala Leu Asp Ile Arg Met Gly Thr Leu Lys Arg Leu Ser
        495                 500                 505 cct cat tat aca caa gcc tgg tct gaa gct gtt ttt ata cat gaa ggt   1587
Pro His Tyr Thr Gln Ala Trp Ser Glu Ala Val Phe Ile His Glu Gly
    510                 515                 520 tat act cat gat gct ggc ttt gac aat gac ata gca ctg att aaa ttg   1635
Tyr Thr His Asp Ala Gly Phe Asp Asn Asp Ile Ala Leu Ile Lys Leu
525                 530                 535 aat aac aaa gtt gta atc aat agc aac atc acg cct att tgt ctg cca   1683
Asn Asn Lys Val Val Ile Asn Ser Asn Ile Thr Pro Ile Cys Leu Pro
540                 545                 550 aga aaa gaa gct gaa tcc ttt atg agg aca gat gac att gga act gca   1731
Arg Lys Glu Ala Glu Ser Phe Met Arg Thr Asp Asp Ile Gly Thr Ala
555                 560                 565                 570 tct gga tgg gga tta acc caa agg ggt ttt ctt gct aga aat cta atg   1779
Ser Gly Trp Gly Leu Thr Gln Arg Gly Phe Leu Ala Arg Asn Leu Met
        575                 580                 585
```

```
tat gtc gac ata ccg att gtt gac cat caa aaa tgt act gct gca tat    1827
Tyr Val Asp Ile Pro Ile Val Asp His Gln Lys Cys Thr Ala Ala Tyr
            590                 595                 600 gaa aag cca ccc tat cca agg gga agt gta act gct aac atg ctt tgt    1875
Glu Lys Pro Pro Tyr Pro Arg Gly Ser Val Thr Ala Asn Met Leu Cys
        605                 610                 615 gct ggc tta gaa agt ggg ggc aag gac agc tgc aga ggt gac agc gga    1923
Ala Gly Leu Glu Ser Gly Gly Lys Asp Ser Cys Arg Gly Asp Ser Gly
    620                 625                 630 ggg gca ctg gtg ttt cta gat agt gaa aca gag agg tgg ttt gtg gga    1971
Gly Ala Leu Val Phe Leu Asp Ser Glu Thr Glu Arg Trp Phe Val Gly
635                 640                 645                 650 gga ata gtg tcc tgg ggt tcc atg aat tgt ggg gaa gca ggt cag tat    2019
Gly Ile Val Ser Trp Gly Ser Met Asn Cys Gly Glu Ala Gly Gln Tyr
                655                 660                 665 gga gtc tac aca aaa gtt att aac tat att ccc tgg atc gag aac ata    2067
Gly Val Tyr Thr Lys Val Ile Asn Tyr Ile Pro Trp Ile Glu Asn Ile
            670                 675                 680 att agt gat ttt taa cttgcgtgtc tgcagtcaag gattcttcat ttttagaaat    2122
Ile Ser Asp Phe
        685 gcctgtgaag accttggcag cgacgtggct cgagaagcat tcatcattac tgtggacatg    2182 gcagttgttg ctccacccaa aaaaacagac tccaggtgag gctgctgtca tttctccact    2242 tgccagttta attccagcct tacccattga ctcaagggga cataaaccac gagagtgaca    2302 gtcatctttg cccacccagt gtaatgtcac tgctcaaatt acatttcatt accttaaaaa    2362 gccagtctct tttcatactg gctgttggca tttctgtaaa ctgcctgtcc atgctctttg    2422 tttttaaact tgttcttatt gaaaaaaaaa aaaaaaaa                           2460

<210> SEQ ID NO 5
<211> LENGTH: 686
<212> TYPE: PRT
<213> ORGANISM: Homo sapiens

<400> SEQUENCE: 5

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160
```

```
Gly Gly Phe Tyr Cys Ser Cys Arg Ala Gly Tyr Val Leu His Arg Asn
                165                 170                 175
Lys Arg Thr Cys Ser Ala Leu Cys Ser Gly Gln Val Phe Thr Gln Arg
            180                 185                 190
Ser Gly Glu Leu Ser Ser Pro Glu Tyr Pro Arg Pro Tyr Pro Lys Leu
        195                 200                 205
Ser Ser Cys Thr Tyr Ser Ile Ser Leu Glu Glu Gly Phe Ser Val Ile
    210                 215                 220
Leu Asp Phe Val Glu Ser Phe Asp Val Glu Thr His Pro Glu Thr Leu
225                 230                 235                 240
Cys Pro Tyr Asp Phe Leu Lys Ile Gln Thr Asp Arg Glu Glu His Gly
                245                 250                 255
Pro Phe Cys Gly Lys Thr Leu Pro His Arg Ile Glu Thr Lys Ser Asn
            260                 265                 270
Thr Val Thr Ile Thr Phe Val Thr Asp Glu Ser Gly Asp His Thr Gly
        275                 280                 285
Trp Lys Ile His Tyr Thr Ser Thr Ala Gln Pro Cys Pro Tyr Pro Met
    290                 295                 300
Ala Pro Pro Asn Gly His Val Ser Pro Val Gln Ala Lys Tyr Ile Leu
305                 310                 315                 320
Lys Asp Ser Phe Ser Ile Phe Cys Glu Thr Gly Tyr Glu Leu Leu Gln
                325                 330                 335
Gly His Leu Pro Leu Lys Ser Phe Thr Ala Val Cys Gln Lys Asp Gly
            340                 345                 350
Ser Trp Asp Arg Pro Met Pro Ala Cys Ser Ile Val Asp Cys Gly Pro
        355                 360                 365
Pro Asp Asp Leu Pro Ser Gly Arg Val Glu Tyr Ile Thr Gly Pro Gly
    370                 375                 380
Val Thr Thr Tyr Lys Ala Val Ile Gln Tyr Ser Cys Glu Glu Thr Phe
385                 390                 395                 400
Tyr Thr Met Lys Val Asn Asp Gly Lys Tyr Val Cys Glu Ala Asp Gly
                405                 410                 415
Phe Trp Thr Ser Ser Lys Gly Glu Lys Ser Leu Pro Val Cys Glu Pro
            420                 425                 430
Val Cys Gly Leu Ser Ala Arg Thr Thr Gly Gly Arg Ile Tyr Gly Gly
        435                 440                 445
Gln Lys Ala Lys Pro Gly Asp Phe Pro Trp Gln Val Leu Ile Leu Gly
    450                 455                 460
Gly Thr Thr Ala Ala Gly Ala Leu Leu Tyr Asp Asn Trp Val Leu Thr
465                 470                 475                 480
Ala Ala His Ala Val Tyr Glu Gln Lys His Asp Ala Ser Ala Leu Asp
                485                 490                 495
Ile Arg Met Gly Thr Leu Lys Arg Leu Ser Pro His Tyr Thr Gln Ala
            500                 505                 510
Trp Ser Glu Ala Val Phe Ile His Glu Gly Tyr Thr His Asp Ala Gly
        515                 520                 525
Phe Asp Asn Asp Ile Ala Leu Ile Lys Leu Asn Asn Lys Val Val Ile
    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                565                 570                 575
Gln Arg Gly Phe Leu Ala Arg Asn Leu Met Tyr Val Asp Ile Pro Ile
```

```
                   580                 585                 590
Val Asp His Gln Lys Cys Thr Ala Ala Tyr Glu Lys Pro Pro Tyr Pro
                595                 600                 605

Arg Gly Ser Val Thr Ala Asn Met Leu Cys Ala Gly Leu Glu Ser Gly
            610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
                660                 665                 670

Ile Asn Tyr Ile Pro Trp Ile Glu Asn Ile Ile Ser Asp Phe
                675                 680                 685

<210> SEQ ID NO 6
<211> LENGTH: 671
<212> TYPE: PRT
<213> ORGANISM: Homo sapiens

<400> SEQUENCE: 6

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
        195                 200                 205

Ile Leu Asp Phe Val Glu Ser Phe Asp Val Glu Thr His Pro Glu Thr
210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
            260                 265                 270
```

-continued

```
Gly Trp Lys Ile His Tyr Thr Ser Thr Ala Gln Pro Cys Pro Tyr Pro
            275                 280                 285

Met Ala Pro Pro Asn Gly His Val Ser Pro Val Gln Ala Lys Tyr Ile
        290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
            340                 345                 350

Pro Pro Asp Asp Leu Pro Ser Gly Arg Val Glu Tyr Ile Thr Gly Pro
        355                 360                 365

Gly Val Thr Thr Tyr Lys Ala Val Ile Gln Tyr Ser Cys Glu Glu Thr
    370                 375                 380

Phe Tyr Thr Met Lys Val Asn Asp Gly Lys Tyr Val Cys Glu Ala Asp
385                 390                 395                 400

Gly Phe Trp Thr Ser Lys Gly Glu Lys Ser Leu Pro Val Cys Glu
                405                 410                 415

Pro Val Cys Gly Leu Ser Ala Arg Thr Thr Gly Gly Arg Ile Tyr Gly
            420                 425                 430

Gly Gln Lys Ala Lys Pro Gly Asp Phe Pro Trp Gln Val Leu Ile Leu
        435                 440                 445

Gly Gly Thr Thr Ala Ala Gly Ala Leu Leu Tyr Asp Asn Trp Val Leu
    450                 455                 460

Thr Ala His Ala Val Tyr Glu Gln Lys His Asp Ala Ser Ala Leu
465                 470                 475                 480

Asp Ile Arg Met Gly Thr Leu Lys Arg Leu Ser Pro His Tyr Thr Gln
                485                 490                 495

Ala Trp Ser Glu Ala Val Phe Ile His Glu Gly Tyr Thr His Asp Ala
            500                 505                 510

Gly Phe Asp Asn Asp Ile Ala Leu Ile Lys Leu Asn Asn Lys Val Val
        515                 520                 525

Ile Asn Ser Asn Ile Thr Pro Ile Cys Leu Pro Arg Lys Glu Ala Glu
    530                 535                 540

Ser Phe Met Arg Thr Asp Asp Ile Gly Thr Ala Ser Gly Trp Gly Leu
545                 550                 555                 560

Thr Gln Arg Gly Phe Leu Ala Arg Asn Leu Met Tyr Val Asp Ile Pro
                565                 570                 575

Ile Val Asp His Gln Lys Cys Thr Ala Ala Tyr Glu Lys Pro Pro Tyr
            580                 585                 590

Pro Arg Gly Ser Val Thr Ala Asn Met Leu Cys Ala Gly Leu Glu Ser
        595                 600                 605

Gly Gly Lys Asp Ser Cys Arg Gly Asp Ser Gly Gly Ala Leu Val Phe
    610                 615                 620

Leu Asp Ser Glu Thr Glu Arg Trp Phe Val Gly Gly Ile Val Ser Trp
625                 630                 635                 640

Gly Ser Met Asn Cys Gly Glu Ala Gly Gln Tyr Gly Val Tyr Thr Lys
                645                 650                 655

Val Ile Asn Tyr Ile Pro Trp Ile Glu Asn Ile Ile Ser Asp Phe
            660                 665                 670

<210> SEQ ID NO 7
<211> LENGTH: 4900
<212> TYPE: DNA
```

<213> ORGANISM: Homo sapiens

<400> SEQUENCE: 7

| | |
|---|---|
| cctgtcctgc ctgcctggaa ctctgagcag gctggagtca tggagtcgat tcccagaatc | 60 |
| ccagagtcag ggaggctggg ggcaggggca ggtcactgga caaacagatc aaaggtgaga | 120 |
| ccagcgtagg actgcagacc aggccaggcc agctggacgg gcacaccatg aggtaggtgg | 180 |
| gcgccacagc ctccctgcag ggtgtggggt gggagcacag gcctgggcct caccgcccct | 240 |
| gccctgccca taggctgctg accctcctgg gccttctgtg tggctcggtg gccaccccct | 300 |
| taggcccgaa gtggcctgaa cctgtgttcg ggcgcctggc atccccggc tttccagggg | 360 |
| agtatgccaa tgaccaggag cggcgctgga ccctgactgc acccccggc taccgcctgc | 420 |
| gcctctactt cacccacttc gacctggagc tctcccacct ctgcgagtac gacttcgtca | 480 |
| aggtgccgtc agacgggagg gctggggttt ctcagggtcg gggggtcccc aaggagtagc | 540 |
| cagggttcag ggacacctgg gagcaggggc caggcttggc caggagggag atcaggcctg | 600 |
| ggtcttgcct tcactccctg tgacacctga ccccacagct gagctcgggg gccaaggtgc | 660 |
| tggccacgct gtgcgggcag gagagcacag acacgagcg ggcccctggc aaggacactt | 720 |
| tctactcgct gggctccagc ctggacatta ccttccgctc cgactactcc aacgagaagc | 780 |
| cgttcacggg gttcgaggcc ttctatgcag ccgagggtga gccaagaggg gtcctgcaac | 840 |
| atctcagtct gcgcagctgg ctgtgggggt aactctgtct taggccaggc agccctgcct | 900 |
| tcagtttccc cacctttccc agggcagggg agaggcctct ggcctgacat catccacaat | 960 |
| gcaaagacca aaacagccgt gacctccatt cacatgggct gagtgccaac tctgagccag | 1020 |
| ggatctgagg acagcatcgc ctcaagtgac gcagggactg gccgggcgcg gcagctcacg | 1080 |
| cctgtaattc cagcactttg ggaggccgag gctggcttga taatttgagg gtcaggagtt | 1140 |
| caaggccagc cagggcaaca cggtgaaact ctatctccac taaaactaca aaaattagct | 1200 |
| gggcgtggtg gtgcgcacct ggaatcccag ctactaggga ggctgaggca ggagaattgc | 1260 |
| ttgaacctgc gaggtggagg ctgcagtgaa cagagattgc accactacac tccacctggg | 1320 |
| cgacagacta gactccgtct caaaaaacaa aaaacaaaaa ccacgcaggg ccgagggccc | 1380 |
| atttacaagc tgacaaagtg ggccctgcca gcgggagcgc tgcaggatgt tgattttca | 1440 |
| gatcccagtc cctgcagaga ccaactgtgt gacctctggc aagtggctca atttctctgc | 1500 |
| tccttagaag ctgctgcaag ggttcagcgc tgtagccccg cccctgggt ttgattgact | 1560 |
| cccctcatta gctgggtgac ctcggccgga cactgaaact cccactggtt taacagaggt | 1620 |
| gatgtttgca tctttctccc agcgctgctg ggagcttgca gcgaccctag gcctgtaagg | 1680 |
| tgattggccc ggcaccagtc ccgcacccta gacaggacct aggcctcctc tgaggtccac | 1740 |
| tctgaggtca tggatctcct gggaggagtc caggctggat cccgcctctt tccctcctga | 1800 |
| cggcctgcct ggccctgcct ctcccccaga cattgacgag tgccaggtgg ccccgggaga | 1860 |
| ggcgcccacc tgcgaccacc actgccacaa ccacctgggc ggtttctact gctcctgccg | 1920 |
| cgcaggctac gtcctgcacc gtaacaagcg cacctgctca ggtgagggag gctgcctggg | 1980 |
| ccccaacgca ccctctcctg ggataccgg ggctcctcag ggccattgct gctctgccca | 2040 |
| ggggtgcgga gggcctgggc ctggacactg ggtgcttcta ggccctgctg cctccagctc | 2100 |
| cccttctcag ccctgcttcc cctcagca gccaggctca tcagtgccac cctgccctag | 2160 |
| cactgagact aattctaaca tcccactgtg tacctggttc cacctgggct ctgggaaccc | 2220 |
| ctcatgtagc cacgggagag tcggggtatc taccctcgtt ccttggactg ggttcctgtt | 2280 |

```
ccctgcactg ggggacgggc cagtgctctg gggcgtgggc agccccaccc tgtggcgctg    2340
accctgctcc cccgactcgg tttctcctct cggggtctct ccttgcctct ctgatctctc    2400
ttccagagca gagcctctag cctcccctgg agctccggct gcccagcagg tcagaagcca    2460
gagccaggct gctggcctca gctccgggtt ggctgagat gctgtgcccc aactcccatt     2520
cacccaccat ggacccaata ataaacctgg ccccacccca cctgctgccg cgtgtctctg    2580
gggtgggagg gtcgggaggc ggtggggcgc gctcctctct gcctaccctc ctcacagcct    2640
catgaacccc aggtctgtgg gagcctcctc catggggcca cacggtcctt ggcctcaccc    2700
cctgttttga agatggggca ctgaggccgg agagggtaa ggcctcgctc gagtccaggt     2760
ccccagaggc tgagcccaga gtaatcttga accacccca ttcagggtct ggcctggagg     2820
agcctgaccc acagaggaga caccctggga gatattcatt gaggggtaat ctggtccccc    2880
gcaaatccag gggtgattcc cactgcccca taggcacagc cacgtggaag aaggcaggca    2940 atgttgggc tcctcacttc ctagaggcct cacaactcaa atgccccca ctgcagctgg      3000 gggtggggtg gtggtatggg atggggacca agccttcctt gaaggataga gcccagccca    3060
acaccccgcc ccgtggcagc agcatcacgt gttccagcga ggaaggagag caccagactc    3120
agtcatgatc actgttgcct tgaacttcca agaacagccc cagggcaagg gtcaaaacag    3180
gggaaagggg gtgatgagag atccttcttc cggatgttcc tccaggaacc aggggctgg     3240 ctggtcttgg ctgggttcgg gtaggagacc catgatgaat aaacttggga atcactgggg    3300
tggctgtaag ggaatttagg ggagctccga aggggcctt aggctcgagg agatgctcct     3360
ctcttttccc gaattccag ggacccagga gagtgtccct tcttcctctt cctgtgtgtc     3420
catccacccc cgcccccgc cctggcagag ctggtggaac tcagtgctct agcccctacc     3480
ctggggttgc gactctggct caggacacca ccacgctccc tgggggtgtg agtgagggcc    3540
tgtgcgctcc atcccgagtg ctgcctgttt cagctaaagc ctcaaagcaa agagaaacccc   3600 ctctctaagc ggcccctcag ccatcgggtg ggtcgtttgg tttctgggta ggcctcaggg    3660
gctggccacc tgcagggccc agcccaaccc agggatgcag atgtcccagc cacatccctg    3720
tcccagtttc ctgctcccca aggcatccac cctgctgttg gtgcgagggc tgatagaggg    3780
cacgccaagt cactcccctg cccttccctc cttccagccc tgtgctccgg ccaggtcttc    3840
acccagaggt ctggggagct cagcagccct gaatacccac ggccgtatcc caaactctcc    3900
agttgcactt acagcatcag cctggaggag gggttcagtg tcattctgga ctttgtggag    3960
tccttcgatg tggagacaca ccctgaaacc ctgtgtccct acgactttct caaggtctgg    4020
ctcctgggcc cctcatcttg tcccagatcc tcccccttca gcccagctgc acccctact     4080 tcctgcagca tggcccccac cacgttcccg tcaccctcgg tgaccccacc tcttcaggtg    4140
ctctatggag gtcaaggctg gggcttcgag tacaagtgtg ggaggcagag tggggagggg    4200 cacccccaatc catggcctgg gttggcctca ttggctgtcc ctgaaatgct gaggaggtgg    4260
gttacttccc tccgcccagg ccagacccag gcagctgctc cccagctttc atgagcttct    4320
ttctcagatt caaacagaca gagaagaaca tggcccattc tgtgggaaga cattgcccca    4380
caggattgaa acaaaaagca acacggtgac catcaccttt gtcacagatg aatcaggaga    4440
ccacacaggc tggaagatcc actacacgag cacagtgagc aagtgggctc agatccttgg    4500
tggaagcgca gagctgcctc tctctggagt gcaaggagc gtagagtgta gggctcttct    4560
gggcaggact aggaagggac accaggttta gtggtgctga ggtctgaggc agcagcttct    4620
```

```
aagggggaagc acccgtgccc tcctcagcag cacccagcat cttcaccact cattcttcaa    4680
ccacccattc acccatcact catcttttac ccacccaccc tttgccactc atccttctgt    4740
ccctcatcct tccaaccatt catcaatcac ccacccatcc atcctttgcc acacaaccat    4800
ccacccattc ttctacctac ccatcctatc catccatcct tctatcagca tccttctacc    4860
acccatcctt cgttcggtca tccatcatca tccatccatc                          4900
```

```
<210> SEQ ID NO 8
<211> LENGTH: 136
<212> TYPE: PRT
<213> ORGANISM: Homo sapiens

<400> SEQUENCE: 8
```

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala
    130                 135

```
<210> SEQ ID NO 9
<211> LENGTH: 181
<212> TYPE: PRT
<213> ORGANISM: Homo sapiens

<400> SEQUENCE: 9
```

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

```
Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
            165                 170                 175

Lys Arg Thr Cys Ser
            180
```

<210> SEQ ID NO 10
<211> LENGTH: 293
<212> TYPE: PRT
<213> ORGANISM: Homo sapiens

<400> SEQUENCE: 10

```
Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
            35                  40                  45

Leu Thr Ala Pro Pro Gly Tyr Arg Leu Arg Leu Tyr Phe Thr His Phe
50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
            85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
            165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
            210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
            275                 280                 285

Trp Lys Ile His Tyr
            290
```

<210> SEQ ID NO 11
<211> LENGTH: 41
<212> TYPE: PRT

<213> ORGANISM: Homo sapiens

<400> SEQUENCE: 11

```
Glu Asp Ile Asp Glu Cys Gln Val Ala Pro Gly Glu Ala Pro Thr Cys
1               5                   10                  15

Asp His His Cys His Asn His Leu Gly Gly Phe Tyr Cys Ser Cys Arg
            20                  25                  30

Ala Gly Tyr Val Leu His Arg Asn Lys
        35                  40
```

<210> SEQ ID NO 12
<211> LENGTH: 242
<212> TYPE: PRT
<213> ORGANISM: Homo sapiens

<400> SEQUENCE: 12

```
Ile Tyr Gly Gly Gln Lys Ala Lys Pro Gly Asp Phe Pro Trp Gln Val
1               5                   10                  15

Leu Ile Leu Gly Gly Thr Thr Ala Ala Gly Ala Leu Leu Tyr Asp Asn
            20                  25                  30

Trp Val Leu Thr Ala Ala His Ala Val Tyr Glu Gln Lys His Asp Ala
        35                  40                  45

Ser Ala Leu Asp Ile Arg Met Gly Thr Leu Lys Arg Leu Ser Pro His
    50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
                85                  90                  95

Lys Val Val Ile Asn Ser Asn Ile Thr Pro Ile Cys Leu Pro Arg Lys
            100                 105                 110

Glu Ala Glu Ser Phe Met Arg Thr Asp Asp Ile Gly Thr Ala Ser Gly
        115                 120                 125

Trp Gly Leu Thr Gln Arg Gly Phe Leu Ala Arg Asn Leu Met Tyr Val
    130                 135                 140

Asp Ile Pro Ile Val Asp His Gln Lys Cys Thr Ala Ala Tyr Glu Lys
145                 150                 155                 160

Pro Pro Tyr Pro Arg Gly Ser Val Thr Ala Asn Met Leu Cys Ala Gly
                165                 170                 175

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
        195                 200                 205

Val Ser Trp Gly Ser Met Asn Cys Gly Glu Ala Gly Gln Tyr Gly Val
    210                 215                 220

Tyr Thr Lys Val Ile Asn Tyr Ile Pro Trp Ile Glu Asn Ile Ile Ser
225                 230                 235                 240

Asp Phe
```

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

```
Gly Lys Asp Ser Cys Arg Gly Asp Ala Gly Gly Ala Leu Val Phe Leu
```

```
1               5               10              15
```

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

```
Thr Pro Leu Gly Pro Lys Trp Pro Glu Pro Val Phe Gly Arg Leu
1               5                   10                  15
```

<210> SEQ ID NO 15
<211> LENGTH: 43
<212> TYPE: PRT
<213> ORGANISM: Artificial Sequence
<220> FEATURE:
<223> OTHER INFORMATION: Synthetic

<400> SEQUENCE: 15

```
Thr Ala Pro Pro Gly Tyr Arg Leu Arg Leu Tyr Phe Thr His Phe Asp
1               5                   10                  15

Leu Glu Leu Ser His Leu Cys Glu Tyr Asp Phe Val Lys Leu Ser Ser
            20                  25                  30

Gly Ala Lys Val Leu Ala Thr Leu Cys Gly Gln
        35                  40
```

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

```
Thr Phe Arg Ser Asp Tyr Ser Asn
1               5
```

<210> SEQ ID NO 17
<211> LENGTH: 25
<212> TYPE: PRT
<213> ORGANISM: Artificial Sequence
<220> FEATURE:
<223> OTHER INFORMATION: Synthetic

<400> SEQUENCE: 17

```
Phe Tyr Ser Leu Gly Ser Ser Leu Asp Ile Thr Phe Arg Ser Asp Tyr
1               5                   10                  15

Ser Asn Glu Lys Pro Phe Thr Gly Phe
            20                  25
```

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

```
Ile Asp Glu Cys Gln Val Ala Pro Gly
1               5
```

<210> SEQ ID NO 19
<211> LENGTH: 25

-continued

```
<212> TYPE: PRT
<213> ORGANISM: Artificial Sequence
<220> FEATURE:
<223> OTHER INFORMATION: Synthetic

<400> SEQUENCE: 19

Ala Asn Met Leu Cys Ala Gly Leu Glu Ser Gly Gly Lys Asp Ser Cys
1               5                   10                  15

Arg Gly Asp Ser Gly Gly Ala Leu Val
            20                  25

<210> SEQ ID NO 20
<211> LENGTH: 960
<212> TYPE: DNA
<213> ORGANISM: Homo sapiens
<220> FEATURE:
<221> NAME/KEY: CDS
<222> LOCATION: (51)..(797)

<400> SEQUENCE: 20
attaactgag attaaccttc cctgagtttt ctcacaccaa ggtgaggacc atg tcc        56
                                                       Met Ser
                                                       1 ctg ttt cca tca ctc cct ctc ctt ctc ctg agt atg gtg gca gcg tct     104
Leu Phe Pro Ser Leu Pro Leu Leu Leu Leu Ser Met Val Ala Ala Ser
        5                   10                  15 tac tca gaa act gtg acc tgt gag gat gcc caa aag acc tgc cct gca     152
Tyr Ser Glu Thr Val Thr Cys Glu Asp Ala Gln Lys Thr Cys Pro Ala
            20                  25                  30 gtg att gcc tgt agc tct cca ggc atc aac ggc ttc cca ggc aaa gat     200
Val Ile Ala Cys Ser Ser Pro Gly Ile Asn Gly Phe Pro Gly Lys Asp
35                  40                  45                  50 ggg cgt gat ggc acc aag gga gaa aag ggg gaa cca ggc caa ggg ctc     248
Gly Arg Asp Gly Thr Lys Gly Glu Lys Gly Glu Pro Gly Gln Gly Leu
                55                  60                  65 aga ggc tta cag ggc ccc cct gga aag ttg ggg cct cca gga aat cca     296
Arg Gly Leu Gln Gly Pro Pro Gly Lys Leu Gly Pro Pro Gly Asn Pro
            70                  75                  80 ggg cct tct ggg tca cca gga cca aag ggc caa aaa gga gac cct gga     344
Gly Pro Ser Gly Ser Pro Gly Pro Lys Gly Gln Lys Gly Asp Pro Gly
        85                  90                  95 aaa agt ccg gat ggt gat agt agc ctg gct gcc tca gaa aga aaa gct     392
Lys Ser Pro Asp Gly Asp Ser Ser Leu Ala Ala Ser Glu Arg Lys Ala
100                 105                 110 ctg caa aca gaa atg gca cgt atc aaa aag tgg ctc acc ttc tct ctg     440
Leu Gln Thr Glu Met Ala Arg Ile Lys Lys Trp Leu Thr Phe Ser Leu
115                 120                 125                 130 ggc aaa caa gtt ggg aac aag ttc ttc ctg acc aat ggt gaa ata atg     488
Gly Lys Gln Val Gly Asn Lys Phe Phe Leu Thr Asn Gly Glu Ile Met
                135                 140                 145 acc ttt gaa aaa gtg aag gcc ttg tgt gtc aag ttc cag gcc tct gtg     536
Thr Phe Glu Lys Val Lys Ala Leu Cys Val Lys Phe Gln Ala Ser Val
            150                 155                 160 gcc acc ccc agg aat gct gca gag aat gga gcc att cag aat ctc atc     584
Ala Thr Pro Arg Asn Ala Ala Glu Asn Gly Ala Ile Gln Asn Leu Ile
        165                 170                 175 aag gag gaa gcc ttc ctg ggc atc act gat gag aag aca gaa ggg cag     632
Lys Glu Glu Ala Phe Leu Gly Ile Thr Asp Glu Lys Thr Glu Gly Gln
180                 185                 190 ttt gtg gat ctg aca gga aat aga ctg acc tac aca aac tgg aac gag     680
Phe Val Asp Leu Thr Gly Asn Arg Leu Thr Tyr Thr Asn Trp Asn Glu
195                 200                 205                 210
```

```
ggt gaa ccc aac aat gct ggt tct gat gaa gat tgt gta ttg cta ctg      728
Gly Glu Pro Asn Asn Ala Gly Ser Asp Glu Asp Cys Val Leu Leu Leu
            215                 220                 225 aaa aat ggc cag tgg aat gac gtc ccc tgc tcc acc tcc cat ctg gcc      776
Lys Asn Gly Gln Trp Asn Asp Val Pro Cys Ser Thr Ser His Leu Ala
            230                 235                 240 gtc tgt gag ttc cct atc tga agggtcatat cactcaggcc ctccttgtct         827
Val Cys Glu Phe Pro Ile
            245 ttttactgca acccacaggc ccacagtatg cttgaaaaga taaattatat caatttcctc    887 atatccagta ttgttccttt tgtgggcaat cactaaaaat gatcactaac agcaccaaca    947 aagcaataat agt                                                        960

<210> SEQ ID NO 21
<211> LENGTH: 248
<212> TYPE: PRT
<213> ORGANISM: Homo sapiens

<400> SEQUENCE: 21

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 22
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 represents
      hydroxyproline
<220> FEATURE:
<221> NAME/KEY: MISC_FEATURE
<222> LOCATION: (4)..(4)
<223> OTHER INFORMATION: Wherein X at position 4 represents hydrophobic
      residue

<400> SEQUENCE: 22

Xaa Gly Lys Xaa Gly Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X represents hydroxyproline

<400> SEQUENCE: 23

Xaa Gly Lys Leu Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(15)
<223> OTHER INFORMATION: Wherein X at positions 9 and 15 represents
      hydroxyproline

<400> SEQUENCE: 24

Gly Leu Arg Gly Leu Gln Gly Pro Xaa Gly Lys Leu Gly Pro Xaa Gly
1               5                   10                  15

<210> SEQ ID NO 25
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(27)
<223> OTHER INFORMATION: Wherein X at positions 3, 6, 15, 21, 24, 27
      represents hydroxyproline

<400> SEQUENCE: 25

Gly Pro Xaa Gly Pro Xaa Gly Leu Arg Gly Leu Gln Gly Pro Xaa Gly
1               5                   10                  15

Lys Leu Gly Pro Xaa Gly Pro Xaa Gly Pro Xaa
                20                  25

<210> SEQ ID NO 26
<211> LENGTH: 53
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 26

Gly Lys Asp Gly Arg Asp Gly Thr Lys Gly Glu Lys Gly Glu Pro Gly
1               5                   10                  15

Gln Gly Leu Arg Gly Leu Gln Gly Pro Xaa Gly Lys Leu Gly Pro Xaa
            20                  25                  30

Gly Asn Xaa Gly Pro Ser Gly Ser Xaa Gly Pro Lys Gly Gln Lys Gly
        35                  40                  45

Asp Xaa Gly Lys Ser
    50

<210> SEQ ID NO 27
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(33)
<223> OTHER INFORMATION: Wherein X at positions 3, 6, 12, 18, 21, 30, 33
      represents hydroxyproline

<400> SEQUENCE: 27

Gly Ala Xaa Gly Ser Xaa Gly Glu Lys Gly Ala Xaa Gly Pro Gln Gly
1               5                   10                  15

Pro Xaa Gly Pro Xaa Gly Lys Met Gly Pro Lys Gly Glu Xaa Gly Asp
            20                  25                  30

Xaa

<210> SEQ ID NO 28
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(45)
<223> OTHER INFORMATION: Wherein X at positions 3, 6, 9, 27, 30, 36, 42,
      45 represents hydroxyproline

<400> SEQUENCE: 28

Gly Cys Xaa Gly Leu Xaa Gly Ala Xaa Gly Asp Lys Gly Glu Ala Gly
1               5                   10                  15
```

```
Thr Asn Gly Lys Arg Gly Glu Arg Gly Pro Xaa Gly Pro Xaa Gly Lys
            20                  25                  30

Ala Gly Pro Xaa Gly Pro Asn Gly Ala Xaa Gly Glu Xaa
        35                  40                  45

<210> SEQ ID NO 29
<211> LENGTH: 24
<212> TYPE: PRT
<213> ORGANISM: Artificial Sequence
<220> FEATURE:
<223> OTHER INFORMATION: Synthetic

<400> SEQUENCE: 29

Leu Gln Arg Ala Leu Glu Ile Leu Pro Asn Arg Val Thr Ile Lys Ala
1               5                   10                  15

Asn Arg Pro Phe Leu Val Phe Ile
            20

<210> SEQ ID NO 30
<211> LENGTH: 559
<212> TYPE: DNA
<213> ORGANISM: Homo sapiens

<400> SEQUENCE: 30
atgaggctgc tgaccctcct gggccttctg tgtggctcgg tggccacccc cttgggcccg      60
aagtggcctg aacctgtgtt cgggcgcctg catccccgg ctttccagg ggagtatgcc       120 aatgaccagg agcggcgctg accctgact gcaccccccg ctaccgcct gcgcctctac       180 ttcacccact cgacctgga gctctcccac ctctgcgagt acgacttcgt caagctgagc      240 tcggggggcca aggtgctggc cacgctgtgc gggcaggaga gcacagacac ggagcgggcc    300
cctggcaagg acactttcta ctcgctgggc tccagcctgg acattacctt ccgctccgac    360
tactccaacg agaagccgtt cacggggttc gaggccttct atgcagccga ggacattgac    420
gagtgccagg tggcccccggg agaggcgccc acctgcgacc accactgcca caaccacctg   480
ggcggtttct actgctcctg ccgcgcaggc tacgtcctgc accgtaacaa gcgcacctgc    540
tcagccctgt gctccggcc                                                  559

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
cgggcacacc atgaggctgc tgaccctcct gggc                                  34

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
gacattacct tccgctccga ctccaacgag aag                                   33

<210> SEQ ID NO 33
<211> LENGTH: 33
<212> TYPE: DNA
<213> ORGANISM: Artificial Sequence
```

```
<220> FEATURE:
<223> OTHER INFORMATION: Synthetic

<400> SEQUENCE: 33
agcagccctg aatacccacg gccgtatccc aaa                                  33

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
cgggatccat gaggctgctg accctc                                          26

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
ggaattccta ggctgcata                                                  19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
ggaattccta cagggcgct                                                  19

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
ggaattccta gtagtggat                                                  19

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
tgcggccgct gtaggtgctg tcttt                                           25

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ggaattcact cgttattctc gga                                             23
```

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
tccgagaata acgagtg                                                  17

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
cattgaaagc tttggggtag aagttgttc                                     29

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
cgcggccgca gctgctcaga gtgtaga                                       27

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
cggtaagctt cactggctca gggaaata                                      28

<210> SEQ ID NO 44
<211> LENGTH: 37
<212> TYPE: DNA
<213> ORGANISM: Artificial Sequence
<220> FEATURE:
<223> OTHER INFORMATION: Synthetic

<400> SEQUENCE: 44
aagaagcttg ccgccaccat ggattggctg tggaact                            37

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
cgggatcctc aaactttctt gtccaccttg g                                  31

<210> SEQ ID NO 46
<211> LENGTH: 36
<212> TYPE: DNA
<213> ORGANISM: Artificial Sequence
<220> FEATURE:
<223> OTHER INFORMATION: Synthetic

```
<400> SEQUENCE: 46
aagaaagctt gccgccacca tgttctcact agctct                                     36

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47 cgggatccttc tccctctaa cactct                                                26

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Glu Pro Lys Ser Cys Asp Lys Thr His
1               5

<210> SEQ ID NO 49
<211> LENGTH: 4960
<212> TYPE: DNA
<213> ORGANISM: Homo Sapiens

<400> SEQUENCE: 49
ccggacgtgg tggcgcatgc ctgtaatccc agctactcgg gaggctgagg caggagaatt           60
gctcgaaccc cggaggcaga ggtttggtgg ctcacacctg taatcccagc actttgcgag          120
gctgaggcag gtgcatcgct ttggctcagg agttcaagac cagcctgggc aacacaggga          180 gaccccccatc tctacaaaaa acaaaaacaa atataaaggg gataaaaaaa aaaaaaagac         240
aagacatgaa tccatgagga cagagtgtgg aagaggaagc agcagcctca agttctgga           300 agctggaaga acagataaac aggtgtgaaa taactgcctg gaaagcaact tctttttttt          360 ttttttttt tttgaggtgg agtctcactc tgtcgtccag gctggagtgc agtggtgcga           420
tctcggatca ctgcaacctc cgcctcccag gctcaagcaa ttctcctgcc tcagcctccc          480
gagtagctgg gattataagt gcgcgctgcc acacctggat gattttttgta ttttttagtag        540 agatgggatt tcaccatgtt ggtcaggctg gtctcaaact cccaacctcg tgatccaccc          600
accttggcct cccaaagtgc tgggattaca ggtataagcc accgagccca gccaaaagcg          660
acttctaagc ctgcaaggga atcgggaatt ggtggcacca ggtccttctg acagggttta          720
agaaattagc cagcctgagg ctgggcacgg tggctcacac ctgtaatccc agcactttgg          780
gaggctaagg caggtggatc acctgagggc aggagttcaa gaccagcctg accaacatgg          840
agaaacccca tccctaccaa aaataaaaaa ttagccaggt gtggtggtgc tcgcctgtaa          900
tcccagctac ttgggaggct gaggtgggag gattgcttga acacaggaag tagaggctgc          960
agtgagctat gattgcagca ctgcactgaa gccggggcaa cagaacaaga tccaaaaaaa         1020
agggaggggt gagggcaga gccaggattt gtttccaggc tgttgttacc taggtccgac          1080
tcctggctcc cagagcagcc tgtcctgcct gcctggaact ctgagcaggc tggagtcatg         1140
gagtcgattc ccagaatccc agagtcaggg aggctggggg caggggcagg tcactggaca         1200
aacagatcaa aggtgagacc agcgtagggc tgcagaccag gccaggccag ctggacgggc         1260
```

```
acaccatgag gtaggtgggc gcccacagcc tccctgcagg gtgtggggtg ggagcacagg    1320
cctgggccct caccgcccct gccctgccca taggctgctg accctcctgg gccttctgtg    1380
tggctcggtg gccacccct  tgggcccgaa gtggcctgaa cctgtgttcg ggcgcctggc    1440 atccccggc  tttccagggg agtatgccaa tgaccaggag cggcgctgga ccctgactgc    1500
accccccggc taccgcctgc gcctctactt cacccacttc gacctggagc tctcccacct    1560
ctgcgagtac gacttcgtca aggtgccgtc aggacgggag ggctgggtt  tctcagggtc    1620 gggggtccc  caaggagtag ccagggttca gggacacctg ggagcagggg ccaggcttgg    1680
ccaggaggga gatcaggcct gggtcttgcc ttcactccct gtgacacctg accccacagc    1740
tgagctcggg ggccaaggtg ctggccacgc tgtgcgggca ggagagcaca gacacggagc    1800
gggcccctgg caaggacact ttctactcgc tgggctccag cctggacatt accttccgct    1860
ccgactactc caacgagaag ccgttcacgg ggttcgaggc cttctatgca gccgagggtg    1920
agccaagagg ggtcctgcaa catctcagtc tgcgcagctg gctgtggggg taactctgtc    1980
ttaggccagg cagccctgcc ttcagttccc ccaccttcc  cagggcaggg gagaggcctc    2040
tggcctgaca tcatccacaa tgcaaagacc aaaacagccg tgacctccat tcacatgggc    2100
tgagtgccaa ctctgagcca gggatctgag gacagcatcg cctcaagtga cgcagggact    2160
ggccgggcgc agcagctcac gcctgtaatt ccagcacttt gggaggccga ggctggctga    2220
tcatttgagg tcaggagttc aaggccagcc agggcaacac ggtgaaactc tatctccact    2280
aaaactacaa aaattagctg gcgtggtgg  tgcgcacctg gaatcccagc tactagggag    2340
gctgaggcag gagaattgct tgaacctgcg aggtggaggc tgcagtgaac agagattgca    2400
ccactacact ccagcctggg cgacagagct agactccgtc tcaaaaaaca aaaaacaaaa    2460
acgacgcagg ggccgagggc cccatttaca gctgacaaag tggggccctg ccagcgggag    2520
cgctgccagg atgtttgatt tcagatccca gtccctgcag agaccaactg tgtgacctct    2580
ggcaagtggc tcaatttctc tgctccttag gaagctgctg caagggttca gcgctgtagc    2640 cccgcccct  gggtttgatt gactcccctc attagctggg tgacctcggg ccggacactg    2700
aaactcccac tggtttaaca gaggtgatgt ttgcatcttt ctcccagcgc tgctgggagc    2760
ttgcagcgac cctaggcctg taaggtgatt ggcccggcac cagtcccgca ccctagacag    2820
gacgaggcct cctctgaggt ccactctgag gtcatggatc tcctgggagg agtccaggct    2880
ggatcccgcc tctttccctc ctgacggcct gcctggccct gcctctcccc cagacattga    2940
cgagtgccag gtggccccgg gagaggcgcc cacctgcgac caccactgcc acaaccacct    3000
gggcggtttc tactgctcct gccgcgcagg ctacgtcctg caccgtaaca agcgcacctg    3060
ctcagccctg tgctccggcc aggtcttcac ccagaggtct ggggagctca gcagccctga    3120
atacccacgg ccgtatccca aactctccag ttgcacttac agcatcagcc tggaggaggg    3180
gttcagtgtc attctggact ttgtggagtc cttcgatgtg gagacacacc ctgaaaccct    3240
gtgtccctac gactttctca agattcaaac agacagagaa gaacatggcc cattctgtgg    3300
gaagacattg ccccacagga ttgaaacaaa aagcaacacg gtgaccatca cctttgtcac    3360
agatgaatca ggagaccaca caggctggaa gatccactac acgagcacag cgcacgcttg    3420
cccttatccg atggcgccac ctaatggcca cgtttcacct gtgcaagcca aatacatcct    3480
gaaagacagc ttctccatct tttgcgagac tggctatgag cttctgcaag gtcacttgcc    3540
cctgaaatcc tttactgcag tttgtcagaa agatggatct tgggaccggc caatgcccgc    3600
```

```
gtgcagcatt gttgactgtg gccctcctga tgatctaccc agtggccgag tggagtacat    3660
cacaggtcct ggagtgacca cctacaaagc tgtgattcag tacagctgtg aagagacctt    3720
ctacacaatg aaagtgaatg atggtaaata tgtgtgtgag gctgatggat tctggacgag    3780
ctccaaagga gaaaaatcac tcccagtctg tgagcctgtt tgtggactat cagcccgcac    3840
aacaggaggg cgtatatatg gagggcaaaa ggcaaaacct ggtgattttc cttggcaagt    3900
cctgatatta ggtggaacca cagcagcagg tgcactttta tatgacaact gggtcctaac    3960
agctgctcat gccgtctatg agcaaaaaca tgatgcatcc gccctggaca ttcgaatggg    4020
caccctgaaa agactatcac ctcattatac acaagcctgg tctgaagctg tttttataca    4080
tgaaggttat actcatgatg ctggctttga caatgacata gcactgatta aattgaataa    4140
caaagttgta atcaatagca acatcacgcc tatttgtctg ccaagaaaag aagctgaatc    4200
ctttatgagg acagatgaca ttggaactgc atctggatgg ggattaaccc aaaggggttt    4260
tcttgctaga aatctaatgt atgtcgacat accgattgtt gaccatcaaa aatgtactgc    4320
tgcatatgaa aagccaccct atccaagggg aagtgtaact gctaacatgc tttgtgctgg    4380
cttagaaagt gggggcaagg acagctgcag aggtgacagc ggaggggcac tggtgtttct    4440
agatagtgaa acagagaggt ggtttgtggg aggaatagtg tcctggggtt ccatgaattg    4500 tgggaagca ggtcagtatg gagtctacac aaaagttatt aactatattc cctggatcga    4560
gaacataatt agtgattttt aacttgcgtg tctgcagtca aggattcttc atttttagaa    4620
atgcctgtga agaccttggc agcgacgtgg ctcgagaagc attcatcatt actgtggaca    4680
tggcagttgt tgctccaccc aaaaaaacag actccaggtg aggctgctgt catttctcca    4740
cttgccagtt taattccagc cttacccatt gactcaaggg gacataaacc acgagagtga    4800
cagtcatctt tgcccaccca gtgtaatgtc actgctcaaa ttacatttca ttaccttaaa    4860
aagccagtct cttttcatac tggctgttgg catttctgta aactgcctgt ccatgctctt    4920 tgttttaaa cttgttctta ttgaaaaaaa aaaaaaaaa                           4960
```

<210> SEQ ID NO 50
<211> LENGTH: 2090
<212> TYPE: DNA
<213> ORGANISM: Murine
<220> FEATURE:
<221> NAME/KEY: CDS
<222> LOCATION: (33)..(2090)

<400> SEQUENCE: 50

```
ggcgctggac tgcagagcta tggtggcaca cc atg agg cta ctc atc ttc ctg      53
                                   Met Arg Leu Leu Ile Phe Leu
                                    1               5 ggt ctg ctg tgg agt ttg gtg gcc aca ctt ctg ggt tca aag tgg cct     101
Gly Leu Leu Trp Ser Leu Val Ala Thr Leu Leu Gly Ser Lys Trp Pro
         10                  15                  20 gaa cct gta ttc ggg cgc ctg gtg tcc cct ggc ttc cca gag aag tat     149
Glu Pro Val Phe Gly Arg Leu Val Ser Pro Gly Phe Pro Glu Lys Tyr
     25                  30                  35 gct gac cat caa gat cga tcc tgg aca ctg act gca ccc cct ggc tac     197
Ala Asp His Gln Asp Arg Ser Trp Thr Leu Thr Ala Pro Pro Gly Tyr
 40                  45                  50                  55 cgc ctg cgc ctc tac ttc acc cac ttt gac ctg gaa ctc tct tac cgc     245
Arg Leu Arg Leu Tyr Phe Thr His Phe Asp Leu Glu Leu Ser Tyr Arg
                 60                  65                  70 tgc gag tat gac ttt gtc aag ttg agc tca ggg acc aag gtg ctg gcc     293
Cys Glu Tyr Asp Phe Val Lys Leu Ser Ser Gly Thr Lys Val Leu Ala
```

```
                    75                  80                  85
aca ctg tgt ggg cag gag agt aca gac act gag cag gca cct ggc aat     341
Thr Leu Cys Gly Gln Glu Ser Thr Asp Thr Glu Gln Ala Pro Gly Asn
         90                  95                 100 gac acc ttc tac tca ctg ggt ccc agc cta aag gtc acc ttc cac tcc     389
Asp Thr Phe Tyr Ser Leu Gly Pro Ser Leu Lys Val Thr Phe His Ser
    105                 110                 115 gac tac tcc aat gag aag ccg ttc aca ggg ttt gag gcc ttc tat gca     437
Asp Tyr Ser Asn Glu Lys Pro Phe Thr Gly Phe Glu Ala Phe Tyr Ala
120                 125                 130                 135 gcg gag gat gtg gat gaa tgc aga gtg tct ctg gga gac tca gtc cct     485
Ala Glu Asp Val Asp Glu Cys Arg Val Ser Leu Gly Asp Ser Val Pro
                140                 145                 150 tgt gac cat tat tgc cac aac tac ttg ggc ggc tac tat tgc tcc tgc     533
Cys Asp His Tyr Cys His Asn Tyr Leu Gly Gly Tyr Tyr Cys Ser Cys
            155                 160                 165 aga gcg ggc tac att ctc cac cag aac aag cac acg tgc tca gcc ctt     581
Arg Ala Gly Tyr Ile Leu His Gln Asn Lys His Thr Cys Ser Ala Leu
        170                 175                 180 tgt tca ggc cag gtg ttc aca gga aga tct ggg tat ctc agt agc cct     629
Cys Ser Gly Gln Val Phe Thr Gly Arg Ser Gly Tyr Leu Ser Ser Pro
    185                 190                 195 gag tac ccg cag cca tac ccc aag ctc tcc agc tgc acc tac agc atc     677
Glu Tyr Pro Gln Pro Tyr Pro Lys Leu Ser Ser Cys Thr Tyr Ser Ile
200                 205                 210                 215 cgc ctg gag gac ggc ttc agt gtc atc ctg gac ttc gtg gag tcc ttc     725
Arg Leu Glu Asp Gly Phe Ser Val Ile Leu Asp Phe Val Glu Ser Phe
                220                 225                 230 gat gtg gag acg cac cct gaa gcc cag tgc ccc tat gac tcc ctc aag     773
Asp Val Glu Thr His Pro Glu Ala Gln Cys Pro Tyr Asp Ser Leu Lys
            235                 240                 245 att caa aca gac aag ggg gaa cac ggc cca ttt tgt ggg aag acg ctg     821
Ile Gln Thr Asp Lys Gly Glu His Gly Pro Phe Cys Gly Lys Thr Leu
        250                 255                 260 cct ccc agg att gaa act gac agc cac aag gtg acc atc acc ttt gcc     869
Pro Pro Arg Ile Glu Thr Asp Ser His Lys Val Thr Ile Thr Phe Ala
    265                 270                 275 act gac gag tcg ggg aac cac aca ggc tgg aag ata cac tac aca agc     917
Thr Asp Glu Ser Gly Asn His Thr Gly Trp Lys Ile His Tyr Thr Ser
280                 285                 290                 295 aca gca cgg ccc tgc cct gat cca acg gcg cca cct aat ggc agc att     965
Thr Ala Arg Pro Cys Pro Asp Pro Thr Ala Pro Pro Asn Gly Ser Ile
                300                 305                 310 tca cct gtg caa gcc acg tat gtc ctg aag gac agg ttt tct gtc ttc    1013
Ser Pro Val Gln Ala Thr Tyr Val Leu Lys Asp Arg Phe Ser Val Phe
            315                 320                 325 tgc aag aca ggc ttc gag ctt ctg caa ggt tct gtc ccc ctg aaa tca    1061
Cys Lys Thr Gly Phe Glu Leu Leu Gln Gly Ser Val Pro Leu Lys Ser
        330                 335                 340 ttc act gct gtc tgt cag aaa gat gga tct tgg gac cgg ccg atg cca    1109
Phe Thr Ala Val Cys Gln Lys Asp Gly Ser Trp Asp Arg Pro Met Pro
    345                 350                 355 gag tgc agc att att gat tgt ggc cct ccc gat gac cta ccc aat ggc    1157
Glu Cys Ser Ile Ile Asp Cys Gly Pro Pro Asp Asp Leu Pro Asn Gly
360                 365                 370                 375 cat gtg gac tat atc aca ggc cct caa gtg act acc tac aaa gct gtg    1205
His Val Asp Tyr Ile Thr Gly Pro Gln Val Thr Thr Tyr Lys Ala Val
                380                 385                 390 att cag tac agc tgt gaa gag act ttc tac aca atg agc agc aat ggt    1253
```

```
Ile Gln Tyr Ser Cys Glu Glu Thr Phe Tyr Thr Met Ser Ser Asn Gly
            395                 400                 405 aaa tat gtg tgt gag gct gat gga ttc tgg acg agc tcc aaa gga gaa        1301
Lys Tyr Val Cys Glu Ala Asp Gly Phe Trp Thr Ser Ser Lys Gly Glu
            410                 415                 420 aaa ctc ccc ccg gtt tgt gag cct gtt tgt ggg ctg tcc aca cac act        1349
Lys Leu Pro Pro Val Cys Glu Pro Val Cys Gly Leu Ser Thr His Thr
        425                 430                 435 ata gga gga cgc ata gtt gga ggg cag cct gca aag cct ggt gac ttt        1397
Ile Gly Gly Arg Ile Val Gly Gly Gln Pro Ala Lys Pro Gly Asp Phe
    440                 445                 450                 455 cct tgg caa gtc ttg ttg ctg ggt caa act aca gca gca gca ggt gca        1445
Pro Trp Gln Val Leu Leu Leu Gly Gln Thr Thr Ala Ala Ala Gly Ala
                460                 465                 470 ctt ata cat gac aat tgg gtc cta aca gcc gct cat gct gta tat gag        1493
Leu Ile His Asp Asn Trp Val Leu Thr Ala Ala His Ala Val Tyr Glu
            475                 480                 485 aaa aga atg gca gcg tcc tcc ctg aac atc cga atg ggc atc ctc aaa        1541
Lys Arg Met Ala Ala Ser Ser Leu Asn Ile Arg Met Gly Ile Leu Lys
        490                 495                 500 agg ctc tca cct cat tac act caa gcc tgg ccc gag gaa atc ttt ata        1589
Arg Leu Ser Pro His Tyr Thr Gln Ala Trp Pro Glu Glu Ile Phe Ile
    505                 510                 515 cat gaa ggc tac act cac ggt gct ggt ttt gac aat gat ata gca ttg        1637
His Glu Gly Tyr Thr His Gly Ala Gly Phe Asp Asn Asp Ile Ala Leu
520                 525                 530                 535 att aaa ctc aag aac aaa gtc aca atc aac gga agc atc atg cct gtt        1685
Ile Lys Leu Lys Asn Lys Val Thr Ile Asn Gly Ser Ile Met Pro Val
            540                 545                 550 tgc cta ccg cga aaa gaa gct gca tcc tta atg aga aca gac ttc act        1733
Cys Leu Pro Arg Lys Glu Ala Ala Ser Leu Met Arg Thr Asp Phe Thr
        555                 560                 565 gga act gtg gct ggc tgg ggg tta acc cag aag ggg ctt ctt gct aga        1781
Gly Thr Val Ala Gly Trp Gly Leu Thr Gln Lys Gly Leu Leu Ala Arg
    570                 575                 580 aac cta atg ttt gtg gac ata cca att gct gac cac caa aaa tgt acc        1829
Asn Leu Met Phe Val Asp Ile Pro Ile Ala Asp His Gln Lys Cys Thr
585                 590                 595 acc gtg tat gaa aag ctc tat cca gga gta aga gta agc gct aac atg        1877
Thr Val Tyr Glu Lys Leu Tyr Pro Gly Val Arg Val Ser Ala Asn Met
600                 605                 610                 615 ctc tgt gct ggc tta gag act ggt ggc aag gac agc tgc aga ggt gac        1925
Leu Cys Ala Gly Leu Glu Thr Gly Gly Lys Asp Ser Cys Arg Gly Asp
            620                 625                 630 agt ggg ggg gca tta gtg ttt cta gat aat gag aca cag cga tgg ttt        1973
Ser Gly Gly Ala Leu Val Phe Leu Asp Asn Glu Thr Gln Arg Trp Phe
        635                 640                 645 gtg gga gga ata gtt tcc tgg ggt tcc att aat tgt ggg gcg gca ggc        2021
Val Gly Gly Ile Val Ser Trp Gly Ser Ile Asn Cys Gly Ala Ala Gly
    650                 655                 660 cag tat ggg gtc tac aca aaa gtc atc aac tat att ccc tgg aat gag        2069
Gln Tyr Gly Val Tyr Thr Lys Val Ile Asn Tyr Ile Pro Trp Asn Glu
665                 670                 675 aac ata ata agt aat ttc taa                                             2090
Asn Ile Ile Ser Asn Phe
680             685

<210> SEQ ID NO 51
<211> LENGTH: 685
<212> TYPE: PRT
```

<213> ORGANISM: Murine

<400> SEQUENCE: 51

```
Met Arg Leu Leu Ile Phe Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Pro Gly Phe Pro Glu Lys Tyr Ala Asp His Gln Asp Arg Ser Trp Thr
        35                  40                  45

Leu Thr Ala Pro Pro Gly Tyr Arg Leu Arg Leu Tyr Phe Thr His Phe
    50                  55                  60

Asp Leu Glu Leu Ser Tyr Arg Cys Glu Tyr Asp Phe Val Lys Leu Ser
65                  70                  75                  80

Ser Gly Thr Lys Val Leu Ala Thr Leu Cys Gly Gln Glu Ser Thr Asp
                85                  90                  95

Thr Glu Gln Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Val
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Ala Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Tyr Leu Ser Ser Pro Glu Tyr Pro Gln Pro Tyr Pro Lys Leu
        195                 200                 205

Ser Ser Cys Thr Tyr Ser Ile Arg Leu Glu Asp Gly Phe Ser Val Ile
    210                 215                 220

Leu Asp Phe Val Glu Ser Phe Asp Val Glu Thr His Pro Glu Ala Gln
225                 230                 235                 240

Cys Pro Tyr Asp Ser Leu Lys Ile Gln Thr Asp Lys Gly Glu His Gly
                245                 250                 255

Pro Phe Cys Gly Lys Thr Leu Pro Pro Arg Ile Glu Thr Asp Ser His
            260                 265                 270

Lys Val Thr Ile Thr Phe Ala Thr Asp Glu Ser Gly Asn His Thr Gly
        275                 280                 285

Trp Lys Ile His Tyr Thr Thr Ala Arg Pro Cys Pro Asp Pro Thr
    290                 295                 300

Ala Pro Pro Asn Gly Ser Ile Ser Pro Val Gln Ala Thr Tyr Val Leu
305                 310                 315                 320

Lys Asp Arg Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350

Ser Trp Asp Arg Pro Met Pro Glu Cys Ser Ile Ile Asp Cys Gly Pro
        355                 360                 365

Pro Asp Asp Leu Pro Asn Gly His Val Asp Tyr Ile Thr Gly Pro Gln
    370                 375                 380

Val Thr Thr Tyr Lys Ala Val Ile Gln Tyr Ser Cys Glu Glu Thr Phe
385                 390                 395                 400
```

Tyr Thr Met Ser Ser Asn Gly Lys Tyr Val Cys Glu Ala Asp Gly Phe
                405                 410                 415

Trp Thr Ser Ser Lys Gly Glu Lys Leu Pro Pro Val Cys Glu Pro Val
            420                 425                 430

Cys Gly Leu Ser Thr His Thr Ile Gly Gly Arg Ile Val Gly Gly Gln
        435                 440                 445

Pro Ala Lys Pro Gly Asp Phe Pro Trp Gln Val Leu Leu Leu Gly Gln
    450                 455                 460

Thr Thr Ala Ala Ala Gly Ala Leu Ile His Asp Asn Trp Val Leu Thr
465                 470                 475                 480

Ala Ala His Ala Val Tyr Glu Lys Arg Met Ala Ala Ser Ser Leu Asn
                485                 490                 495

Ile Arg Met Gly Ile Leu Lys Arg Leu Ser Pro His Tyr Thr Gln Ala
            500                 505                 510

Trp Pro Glu Glu Ile Phe Ile His Glu Gly Tyr Thr His Gly Ala Gly
        515                 520                 525

Phe Asp Asn Asp Ile Ala Leu Ile Lys Leu Lys Asn Lys Val Thr Ile
    530                 535                 540

Asn Gly Ser Ile Met Pro Val Cys Leu Pro Arg Lys Glu Ala Ala Ser
545                 550                 555                 560

Leu Met Arg Thr Asp Phe Thr Gly Thr Val Ala Gly Trp Gly Leu Thr
                565                 570                 575

Gln Lys Gly Leu Leu Ala Arg Asn Leu Met Phe Val Asp Ile Pro Ile
            580                 585                 590

Ala Asp His Gln Lys Cys Thr Thr Val Tyr Glu Lys Leu Tyr Pro Gly
        595                 600                 605

Val Arg Val Ser Ala Asn Met Leu Cys Ala Gly Leu Glu Thr Gly Gly
    610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Ala Ala Gly Gln Tyr Gly Val Tyr Thr Lys Val Ile
            660                 665                 670

Asn Tyr Ile Pro Trp Asn Glu Asn Ile Ile Ser Asn Phe
        675                 680                 685

<210> SEQ ID NO 52
<211> LENGTH: 670
<212> TYPE: PRT
<213> ORGANISM: Murine

<400> SEQUENCE: 52

Thr Leu Leu Gly Ser Lys Trp Pro Glu Pro Val Phe Gly Arg Leu Val
1               5                   10                  15

Ser Pro Gly Phe Pro Glu Lys Tyr Ala Asp His Gln Asp Arg Ser Trp
            20                  25                  30

Thr Leu Thr Ala Pro Pro Gly Tyr Arg Leu Arg Leu Tyr Phe Thr His
        35                  40                  45

Phe Asp Leu Glu Leu Ser Tyr Arg Cys Glu Tyr Asp Phe Val Lys Leu
    50                  55                  60

Ser Ser Gly Thr Lys Val Leu Ala Thr Leu Cys Gly Gln Glu Ser Thr
65                  70                  75                  80

Asp Thr Glu Gln Ala Pro Gly Asn Asp Thr Phe Tyr Ser Leu Gly Pro
                85                  90                  95

```
Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
            115                 120                 125

Val Ser Leu Gly Asp Ser Val Pro Cys Asp His Tyr Cys His Asn Tyr
            130                 135                 140

Leu Gly Gly Tyr Tyr Cys Ser Cys Arg Ala Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Tyr Leu Ser Ser Pro Glu Tyr Pro Gln Pro Tyr Pro Lys
            180                 185                 190

Leu Ser Ser Cys Thr Tyr Ser Ile Arg Leu Glu Asp Gly Phe Ser Val
            195                 200                 205

Ile Leu Asp Phe Val Glu Ser Phe Asp Val Glu Thr His Pro Glu Ala
            210                 215                 220

Gln Cys Pro Tyr Asp Ser Leu Lys Ile Gln Thr Asp Lys Gly Glu His
225                 230                 235                 240

Gly Pro Phe Cys Gly Lys Thr Leu Pro Pro Arg Ile Glu Thr Asp Ser
                245                 250                 255

His Lys Val Thr Ile Thr Phe Ala Thr Asp Glu Ser Gly Asn His Thr
            260                 265                 270

Gly Trp Lys Ile His Tyr Thr Ser Thr Ala Arg Pro Cys Pro Asp Pro
            275                 280                 285

Thr Ala Pro Pro Asn Gly Ser Ile Ser Pro Val Gln Ala Thr Tyr Val
            290                 295                 300

Leu Lys Asp Arg Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Met Pro Glu Cys Ser Ile Ile Asp Cys Gly
            340                 345                 350

Pro Pro Asp Asp Leu Pro Asn Gly His Val Asp Tyr Ile Thr Gly Pro
            355                 360                 365

Gln Val Thr Thr Tyr Lys Ala Val Ile Gln Tyr Ser Cys Glu Glu Thr
            370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Ser Leu Pro Val Cys Glu Pro
                405                 410                 415

Val Cys Gly Leu Ser Thr His Thr Ser Gly Gly Arg Ile Val Gly Gly
            420                 425                 430

Gln Pro Ala Lys Pro Gly Asp Phe Pro Trp Gln Val Leu Leu Leu Gly
            435                 440                 445

Gln Thr Thr Ala Ala Ala Gly Ala Leu Ile His Asp Asn Trp Val Leu
            450                 455                 460

Thr Ala Ala His Ala Val Tyr Glu Lys Arg Met Ala Ala Ser Ser Leu
465                 470                 475                 480

Asn Ile Arg Met Gly Ile Leu Lys Arg Leu Ser Pro His Tyr Thr Gln
                485                 490                 495

Ala Trp Pro Glu Glu Ile Phe Ile His Glu Gly Tyr Thr His Gly Ala
            500                 505                 510
```

```
Gly Phe Asp Asn Asp Ile Ala Leu Ile Lys Leu Lys Asn Lys Val Thr
            515                 520                 525

Ile Asn Gly Ser Ile Met Pro Val Cys Leu Pro Arg Lys Glu Ala Ala
    530                 535                 540

Ser Leu Met Arg Thr Asp Phe Thr Gly Thr Val Ala Gly Trp Gly Leu
545                 550                 555                 560

Thr Gln Lys Gly Leu Leu Ala Arg Asn Leu Met Phe Val Asp Ile Pro
                565                 570                 575

Ile Ala Asp His Gln Lys Cys Thr Thr Val Tyr Glu Lys Leu Tyr Pro
            580                 585                 590

Gly Val Arg Val Ser Ala Asn Met Leu Cys Ala Gly Leu Glu Thr Gly
        595                 600                 605

Gly Lys Asp Ser Cys Arg Gly Asp Ser Gly Gly Ala Leu Val Phe Leu
    610                 615                 620

Asp Asn Glu Thr Gln Arg Trp Phe Val Gly Ile Val Ser Trp Gly
625                 630                 635                 640

Ser Ile Asn Cys Gly Ala Ala Gly Gln Tyr Gly Val Tyr Thr Lys Val
                645                 650                 655

Ile Asn Tyr Ile Pro Trp Asn Glu Asn Ile Ile Ser Asn Phe
            660                 665                 670

<210> SEQ ID NO 53
<211> LENGTH: 2091
<212> TYPE: DNA
<213> ORGANISM: Rat
<220> FEATURE:
<221> NAME/KEY: CDS
<222> LOCATION: (10)..(2067)

<400> SEQUENCE: 53 tggcacaca atg agg cta ctg atc gtc ctg ggt ctg ctt tgg agt ttg gtg      51
          Met Arg Leu Leu Ile Val Leu Gly Leu Leu Trp Ser Leu Val
            1               5                   10 gcc aca ctt ttg ggc tcc aag tgg cct gag cct gta ttc ggg cgc ctg        99
Ala Thr Leu Leu Gly Ser Lys Trp Pro Glu Pro Val Phe Gly Arg Leu
15                  20                  25                  30 gtg tcc ctg gcc ttc cca gag aag tat ggc aac cat cag gat cga tcc       147
Val Ser Leu Ala Phe Pro Glu Lys Tyr Gly Asn His Gln Asp Arg Ser
                35                  40                  45 tgg acg ctg act gca ccc cct ggc ttc cgc ctg cgc ctc tac ttc acc       195
Trp Thr Leu Thr Ala Pro Pro Gly Phe Arg Leu Arg Leu Tyr Phe Thr
            50                  55                  60 cac ttc aac ctg gaa ctc tct tac cgc tgc gag tat gac ttt gtc aag       243
His Phe Asn Leu Glu Leu Ser Tyr Arg Cys Glu Tyr Asp Phe Val Lys
        65                  70                  75 ttg acc tca ggg acc aag gtg cta gcc acg ctg tgt ggg cag gag agt       291
Leu Thr Ser Gly Thr Lys Val Leu Ala Thr Leu Cys Gly Gln Glu Ser
    80                  85                  90 aca gat act gag cgg gca cct ggc aat gac acc ttc tac tca ctg ggt       339
Thr Asp Thr Glu Arg Ala Pro Gly Asn Asp Thr Phe Tyr Ser Leu Gly
95                  100                 105                 110 ccc agc cta aag gtc acc ttc cac tcc gac tac tcc aat gag aag cca       387
Pro Ser Leu Lys Val Thr Phe His Ser Asp Tyr Ser Asn Glu Lys Pro
                115                 120                 125 ttc aca gga ttt gag gcc ttc tat gca gcg gag gat gtg gat gaa tgc       435
Phe Thr Gly Phe Glu Ala Phe Tyr Ala Ala Glu Asp Val Asp Glu Cys
            130                 135                 140 aga aca tcc ctg gga gac tca gtc cct tgt gac cat tat tgc cac aac       483
Arg Thr Ser Leu Gly Asp Ser Val Pro Cys Asp His Tyr Cys His Asn
```

```
                145                 150                 155
tac ctg ggc ggc tac tac tgc tcc tgc cga gtg ggc tac att ctg cac      531
Tyr Leu Gly Gly Tyr Tyr Cys Ser Cys Arg Val Gly Tyr Ile Leu His
    160                 165                 170 cag aac aag cat acc tgc tca gcc ctt tgt tca ggc cag gtg ttc act      579
Gln Asn Lys His Thr Cys Ser Ala Leu Cys Ser Gly Gln Val Phe Thr
175                 180                 185                 190 ggg agg tct ggc ttt ctc agt agc cct gag tac cca cag cca tac ccc      627
Gly Arg Ser Gly Phe Leu Ser Ser Pro Glu Tyr Pro Gln Pro Tyr Pro
                195                 200                 205 aaa ctc tcc agc tgc gcc tac aac atc cgc ctg gag gaa ggc ttc agt      675
Lys Leu Ser Ser Cys Ala Tyr Asn Ile Arg Leu Glu Glu Gly Phe Ser
                210                 215                 220 atc acc ctg gac ttc gtg gag tcc ttt gat gtg gag atg cac cct gaa      723
Ile Thr Leu Asp Phe Val Glu Ser Phe Asp Val Glu Met His Pro Glu
            225                 230                 235 gcc cag tgc ccc tac gac tcc ctc aag att caa aca gac aag agg gaa      771
Ala Gln Cys Pro Tyr Asp Ser Leu Lys Ile Gln Thr Asp Lys Arg Glu
        240                 245                 250 tac ggc ccg ttt tgt ggg aag acg ctg ccc ccc agg att gaa act gac      819
Tyr Gly Pro Phe Cys Gly Lys Thr Leu Pro Pro Arg Ile Glu Thr Asp
255                 260                 265                 270 agc aac aag gtg acc att acc ttt acc acc gac gag tca ggg aac cac      867
Ser Asn Lys Val Thr Ile Thr Phe Thr Thr Asp Glu Ser Gly Asn His
                275                 280                 285 aca ggc tgg aag ata cac tac aca agc aca gca cag ccc tgc cct gat      915
Thr Gly Trp Lys Ile His Tyr Thr Ser Thr Ala Gln Pro Cys Pro Asp
                290                 295                 300 cca acg gcg cca cct aat ggt cac att tca cct gtg caa gcc acg tat      963
Pro Thr Ala Pro Pro Asn Gly His Ile Ser Pro Val Gln Ala Thr Tyr
            305                 310                 315 gtc ctg aag gac agc ttt tct gtc ttc tgc aag act ggc ttc gag ctt     1011
Val Leu Lys Asp Ser Phe Ser Val Phe Cys Lys Thr Gly Phe Glu Leu
        320                 325                 330 ctg caa ggt tct gtc ccc ctg aag tca ttc act gct gtc tgt cag aaa     1059
Leu Gln Gly Ser Val Pro Leu Lys Ser Phe Thr Ala Val Cys Gln Lys
335                 340                 345                 350 gat gga tct tgg gac cgg ccg ata cca gag tgc agc att att gac tgt     1107
Asp Gly Ser Trp Asp Arg Pro Ile Pro Glu Cys Ser Ile Ile Asp Cys
                355                 360                 365 ggc cct ccc gat gac cta ccc aat ggc cac gtg gac tat atc aca ggc     1155
Gly Pro Pro Asp Asp Leu Pro Asn Gly His Val Asp Tyr Ile Thr Gly
                370                 375                 380 cct gaa gtg acc acc tac aaa gct gtg att cag tac agc tgt gaa gag     1203
Pro Glu Val Thr Thr Tyr Lys Ala Val Ile Gln Tyr Ser Cys Glu Glu
            385                 390                 395 act ttc tac aca atg agc agc aat ggt aaa tat gtg tgt gag gct gat     1251
Thr Phe Tyr Thr Met Ser Ser Asn Gly Lys Tyr Val Cys Glu Ala Asp
        400                 405                 410 gga ttc tgg acg agc tcc aaa gga gaa aaa tcc ctc ccg gtt tgc aag     1299
Gly Phe Trp Thr Ser Ser Lys Gly Glu Lys Ser Leu Pro Val Cys Lys
415                 420                 425                 430 cct gtc tgt gga ctg tcc aca cac act tca gga ggc cgt ata att gga     1347
Pro Val Cys Gly Leu Ser Thr His Thr Ser Gly Gly Arg Ile Ile Gly
                435                 440                 445 gga cag cct gca aag cct ggt gac ttt cct tgg caa gtc ttg tta ctg     1395
Gly Gln Pro Ala Lys Pro Gly Asp Phe Pro Trp Gln Val Leu Leu Leu
                450                 455                 460 ggt gaa act aca gca gca ggt gct ctt ata cat gac gac tgg gtc cta     1443
```

```
                Gly Glu Thr Thr Ala Ala Gly Ala Leu Ile His Asp Asp Trp Val Leu
                            465                 470                 475 aca gcg gct cat gct gta tat ggg aaa aca gag gcg atg tcc tcc ctg          1491
Thr Ala His Ala Val Tyr Gly Lys Thr Glu Ala Met Ser Ser Leu
    480                 485                 490 gac atc cgc atg ggc atc ctc aaa agg ctc tcc ctc att tac act caa          1539
Asp Ile Arg Met Gly Ile Leu Lys Arg Leu Ser Leu Ile Tyr Thr Gln
495                 500                 505                 510 gcc tgg cca gag gct gtc ttt atc cat gaa ggc tac act cac gga gct          1587
Ala Trp Pro Glu Ala Val Phe Ile His Glu Gly Tyr Thr His Gly Ala
                515                 520                 525 ggt ttt gac aat gat ata gca ctg att aaa ctc aag aac aaa gtc aca          1635
Gly Phe Asp Asn Asp Ile Ala Leu Ile Lys Leu Lys Asn Lys Val Thr
            530                 535                 540 atc aac aga aac atc atg ccg att tgt cta cca aga aaa gaa gct gca          1683
Ile Asn Arg Asn Ile Met Pro Ile Cys Leu Pro Arg Lys Glu Ala Ala
545                 550                 555 tcc tta atg aaa aca gac ttc gtt gga act gtg gct ggc tgg ggg tta          1731
Ser Leu Met Lys Thr Asp Phe Val Gly Thr Val Ala Gly Trp Gly Leu
    560                 565                 570 acc cag aag ggg ttt ctt gct aga aac cta atg ttt gtg gac ata cca          1779
Thr Gln Lys Gly Phe Leu Ala Arg Asn Leu Met Phe Val Asp Ile Pro
575                 580                 585                 590 att gtt gac cac caa aaa tgt gct act gcg tat aca aag cag ccc tac          1827
Ile Val Asp His Gln Lys Cys Ala Thr Ala Tyr Thr Lys Gln Pro Tyr
                595                 600                 605 cca gga gca aaa gtg act gtt aac atg ctc tgt gct ggc cta gac cgc          1875
Pro Gly Ala Lys Val Thr Val Asn Met Leu Cys Ala Gly Leu Asp Arg
            610                 615                 620 ggt ggc aag gac agc tgc aga ggt gac agc gga ggg gca tta gtg ttt          1923
Gly Gly Lys Asp Ser Cys Arg Gly Asp Ser Gly Gly Ala Leu Val Phe
625                 630                 635 cta gac aat gaa aca cag aga tgg ttt gtg gga gga ata gtt tcc tgg          1971
Leu Asp Asn Glu Thr Gln Arg Trp Phe Val Gly Gly Ile Val Ser Trp
    640                 645                 650 ggt tct att aac tgt ggg ggg tca gaa cag tat ggg gtc tac acg aaa          2019
Gly Ser Ile Asn Cys Gly Gly Ser Glu Gln Tyr Gly Val Tyr Thr Lys
655                 660                 665                 670 gtc acg aac tat att ccc tgg att gag aac ata ata aat aat ttc taa          2067
Val Thr Asn Tyr Ile Pro Trp Ile Glu Asn Ile Ile Asn Asn Phe
                675                 680                 685 tttgcaaaaa aaaaaaaaaa aaaa                                               2091

<210> SEQ ID NO 54
<211> LENGTH: 685
<212> TYPE: PRT
<213> ORGANISM: Rat

<400> SEQUENCE: 54

Met Arg Leu Leu Ile Val Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Leu Ala Phe Pro Glu Lys Tyr Gly Asn His Gln Asp Arg Ser Trp Thr
        35                  40                  45

Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80
```

```
Ser Gly Thr Lys Val Leu Ala Thr Leu Cys Gly Gln Glu Ser Thr Asp
            85                  90                  95

Thr Glu Arg Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
            115                 120                 125

Gly Phe Glu Ala Phe Tyr Ala Ala Glu Asp Val Asp Glu Cys Arg Thr
        130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
                180                 185                 190

Ser Gly Phe Leu Ser Ser Pro Glu Tyr Pro Gln Pro Tyr Pro Lys Leu
            195                 200                 205

Ser Ser Cys Ala Tyr Asn Ile Arg Leu Glu Glu Gly Phe Ser Ile Thr
    210                 215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
                260                 265                 270

Lys Val Thr Ile Thr Phe Thr Thr Asp Glu Ser Gly Asn His Thr Gly
            275                 280                 285

Trp Lys Ile His Tyr Thr Ser Thr Ala Gln Pro Cys Pro Asp Pro Thr
            290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350

Ser Trp Asp Arg Pro Ile Pro Glu Cys Ser Ile Ile Asp Cys Gly Pro
            355                 360                 365

Pro Asp Asp Leu Pro Asn Gly His Val Asp Tyr Ile Thr Gly Pro Glu
            370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
            420                 425                 430

Cys Gly Leu Ser Thr His Thr Ser Gly Gly Arg Ile Ile Gly Gly Gln
            435                 440                 445

Pro Ala Lys Pro Gly Asp Phe Pro Trp Gln Val Leu Leu Leu Gly Glu
            450                 455                 460

Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495
```

```
Arg Met Gly Ile Leu Lys Arg Leu Ser Leu Ile Tyr Thr Gln Ala Trp
                500                 505                 510

Pro Glu Ala Val Phe Ile His Glu Gly Tyr Thr His Gly Ala Gly Phe
            515                 520                 525

Asp Asn Asp Ile Ala Leu Ile Lys Leu Lys Asn Lys Val Thr Ile Asn
        530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
            580                 585                 590

Asp His Gln Lys Cys Ala Thr Ala Tyr Thr Lys Gln Pro Tyr Pro Gly
        595                 600                 605

Ala Lys Val Thr Val Asn Met Leu Cys Ala Gly Leu Asp Arg Gly Gly
        610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Gly Ser Glu Gln Tyr Gly Val Tyr Thr Lys Val Thr
            660                 665                 670

Asn Tyr Ile Pro Trp Ile Glu Asn Ile Ile Asn Phe
            675                 680                 685

<210> SEQ ID NO 55
<211> LENGTH: 670
<212> TYPE: PRT
<213> ORGANISM: Rat

<400> SEQUENCE: 55

Thr Leu Leu Gly Ser Lys Trp Pro Glu Pro Val Phe Gly Arg Leu Val
1               5                   10                  15

Ser Leu Ala Phe Pro Glu Lys Tyr Gly Asn His Gln Asp Arg Ser Trp
            20                  25                  30

Thr Leu Thr Ala Pro Pro Gly Phe Arg Leu Arg Leu Tyr Phe Thr His
        35                  40                  45

Phe Asn Leu Glu Leu Ser Tyr Arg Cys Glu Tyr Asp Phe Val Lys Leu
    50                  55                  60

Thr Ser Gly Thr Lys Val Leu Ala Thr Leu Cys Gly Gln Glu Ser Thr
65                  70                  75                  80

Asp Thr Glu Arg Ala Pro Gly Asn Asp Thr Phe Tyr Ser Leu Gly Pro
                85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
        115                 120                 125

Thr Ser Leu Gly Asp Ser Val Pro Cys Asp His Tyr Cys His Asn Tyr
    130                 135                 140

Leu Gly Gly Tyr Tyr Cys Ser Cys Arg Val Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Phe Leu Ser Ser Pro Glu Tyr Pro Gln Pro Tyr Pro Lys
            180                 185                 190
```

-continued

```
Leu Ser Ser Cys Ala Tyr Asn Ile Arg Leu Glu Glu Gly Phe Ser Ile
        195                 200                 205

Thr Leu Asp Phe Val Glu Ser Phe Asp Val Glu Met His Pro Glu Ala
    210                 215                 220

Gln Cys Pro Tyr Asp Ser Leu Lys Ile Gln Thr Asp Lys Arg Glu Tyr
225                 230                 235                 240

Gly Pro Phe Cys Gly Lys Thr Leu Pro Pro Arg Ile Glu Thr Asp Ser
            245                 250                 255

Asn Lys Val Thr Ile Thr Phe Thr Thr Asp Glu Ser Gly Asn His Thr
                260                 265                 270

Gly Trp Lys Ile His Tyr Thr Ser Thr Ala Gln Pro Cys Pro Asp Pro
            275                 280                 285

Thr Ala Pro Pro Asn Gly His Ile Ser Pro Val Gln Ala Thr Tyr Val
        290                 295                 300

Leu Lys Asp Ser Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
            325                 330                 335

Gly Ser Trp Asp Arg Pro Ile Pro Glu Cys Ser Ile Ile Asp Cys Gly
            340                 345                 350

Pro Pro Asp Asp Leu Pro Asn Gly His Val Asp Tyr Ile Thr Gly Pro
            355                 360                 365

Glu Val Thr Thr Tyr Lys Ala Val Ile Gln Tyr Ser Cys Glu Glu Thr
        370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Ser Leu Pro Val Cys Lys Pro
            405                 410                 415

Val Cys Gly Leu Ser Thr His Thr Ser Gly Gly Arg Ile Ile Gly Gly
                420                 425                 430

Gln Pro Ala Lys Pro Gly Asp Phe Pro Trp Gln Val Leu Leu Leu Gly
            435                 440                 445

Glu Thr Thr Ala Ala Gly Ala Leu Ile His Asp Asp Trp Val Leu Thr
        450                 455                 460

Ala Ala His Ala Val Tyr Gly Lys Thr Glu Ala Met Ser Ser Leu Asp
465                 470                 475                 480

Ile Arg Met Gly Ile Leu Lys Arg Leu Ser Leu Ile Tyr Thr Gln Ala
            485                 490                 495

Trp Pro Glu Ala Val Phe Ile His Glu Gly Tyr Thr His Gly Ala Gly
            500                 505                 510

Phe Asp Asn Asp Ile Ala Leu Ile Lys Leu Lys Asn Lys Val Thr Ile
            515                 520                 525

Asn Arg Asn Ile Met Pro Ile Cys Leu Pro Arg Lys Glu Ala Ala Ser
            530                 535                 540

Leu Met Lys Thr Asp Phe Val Gly Thr Val Ala Gly Trp Gly Leu Thr
545                 550                 555                 560

Gln Lys Gly Phe Leu Ala Arg Asn Leu Met Phe Val Asp Ile Pro Ile
            565                 570                 575

Val Asp His Gln Lys Cys Ala Thr Ala Tyr Thr Lys Gln Pro Tyr Pro
            580                 585                 590

Gly Ala Lys Val Thr Val Asn Met Leu Cys Ala Gly Leu Asp Arg Gly
            595                 600                 605
```

```
Gly Lys Asp Ser Cys Arg Gly Asp Ser Gly Gly Ala Leu Val Phe Leu
        610                 615                 620

Asp Asn Glu Thr Gln Arg Trp Phe Val Gly Gly Ile Val Ser Trp Gly
625                 630                 635                 640

Ser Ile Asn Cys Gly Gly Ser Glu Gln Tyr Gly Val Tyr Thr Lys Val
                645                 650                 655

Thr Asn Tyr Ile Pro Trp Ile Glu Asn Ile Ile Asn Asn Phe
                660                 665                 670
```

<210> SEQ ID NO 56
<211> LENGTH: 28
<212> TYPE: DNA
<213> ORGANISM: Artificial Sequence
<220> FEATURE:
<223> OTHER INFORMATION: Homo Sapiens

<400> SEQUENCE: 56
atgaggctgc tgaccctcct gggccttc                                    28

<210> SEQ ID NO 57
<211> LENGTH: 23
<212> TYPE: DNA
<213> ORGANISM: Artificial Sequence
<220> FEATURE:
<223> OTHER INFORMATION: Homo Sapiens

<400> SEQUENCE: 57
gtgcccctcc tgcgtcacct ctg                                         23

<210> SEQ ID NO 58
<211> LENGTH: 23
<212> TYPE: DNA
<213> ORGANISM: Artificial Sequence
<220> FEATURE:
<223> OTHER INFORMATION: Homo Sapiens

<400> SEQUENCE: 58
cagaggtgac gcaggagggg cac                                         23

<210> SEQ ID NO 59
<211> LENGTH: 27
<212> TYPE: DNA
<213> ORGANISM: Artificial Sequence
<220> FEATURE:
<223> OTHER INFORMATION: Homo Sapiens

<400> SEQUENCE: 59
ttaaaatcac taattatgtt ctcgatc                                     27

<210> SEQ ID NO 60
<211> LENGTH: 22
<212> TYPE: DNA
<213> ORGANISM: Artificial Sequence
<220> FEATURE:
<223> OTHER INFORMATION: Murine

<400> SEQUENCE: 60
atgaggctac tcatcttcct gg                                          22

<210> SEQ ID NO 61
<211> LENGTH: 23
<212> TYPE: DNA
<213> ORGANISM: Artificial Sequence
<220> FEATURE:
<223> OTHER INFORMATION: Murine

```
<400> SEQUENCE: 61
ctgcagaggt gacgcagggg ggg                                           23

<210> SEQ ID NO 62
<211> LENGTH: 23
<212> TYPE: DNA
<213> ORGANISM: Artificial Sequence
<220> FEATURE:
<223> OTHER INFORMATION: Murine

<400> SEQUENCE: 62 cccccctgc gtcacctctg cag                                            23

<210> SEQ ID NO 63
<211> LENGTH: 29
<212> TYPE: DNA
<213> ORGANISM: Artificial Sequence
<220> FEATURE:
<223> OTHER INFORMATION: Murine

<400> SEQUENCE: 63
ttagaaatta cttattatgt tctcaatcc                                     29

<210> SEQ ID NO 64
<211> LENGTH: 29
<212> TYPE: DNA
<213> ORGANISM: Artificial Sequence
<220> FEATURE:
<223> OTHER INFORMATION: Rat

<400> SEQUENCE: 64
gaggtgacgc aggagggca ttagtgttt                                      29

<210> SEQ ID NO 65
<211> LENGTH: 37
<212> TYPE: DNA
<213> ORGANISM: Artificial Sequence
<220> FEATURE:
<223> OTHER INFORMATION: Rat

<400> SEQUENCE: 65
ctagaaacac taatgcccct cctgcgtcac ctctgca                            37
```

METHODS FOR TREATING CONDITIONS ASSOCIATED WITH MASP-2 DEPENDENT COMPLEMENT ACTIVATION

CROSS-REFERENCES TO RELATED APPLICATION

This application claims the benefit of Provisional Application No. 61/473,698 filed Apr. 8, 2011, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0126_US2_SequenceListingasFiled.txt. The text file is 110 KB; was created on Mar. 30, 2012; and is being submitted via EFS-Web with the filing of the specification.

BACKGROUND

The complement system provides an early acting mechanism to initiate, amplify and orchestrate the immune response to microbial infection and other acute insults (M. K. Liszewski and J. P. Atkinson, 1993, in *Fundamental Immunology*, Third Edition, edited by W. E. Paul, Raven Press, Ltd., New York), in humans and other vertebrates. While complement activation provides a valuable first-line defense against potential pathogens, the activities of complement that promote a protective immune response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, C3 and C5 proteolytic products recruit and activate neutrophils. While indispensable for host defense, activated neutrophils are indiscriminate in their release of destructive enzymes and may cause organ damage. In addition, complement activation may cause the deposition of lytic complement components on nearby host cells as well as on microbial targets, resulting in host cell lysis.

The complement system has also been implicated in the pathogenesis of numerous acute and chronic disease states, including: myocardial infarction, stroke, ARDS, reperfusion injury, septic shock, capillary leakage following thermal burns, postcardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states. The growing recognition of the importance of complement-mediated tissue injury in a variety of disease states underscores the need for effective complement inhibitory drugs. To date, Eculizumab (Solaris®), an antibody against C5, is the only complement-targeting drug that has been approved for human use. Yet, C5 is one of several effector molecules located "downstream" in the complement system, and blockade of C5 does not inhibit activation of the complement system. Therefore, an inhibitor of the initiation steps of complement activation would have significant advantages over a "downstream" complement inhibitor.

Currently, it is widely accepted that the complement system can be activated through three distinct pathways: the classical pathway, the lectin pathway, and the alternative pathway. The classical pathway is usually triggered by a complex composed of host antibodies bound to a foreign particle (i.e., an antigen) and thus requires prior exposure to an antigen for the generation of a specific antibody response. Since activation of the classical pathway depends on a prior adaptive immune response by the host, the classical pathway is part of the acquired immune system. In contrast, both the lectin and alternative pathways are independent of adaptive immunity and are part of the innate immune system.

The activation of the complement system results in the sequential activation of serine protease zymogens. The first step in activation of the classical pathway is the binding of a specific recognition molecule, C1q, to antigen-bound IgG and IgM molecules. C1q is associated with the C1r and C1s serine protease proenzymes as a complex called C1. Upon binding of C1q to an immune complex, autoproteolytic cleavage of the Arg-Ile site of C1r is followed by C1r-mediated cleavage and activation of C1s, which thereby acquires the ability to cleave C4 and C2. C4 is cleaved into two fragments, designated C4a and C4b, and, similarly, C2 is cleaved into C2a and C2b. C4b fragments are able to form covalent bonds with adjacent hydroxyl or amino groups and generate the C3 convertase (C4b2a) through noncovalent interaction with the C2a fragment of activated C2. C3 convertase (C4b2a) activates C3 by proteolytic cleavage into C3a and C3b subcomponents leading to generation of the C5 convertase (C4b2a3b), which, by cleaving C5 leads to the formation of the membrane attack complex (C5b combined with C6, C7, C8 and C-9, also referred to as "MAC") that can disrupt cellular membranes leading to cell lysis. The activated forms of C3 and C4 (C3b and C4b) are covalently deposited on the foreign target surfaces, which are recognized by complement receptors on multiple phagocytes.

Independently, the first step in activation of the complement system through the lectin pathway is also the binding of specific recognition molecules, which is followed by the activation of associated serine protease proenzymes. However, rather than the binding of immune complexes by C1q, the recognition molecules in the lectin pathway comprise a group of carbohydrate-binding proteins (mannan-binding lectin (MBL), H-ficolin, M-ficolin, L-ficolin and C-type lectin CL-11), collectively referred to as lectins. See J. Lu et al., *Biochim. Biophys. Acta* 1572:387-400, (2002); Holmskov et al., *Annu. Rev. Immunol.* 21:547-578 (2003); Teh et al., *Immunology* 101:225-232 (2000)). See also J. Lu et al., *Biochim Biophys Acta* 1572:387-400 (2002); Holmskov et al, *Annu Rev Immunol* 21:547-578 (2003); Teh et al., *Immunology* 101:225-232 (2000); Hansen et al, *J. Immunol* 185(10):6096-6104 (2010).

Ikeda et al. first demonstrated that, like C1q, MBL could activate the complement system upon binding to yeast mannan-coated erythrocytes in a C4-dependent manner (Ikeda et al., *J. Biol. Chem.* 262:7451-7454, (1987)). MBL, a member of the collectin protein family, is a calcium-dependent lectin that binds carbohydrates with 3- and 4-hydroxy groups oriented in the equatorial plane of the pyranose ring. Prominent ligands for MBL are thus D-mannose and N-acetyl-D-glucosamine, while carbohydrates not fitting this steric requirement have undetectable affinity for MBL (Weis et al., *Nature* 360:127-134, (1992)). The interaction between MBL and monovalent sugars is extremely weak, with dissociation constants typically in the single-digit millimolar range. MBL achieves tight, specific binding to glycan ligands by avidity, i.e., by interacting simultaneously with multiple monosaccharide residues located in close proximity to each other (Lee et al., *Archiv. Biochem. Biophys.* 299:129-136, (1992)). MBL recognizes the carbohydrate patterns that commonly decorate microorganisms such as bacteria, yeast, parasites and certain viruses. In contrast, MBL does not recognize D-galactose and sialic acid, the penultimate and ultimate sugars that usually decorate "mature" complex glycoconjugates present on mammalian plasma and cell surface glycoproteins. This binding specificity is thought to promote recognition of "foreign" surfaces and help protect from "self-activation." However, MBL does bind with high affinity to clusters of high-mannose "precursor" glycans on N-linked glycoproteins and glycolipids sequestered in the endoplasmic reticulum and Golgi of mammalian cells (Maynard et al., *J. Biol. Chem.* 257:3788-3794, (1982)). Therefore, damaged cells are potential targets for lectin pathway activation via MBL binding.

The ficolins possess a different type of lectin domain than MBL, called the fibrinogen-like domain. Ficolins bind sugar residues in a $Ca^{++}$-independent manner. In humans, three kinds of ficolins (L-ficolin, M-ficolin and H-ficolin) have been identified. The two serum ficolins, L-ficolin and H-ficolin, have in common a specificity for N-acetyl-D-glucosamine; however, H-ficolin also binds N-acetyl-D-galactosamine. The difference in sugar specificity of L-ficolin, H-ficolin, CL-11, and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch et al., *J. Immunol.* 172:1198-1202; (2004)). The collectins (i.e., MBL) and the ficolins bear no significant similarity in amino acid sequence. However, the two groups of proteins have similar domain organizations and, like C1q, assemble into oligomeric structures, which maximize the possibility of multisite binding.

The serum concentrations of MBL are highly variable in healthy populations and this is genetically controlled by polymorphisms/mutations in both the promoter and coding regions of the MBL gene. As an acute phase protein, the expression of MBL is further upregulated during inflammation. L-ficolin is present in serum at concentrations similar to those of MBL. Therefore, the L-ficolin branch of the lectin pathway is potentially comparable to the MBL arm in strength. MBL and ficolins can also function as opsonins, which allow phagocytes to target MBL- and ficolin-decorated surfaces (see Jack et al., *J Leukoc Biol.*, 77(3):328-36 (2004), Matsushita and Fujita, *Immunobiology*, 205(4-5):490-7 (2002), Aoyagi et al., *J Immunol*, 174(1):418-25 (2005). This opsonization requires the interaction of these proteins with phagocyte receptors (Kuhlman et al., *J. Exp. Med.* 169:1733, (1989); Matsushita et al., *J. Biol. Chem.* 271:2448-54, (1996)), the identity of which has not been established.

Human MBL forms a specific and high-affinity interaction through its collagen-like domain with unique C1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Matsushita et al., *J Exp Med* 176(6):1497-1502 (1992); Ji et al., *J. Immunol.* 150:571-578, (1993)). It was subsequently determined that the MASP activity was, in fact, a mixture of two proteases: MASP-1 and MASP-2 (Thiel et al., *Nature* 386:506-510, (1997)). However, it was demonstrated that the MBL-MASP-2 complex alone is sufficient for complement activation (Vorup-Jensen et al., *J. Immunol.* 165:2093-2100, (2000)). Furthermore, only MASP-2 cleaved C2 and C4 at high rates (Ambrus et al., *J. Immunol.* 170:1374-1382, (2003)). Therefore, MASP-2 is the protease responsible for activating C4 and C2 to generate the C3 convertase, C4b2a. This is a significant difference from the C1 complex of the classical pathway, where the coordinated action of two specific serine proteases (C1r and C1s) leads to the activation of the complement system. In addition, a third novel protease, MASP-3, has been isolated (Dahl, M. R., et al., *Immunity* 15:127-35, 2001). MASP-1 and MASP-3 are alternatively spliced products of the same gene.

MASPs share identical domain organizations with those of C1r and C1s, the enzymatic components of the C1 complex (Sim et al., *Biochem. Soc. Trans.* 28:545, (2000)). These domains include an N-terminal C1r/C1s/sea urchin VEGF/bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain.

MBL can also associate with an alternatively sliced form of MASP-2, known as MBL-associated protein of 19 kDa (MAp19) or small MBL-associated protein (sMAP), which lacks the catalytic activity of MASP2. (Stover, *J. Immunol.* 162:3481-90, (1999); Takahashi et al., *Int. Immunol.* 11:859-863, (1999)). MAp19 comprises the first two domains of MASP-2, followed by an extra sequence of four unique amino acids. The function of Map19 is unclear (Degn et al., *J Immunol. Methods,* 2011). The MASP-1 and MASP-2 genes are located on human chromosomes 3 and 1, respectively (Schwaeble et al., *Immunobiology* 205:455-466, (2002)).

Several lines of evidence suggest that there are different MBL-MASP complexes and a large fraction of the MASPs in serum is not complexed with MBL (Thiel, et al., *J. Immunol.* 165:878-887, (2000)). Both H- and L-ficolin bind to all MASPs and activate the lectin complement pathway, as does MBL (Dahl et al., *Immunity* 15:127-35, (2001); Matsushita et al., *J. Immunol.* 168:3502-3506, (2002)). Both the lectin and classical pathways form a common C3 convertase (C4b2a) and the two pathways converge at this step.

The lectin pathway is widely thought to have a major role in host defense against infection in the naïve host. Strong evidence for the involvement of MBL in host defense comes from analysis of patients with decreased serum levels of functional MBL (Kilpatrick, *Biochim. Biophys. Acta* 1572:401-413, (2002)). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

In contrast to the classical and lectin pathways, no initiators of the alternative pathway have been found to fulfill the recognition functions that C1q and lectins perform in the other two pathways. Currently it is widely accepted that the alternative pathway spontaneously undergoes a low level of turn-over activation, which can be readily amplified on foreign or other abnormal surfaces (bacteria, yeast, virally infected cells, or damaged tissue) that lack the proper molecular elements that keep spontaneous complement activation in check.

There are four plasma proteins directly involved in the activation of the alternative pathway: C3, factors B and D, and properdin.

Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard et al., *Am. J. Pathol.* 156:1549-1556, (2000)). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan et al., *Circulation* 104:1413-1418, (2001)). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard et al., *Am. J. Pathol.* 159:1045-1054, (2001)). Other studies have implicated the classical and alternative pathways in the pathogenesis of ischemia/reperfusion injury and the role of the lectin pathway in this disease remains controversial (Riedermann, N. C., et al., *Am. J. Pathol.* 162:363-367, 2003).

A recent study has shown that MASP-1 (and possibly also MASP-3) is required to convert the alternative pathway activation enzyme Factor D from its zymogen form into its enzymatically active form (see Takahashi M. et al., *J Exp Med* 207(1):29-37 (2010)). The physiological importance of this process is underlined by the absence of alternative pathway functional activity in plasma of MASP-1/3-deficient mice. Proteolytic generation of C3b from native C3 is required for the alternative pathway to function. Since the alternative pathway C3 convertase (C3bBb) contains C3b as an essential subunit, the question regarding the origin of the first C3b via the alternative pathway has presented a puzzling problem and has stimulated considerable research.

C3 belongs to a family of proteins (along with C4 and α-2 macroglobulin) that contain a rare posttranslational modification known as a thioester bond. The thioester group is composed of a glutamine whose terminal carbonyl group forms a covalent thioester linkage with the sulfhydryl group of a cysteine three amino acids away. This bond is unstable and the electrophilic glutamyl-thioester can react with nucleophilic moieties such as hydroxyl or amino groups and thus form a covalent bond with other molecules. The thioester bond is reasonably stable when sequestered within a hydrophobic pocket of intact C3. However, proteolytic cleavage of C3 to C3a and C3b results in exposure of the highly reactive thioester bond on C3b and, following nucleophilic attack by adjacent moieties comprising hydroxyl or amino groups, C3b becomes covalently linked to a target. In addition to its well-documented role in covalent attachment of C3b to complement targets, the C3 thioester is also thought to have a pivotal role in triggering the alternative pathway. According to the widely accepted "tick-over theory", the alternative pathway is initiated by the generation of a fluid-phase convertase, iC3Bb, which is formed from C3 with hydrolyzed thioester (iC3; $C3(H_2O)$) and factor B (Lachmann, P. J., et al., *Springer Semin. Immunopathol.* 7:143-162, (1984)). The C3b-like $C3(H_2O)$ is generated from native C3 by a slow spontaneous hydrolysis of the internal thioester in the protein (Pangburn, M. K., et al., *J. Exp. Med.* 154:856-867, 1981). Through the activity of the $C3(H_2O)$Bb convertase, C3b molecules are deposited on the target surface thereby initiating the alternative pathway.

Very little is known about the initiators of activation of the alternative pathway. Activators are thought to include yeast cell walls (zymosan), many pure polysaccharides, rabbit erythrocytes, certain immunoglobulins, viruses, fungi, bacteria, animal tumor cells, parasites, and damaged cells. The only feature common to these activators is the presence of carbohydrate, but the complexity and variety of carbohydrate structures has made it difficult to establish the shared molecular determinants which are recognized. It has been widely accepted that alternative pathway activation is controlled through the fine balance between inhibitory regulatory components of this pathway, such as Factor H, Factor I, DAF, and CR1, and properdin, which is the only positive regulator of the alternative pathway (see Schwaeble W. J. and Reid K. B., *Immunol Today* 20(1):17-21 (1999)).

In addition to the apparently unregulated activation mechanism described above, the alternative pathway can also provide a powerful amplification loop for the lectin/classical pathway C3 convertase (C4b2a) since any C3b generated can participate with factor B in forming additional alternative pathway C3 convertase (C3bBb). The alternative pathway C3 convertase is stabilized by the binding of properdin. Properdin extends the alternative pathway C3 convertase half-life six to ten fold. Addition of C3b to the alternative pathway C3 convertase leads to the formation of the alternative pathway C5 convertase.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites, and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

In addition to its essential role in immune defense, the complement system contributes to tissue damage in many clinical conditions. Thus, there is a pressing need to develop therapeutically effective complement inhibitors to prevent these adverse effects.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a method of inhibiting the adverse effects of MASP-2-dependent complement activation in a living subject. The method includes the step of administering to a subject in need thereof, an amount of a MASP-2 inhibitory agent effective to inhibit MASP-2-dependent complement activation. In another aspect of the invention, the MASP-2 inhibitory agent inhibits complement activation via the lectin-dependent MASP-2 system without substantially inhibiting complement activation via the classical or C1q-dependent system, such that the C1q-dependent system remains functional.

In some embodiments of these aspects of the invention, the MASP-2 inhibitory agent is an anti-MASP-2 antibody or fragment thereof. In further embodiments, the anti-MASP-2 antibody has reduced effector function. In some embodiments, the MASP-2 inhibitory agent is a MASP-2 inhibitory peptide or a non-peptide MASP-2 inhibitor.

In another aspect, the present invention provides compositions for inhibiting the adverse effects of MASP-2-dependent complement activation, comprising a therapeutically effective amount of a MASP-2 inhibitory agent and a pharmaceutically acceptable carrier. Methods are also provided for manufacturing a medicament for use in inhibiting the adverse effects of MASP-2-dependent complement activation in living subjects in need thereof, comprising a therapeutically effective amount of a MASP-2 inhibitory agent in a pharmaceutical carrier. Methods are also provided for manufacturing medicaments for use in inhibiting MASP-2-dependent complement activation for treatment of each of the conditions, diseases and disorders described herein below.

The methods, compositions and medicaments of the invention are useful for inhibiting the adverse effects of MASP-2-dependent complement activation in vivo in mammalian subjects, including humans suffering from an acute or chronic pathological condition or injury as further described herein.

In another aspect of the invention, methods are provided for inhibiting MASP-2-dependent complement activation in a subject suffering from paroxysmal nocturnal hemoglobinuria, comprising administering to the subject a composition comprising an amount of a MASP-2 inhibitory agent effective to inhibit MASP-2 dependent complement activation.

In another aspect, the invention provides a method of inhibiting MASP-2-dependent complement activation in a subject suffering from or at risk for developing non-Factor H-dependent atypical hemolytic uremic syndrome (aHUS), comprising administering to the subject a composition comprising an amount of a MASP-2 inhibitory agent effective to inhibit MASP-2 dependent complement activation.

In another aspect, the invention provides a method for reducing the likelihood that a subject at risk for developing atypical hemolytic uremic syndrome (aHUS) will suffer clinical symptoms associated with aHUS comprising: (a) determining the presence of a genetic marker in the subject known to be associated with aHUS; (b) periodically monitoring the subject to determine the presence or absence of at least one symptom selected from the group consisting of anemia, thrombocytopenia, renal insufficiency and rising creatinine; and (c) administering to the subject a composition comprising an amount of a MASP-2 inhibitory agent effective to inhibit MASP-2-dependent complement activation upon the determination of the presence of at least one of anemia, thrombocytopenia, renal insufficiency or rising creatinine, wherein the composition is administered in an effective amount and for a sufficient time period to improve said one or more symptoms.

In another aspect, the invention provides a method of inhibiting MASP-2-dependent complement activation in a subject suffering from, or at risk for developing, atypical hemolytic uremic syndrome (aHUS) secondary to an infection, comprising administering to the subject a composition comprising an amount of a MASP-2 inhibitory agent effective to inhibit MASP-2 complement activation.

In another aspect, the invention provides a method of treating a subject suffering from atypical hemolytic uremic syndrome (aHUS) comprising administering to the subject a composition comprising an amount of a MASP-2 inhibitory agent effective to inhibit MASP-2 dependent complement activation, wherein the administration of the MASP-2 inhibitory agent is administered via an intravenous catheter or other catheter delivery method.

In another aspect, the invention provides a method for decreasing the likelihood of developing impaired renal function in a subject at risk for developing hemolytic uremic syndrome (HUS) comprising administering to the subject a composition comprising an amount of a MASP-2 inhibitory agent effective to inhibit MASP-2 dependent complement activation.

In another aspect, the invention provides a method of treating a subject suffering from hemolytic uremic syndrome (HUS) comprising administering to the subject a composition comprising an amount of a MASP-2 inhibitory agent effective to inhibit MASP-2-dependent complement activation, wherein the administration of the MASP-2 inhibitory agent is administered to the subject via an intravenous catheter or other catheter delivery method.

In another aspect, the invention provides a method of treating a subject suffering from thrombotic thrombocytopenic purpura (TTP), or exhibiting symptoms consistent with a diagnosis of TTP, comprising administering to the subject a composition comprising an amount of a MASP-2 inhibitory agent effective to inhibit MASP-2-dependent complement activation, wherein the administration of the MASP-2 inhibitory agent is administered to the subject via an intravenous catheter or other catheter delivery method.

In another aspect, the invention provides a method of treating a subject suffering from refractory thrombotic thrombocytopenic purpura (TTP) comprising administering to the subject a composition comprising an amount of a MASP-2 inhibitory agent effective to inhibit MASP-2 dependent complement activation.

In another aspect of the invention, methods are provided for inhibiting MASP-2-dependent complement activation in a subject suffering from cryoglobulinemia, comprising administering to the subject a composition comprising an amount of a MASP-2 inhibitory agent effective to inhibit MASP-2 dependent complement activation.

In another aspect of the invention, methods are provided for inhibiting MASP-2-dependent complement activation in a subject suffering from cold agglutinin disease, comprising administering to the subject a composition comprising an amount of a MASP-2 inhibitory agent effective to inhibit MASP-2 dependent complement activation.

In another aspect of the invention, methods are provided for inhibiting MASP-2 dependent complement activation in a subject suffering from glaucoma, comprising administering to the subject a composition comprising an amount of a MASP-2 inhibitory agent effective to inhibit MASP-2 dependent complement activation.

In another aspect of the invention, methods are provided for inhibiting MASP-2 dependent complement activation in a subject at risk for developing or suffering from acute radiation syndrome comprising administering to the subject a composition comprising an amount of a MASP-2 inhibitory agent effective to inhibit MASP-2 dependent complement activation. In some embodiments, the anti-MASP-2 inhibitory agent is an anti-MASP-2 antibody. In some embodiments, the MASP-2 inhibitory agent is administered prophylactically to the subject prior to radiation exposure (such as prior to treatment with radiation, or prior to an expected exposure to radiation). In some embodiments, the MASP-2 inhibitory agent is administered within 24 to 48 hours after exposure to radiation. In some embodiments, the MASP-2 inhibitory agent is administered prior to and/or after exposure to radiation in an amount sufficient to ameliorate one or more symptoms associated with acute radiation syndrome.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is a schematic diagram illustrating the domain structure of human MASP-2 protein;

FIG. 2B is a schematic diagram illustrating the domain structure of human MAp19 protein;

DESCRIPTION OF THE SEQUENCE LISTING

Figure 1:
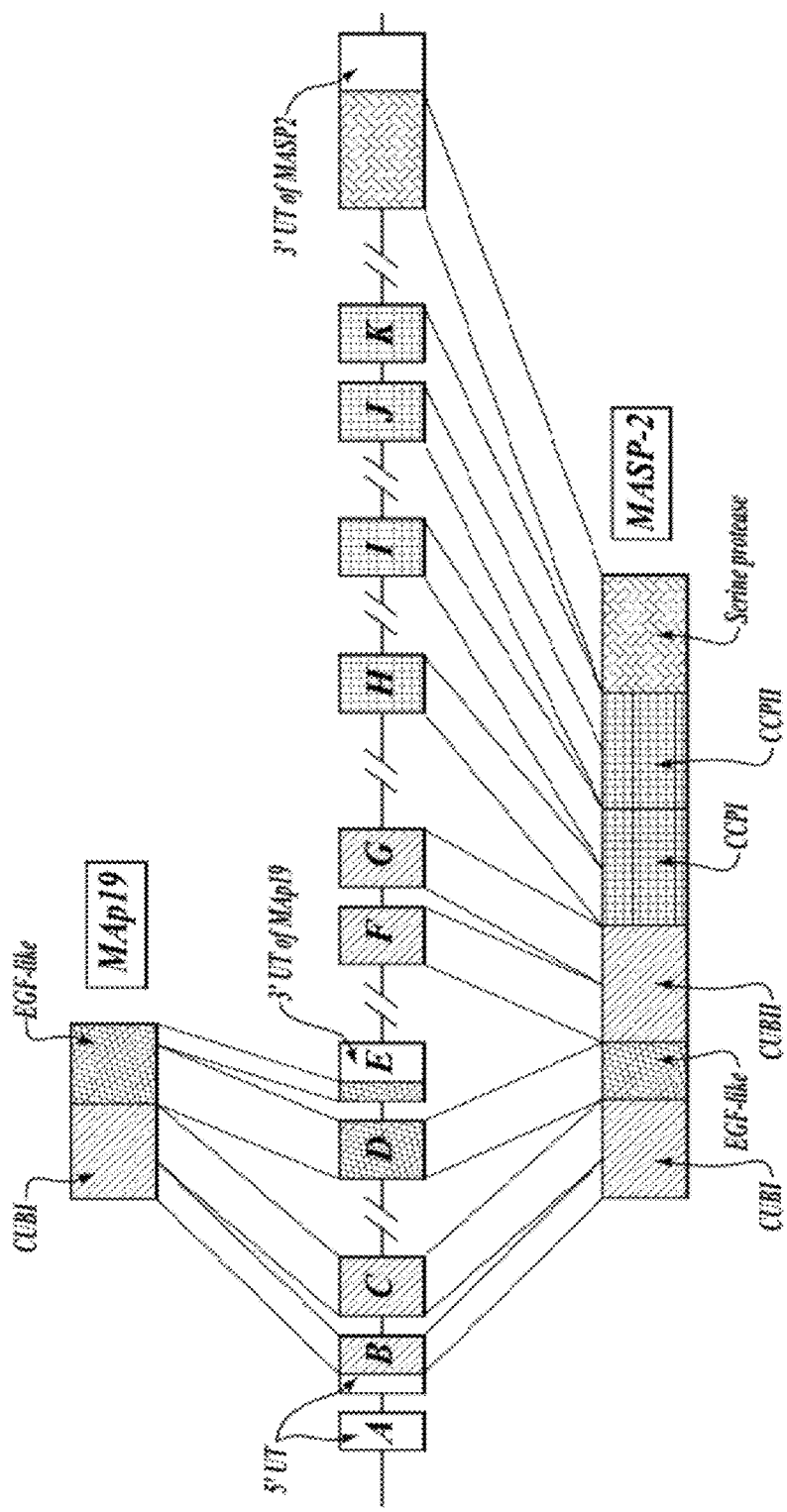
FIG. 1 is a diagram illustrating the genomic structure of human MASP-2.

SEQ ID NO:1 human MAp19 cDNA
SEQ ID NO:2 human MAp19 protein (with leader)
SEQ ID NO:3 human MAp19 protein (mature)
SEQ ID NO:4 human MASP-2 cDNA
SEQ ID NO:5 human MASP-2 protein (with leader)
SEQ ID NO:6 human MASP-2 protein (mature)
SEQ ID NO:7 human MASP-2 gDNA (exons 1-6)
Antigens: (In Reference to the MASP-2 Mature Protein)
 SEQ ID NO:8 CUBI sequence (aa 1-121)
 SEQ ID NO:9 CUBEGF sequence (aa 1-166)
 SEQ ID NO:10 CUBEGFCUBII (aa 1-293)
 SEQ ID NO:11 EGF region (aa 122-166)
 SEQ ID NO:12 serine protease domain (aa 429-671)
 SEQ ID NO:13 serine protease domain inactive (aa 610-625 with Ser618 to Ala mutation)
 SEQ ID NO:14 TPLGPKWPEPVFGRL (CUBI peptide)
 SEQ ID NO:15 TAPPGYRLRLYFTHFDLELSHLCEYD-FVKLSSGAKVLATLCGQ (CUBI peptide)
 SEQ ID NO:16 TFRSDYSN (MBL binding region core)
 SEQ ID NO:17 FYSLGSSLDITFRSDYSNEKPFTGF (MBL binding region)
 SEQ ID NO:18 IDECQVAPG (EGF PEPTIDE)
 SEQ ID NO:19 ANMLCAGLESGGKDSCRGDSG-GALV (serine protease binding core) Detailed Description
Peptide Inhibitors:
 SEQ ID NO:20 MBL full length cDNA
 SEQ ID NO:21 MBL full length protein
 SEQ ID NO:22 OGK-X-GP (consensus binding)
 SEQ ID NO:23 OGKLG
 SEQ ID NO:24 GLR GLQ GPO GKL GPO G
 SEQ ID NO:25 GPO GPO GLR GLQ GPO GKL GPO GPO GPO
 SEQ ID NO:26 GKDGRDGTKGEKGEPGQGLRGLQG-POGKLGPOG
 SEQ ID NO:27 GAOGSOGEKGAOGPQGPOGPOGK-MGPKGEOGDO (human h-ficolin)
 SEQ ID NO:28 GCOGLOGAOGDKGEAGTNGKRGERGPOG-POGKAGPOGPNGAOGEO (human ficolin p35)
 SEQ ID NO:29 LQRALEILPNRVTIKANRPFLVFI (C4 cleavage site)
Expression Inhibitors:
 SEQ ID NO:30 cDNA of CUBI-EGF domain (nucleotides 22-680 of SEQ ID NO:4)
 SEQ ID NO:31
  5' CGGGCACACCATGAGGCTGCTGACCCTC-CTGGGC 3' Nucleotides 12-45 of SEQ ID NO:4 including the MASP-2 translation start site (sense)
 SEQ ID NO:32
  5'GACATTACCTTCCGCTCCGACTCCAAC-GAGAAG3' Nucleotides 361-396 of SEQ ID NO:4 encoding a region comprising the MASP-2 MBL binding site (sense)
 SEQ ID NO:33
  5'AGCAGCCCTGAATACCCACGGCCGTATC-CAAAA3' Nucleotides 610-642 of SEQ ID NO:4 encoding a region comprising the CUBII domain
Cloning Primers:
 SEQ ID NO:34 CGGGATCCATGAGGCTGCTGAC-CCTC (5' PCR for CUB)
 SEQ ID NO:35 GGAATTCCTAGGCTGCATA (3' PCR FOR CUB)
 SEQ ID NO:36 GGAATTCCTACAGGGCGCT (3' PCR FOR CUBIEGF)
 SEQ ID NO:37 GGAATTCCTAGTAGTGGAT (3' PCR FOR CUBIEGFCUBII)
 SEQ ID NOS:38-47 are cloning primers for humanized antibody
 SEQ ID NO:48 is 9 aa peptide bond
Expression Vector:
 SEQ ID NO:49 is the MASP-2 minigene insert
 SEQ ID NO: 50 is the murine MASP-2 cDNA
 SEQ ID NO: 51 is the murine MASP-2 protein (w/leader)
 SEQ ID NO: 52 is the mature murine MASP-2 protein
 SEQ ID NO: 53 the rat MASP-2 cDNA
 SEQ ID NO: 54 is the rat MASP-2 protein (w/leader)
 SEQ ID NO: 55 is the mature rat MASP-2 protein
 SEQ ID NO: 56-59 are the oligonucleotides for site-directed mutagenesis of human MASP-2 used to generate human MASP-2A
 SEQ ID NO: 60-63 are the oligonucleotides for site-directed mutagenesis of murine MASP-2 used to generate murine MASA-2A
 SEQ ID NO: 64-65 are the oligonucleotides for site-directed mutagenesis of rat MASP-2 used to generate rat MASP-2A

DETAILED DESCRIPTION

The present invention is based upon the surprising discovery by the present inventors that it is possible to inhibit the lectin mediated MASP-2 pathway while leaving the classical pathway intact. The present invention also describes the use of MASP-2 as a therapeutic target for inhibiting cellular injury associated with lectin-mediated complement pathway activation while leaving the classical (C1q-dependent) pathway component of the immune system intact.

I. DEFINITIONS

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "MASP-2-dependent complement activation" comprises MASP-2-dependent activation of the lectin pathway, which occurs under physiological conditions (i.e., in the presence of $Ca^{++}$) leading to the formation of the lectin pathway C3 convertase C4b2a and upon accumulation of the C3 cleavage product C3b subsequently to the C5 convertase C4b2a(C3b)n, which has been determined to primarily cause opsonization.

As used herein, the term "alternative pathway" refers to complement activation that is triggered, for example, by zymosan from fungal and yeast cell walls, lipopolysaccharide (LPS) from Gram negative outer membranes, and rabbit erythrocytes, as well as from many pure polysaccharides, rabbit erythrocytes, viruses, bacteria, animal tumor cells, parasites and damaged cells, and which has traditionally been thought to arise from spontaneous proteolytic generation of C3b from complement factor C3.

As used herein, the term "lectin pathway" refers to complement activation that occurs via the specific binding of serum and non-serum carbohydrate-binding proteins including mannan-binding lectin (MBL), CL-11 and the ficolins (H-ficolin, M-ficolin, or L-ficolin).

As used herein, the term "classical pathway" refers to complement activation that is triggered by antibody bound to a foreign particle and requires binding of the recognition molecule C1q.

As used herein, the term "MASP-2 inhibitory agent" refers to any agent that binds to or directly interacts with MASP-2 and effectively inhibits MASP-2-dependent complement activation, including anti-MASP-2 antibodies and MASP-2 binding fragments thereof, natural and synthetic peptides, small molecules, soluble MASP-2 receptors, expression inhibitors and isolated natural inhibitors, and also encompasses peptides that compete with MASP-2 for binding to another recognition molecule (e.g., MBL, M-ficolin, or L-ficolin) in the lectin pathway, but does not encompass antibodies that bind to such other recognition molecules. MASP-2 inhibitory agents useful in the method of the invention may reduce MASP-2-dependent complement activation by greater than 20%, such as greater than 50%, such as greater than 90%. In one embodiment, the MASP-2 inhibitory agent reduces MASP-2-dependent complement activation by greater than 90% (i.e., resulting in MASP-2 complement activation of only % or less).

As used herein, the term "antibody" encompasses antibodies and antibody fragments thereof, derived from any antibody-producing mammal (e.g., mouse, rat, rabbit, and primate including human), or from a hybridoma, phage selection, recombinant expression or transgenic animals (or other methods of producing antibodies or antibody fragments"), that specifically bind to a target polypeptide, such as, for example, MASP-2, polypeptides or portions thereof. It is not intended that the term "antibody" limited as regards to the source of the antibody or the manner in which it is made (e.g., by hybridoma, phage selection, recombinant expression, transgenic animal, peptide synthesis, etc). Exemplary antibodies include polyclonal, monoclonal and recombinant antibodies; pan-specific, multispecific antibodies (e.g., bispecific antibodies, trispecific antibodies); humanized antibodies; murine antibodies; chimeric, mouse-human, mouse-primate, primate-human monoclonal antibodies; and anti-idiotype antibodies, and may be any intact antibody or fragment thereof. As used herein, the term "antibody" encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity.

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific for the target antigen. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

As used herein, the term "antibody fragment" refers to a portion derived from or related to a full-length antibody, such as, for example, an anti-MASP-2 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "mannan-binding lectin" ("MBL") is equivalent to mannan-binding protein ("MBP").

As used herein, the "membrane attack complex" ("MAC") refers to a complex of the terminal five complement components (C5b combined with C6, C7, C8 and C-9) that inserts into and disrupts membranes (also referred to as C5b-9).

As used herein, "a subject" includes all mammals, including without limitation humans, non-human primates, dogs, cats, horses, sheep, goats, cows, rabbits, pigs and rodents.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "oligonucleotide" as used herein refers to an oligomer or polymer of ribonucleic acid (RNA) or deoxyribonucleic acid (DNA) or mimetics thereof. This term also covers those oligonucleobases composed of naturally-occurring nucleotides, sugars and covalent internucleoside (backbone) linkages as well as oligonucleotides having non-naturally-occurring modifications.

As used herein, an "epitope" refers to the site on a protein (e.g., a human MASP-2 protein) that is bound by an antibody. "Overlapping epitopes" include at least one (e.g., two, three, four, five, or six) common amino acid residue(s), including linear and non-linear epitopes.

As used herein, the terms "polypeptide," "peptide," and "protein" are used interchangeably and mean any peptide-linked chain of amino acids, regardless of length or post-translational modification. The MASP-2 protein described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments, the human MASP-2 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human MASP-2 protein having the amino acid sequence set forth in SEQ ID NO: 5.

In some embodiments, peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120; 130, 140, 150, 160, 170, 180, 190, 200, 250, 300, 350, 400, 450, 500, or 600 or more) amino acid residues in length (e.g., at least 6 contiguous amino acid residues of SEQ ID NO: 5). In some embodiments, an antigenic peptide fragment of a human MASP-2 protein is fewer than 500 (e.g., fewer than 450, 400, 350, 325, 300, 275, 250, 225, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6) amino acid residues in length (e.g., fewer than 500 contiguous amino acid residues in any one of SEQ ID NOS: 5).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent, sequence identity can be achieved in various ways that are within the skill in the art, for instance, using publicly available computer software such as BLAST, BLAST-2, ALIGN, ALIGN-2 or Megalign (DNAS-TAR) software. Appropriate parameters for measuring alignment, including any algorithms needed to achieve maximal alignment over the full-length of the sequences being compared can be determined by known methods.

II. OVERVIEW OF THE INVENTION

Lectins (MBL, M-ficolin, H-ficolin, L-ficolin and CL-11) are the specific recognition molecules that trigger the innate complement system and the system includes the lectin initiation pathway and the associated terminal pathway amplification loop that amplifies lectin-initiated activation of terminal complement effector molecules. C1q is the specific recognition molecule that triggers the acquired complement system and the system includes the classical initiation pathway and associated terminal pathway amplification loop that amplifies C1q-initiated activation of terminal complement effector molecules. We refer to these two major complement activation systems as the lectin-dependent complement system and the C1q-dependent complement system, respectively.

In addition to its essential role in immune defense, the complement system contributes to tissue damage in many clinical conditions. Thus, there is a pressing need to develop therapeutically effective complement inhibitors to prevent these adverse effects. With the recognition that it is possible to inhibit the lectin mediated MASP-2 pathway while leaving the classical pathway intact comes the realization that it would be highly desirable to specifically inhibit only the complement activation system causing a particular pathology without completely shutting down the immune defense capabilities of complement. For example, in disease states in which complement activation is mediated predominantly by the lectin-dependent complement system, it would be advantageous to specifically inhibit only this system. This would leave the C1q-dependent complement activation system intact to handle immune complex processing and to aid in host defense, against infection.

The preferred protein component to target in the development of therapeutic agents to specifically inhibit the lectin-dependent complement system is MASP-2. Of all the known protein components of the lectin-dependent complement system (MBL, H-ficolin, M-ficolin, L-ficolin, MASP-2, C2-C9, Factor B, Factor D), and properdin), only MASP-2 is both unique to the lectin-dependent complement system and required for the system to function. The lectins (MBL, H-ficolin, M-ficolin, L-ficolin and CL-11) are also unique components in the lectin-dependent complement system. However, loss of any one of the lectin components would not necessarily inhibit activation of the system due to lectin redundancy. It would be necessary to inhibit all five lectins in order to guarantee inhibition of the lectin-dependent complement activation system. Furthermore, since MBL and the ficolins are also known to have opsonic activity independent of complement, inhibition of lectin function would result in the loss of this beneficial host defense mechanism against infection. In contrast, this complement-independent lectin opsonic activity would remain intact if MASP-2 was the inhibitory target. An added benefit of MASP-2 as the therapeutic target to inhibit the lectin-dependent complement activation system is that the plasma concentration of MASP-2 is among the lowest of any complement protein (≈500 ng/ml); therefore, correspondingly low concentrations of high-affinity inhibitors of MASP-2 may be sufficient to obtain full inhibition (Moller-Kristensen, M., et al., *J. Immunol. Methods* 282:159-167, 2003).

III. ROLE OF MASP-2 IN VARIOUS DISEASES AND CONDITIONS AND THERAPEUTIC METHODS USING MASP-2 INHIBITORY AGENTS

Renal Conditions

Activation of the complement system has been implicated in the pathogenesis of a wide variety of renal diseases; including, mesangioproliferative glomerulonephritis (IgA-nephropathy, Berger's disease) (Endo, M., et al., *Clin. Nephrology* 55:185-191, 2001), membranous glomerulonephritis (Kerjashki, D., *Arch B Cell Pathol.* 58:253-71, 1990; Brenchley, P. E., et al., *Kidney Int.*, 41:933-7, 1992; Salant, D. J., et al., *Kidney Int.* 35:976-84, 1989), membranoproliferative glomerulonephritis (mesangiocapillary glomerulonephritis) (Bartlow, B. G., et al., *Kidney Int.* 15:294-300, 1979; Meri, S., et al., *J. Exp. Med.* 175:939-50, 1992), acute postinfectious glomerulonephritis (poststreptococcal glomerulonephritis), cryoglobulinemic glomerulonephritis (Ohsawa, I., et al., *Clin Immunol.* 101:59-66, 2001), lupus nephritis (Gatenby, P. A., *Autoimmunity* 11:61-6, 1991), and Henoch-Schonlein purpura nephritis (Endo, M., et al., *Am. J. Kidney Dis.* 35:401-407, 2000). The involvement of complement in renal disease has been appreciated for several decades but there is still a major discussion on its exact role in the onset, the development and the resolution phase of renal disease. Under normal conditions the contribution of complement is beneficial to the host, but inappropriate activation and deposition of complement may contribute to tissue damage.

There is substantial evidence that glomerulonephritis, inflammation of the glomeruli, is often initiated by deposition of immune complexes onto glomerular or tubular structures which then triggers complement activation, inflammation and tissue damage. Kahn and Sinniah demonstrated increased deposition of C5b-9 in tubular basement membranes in biopsies taken from patients with various forms of glomerulonephritis (Kahn, T. N., et al., *Histopath.* 26:351-6, 1995). In a study of patients with IgA nephrology (Alexopoulos, A., et al., *Nephrol. Dial. Transplant* 10:1166-1172, 1995), C5b-9 deposition in the tubular epithelial/basement membrane structures correlated with plasma creatinine levels. Another study of membranous nephropathy demonstrated a relationship between clinical outcome and urinary sC5b-9 levels (Kon, S. P., et al., *Kidney Int.* 48:1953-58, 1995). Elevated sC5b-9 levels were correlated positively with poor prognosis. Lehto et al., measured elevated levels of CD59, a complement regulatory factor that inhibits the membrane attack complex in plasma membranes, as well as C5b-9 in urine from patients with membranous glomerulonephritis (Lehto, T., et al., *Kidney Int.* 47:1403-11, 1995). Histopathological analysis of biopsy samples taken from these same patients demonstrated deposition of C3 and C9 proteins in the glomeruli, whereas expression of CD59 in these tissues was diminished compared to that of normal kidney tissue. These various studies suggest that ongoing complement-mediated glomerulonephritis results in urinary excretion of complement proteins that correlate with the degree of tissue damage and disease prognosis.

Inhibition of complement activation in various animal models of glomerulonephritis has also demonstrated the importance of complement activation in the etiology of the disease. In a model of membranoproliferative glomerulonephritis (MPGN), infusion of anti-Thy1 antiserum in C6-deficient rats (that cannot form C5b-9) resulted in 90% less glomerular cellular proliferation, 80% reduction in platelet and macrophage infiltration, diminished collagen type IV synthesis (a marker for mesangial matrix expansion), and 50% less proteinuria than in C6+ normal rats (Brandt, J., et al., *Kidney Int.* 49:335-343, 1996). These results implicate C5b-9 as a major mediator of tissue damage by complement in this rat anti-thymocyte serum model. In another model of glomerulonephritis, infusion of graded dosages of rabbit anti-rat glomerular basement membrane produced a dose-dependent influx of polymorphonuclear leukocytes (PMN) that was attenuated by prior treatment with cobra venom factor (to consume complement) (Scandrett, A. L., et al., *Am. J. Physiol.* 268:F256-F265, 1995). Cobra venom factor-treated rats also showed diminished histopathology, decreased long-term proteinuria, and lower creatinine levels than control rats. Employing three models of GN in rats (anti-thymocyte serum, Con A anti-Con A, and passive Heymann nephritis), Couser et al., demonstrated the potential therapeutic efficacy of approaches to inhibit complement by using the recombinant sCR1 protein (Couser, W. G., et al., *J. Am. Soc. Nephrol.* 5:1888-94, 1995). Rats treated with sCR1 showed significantly diminished PMN, platelet and macrophage influx, decreased mesangiolysis, and proteinuria versus control rats. Further evidence for the importance of complement activation in glomerulonephritis has been provided by the use of an anti-C5 MoAb in the NZB/W F1 mouse model. The anti-C5 MoAb inhibits cleavage of C5, thus blocking generation of C5a and C5b-9. Continuous therapy with anti-C5 MoAb for 6 months resulted in significant amelioration of the course of glomerulonephritis. A humanized anti-C5 MoAb monoclonal antibody (5G1.1) that prevents the cleavage of human complement component C5 into its pro-inflammatory components is under development by Alexion Pharmaceuticals, Inc., New Haven, Conn., as a potential treatment for glomerulonephritis.

Direct evidence for a pathological role of complement in renal injury is provided by studies of patients with genetic deficiencies in specific complement components. A number of reports have documented an association of renal disease with deficiencies of complement regulatory, factor H (Ault, B. H., *Nephrol.* 14:1045-1053, 2000; Levy, M., et al., *Kidney Int.* 30:949-56, 1986; Pickering, M. C., et al., *Nat. Genet.* 31:424-8, 2002). Factor H deficiency results in low plasma levels of factor B and C3 and in consumption of C5b-9. Both atypical membranoproliferative glomerulonephritis (MPGN) and idiopathic hemolytic uremic syndrome (HUS) are associated with factor H deficiency. Factor H deficient pigs (Jansen, J. H., et al., *Kidney Int.* 53:331-49, 1998) and factor H knockout mice (Pickering, M. C., 2002) display MPGN-like symptoms, confirming the importance of factor in complement regulation. Deficiencies of other complement components are associated with renal disease, secondary to the development of systemic lupus erythematosus (SLE) (Walport, M. J., Davies, et al., *Ann. N.Y. Acad. Sci.* 815:267-81, 1997). Deficiency for C1q, C4 and C2 predispose strongly to the development of SLE via mechanisms relating to defective clearance of immune complexes and apoptotic material. In many of these SLE patients lupus nephritis occurs, characterized by the deposition of immune complexes throughout the glomerulus.

Further evidence linking complement activation and renal disease has been provided by the identification in patients of autoantibodies directed against complement components, some of which have been directly related to renal disease (Trouw, L. A., et al., *Mol. Immunol.* 38:199-206, 2001). A number of these autoantibodies show such a high degree of correlation with renal disease that the term nephritic factor (NeF) was introduced to indicate this activity. In clinical studies, about 50% of the patients positive for nephritic factors developed MPGN (Spitzer, R. E., et al., *Clin. Immunol. Immunopathol.* 64:177-83, 1992). C3NeF is an autoantibody directed against the alternative pathway C3 convertase (C3bBb) and it stabilizes this convertase, thereby promoting alternative pathway activation (Daha, M. R., et al., *J. Immunol.* 116:1-7, 1976). Likewise, autoantibody with a specificity for the classical pathway C3 convertase (C4b2a), called C4NeF, stabilizes this convertase and thereby promotes classical pathway activation (Daha, M. R. et al., *J. Immunol.* 125:2051-2054, 1980; Halbwachs, L., et al., *J. Clin. Invest.* 65:1249-56, 1980). Anti-C1q autoantibodies have been described to be related to nephritis in SLE patients (Hovath, L., et al., *Clin. Exp. Rheumatol.* 19:667-72, 2001; Siegert, C., et al., *J. Rheumatol.* 18:230-34, 1991; Siegert, C., et al., *Clin. Exp. Rheumatol.* 10:19-23, 1992), and a rise in the titer of these anti-C1q autoantibodies was reported to predict a flare of nephritis (Coremans, I. E., et al., *Am. J. Kidney Dis.* 26:595-601, 1995). Immune deposits eluted from postmortem kidneys of SLE patients revealed the accumulation of these anti-C1q autoantibodies (Mannick, M., et al., *Arthritis Rheumatol.* 40:1504-11, 1997). All these facts point to a pathological role for these autoantibodies. However, not all patients with anti-C1q autoantibodies develop renal disease and also some healthy individuals have low titer anti-C1q autoantibodies (Siegert, C. E., et al., *Clin. Immunol. Immunopathol.* 67:204-9, 1993).

In addition to the alternative and classical pathways of complement activation, the lectin pathway may also have an important pathological role in renal disease. Elevated levels of MBL, MBL-associated serine protease and complement activation products have been detected by immunohistochemical techniques on renal biopsy material obtained from patients diagnosed with several different renal diseases, including Henoch-Schonlein purpura nephritis (Endo, M., et al., *Am. J. Kidney Dis.* 35:401-407, 2000), cryoglobulinemic glomerulonephritis (Ohsawa, I., et al., *Clin. Immunol.* 101:59-66, 2001) and IgA neuropathy (Endo, M., et al., *Clin. Nephrology* 55:185-191, 2001). Therefore, despite the fact that an association between complement and renal diseases has been known for several decades, data on how complement exactly influences these renal diseases is far from complete.

One aspect of the invention is thus directed to the treatment of renal conditions including but not limited to mesangioproliferative glomerulonephritis, membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, Henoch-Schonlein purpura nephritis or IgA nephropathy, by administering a composition comprising a therapeutically effective amount of a MASP-2 inhibitory agent in a pharmaceutical carrier to a subject suffering from such a disorder. The MASP-2 inhibitory agent may be administered to the subject systemically, such as by intra-arterial, intravenous, intramuscular, subcutaneous or other parenteral administration, or potentially by oral administration for non-peptidergic agents. The MASP-2 inhibitory agent may be administered periodically over an extended period of time for treatment or control of a chronic condition, or may be by single or repeated administration in the period before, during or following acute trauma or injury.

Blood Disorders

Sepsis is caused by an overwhelming reaction of the patient to invading microorganisms. A major function of the complement system is to orchestrate the inflammatory response to invading bacteria and other pathogens. Consistent with this physiological role, complement activation has been shown in numerous studies to have a major role in the pathogenesis of sepsis (Bone, R. C., *Annals. Internal. Med.* 115:457-469, 1991). The definition of the clinical manifestations of sepsis is ever evolving. Sepsis is usually defined as the systemic host response to an infection. However, on many occasions, no clinical evidence for infection (e.g., positive bacterial blood cultures) is found in patients with septic symptoms. This discrepancy was first taken into account at a Consensus Conference in 1992 when the term "systemic inflammatory response syndrome" (SIRS) was established, and for which no definable presence of bacterial infection was required (Bone, R. C., et al., *Crit. Care Med* 20:724-726, 1992). There is now general agreement that sepsis and SIRS are accompanied by the inability to regulate the inflammatory response. For the purposes of this brief review, we will consider the clinical definition of sepsis to also include severe sepsis, septic shock, and SIRS.

The predominant source of infection in septic patients before the late 1980s was Gram-negative bacteria. Lipopolysaccharide (LPS), the main component of the Gram-negative bacterial cell wall, was known to stimulate release of inflammatory mediators from various cell types and induce acute infectious symptoms when injected into animals (Haeney, M. R., et al., *Antimicrobial Chemotherapy* 41(Suppl. A):41-6, 1998). Interestingly, the spectrum of responsible microorganisms appears to have shifted from predominantly Gram-negative bacteria in the late 1970s and 1980s to predominantly Gram-positive bacteria at present, for reasons that are currently unclear (Martin, G. S., et al., *N. Eng. J. Med.* 348:1546-54, 2003).

Many studies have shown the importance of complement activation in mediating inflammation and contributing to the features of shock, particularly septic and hemorrhagic shock. Both Gram-negative and Gram-positive organisms commonly precipitate septic shock. LPS is a potent activator of complement, predominantly via the alternative pathway, although classical pathway activation mediated by antibodies also occurs (Fearon, D. T., et al., *N. Engl. J. Med.* 292:937-400, 1975). The major components of the Gram-positive cell wall are peptidoglycan and lipoteichoic acid, and both components are potent activators of the alternative complement pathway, although in the presence of specific antibodies they can also activate the classical complement pathway (Joiner, K. A., et al., *Ann. Rev. Immunol.* 2:461-2, 1984).

The complement system was initially implicated in the pathogenesis of sepsis when it was noted by researchers that anaphylatoxins C3a and C5a mediate a variety of inflammatory reactions that might also occur during sepsis. These anaphylatoxins evoke vasodilation and an increase in microvascular permeability, events that play a central role in septic shock (Schumacher, W. A., et al., *Agents Actions* 34:345-349, 1991). In addition, the anaphylatoxins induce bronchospasm, histamine release from mast cells, and aggregation of platelets. Moreover, they exert numerous effects on granulocytes, such as chemotaxis, aggregation, adhesion, release of lysosomal enzymes, generation of toxic super oxide anion and formation of leukotrienes (Shin, U. S., et al., *Science* 162:361-363, 1968; Vogt, W., *Complement* 3:177-86, 1986). These biologic effects are thought to play a role in development of complications of sepsis such as shock or acute respiratory distress syndrome (ARDS) (Hammerschmidt, D. E., et al., *Lancet* 1:947-949, 1980; Slotman, G. T., et al., *Surgery* 99:744-50, 1986). Furthermore, elevated levels of the anaphylatoxin C3a is associated with a fatal outcome in sepsis (Hack, C. E., et al., *Am. J. Med.* 86:20-26, 1989). In some animal models of shock, certain complement-deficient strains (e.g., C5-deficient ones) are more resistant to the effects of LPS infusions (Hseuh, W., et al., *Immunol.* 70:309-14, 1990).

Blockade of C5a generation with antibodies during the onset of sepsis in rodents has been shown to greatly improve survival (Czermak, B. J., et al., *Nat. Med.* 5:788-792, 1999). Similar findings were made when the C5a receptor (C5aR) was blocked, either with antibodies or with a small molecular inhibitor (Huber-Lang, M. S., et al., *FASEB J.* 16:1567-74, 2002; Riedemann, N. C., et al., *J. Clin. Invest.* 110:101-8, 2002). Earlier experimental studies in monkeys have suggested that antibody blockade of C5a attenuated *E. coli*-induced septic shock and adult respiratory distress syndrome (Hangen, D. H., et al., *J. Surg. Res.* 46:195-9, 1989; Stevens, J. H., et al., *J. Clin. Invest.* 77:1812-16, 1986). In humans with sepsis, C5a was elevated and associated with significantly reduced survival rates together with multiorgan failure, when compared with that in less severely septic patients and survivors (Nakae, H., et al., *Res. Commun. Chem. Pathol. Pharmacol.* 84:189-95, 1994; Nakae, et al., *Surg. Today* 26:225-29, 1996; Bengtson, A., et al., *Arch. Surg.* 123:645-649, 1988). The mechanisms by which C5a exerts its harmful effects during sepsis are yet to be investigated in greater detail, but recent data suggest the generation of C5a during sepsis significantly compromises innate immune functions of blood neutrophils (Huber-Lang, M. S., et al., *J. Immunol.* 169:3223-31, 2002), their ability to express a respiratory burst, and their ability to generate cytokines (Riedemann, N. C., et al, *Immunity* 19:193-202, 2003). In addition, C5a generation during sepsis appears to have procoagulant effects (Laudes, I. J., et al., *Am. J. Pathol.* 160:1867-75, 2002). The complement-modulating protein CI INH has also shown efficacy in animal models of sepsis and ARDS (Dickncite, G., *Behring Ins. Mitt.* 93:299-305, 1993).

The lectin pathway may also have a role in pathogenesis of sepsis. MBL has been shown to bind to a range of clinically important microorganisms including both Gram-negative and Gram-positive bacteria, and to activate the lectin pathway (Neth, O., et al., *Infect. Immun.* 68:688, 2000). Lipoteichoic acid (LTA) is increasingly regarded as the Gram-positive counterpart of LPS. It is a potent immunostimulant that induces cytokine release from mononuclear phagocytes and whole blood (Morath, S., et al., *J. Exp. Med.* 195:1635, 2002; Morath, S., et al., *Infect. Immun.* 70:938, 2002). Recently it was demonstrated that L-ficolin specifically binds to LTA isolated from numerous Gram-positive bacteria species, including *Staphylococcus aureus*, and activates the lectin pathway (Lynch, N. J., et al., *J. Immunol.* 172:1198-02, 2004). MBL also has been shown to bind to LTA from *Enterococcus* spp in which the polyglycerophosphate chain is substituted with glycosyl groups), but not to LTA from nine other species including *S. aureus* (Polotsky, V. Y., et al., *Infect. Immun.* 64:380, 1996).

An aspect of the invention thus provides a method for treating sepsis or a condition resulting from sepsis, by administering a composition comprising a therapeutically effective amount of a MASP-2 inhibitory agent in a pharmaceutical carrier to a subject suffering from sepsis or a condition resulting from sepsis including without limitation severe sepsis, septic shock, acute respiratory distress syndrome resulting from sepsis, and systemic inflammatory response syndrome. Related methods are provided for the treatment of other blood disorders, including hemorrhagic shock, hemolytic anemia, autoimmune thrombotic thrombocytopenic purpura (TTP), hemolytic uremic syndrome (HUS), atypical hemolytic uremic syndrome (aHUS), or other marrow/blood destructive conditions, by administering a composition comprising a therapeutically effective amount of a MASP-2 inhibitory agent in a pharmaceutical carrier to a subject suffering from such a condition. The MASP-2 inhibitory agent is administered to the subject systemically, such as by intra-arterial, intravenous, intramuscular, inhalational (particularly in the case of ARDS), subcutaneous or other parenteral administration, or potentially by oral administration for non-peptidergic agents. The MASP-2 inhibitory agent composition may be combined with one or more additional therapeutic agents to combat the sequelae of sepsis and/or shock. For advanced sepsis or shock or a distress condition resulting therefrom, the MASP-2 inhibitory composition may suitably be administered in a fast-acting dosage form, such as by intravenous or intra-arterial delivery of a bolus of a solution containing the MASP-2 inhibitory agent composition. Repeated administration may be carried out as determined by a physician until the condition has been resolved.

The Role of MASP-2 in Paroxysmal Nocturnal Hemoglobinurina and Therapeutic Methods Using MASP-2 Inhibitory Agents Overview of PNH Paroxysmal nocturnal hemoglobinuria (PNH), sometimes also referred to as Marchiafava-Micheli syndrome, is an acquired, potentially life-threatening disease of the blood. PNH may develop on its own, referred to as "primary PNH" or in the context of other bone marrow disorders such as aplastic anemia, referred to as "secondary PNH." The majority of cases are primary PNH. PNH is characterized by complement-induced destruction of red blood cells (hemolysis), low red blood cell counts (anemia), thrombosis and bone marrow failure. Laboratory findings in PNH show changes consistent with intravascular hemolytic anemia: low hemoglobin, raised lactate dehydrogenase, raised reticulocyte counts (immature red cells released by the bone marrow to replace the destroyed cells), raised bilirubin (a breakdown product of hemoglobin), in the absence of autoreactive RBC-binding antibodies as a possible cause.

The hallmark of PNH is the chronic complement-mediated hemolysis caused by the unregulated activation of terminal complement components, including the membrane attack complex, on the surface of circulating RBCs. PNH RBCs are subject to uncontrolled complement activation and hemolysis due to the absence of the complement regulators CD55 and CD59 on their surface (Lindorfer, M. A., et al., *Blood* 115 (11):2283-91 (2010), Risitano, et al., *Mini-Reviews in Medicinal Chemistry*, 11:528-535 (2011)). CD55 and CD59 are abundantly expressed on normal RBCs and control complement activation. CD55 acts as a negative regulator of the alternative pathway, inhibiting the assembly of the alternative pathway C3 convertase (C3bBb) complex and accelerating the decay of preformed convertase, thus blocking the formation of the membrane attack complex (MAC). CD59 inhibits the complement membrane attack complex directly by binding the C5b678 complex and preventing C9 from binding and polymerizing.

While hemolysis and anemia are the dominant clinical features of PNH, the disease is a complex hematologic disorder that further includes thrombosis and bone marrow failure as part of the clinical findings (Risitano et al, *Mini Reviews in Med Chem* 11:528-535 (2011)). At the molecular level, PNH is caused by the abnormal clonal expansion of hematopoietic stem cells lacking a functional PIG A gene. PIG A is an X-linked gene encoding a glycosyl-phosphatidyl inositol (GPI) transferase required for the stable surface expression of GPI-anchored class A glycoproteins, including CD55 and CD59. For reasons that are presently under investigation, hematopoietic stem cells with a dysfunctional PIG A gene that arise as the result of spontaneous somatic mutations can undergo clonal expansion to the point where their progeny constitute a significant portion of the peripheral hematopoietic cell pool. While both erythrocyte and lymphocyte progeny of the mutant stem cell clone lack CD55 and CD59, only the RBCs undergo overt lysis after they enter the circulation.

Current treatment for PNH includes blood transfusion for anemia, anticoagulation for thrombosis and the use of the monoclonal antibody eculizumab (Soliris®), which protects blood cells against immune destruction by inhibiting the complement system (Hillmen P. et al., *N. Engl. J. Med.* 350 (6):552-559 (2004)). Eculizumab (Soliris®) is a humanized monoclonal antibody that targets the complement component C5, blocking its cleavage by C5 convertases, thereby preventing the production of C5a and the assembly of the MAC. Treatment of PNH patients with eculizumab has resulted in a reduction of intravascular hemolysis, as measured by lactate dehydrogenase (LDH), leading to hemoglobin stabilization and transfusion independence in about half of the patients (Risitano et al, *Mini-Reviews in Medicinal Chemistry*, 11(6) (2011)). While nearly all patients undergoing therapy with eculizumab achieve normal or almost normal LDH levels (due to control of intravascular hemolysis), only about one third of the patients reach a hemoglobin value about 11 gr/dL, and the remaining patients on eculizumab continue to exhibit moderate to severe (i.e., transfusion-dependent) anemia, in about equal proportions (Risitano A. M. et al., *Blood* 113: 4094-100 (2009)). As described in Risitano et al., *Mini-Reviews in Medicinal Chemistry* 11:528-535 (2011), it was demonstrated that PNH patients on eculizumab contained large amounts of C3 fragments bound to their PNH erythrocytes (while untreated patients did not). This finding led to the recognition that in eculizumab-treated PNH patients, PNH RBCs that are no longer hemolyzed due to C5 blockade now can accumulate copious amounts of membrane-bound C3 fragments, which operate as opsonins, resulting in their entrapment in the reticuloendothelial cells through specific C3 receptors and subsequent extravascular hemolysis. Thus, while preventing intravascular hemolysis and the resulting sequelae, eculizumab therapy simply diverts the disposition of these RBCs from intravascular to extravascular hemolysis, resulting in substantial residual untreated anemia in many patients (Risitano A. M. et al., *Blood* 113:4094-100 (2009)). Therefore, therapeutic strategies in addition to the use of eculizumab are needed for those patients developing C3-fragment mediated extravascular hemolysis, because they continue to require red cell transfusions. Such C3 fragment targeting approaches have demonstrated utility in experimental systems (Lindorfer et al., *Blood* 115:2283-91, 2010).

Complement-Initiating Mechanisms in PNH

The causal link between defective expression of the negative complement regulators CD55 and CD59 in PNH, combined with the effectiveness of eculizumab in preventing intravascular hemolysis, clearly define PNH as a condition caused by the complement system. While this paradigm is widely accepted, the nature of the events initiating complement activation, and the complement activation pathway(s) involved remain unresolved. Because CD55 and CD59 negatively regulate the terminal amplification steps in the complement cascade common to all complement initiation pathways, deficiency of these molecules will lead to exaggerated terminal complement activation regardless of whether complement activation is initiated by the lectin pathway, by the classical pathway or by spontaneous turnover of the alternative pathway. Thus, in PNH patients, any complement activation events that lead to C3b deposition on the RBC surface can trigger subsequent amplification and pathological hemolysis (intravascular and/or extravascular) and precipitate a hemolytic crisis. A clear mechanistic understanding of the molecular events triggering hemolytic crisis in PNH patients has remained elusive. Because no complement initiating event is overtly evident in PNH patients undergoing a hemolytic crisis, the prevailing view is that complement activation in PNH may occur spontaneously owing to low level tick-over activation of the alternative pathway, which is subsequently magnified by inappropriate control of terminal complement activation due to lack of CD55 and CD59.

However, it is important to note that in its natural history, PNH usually develops or exacerbates after certain events, such as an infection or an injury (Risitano, *Biologics* 2:205-222 (2008)), which have been shown to trigger complement activation. This complement activation response is not dependent on prior immunity of the host towards the inciting pathogen, and hence likely does not involve the classical pathway. Rather, it appears that this complement activation response is initiated by lectin binding to foreign or "altered self" carbohydrate patterns expressed on the surface of microbial agents or damaged host tissue. Thus, the events precipitating hemolytic crisis in PNH are tightly linked to complement activation initiated via lectins. This makes it very likely that lectin activation pathways provide the initiating trigger that ultimately leads to hemolysis in PNH patients.

MASP-2 Inhibitors to Block Opsonization and Extravascular Hemolysis of PNH RBCs Through the Reticuloendothelial System This section describes the inhibitory effects of MASP-2 inhibitory agents on hemolysis in an in vitro model of PNH. The findings support the utility of MASP-2-blocking agents (including, but not limited to, antibodies that bind to and block the function of MASP-2) to treat subjects suffering from aspects of PNH, and also the use of inhibitors of MASP-2 to ameliorate the effects of C3-fragment-mediated extravascular hemolysis in PNH patients undergoing therapy with a C5-inhibitor such as eculizumab.

As detailed above, PNH patients become anemic owing to two distinct mechanisms of RBC clearance from circulation: intravascular hemolysis via activation of the membrane attack complex (MAC), and extravascular hemolysis following opsonization with C3b and subsequent clearance following complement receptor binding and uptake by the reticuloendothelial system. The intravascular hemolysis is largely prevented when a patient is treated with eculizumab. Because eculizumab blocks the terminal lytic effector mechanism that occurs downstream of both the complement-initiating activation event as well as the ensuing opsonization, eculizumab does not block extravascular hemolysis (Risitano A. M. et al., Blood 113:4094-100 (2009)). Instead, RBCs that would have undergone hemolysis in untreated PNH patients now can accumulate activated C3b proteins on their surface, which augments uptake by the reticuloendothelial system and enhances their extravascular hemolysis. Thus, eculizumab treatment effectively diverts RBC disposition from intravascular hemolysis to extravascular hemolysis. As a result, some eculizumab-treated PNH patients remain anemic. It follows that agents that block complement activation upstream and prevent the opsonization of PNH RBCs may be particularly suitable to block the extravascular hemolysis not prevented by eculizumab.

The data presented here demonstrate that MASP-2 dependent complement activation is the dominant route for lectin-dependent opsonization. Therefore, MASP-2 inhibitory agents are expected to be effective at limiting opsonization and inhibiting extravascular hemolysis in PNH.

Figure 40:
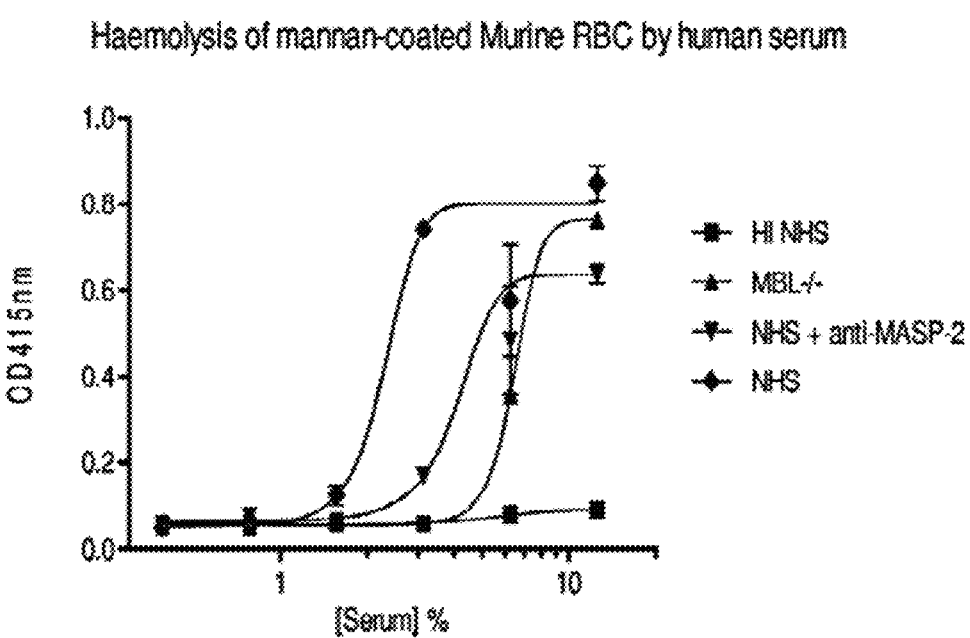
FIG. 40 graphically illustrates hemolysis (as measured by hemoglobin release of lysed mouse erythrocytes (Crry/C3−/−) into the supernatant measured by photometry) of mannan-coated murine erythrocytes by human serum over a range of serum concentrations The sera tested included heat-inactivated (HI) NHS, MBL−/−, NHS +anti-MASP-2 antibody and NHS control, as described in Example 33.
Figure 42:
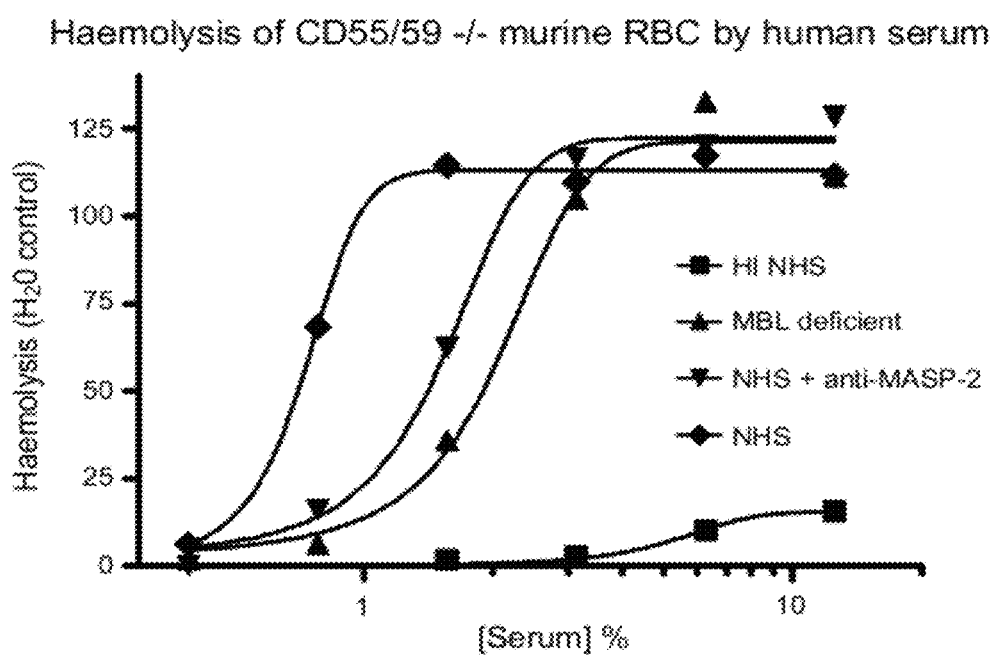
FIG. 42 graphically illustrates hemolysis (as measured by hemoglobin release of lysed mouse erythrocytes (CD55/59−/−) into the supernatant measured by photometry) of non-coated murine erythrocytes by human serum over a range of serum concentrations. The sera tested included heat-inactivated (HI) NHS, MBL−/−, NHS +anti-MASP-2 antibody and NHS control, as described in Example 33.

Using an in vitro model of PNH, we demonstrated that complement activation and the resulting hemolysis in PNH are indeed initiated, at least in part, by MASP-2 dependent complement activation and that it is not an independent function of the alternative pathway. These studies used mannan-sensitized RBCs of various mouse strains, including RBCs from Crry-deficient mice (an important negative regulator of the terminal complement pathway in mice) as well as RBCs from CD55/CD59-deficient mice, which lack the same complement regulators that are absent in PNH patients). When Mannan-sensitized Crry-deficient RBCs were exposed to complement-sufficient human serum, the RBCs effectively hemolysed at a serum concentration of 3% (FIG. 40) while complement-deficient serum (HI: heat-inactivated) was not hemolytic. Remarkably, complement-sufficient scrum in the presence of anti-MASP-2 antibody had reduced hemolytic activity, and 6% serum was needed for effective hemolysis (FIG. 40). Similar observations were made when CD55/CD59-deficient RBCs were tested (FIG. 42). Complement-sufficient human serum supplemented with anti-MASP-2 monoclonal antibody was about two-fold less effective than untreated serum in supporting hemolysis. Furthermore, higher concentrations of serum treated with anti-MASP-2 monoclonal antibody were needed to promote effective hemolysis of untreated WT RBCs compared to untreated serum (FIG. 40). Collectively, these data indicate that MASP-2 dependent complement activation contributes significantly to the hemolysis response. The data presented herein reveals the following pathogenic mechanisms for anemia in PNH: intravascular hemolysis due to unregulated activation of terminal complement components and lysis of RBC by formation of MAC, and extravascular hemolysis caused by opsonization of RBCs by C3b, which is initiated predominately by MASP-2 dependent complement activation. Thus, MASP-2-inhibitory agents are expected to significantly reduce intravascular hemolysis in PNH patients.

Extravascular hemolysis, a less dramatic, yet equally important mechanism of RBC destruction that leads to anemia in PNH, is primarily the result of opsonization by C3b, which is predominantly mediated by MASP-2 dependent complement activation. Thus, MASP-2-inhibitory agents will preferentially block RBC opsonization and C3b and the ensuing extravascular hemolysis in PNH. This unique therapeutic activity of MASP-2-inhibitory agents is expected to provide a significant treatment benefit to all PNH patients as no treatment currently exists for this pathogenic process.

MASP-2 Inhibitors as Adjunct Treatment to Terminal Complement Blocking Agents:

The data presented herein detail two pathogenic mechanisms for RBC clearance and anemia in PNH: the intravascular hemolysis initiated, at least in part, by MASP-2 dependent complement activation, and thus expected to be effectively inhibited by a MASP-2-inhibitory agent, and extravascular hemolysis due to C3b opsonization driven by MASP-2, and thus effectively prevented by a MASP-2-inhibitory agent.

It is well documented that both intravascular and extravascular mechanisms of hemolysis lead to anemia in PNH patients (Risitano et al., Blood 113:4094-4100 (2009)). Therefore, in the setting of PNH, inhibition of MASP-2 would be expected to address both intravascular and extravascular hemolysis, providing a significant advantage over the C5 inhibitor eculizumab. Accordingly, it is expected that a MASP-2-blocking agent that inhibits intravascular hemolysis and prevents extravascular hemolysis is expected to be effective in preventing the degree of anemia that develops in PNH patients.

It is also known that C5-blocking agents (such as eculizumab) effectively block intravascular hemolysis but do not interfere with opsonization. This leaves anti-C5-treated PNH patients with substantial residual anemia due to extravascular hemolysis mediated by MASP-2 dependent complement activation that remains untreated. Therefore, it is expected that a C5-blocking agent (such as eculizumab) that prevents intravascular hemolysis in combination with a MASP-2 inhibitory agent that prevents extravascular hemolysis will be more effective than either agent alone in preventing the anemia that develops in PNH patients. In fact, the combination of an anti-C5 and a MASP-2-inhibitory agent is expected to prevent all relevant mechanisms of RBC destruction in PNH and thus reduce or block all symptoms of anemia in PNH.

Other agents that block the terminal amplification loop of the complement system leading to C5 activation and MAC deposition (including, but not limited to agents that block Properdin, factor B or factor D or enhance the inhibitory activity of factor I, factor H or other complement inhibitory factors) are also expected to inhibit intravascular hemolysis. However, these agents are not expected to interfere with MASP-2-mediated opsonization in PNH patients. This leaves PNH patients treated with such agents with substantial residual anemia due to extravascular hemolysis mediated by MASP-2 dependent complement activation that remains untreated. Therefore, it is expected that treatment with such agents that prevent intravascular hemolysis in combination with a MASP-2-inhibitory agent that prevents extravascular hemolysis will be more effective than either agent alone in preventing the anemia that develops in PNH patients. In fact, the combination of such agents and a MASP-2 inhibitory agent is expected to prevent all or a large majority of the relevant mechanisms of RBC destruction in PNH and thus block all or a large majority of the symptoms of anemia in PNH.

Inhibition of MASP-2 Improves Survival in Subjects Infected with *Neisseria Meningitidis*

Figure 33:
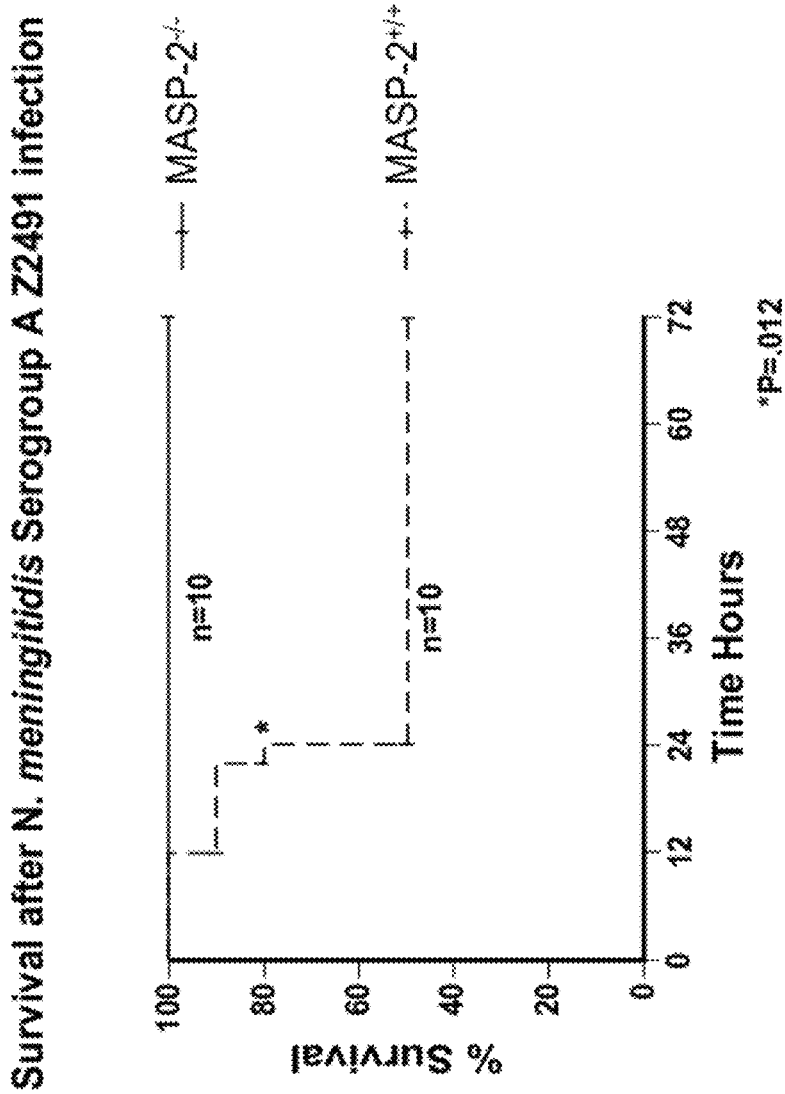
FIG. 33 is a Kaplan-Meyer plot graphically illustrating the percent survival of MASP-2 KO and WT mice after administration of an infective dose of 2.6×10⁷ cfu of *N. meningitidis* serogroup A 22491, demonstrating that MASP-2 deficient mice are protected from *N. meningitidis* induced mortality, as described in Example 30.
Figure 34:
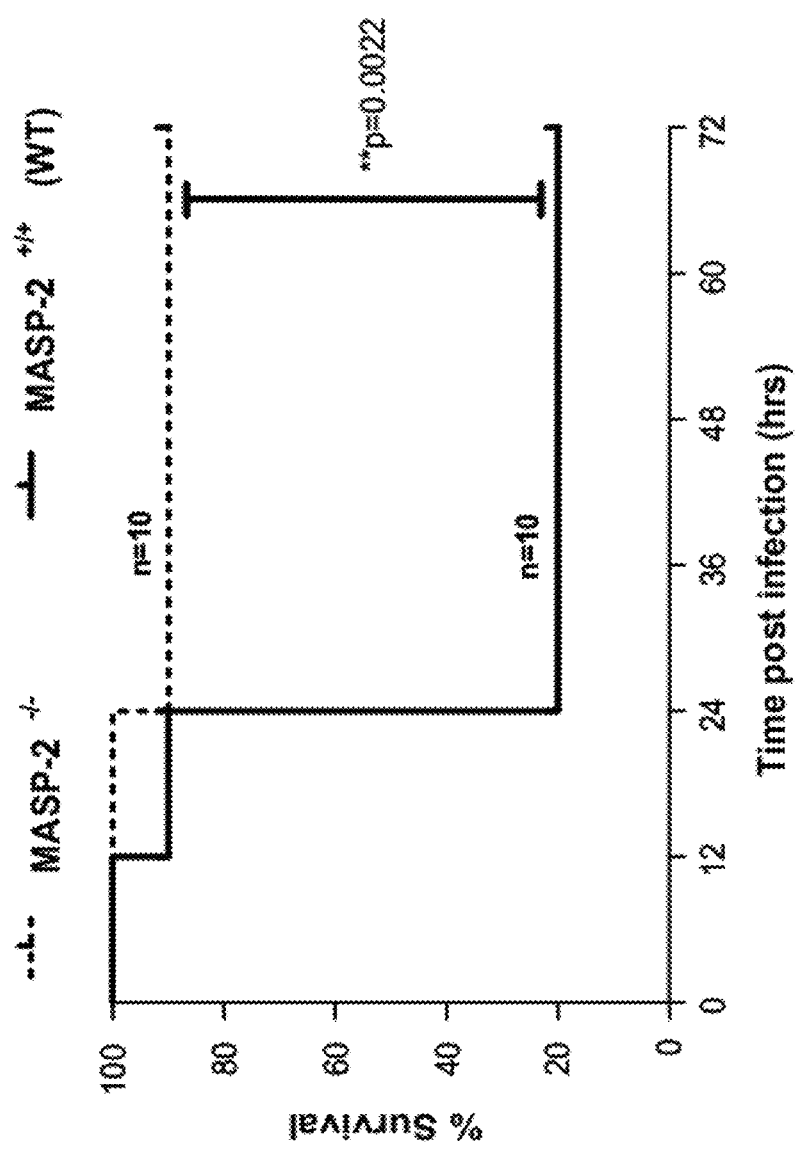
FIG. 34 is a Kaplan-Meyer plot graphically illustrating the percent survival of MASP-2 KO and WT mice after administration of an infective dose of 6×10⁶ cfu of *N. meningitidis* serogroup B strain MC58, demonstrating that MASP-2-deficient mice are protected from *N. meningitidis* serogroup B strain MC58 induced mortality, as described in Example 30.
Figure 35:
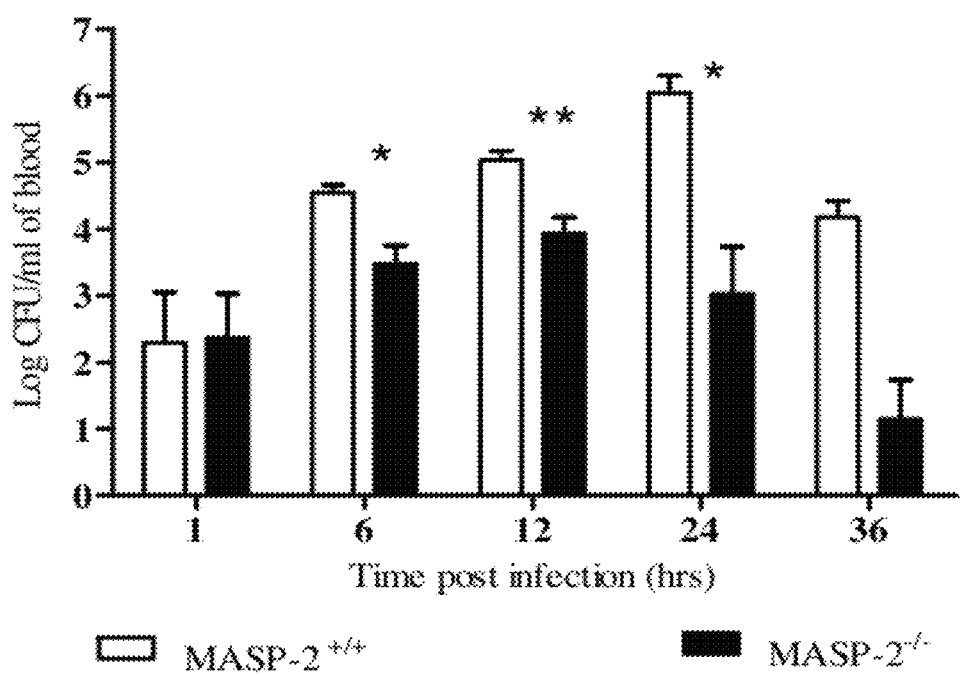
FIG. 35 graphically illustrates the log cfu/ml of *N. meningitidis* serogroup B strain MC58 recovered at different time points in blood samples taken from the MASP-2 KO and WT mice after i.p. infection with 6×10⁶ cfu of *N. meningitidis* serogroup B strain MC58 (n=3 at different time points for both groups of mice, results are expressed as Means±SEM) demonstrating that although the MASP-2 KO mice were infected with the same dose of *N. meningitidis* serogroup B strain MC58 as the WI mice, the MASP-2 KO mice have enhanced clearance of bacteraemia as compared to WT, as described in Example 30.

As described in Examples 30-32 and shown in FIGS. 33-37, inhibition of MASP-2 does not reduce survival following infection with *Neisseria meningitidis*. To the contrary, it was surprisingly discovered that MASP-2 inhibition significantly improved survival (FIGS. 33 and 34) as well as illness scores (FIG. 36) in these studies. Administration of anti- MASP2 antibody yielded the same result (FIG. 37), eliminating secondary or compensatory effects in the knockout-mouse strain as a possible cause. These favorable outcomes in MASP-2-ablated animals were associated with a more rapid elimination of *Neisseria* from the blood (FIG. 35). Also, as described herein, incubation of *Neisseria* with human scrum killed *Neisseria* (FIG. 38). Furthermore, addition of a functional monoclonal antibody specific for human MASP-2 that blocks MASP-2-dependent lectin pathway complement activation, but not administration of an isotype control monoclonal antibody, enhanced this killing response. In the context of lectin-dependent complement activation by *Neisseria*, blockade of MASP-2-enhanced lytic destruction of the organism in vitro (FIG. 38). Because lysis of *Neisseria* is the main protective mechanism in the naïve host, blockade of MASP-2 in vivo increases *Neisseria* clearance and leads to enhanced killing. These results are surprising, and provide a significant advantage over treatment with eculizumab, which has been shown to increase susceptibility to life-threatening and fatal meningococcal infections (Dmytrijuk A., et al., *The Oncologist* 13:993-1000 (2008)).

In accordance with the foregoing, in one aspect, the invention provides a method for treating paroxysmal nocturnal hemoglobinuria (PNH) by administering a composition comprising a therapeutically effective amount of a MASP-2 inhibitory agent in a pharmaceutical carrier to a subject suffering from PNH or a condition resulting from PNH (e.g., anemia, hemoglobin in the urine and thrombosis). The MASP-2 inhibitory agent is administered systemically to the subject suffering from PNH or a condition resulting from PNH, such as by intra-arterial, intravenous, intramuscular, inhalational, subcutaneous or other parenteral administration, or potentially by oral administration for non-peptidergic agents.

The Role of MASP-2 in Thrombotic Microangiopathies, Including Hemolytic Uremic Syndrome (HUS), Atypical Hemolytic Uremic Syndrome (AHUS) and Thrombotic Thrombocytopenic Purpura (TTP), and Therapeutic Methods Using MASP-2 Inhibitory Agents Overview Thrombotic microangiopathy (TMA) is a pathology characterized by blood clots in small blood vessels (Benz, K.; et al., *Curr Opin Nephrol Hypertens* 19(3):242-7 (2010)). Stress or injury to the underlying vascular endothelium is believed to be a primary driver. Clinical and laboratory findings of TMA include thrombocytopenia, anemia, purpura, and renal failure. The classic TMAs are hemolytic uremic syndrome (HUS) and thrombotic thrombocytopenic purpura (TTP). The characteristic underlying pathological feature of TMAs are platelet activation and the formation of microthrombi in the small arterioles and venules.

Direct evidence for a pathological role of complement in a host of nephritides is provided by studies of patients with genetic deficiencies in specific complement components. A number of reports have documented an association of renal injury with deficiencies of complement regulatory factor H (Ault, B. H., *Nephrol.* 14:1045-1053, 2000; Levy, M., et al., *Kidney Int.* 30:949-56, 1986; Pickering, M. C., et al., *Nat. Genet.* 31:424-8, 2002). Factor H deficiency results in low plasma levels of factor B and C3 due to activation-related consumption of these components. Circulating levels of C5b-9 are also elevated in the serum of these patients, implying complement activation. Membranoproliferative glomerulonephritis (MPGN) and idiopathic hemolytic uremic syndrome (HUS) are associated with factor H deficiency or mutations of factor H. Factor H-deficient pigs (Jansen, J. H., et al., *Kidney Int.* 53:331-49, 1998) and factor-H knockout mice (Pickering, M. C., 2002) display MPGN-like symptoms, confirming the importance of factor H in complement regulation. Deficiencies of other complement components are associated with renal disease, secondary to the development of systemic lupus erythematosus (SLE) (Walport, M. J., Davies, et al., *Ann. N.Y. Acad. Sci.* 815:267-81, 1997). Deficiency for C1q, C4 and C2 predispose strongly to the development of SLE via mechanisms relating to defective clearance of immune complexes and apoptotic material. In many of these SLE patients lupus nephritis occurs, characterized by the deposition of immune complexes throughout the glomerulus.

aHUS

Atypical hemolytic uremic syndrome (aHUS) is part of a group of conditions termed "Thrombotic microangiopathies." In the atypical form of HUS (aHUS), the disease is associated with defective complement regulation and can be either sporadic or familial. Familial cases of aHUS are associated with mutations in genes coding for complement activation or complement regulatory proteins, including complement factor H, factor 1, factor B, membrane cofactor CD46 as well as complement factor H-related protein 1 (CFHR1) and complement factor H-related protein 3 (CFHR3). (Zipfel, P. F., et al., *PloS Genetics* 3(3):e41 (2007)). The unifying feature of this diverse array of genetic mutations associated with aHUS is a predisposition to enhanced complement activation on cellular or tissue surfaces. Therefore, one aspect of the present invention comprises treating a patient suffering with aHUS that is associated with a factor H defiency by administering an effective amount of a MASP-2 inhibitory agent. Another aspect of the present invention comprises treating a patient suffering with HUS that is associated with a factor I, factor B, membrane cofactor CD46, CFHR1 or CFHR3 deficiency by administering an effective amount of a MASP-2 inhibitory agent.

Significant progress has been made recently toward the understanding of the molecular pathophysiology underlying enhanced complement activation in aHUS caused by the diverse set of mutant complement factors. This mechanism is best understood for factor H mutations. Factor H is an abundant serum protein comprising 20 short consensus repeat (SCR) domains that acts as a negative regulator of complement activation both in solution as well as on host cell surfaces. It targets the activated form of C3 and, together with factor I and other cofactors, promotes its inactivation, forestalling further complement activation. To effectively control complement activation on host cell surfaces, factor H needs to interact with host cells, which is mediated by SCR domains 16-20. All factor H mutations associated with aHUS described to date are clustered in the C-terminal region encompassing (SCR) domains 16-20. These mutant factor H proteins are fully functional in controlling C3 activation in solution, but are unable to interact with host cell surfaces and consequently cannot control C3 activation on cellular surfaces (Exp Med 204(6):1249-56 (2007)). Thus, certain mutations of factor H are associated with aHUS because the mutant factor H protein fails to interact with host cell surfaces and thus cannot effectively down modulate complement activation on host cell surfaces, including the microvascular endothelium. As a result, once initial C3 activation has occurred, subsequent complement activation on microvascular endothelial surfaces proceeds unabated in patients with factor H mutations. This uncontrolled activation of complement ultimately leads to progressive injury to the vascular endothelium, subsequent platelet aggregation and microvascular coagulation, and hemolysis caused by sheer stress of RBC passage through partially occluded microvessels. Thus, aHUS disease manifestations and clinical and laboratory findings are directly linked to a defect in the negative regulation of complement on the surface of the microvascular endothelium.

Analogous to factor H mutation, loss-of-function mutations in the negative complement modulators factor I and membrane cofactor protein (CD46) are also linked to aHUS. The opposite has been observed for factor B the C3 protein in that aHUS was found to be associated with gain-of-function mutations in these proteins (Pediatr Nephrol 25(12):2431-42 (2010)). Thus, a host of converging data implicates complement activation in aHUS pathogenesis. This notion is most convincingly supported by the therapeutic efficacy of eculizumab, a monoclonal antibody that blocks the terminal complement protein C5 in the treatment of aHUS.

While the central role of complement as an effector mechanism in aHUS is widely accepted, the triggers initiating complement activation and the molecular pathways involved are unresolved. Not all individuals carrying the above described mutations develop aHUS. In fact, familial studies have suggested that the penetrance of aHUS is only ~50% (Ann Hum Genet 74(1):17-26 (2010)). The natural history of the disease suggests that aHUS most often develops after an initiating event such as an infectious episode or an injury. Infectious agents are well known to activate the complement system. In the absence of pre-existing adaptive immunity, complement activation by infectious agents may be primarily initiated via the lectin pathway. Thus, lectin pathway activation triggered by an infection may represent the initiating trigger for subsequent pathological amplification of complement activation in aHUS-predisposed individuals, which may ultimately lead to disease progression. Accordingly, another aspect of the present invention comprises treating a patient suffering with aHUS secondary to an infection by administering an effective amount of a MASP-2 inhibitory agent.

Other forms of injury to host tissue will activate complement via the lectin pathway, in particular injury to the vascular endothelium. Human vascular endothelial cells subject to oxidative stress for example respond by expressing surface moieties that bind lectins and activate the lectin pathway of complement (Am J. Pathol 156(6):1549-56 (2000)). Vascular injury following ischemia/reperfusion also activates complement via the lectin pathway in vivo (Scand J Immunol 61(5): 426-34 (2005)). Lectin pathway activation in this setting has pathological consequences for the host, and inhibition of the lectin pathway by blocking MASP-2 prevents further host tissue injury and adverse outcomes (Schwaeble PNAS 2011).

Thus, other processes that precipitate aHUS are also known to activate the lectin pathway of complement. It is therefore likely that the lectin pathway may represent the initial complement activating mechanism that is inappropriately amplified in a deregulated fashion in individuals genetically predisposed to aHUS, thus initiating aHUS pathogenesis. By inference, agents that block activation of complement via the lectin pathway, including anti-MASP-2 antibodies, are expected to prevent disease progression or reduce exacerbations in aHUS susceptible individuals.

In further support of this concept, recent studies have identified *S. pneumonia* as an important etiological agent in pediatric cases of aHUS. (Nephrology (Carlton), 17:48-52 (2012); Pediatr Infect Dis J. 30(9):736-9 (2011)). This particular etiology appears to have an unfavorable prognosis, with significant mortality and long-term morbidity. Notably, these cases involved non-enteric infections leading to manifestations of microangiopathy, uremia and hemolysis without evidence of concurrent mutations in complement genes known to predispose to aHUS. It is important to note that *S. pneumonia* is particularly effective at activating complement, and does so predominantly through the lectin pathway. Thus, in cases of non-enteric HUS associated with pneumococcal infection, manifestations of microangiopathy, uremia and hemolysis are expected to be driven predominantly by activation of the lectin pathway, and agents that block the lectin pathway, including anti-MASP-2 antibodies, are expected to prevent progression of aHUS or reduce disease severity in these patients. Accordingly, another aspect of the present invention comprises treating a patient suffering with non-enteric aHUS that is associated with *S. pneumonia* infection by administering an effective amount of a MASP-2 inhibitory agent.

In accordance with the foregoing, in some embodiments, in the setting of a subject at risk for developing renal failure associated with aHUS, a method is provided for decreasing the likelihood of developing aHUS, or of developing renal failure associated with aHUS, comprising administering an amount of an MASP-2 inhibitory agent for a time period effective to ameliorate or prevent renal failure in the subject. In some embodiments, the method further comprises the step of determining whether a subject is at risk for developing aHUS prior to the onset of any symptoms associated with aHUS. In other embodiments, the method comprises determining whether a subject is a risk for developing aHUS upon the onset of at least one or more symptoms indicative of aHUS (e.g., the presence of anemia, thrombocytopenia and/or renal insufficiency) and/or the presence of thrombotic microangiopathy in a biopsy obtained from the subject. The determination of whether a subject is at risk for developing aHUS comprises determining whether the subject has a genetic predisposition to developing aHUS, which may be carried out by assessing genetic information (e.g. from a database containing the genotype of the subject), or performing at least one genetic screening test on the subject to determine the presence or absence of a genetic marker associated with aHUS (i.e., determining the presence or absence of a genetic mutation associated with aHUS in the genes encoding complement factor H (CFH), factor I (CFI), factor B (CFB), membrane cofactor CD46, C3, complement factor H-related protein 1 (CFHR1), or THBD (encoding the anticoagulant protein thrombodulin) or complement factor H-related protein 3 (CFHR3), or complement factor H-related protein 4 (CFHR4)) either via genome sequencing or gene-specific analysis (e.g., PCR analysis), and/or determining whether the subject has a family history of aHUS. Methods of genetic screening for the presence or absence of a genetic mutation associated with aHUS are well established, for example, see Noris M et al. "Atypical Hemolytic-Uremic Syndrome," 2007 Nov. 16 [Updated 2011 Mar. 10]. In: Pagon R A, Bird T D, Dolan C R, et al., editors. GeneReviews™, Seattle (WA): University of Washington, Seattle.

For example, overall the penetrance of the disease in those with mutations of complement factor H (CFH) is 48%, and the penetrance for mutations in CD46 is 53%, for mutations in CFI is 50%, for mutations in C3 is 56% and for mutations in THBD is 64% (Caprioli J. et al., *Blood*, 108:1267-79 (2006); Noris et al., Clin J Am Soc Nephrol 5:1844-59 (2010)). As described in Caprioli et al., (2006), supra, a substantial number of individuals with a mutation in complement Factor H (CFH) never develop aHUS, and it is postulated that suboptimal CFH activity in these individuals is sufficient to protect the host from the effects of complement activation in physiological conditions, however, suboptimal CFH activity is not sufficient to prevent C3b from being deposited on vascular endothelial cells when exposure to an agent that activates complement produces higher than normal amounts of C3b.

Accordingly, in one embodiment, a method is provided for inhibiting MASP-2-dependent complement activation in a subject suffering from, or at risk for developing non-Factor H-dependent atypical hemolytic uremic syndrome, comprising administering to the subject a composition comprising an amount of a MASP-2 inhibitory agent effective to inhibit MASP-2-dependent complement activation. In another embodiment, a method is provided for inhibiting MASP-2-dependent complement activation in a subject at risk for developing Factor H-dependent atypical hemolytic uremic syndrome, comprising periodically monitoring the subject to determine the presence or absence of anemia, thrombocytopenia or rising creatinine, and treating with a MASP-2 inhibitory agent upon the determination of the presence of anemia thrombocytopenia, or rising creatinine. In another embodiment, a method is provided for reducing the likelihood that a subject at risk for developing Factor H-dependent aHUS will suffer clinical symptoms associated with aHUS, comprising administering a MASP-2 inhibitory agent prior to, or during, or after an event known to be associated with triggering aHUS clinical symptoms, for example, drug exposure (e.g., chemotherapy), infection (e.g., bacterial infection), malignancy, an injury, organ or tissue transplant, or pregnancy.

In one embodiment, a method is provided for reducing the likelihood that a subject at risk for developing aHUS will suffer clinical symptoms associated with aHUS, comprising periodically monitoring the subject to determine the presence or absence of anemia, thrombocytopenia or rising creatinine, and treating with a MASP-2 inhibitory agent upon the determination of the presence of anemia, thrombocytopenia, or rising creatinine.

In another embodiment, a method is provided for reducing the likelihood that a subject at risk for developing aHUS will suffer clinical symptoms associated with aHUS comprising administering a MASP-2 inhibitory agent prior to, or during, or after an event known to be associated with triggering aHUS clinical symptoms, for example, drug exposure (e.g., chemotherapy), infection (e.g., bacterial infection), malignancy, an injury, organ or tissue transplant, or pregnancy.

In some embodiments, the MASP-2 inhibitory agent is administered for a time period of at least one, two, three, four days, or longer, prior to, during, or after the event associated with triggering aHUS clinical symptoms and may be repeated as determined by a physician until the condition has been resolved or is controlled. In a pre-aHUS setting, the MASP-2 inhibitory agent may be administered to the subject systemically, such as by intra-arterial, intravenous, intramuscular, inhalational, nasal, subcutaneous or other parenteral administration.

In some embodiments, in the setting of initial diagnosis of aHUS, or in a subject exhibiting one or more symptoms consistent with a diagnosis of aHUS (e.g., the presence of anemia, thrombocytopenia and/or renal insufficiency), the subject is treated with an effective amount of a MASP-2 inhibitory agent (e.g., an anti-MASP-2 antibody) as a first line therapy in the absence of plasmapheresis, or in combination with plasmapheresis. As a first line therapy, the MASP-2 inhibitory agent may be administered to the subject systemically, such as by intra-arterial, intravenous, intramuscular, inhalational, nasal, subcutaneous or other parenteral administration. In some embodiments, the MASP-2 inhibitory agent is administered to a subject as a first line therapy in the absence of plasmaphersis to avoid the potential complications of plasmaphersis including hemorrhage, infection, and exposure to disorders and/or allergies inherent in the plasma donor, or in a subject otherwise averse to plasmapheresis, or in a setting where plasmapheresis is unavailable.

In some embodiments, the method comprises administering a MASP-2 inhibitory agent to a subject suffering from aHUS via a catheter (e.g., intravenously) for a first time period (e.g., at least one day to a week or two weeks) followed by administering a MASP-2 inhibitory agent to the subject subcutaneously for a second time period (e.g., a chronic phase of at least two weeks or longer). In some embodiments, the administration in the first and/or second time period occurs in the absence of plasmapheresis. In some embodiments, the method further comprises determining the level of at least one complement factor (e.g., C3, C5) in the subject prior to treatment, and optionally during treatment, wherein the determination of a reduced level of at least one complement factor in comparison to a standard value or healthy control subject is indicative of the need for continued treatment with the MASP-2 inhibitory agent.

In some embodiments, the method comprises administering a MASP-2 inhibitory agent, such as an anti-MASP-2 antibody, to a subject suffering from, or at risk for developing, aHUS either intravenously, intramuscularly, or preferably, subcutaneously. Treatment may be chronic and administered daily to monthly, but preferably every two weeks. The anti-MASP-2 antibody may be administered alone, or in combination with a C5 inhibitor, such as eculizamab.

HUS

Like atypical HUS, the typical form of HUS displays all the clinical and laboratory findings of a TMA. Typical HUS, however, is often a pediatric disease and usually has no familial component or direct association with mutations in complement genes. The etiology of typical HUS is tightly linked to infection with certain intestinal pathogens. The patients typically present with acute renal failure, hemoglobinuria, and thrombocytopenia, which typically follows an episode of bloody diarrhea. The condition is caused by an enteric infection with *Shigella dissenteria, Salmonella* or shiga toxin-like producing enterohemorrhagic strains of *E. Coli* such as *E. Coli* O157:H7. The pathogens are acquired from contaminated food or water supply. HUS is a medical emergency and carries a 5-10% mortality. A significant portion of survivors develop chronic kidney disease (Corrigan and Boineau, *Pediatr Rev* 22 (11): 365-9 (2011)) and may require kidney transplantation.

The microvascular coagulation in typical HUS occurs predominantly, though not exclusively, in the renal microvasculature. The underlying pathophysiology is mediated by Shiga toxin (STX). Excreted by enteropathic microbes into the intestinal lumen, STX crosses the intestinal barrier, enters the bloodstream and binds to vascular endothelial cells via the blobotriaosyl ceramide receptor CD77 (Boyd and Lingwood *Nephron* 51:207 (1989)), which is preferentially expressed on glomerular endothelium and mediates the toxic effect of STX. Once bound to the endothelium, SIX induces a series of events that damage vascular endothelium, activate leukocytes and cause vWF-dependent thrombus formation (Forsyth et al., *Lancet* 2: 411-414 (1989); Zoja et al., *Kidney Int.* 62: 846-856 (2002); Zanchi et al., *J. Immunol.* 181:1460-1469 (2008); Morigi et al., *Blood* 98: 1828-1835 (2001); Guessou et al., *Infect. Immun.*, 73: 8306-8316 (2005)). These microthrombi obstruct or occlude the arterioles and capillaries of the kidney and other organs. The obstruction of blood flow in arterioles and capillaries by microthrombi increases the shear force applied to RBCs as they squeeze through the narrowed blood vessels. This can result in destruction of RBC by shear force and the formation of RBC fragments called schistocytes. The presence of schistocytes is a characteristic finding in HUS. This mechanism is known as microangiopathic hemolysis. In addition, obstruction of blood flow results in ischemia, initiating a complement-mediated inflammatory response that causes additional damage to the affected organ.

The lectin pathway of complement contributes to the pathogenesis of HUS by two principle mechanisms: 1) MASP-2-mediated direct activation of the coagulation cascade caused by endothelial injury, and 2) lectin-mediated subsequent complement activation induced by the ischemia resulting from the initial occlusion of microvascular blood flow.

STX injures microvascular endothelial cells, and injured endothelial cells are known to activate the complement system. As detailed above, complement activation following endothelial cell injury is driven predominantly by the lectin pathway. Human vascular endothelial cells subject to oxidative stress respond by expressing surface moieties that bind lectins and activate the lectin pathway of complement (Collard et al., *Am J Pathol.* 156(5):1549-56 (2000)). Vascular injury following ischemia reperfusion also activates complement via the lectin pathway in vivo (Scand J Immunol 61(5): 426-34 (2005)). Lectin pathway activation in this setting has pathological consequences for the host, and inhibition of the lectin pathway by blockade of MASP-2 prevents further host tissue injury and adverse outcomes (Schwaeble et al., *PNAS* (2011)). In addition to complement activation, lectin-dependent activation of MASP-2 has been shown to result in cleavage of prothrombin to form thrombin and to promote coagulation. Thus, activation of the lectin pathway of complement by injured endothelial cells can directly activate the coagulation system. The lectin pathway of complement, by virtue of MASP-2-mediated prothombin activation, therefore is likely the dominant molecular pathway linking the initial endothelial injury by STX to the coagulation and microvascular thrombosis that occurs in HUS. It is therefore expected that lectin pathway inhibitors, including, but not limited to, antibodies that block MASP-2 function, will prevent or mitigate microvascular coagulation, thrombosis and hemolysis in patients suffering from HUS. Indeed, administration of anti-MASP-2 antibody profoundly protects mice in a model of typical HUS. As described in Example 36 and shown in FIG. 45, all control mice exposed to STX and LPS developed severe HUS and became moribund or died within 48 hours. On the other hand, as further shown in FIG. 45, all mice treated with an anti-MASP-2 antibody and then exposed to STX and LPS survived (Fisher's exact p<0.01; N=5). Thus, anti-MASP-2 therapy profoundly protects mice in this model of HUS. It is expected that administration of a MASP-2 inhibitory agent, such as a MASP-2 antibody, will be effective in the treatment of HUS patients and provide protection from microvascular coagulation, thrombosis, and hemolysis caused by infection with enteropathic *E. coli* or other STX-producing pathogens.

While shown here for HUS caused by STX, it is expected that anti-MASP-2 therapy will also be beneficial for HUS-like syndromes due to endothelial injury caused by other toxic agents. This includes agents such as mitomycin, ticlopidine, cycplatin, quinine, cyclosporine, bleomycin as well as other chemotherapy drugs and immunosuppressive drugs. Thus, it is expected that anti-MASP-2 antibody therapy, or other modalities that inhibit MASP-2 activity, will effectively prevent or limit coagulation, thrombus formation, and RBC destruction and prevent renal failure in HUS and other TMA related diseases (i.e., aHUS and TTP).

Patients suffering from HUS often present with diarrhea and vomiting, their platelet counts are usually reduced (thrombocytopenia), and RBCs are reduced (anemia). A pre-HUS diarrhea phase typically lasts for about four days, during which subjects at risk for developing HUS typically exhibit one or more of the following symptoms in addition to severe diarrhea: a hematocrit level below 30% with smear evidence of intravascular erythrocyte destruction, thrombocytopenia (platelet count <$150\times10^3$/mm$^3$), and/or the presence of impaired renal function (serum creatinine concentration greater than the upper limit of reference range for age). The presence of oligoanuria (urine output ≤0.5 mL/kg/h for >1 day) can be used as a measure for progression towards developing HUS (see C. Hickey et al., *Arch Pediatr Adolesc Med* 165(10):884-889 (2011)). Testing is typically carried out for the presence of infection with *E. coli* bacteria (*E. coli* 0157: 1-17), or *Shigella* or *Salmonella* species. In a subject testing positive for infection with enterogenic *E. coli* (e.g., *E. coli* 0157:H7), the use of antibiotics is contra-indicated because the use of antibiotics may increase the risk of developing HUS through increased STX production (See Wong C. et al., *N Engl J. Med* 342:1930-1936 (2000). For subjects testing positive for *Shigella* or *Salmonella*, antibiotics are typically administered to clear the infection. Other well established first-line therapy for HUS includes volume expansion, dialysis and plasmapheresis.

In accordance with the foregoing, in some embodiments, in the setting of a subject suffering from one or more symptoms associated with a pre-HUS phase and at risk for developing HUS (i.e., the subject exhibits one or more of the following: diarrhea, a hematocrit level less than 30% with smear evidence of intravascular erythrocyte destruction, thrombocytopenia (platelet count less than $150\times10^3$/mm$^3$), and/or the presence of impaired renal function (serum creatinine concentration greater than the upper limit of reference range for age)), a method is provided for decreasing the risk of developing HUS, or of decreasing the likelihood of renal failure in the subject, comprising administering an amount of an MASP-2 inhibitory agent for a time period effective to ameliorate or prevent impaired renal function. In some embodiments, the MASP-2 inhibitory agent is administered for a time period of at least one, two, three, four or more days, and may be repeated as determined by a physician until the condition has been resolved or is controlled. In a pre-HUS setting, the MASP-2 inhibitory agent may be administered to the subject systemically, such as by intra-arterial, intravenous, intramuscular, inhalational, nasal, oral, subcutaneous or other parenteral administration.

The treatment of *E. coli* 0157:H7 infection with bactericidal antibiotics, particularly β-lactams, has been associated with an increased risk of developing HUS (Smith et al., Pediatr Infect Dis J 31(1):37-41 (2012). In some embodiments, in the setting of a subject suffering from symptoms associated with a pre-HUS phase, wherein the subject is known to have an infection with enterogenic *E. coli* for which the use of antibiotics is contra-indicated (e.g., *E. coli* 0157:H7), a method is provided for decreasing the risk of developing HUS, or of decreasing the likelihood of renal failure in the subject, comprising administering an amount of a MASP-2 inhibitory agent for a first time period effective to inhibit or prevent the presence of oligoanuria in the subject (e.g., at least one, two, three or four days), wherein the administration of the MASP-2 inhibitory agent during the first time period occurs in the absence of an antibiotic. In some embodiments, the method further comprises administering the MASA-2 inhibitory agent to the subject in combination with an antibiotic for a second time period (such as at least one to two weeks).

In other embodiments, in the setting of a subject suffering from symptoms associated with a pre-HUS phase, wherein the subject is known to have an infection with *Shigella* or *Salmonella*, a method is provided for decreasing the risk of developing HUS, or of decreasing the likelihood of renal failure in the subject, comprising administering an amount of a MASP-2 inhibitory agent and for a time period effective to inhibit or prevent the presence of oligoanuria in the subject, wherein the administration of the MASP-2 inhibitory agent is either in the presence or in the absence of a suitable antibiotic.

In some embodiments, in the setting of an initial diagnosis of HUS, or in a subject exhibiting one or more symptoms consistent with a diagnosis of HUS (e.g., the presence of renal failure, or microangiopathic hemolytic anemia in the absence of low fibrinogen, or thrombocytopenia) the subject is treated with an effective amount of a MASP-2 inhibitory agent (e.g. a anti-MASP-2 antibody) as a first-line therapy in the absence of plasmapheresis, or in combination with plasmapheresis. As a first-line therapy, the MASP-2 inhibitory agent may be administered to the subject systemically, such as by intra-arterial, intravenous, intramuscular, inhalational, nasal, subcutaneous or other parenteral administration. In some embodiments, the MASP-2 inhibitory agent is administered to a subject as a first line therapy in the absence of plasmapheresis to avoid the complications of plasmapheresis such as hemorrhage, infection, and exposure to disorders and/or allergies inherent in the plasma donor, or in a subject otherwise averse to plasmaphoresis, or in a setting where plasmapheresis is unavailable.

In some embodiments, the method comprises administering a MASP-2 inhibitory agent to a subject suffering from HUS via a catheter (e.g., intravenously) for a first time period (e.g., an acute phase lasting at least one day to a week or two weeks) followed by administering a MASP-2 inhibitory agent to the subject subcutaneously for a second time period (e.g., a chronic phase of at least two weeks or longer). In some embodiments, the administration in the first and/or second time period occurs in the absence of plasmapheresis. In some embodiments, the method further comprises determining the level of at least one complement factor (e.g., C3, C5) in the subject prior to treatment, and optionally during treatment, wherein the determination of a reduced level of the at least one complement factor in comparison to a standard value or healthy control subject is indicative of the need for treatment, and wherein the determination of a normal level is indicative of improvement.

In some embodiments, the method comprises administering a MASP-2 inhibitory agent, such as an anti-MASP-2 antibody, to a subject suffering from, or at risk for developing, HUS either subcutaneously or intravenously. Treatment is preferably daily, but can be as infrequent as weekly or monthly. Treatment will continue for at least one week and as long as 3 months. The anti-MASP-2 antibody may be administered alone, or in combination with a C5 inhibitor, such as eculizamab.

TTP:

Thrombotic thrombocytopenic purpura (TTP) is a life threatening disorder of the blood-coagulation system, caused by autoimmune or hereditary dysfunctions that activate the coagulation cascade or the complement system (George, J N, *N Engl J Med;* 354:1927-35 (2006)). This results in numerous microscopic clots, or thomboses, in small blood vessels throughout the body. Red blood cells are subjected to shear stress which damages their membranes, leading to intravascular hemolysis. The resulting reduced blood flow and endothelial injury results in organ damage, including brain, heart, and kidneys. TTP is clinically characterized by thrombocytopenia, microangiopathic hemolytic anemia, neurological changes, renal failure and fever. In the era before plasma exchange, the fatality rate was 90% during acute episodes. Even with plasma exchange, survival at six months is about 80%.

TTP may arise from genetic or acquired inhibition of the enzyme ADAMTS-13, a metalloprotease responsible for cleaving large multimers of von Willebrand factor (vWF) into smaller units. ADAMTS-13 inhibition or deficiency ultimately results in increased coagulation (Tsai, H. *J Am Soc Nephrol* 14: 1072-1081, (2003)). ADAMTS-13 regulates the activity of vWF; in its absence, vWF forms large multimers which are more likely to bind platelets and predisposes patients to platelet aggregation and thrombosis in the microvasculature.

Numerous mutations in ADAMTS13 have been identified in individuals with TTP. The disease can also develop due to auto-antibodies against ADAMTS-13. In addition, TTP can develop during breast, gastrointestinal tract, or prostate cancer (George J N., *Oncology* (Williston Park). 25:908-14 (2011)), pregnancy (second trimester or postpartum), George J N., *Curr Opin Hematol* 10:339-344 (2003)), or is associated with diseases, such as HIV or autoimmune diseases like systemic lupus erythematosis (Hamasaki K, et al., *Clin Rheumatol.* 22:355-8 (2003)). TTP can also be caused by certain drug therapies, including heparin, Quinine, immunemediated ingredient, cancer chemotherapeutic agents (bleomycin, cisplatin, cytosine arabinoside, daunomycin gemcitabine, mitomycin C, and tamoxifen), cyclosporine A, oral contraceptives, penicillin, rifampin and anti-platelet drugs including ticlopidine and clopidogrel (Azarm, T. et al., *J Res Med Sci.,* 16: 353-357 (2011)). Other factors or conditions associated with TTP are toxins such as bee venoms, sepsis, splenic sequestration, transplantion, vasculitis, vascular surgery, and infections like *Streptococcus pneumonia* and cytomegalovirus (Moake J L., *N Engl J Med.,* 347:589-600 (2002)). TTP due to transient functional ADAMTS-13 deficiency can occur as a consequence of endothelial cell injury associated with *S. pneumonia* infection (*Pediatr Nephrol.,* 26:631-5 (2011)).

Plasma exchange is the standard treatment for TTP (Rock G A, et al., *N Engl J Med* 325:393-397 (1991)). Plasma exchange replaces ADAMTS-13 activity in patients with genetic defects and removes ADAMTS-13 autoantibodies in those patients with acquired autoimmune TTP (Tsai, H-M, *Hematol Oncol Clin North Am.,* 21(4): 609-v (2007)). Additional agents such as immunosuppressive drugs are routinely added to therapy (George, J N, *N Engl J Med,* 354:1927-35 (2006)). However, plasma exchange is not successful for about 20% of patients, relapse occurs in more than a third of patients, and plasmapheresis is costly and technically demanding. Furthermore, many patients are unable to tolerate plasma exchange. Consequently there remains a critical need for additional and better treatments for TTP.

Because TTP is a disorder of the blood coagulation cascade, treatment with antagonists of the complement system may aid in stabilizing and correcting the disease. While pathological activation of the alternative complement pathway is linked to aHUS, the role of complement activation in TTP is less clear. The functional deficiency of ADAMTS13 is important for the susceptibility of TTP, however it is not sufficient to cause acute episodes. Environmental factors and/ or other genetic variations may contribute to the manifestation of TTP. For example, genes encoding proteins involved in the regulation of the coagulation cascade, vWF, platelet function, components of the endothelial vessel surface, or the complement system may be implicated in the development of acute thrombotic microangiopathy (Galbusera, M. et al., *Haematologica,* 94: 166-170 (2009)). In particular, complement activation has been shown to play a critical role; serum from thrombotic microangiopathy associated with ADAMTS-13 deficiency has been shown to cause C3 and MAC deposition and subsequent neutrophil activation which could be abrogated by complement inactivation (Ruiz-Torres M P, et al., *Thromb Haemost,* 93:443-52 (2005)). In addition, it has recently been shown that during acute episodes of TTP there are increased levels of C4d, C3bBbP, and C3a (M. Réti et al., *J Thromb Haemost*. Feb. 28 (2012) doi: 10.1111/j.1538-7836.2012.04674.x. [Epub ahead of print]), consistent with activation of the classical/lectin and alternative pathways. This increased amount of complement activation in acute episodes may initiate the terminal pathway activation and be responsible for further exacerbation of TTP.

The role of ADAMTS-13 and vWF in TTP clearly is responsible for activation and aggregation of platelets and their subsequent role in shear stress and deposition in microangiopathies. Activated platelets interact with and trigger both the classical and alternative pathways of complement. Platelet mediated complement activation increases the inflammatory mediators C3a and C5a (Peerschke E et al., *Mol Immunol,* 47:2170-5 (2010)). Platelets may thus serve as targets of classical complement activation in inherited or autoimmune TTP.

As described above, the lectin pathway of complement, by virtue of MASP-2 mediated prothombin activation, is the dominant molecular pathway linking endothelial injury to the coagulation and microvascular thrombosis that occurs in HUS. Similarly, activation of the lectin pathway of complement may directly drive the coagulation system in TTP. Lectin pathway activation may be initiated in response to the initial endothelium injury caused by ADAMTS-13 deficiency in TTP. It is therefore expected that lectin pathway inhibitors, including but not limited to antibodies that block MASP-2 function, will mitigate the microangiopathies associated with microvascular coagulation, thrombosis, and hemolysis in patients suffering from TTP.

Patients suffering from TTP typically present in the emergency room with one or more of the following: purpura, renal failure, low platelets, anemia and/or thrombosis, including stroke. The current standard of care for TTP involves intra-catheter delivery (e.g., intravenous or other form of catheter) of replacement plasmapheresis for a period of two weeks or longer, typically three times a week, but up to daily. If the subject tests positive for the presence of an inhibitor of ADAMTS13 (i.e., an endogenous antibody against ADAMTS13), then the plasmapheresis may be carried out in combination with immunosuppressive therapy (e.g., corticosteroids, rituxan, or cyclosporine). Subjects with refractory TTP (approximately 20% of TTP patients) do not respond to at least two weeks of plasmapheresis therapy.

In accordance with the foregoing, in one embodiment, in the setting of an initial diagnosis of TTP, or in a subject exhibiting one or more symptoms consistent with a diagnosis of TTP (e.g., central nervous system involvement, severe thrombocytopenia (a platelet count of less that or equal to 5000/µL if off aspirin, less than or equal to 20,000/µL if on aspirin), severe cardiac involvement, severe pulmonary involvement, gastro-intestinal infarction or gangrene), a method is provided for treating the subject with an effective amount of a MASP-2 inhibitory agent (e.g., a anti-MASP-2 antibody) as a first line therapy in the absence of plasmapheresis, or in combination with plasmapheresis. As a first-line therapy, the MASP-2 inhibitory agent may be administered to the subject systemically, such as by intra-arterial, intravenous, intramuscular, inhalational, nasal, subcutaneous or other parenteral administration. In some embodiments, the MASP-2 inhibitory agent is administered to a subject as a first-line therapy in the absence of plasmapheresis to avoid the potential complications of plasmapheresis, such as hemorrhage, infection, and exposure to disorders and/or allergies inherent in the plasma donor, or in a subject otherwise averse to plasmapheresis, or in a setting where plasmapheresis is unavailable. In some embodiments, the MASP-2 inhibitory agent is administered to the subject suffering from TTP in combination (including co-administration) with an immunosuppressive agent (e.g., corticosteroids, rituxan or cyclosporine) and/or in combination with concentrated ADAMTS-13.

In some embodiments, the method comprises administering a MASP-2 inhibitory agent to a subject suffering from TTP via a catheter (e.g., intravenously) for a first time period (e.g., an acute phase lasting at least one day to a week or two weeks) followed by administering a MASP-2 inhibitory agent to the subject subcutaneously for a second time period (e.g., a chronic phase of at least two weeks or longer). In some embodiments, the administration in the first and/or second time period occurs in the absence of plasmapheresis. In some embodiments, the method is used to maintain the subject to prevent the subject from suffering one or more symptoms associated with TTP.

In another embodiment, a method is provided for treating a subject suffering from refractory TTP (i.e., a subject that has not responded to at least two weeks of plasmaphorsis therapy), by administering an amount of a MASP-2 inhibitor effective to reduce one or more symptoms of TTP. In one embodiment, the MASP-2 inhibitor (e.g., an anti-MASP-2 antibody) is administered to a subject with refractory TTP on a chronic basis, over a time period of at least two weeks or longer via subcutaneous or other parenteral administration. Administration may be repeated as determined by a physician until the condition has been resolved or is controlled.

In some embodiments, the method further comprises determining the level of at least one complement factor (e.g., C3, C5) in the subject prior to treatment, and optionally during treatment, wherein the determination of a reduced level of the at least one complement factor in comparison to a standard value or healthy control subject is indicative of the need for continued treatment with the MASP-2 inhibitory agent.

In some embodiments, the method comprises administering a MASP-2 inhibitory agent, such as an anti-MASP-2 antibody, to a subject suffering from, or at risk for developing, TTP either subcutaneously or intravenously. Treatment is preferably daily, but can be as infrequent as biweekly. Treatment is continued until the subject's platelet count is greater than 150,000/ml for at least two consecutive days. The anti-MASP-2 antibody may be administered alone, or in combination with a C5 inhibitor, such as eculizamab.

Another aspect of the invention provides methods for treating Cryoglobulinemia by administering a composition comprising a therapeutically effective amount of a MASP-2 inhibitory agent in a pharmaceutical carrier to a subject suffering from Cryoglobulinemia or a condition resulting from Cryoglobulinemia. Cryoglobulinemia is characterized by the presence of cryoglobulins in the serum, which are single or mixed immunoglobulins (typically IgM antibodies) that undergo reversible aggregation at low temperatures. Conditions resulting from Cryoglobulinemia include vasculitis, glomerulonepthritis, and systemic inflammation. The MASP-2 inhibitory agent is administered systemically to the subject suffering from Cryoglobulinemia or a condition resulting from Cryoglobulinemia, such as by intra-arterial, intravenous, intramuscular, inhalational, subcutaneous or other parenteral administration, or potentially by oral administration for non-peptidergic agents.

In another aspect, the invention provides methods for treating Cold Agglutinin disease (CAD) by administering a composition comprising a therapeutically effective amount of a MASP-2 inhibitory agent in a pharmaceutical carrier to a subject suffering from CAD or a condition resulting from CAD. CAD disease manifests as anemia and can be caused by an underlying disease or disorder, referred to as "Secondary CAD" such as an infectious disease, lymphoproliferative disease or connective tissue disorder. These patients develop IgM antibodies against their red blood cells that trigger an agglutination reaction at low temperatures. The MASP-2 inhibitory agent is administered systemically to the subject suffering from CAD or a condition resulting from CAD, such as by intra-arterial, intravenous, intramuscular, inhalational, subcutaneous or other parenteral administration, or potentially by oral administration for non-peptidergic agents.

Coagulopathies

Evidence has been developed for the role of the complement system in disseminated intravascular coagulation ("DIC"), such as DIC secondary to significant bodily trauma.

Figure 30:
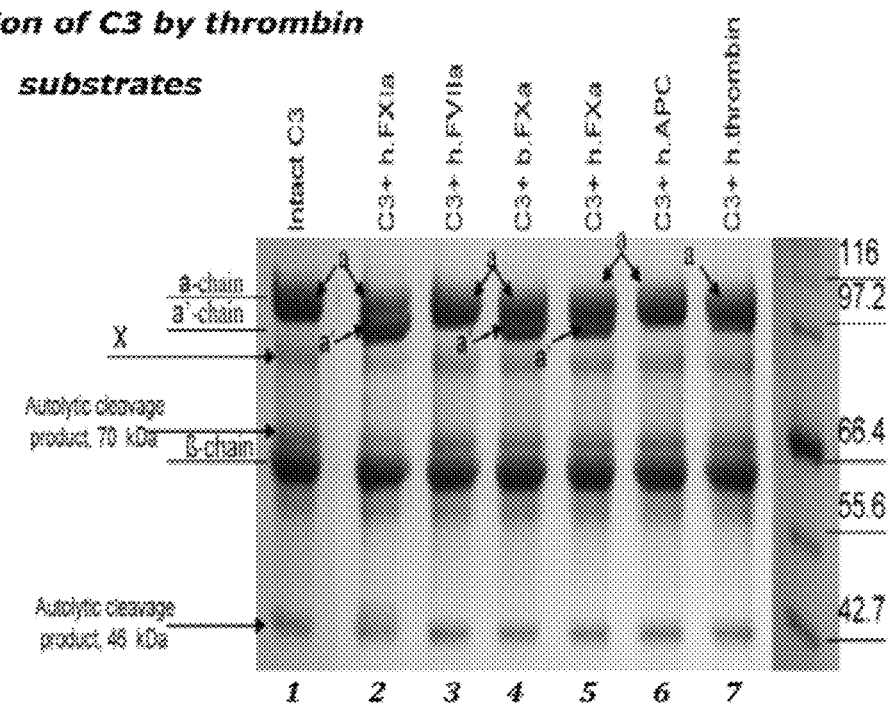
FIG. 30 illustrates the results of a Western blot analysis showing activation of human C3, shown by the presence of the a' chain, by thrombin substrates FX1a and FXa, as described in Example 23.

Previous studies have shown that C4−/− mice are not protected from renal reperfusion injury. (Zhou, W., et al, "Predominant role for C5b-9 in renal ischemia/reperfusion injury," *J Clin Invest* 105:1363-1371 (2000)) In order to investigate whether C4−/− mice may still be able to activate complement via either the classical or the lectin pathway, C3 turn-over in C4−/− plasma was measured in assays specific for either the classical, or the lectin pathway activation route. While no C3 cleavage could be observed when triggering activation via the classical, a highly efficient lectin pathway-dependent activation of C3 in C4 deficient serum was observed (FIG. 30). It can be seen that C3b deposition on mannan and zymosan is severely compromised in MASP-2−/− mice, even under experimental conditions, that according to many previously published papers on alternative pathway activation, should be permissive for all three pathways. When using the same sera in wells coated with immunoglobulin complexes instead of mannan or zymosan, C3b deposition and Factor B cleavage are seen in MASP-2+/+ mouse sera and MASP-2−/− sera, but not in C1q depleted sera. This indicates that alternate pathway activation is facilitated in MASP-2−/− sera when the initial C3b is provided via classical activity. FIG. 30C depicts the surprising finding that C3 can efficiently be activated in a lectin pathway-dependent fashion in C4 deficient plasma.

This "C4 bypass" is abolished by the inhibition of lectin pathway-activation through preincubation of plasma with soluble mannan or mannose.

Aberrant, non-immune, activation of the complement system is potentially hazardous to man and may also play an important role in hematological pathway activation, particularly in severe trauma situations wherein both inflammatory and hematological pathways are activated. In normal health, C3 conversion is <5% of the total plasma C3 protein. In rampant infection, including septicaemia and immune complex disease, C3 conversion re-establishes itself at about 30% with complement levels frequently lower than normal, due to increased utilization and changes in pool distribution. Immediate C3 pathway activation of greater than 30% generally produces obvious clinical evidence of vasodilatation and of fluid loss to the tissues. Above 30% C3 conversion, the initiating mechanisms are predominantly non-immune and the resulting clinical manifestations are harmful to the patient. Complement C5 levels in health and in controlled disease appear much more stable than C3. Significant decreases and or conversion of C5 levels are associated with the patient's response to abnormal polytrauma (e.g., road traffic accidents) and the likely development of shock lung syndromes. Thus, any evidence of either complement C3 activation beyond 30% of the vascular pool or of any C5 involvement, or both, may be considered likely to be a harbinger of a harmful pathological change in the patient.

Both C3 and C5 liberate anaphylatoxins (C3a and C5a) that act on mast cells and basophils releasing vasodilatory chemicals. They set up chemotactic gradients to guide polymorphonuclear cells (PMN) to the center of immunological disturbances (a beneficial response), but here they differ because C5a has a specific clumping (aggregating) effect on these phagocytic cells, preventing their random movement away from the reaction site. In normal control of infection, C3 activates C5. However, in polytrauma, C5 appears to be widely activated, generating C5a anaphylatoxins systemically. This uncontrolled activity causes polymorphs to clump within the vascular system, and these clumps are then swept into the capillaries of the lungs, which they occlude and generate local damaging effects as a result of superoxide liberation. While not wishing to be limited by theory, the mechanism is probably important in the pathogenesis of acute respiratory distress syndrome (ARDS), although this view has recently been challenged. The C3a anaphylatoxins in vitro can be shown to be potent platelet aggregators, but their involvement in vivo is less defined and the release of platelet substances and plasmin in wound repair may only secondarily involve complement C3. It is possible that prolonged elevation of C3 activation is necessary to generate DIC.

In addition to cellular and vascular effects of activated complement component outlined above that could explain the link between trauma and DIC, emerging scientific discoveries have identified direct molecular links and functional cross-talk between complement and coagulation systems. Supporting data has been obtained from studies in C3 deficient mice. Because C3 is the shared component for each of the complement pathways, C3 deficient mice are predicted to lack all complement function. Surprisingly, however, C3 deficient mice are perfectly capable of activating terminal complement components. (Huber-Lang, M., et al., "Generation of C5a in the absence of C3: a new complement activation pathway," *Nat. Med.* 12:682-687 (2006)) In depth studies revealed that C3-independent activation of terminal complement components is mediated by thrombin, the rate limiting enzyme of the coagulation cascade. (Huber et al., 2006) The molecular components mediating thrombin activation following initial complement activation remained elusive.

The present inventors have elucidated what is believed to be the molecular basis for cross-talk between complement and clotting cascades and identified MASP-2 as a central control point linking the two systems. Biochemical studies into the substrate specificity of MASP-2 have identified prothrombin as a possible substrate, in addition to the well known C2 and C4 complement proteins. MASP-2 specifically cleaves prothrombin at functionally relevant sites, generating thrombin, the rate limiting enzyme of the coagulation cascade. (Krarup, A., et al., "Simultaneous Activation of Complement and Coagulation by MBL-Associated Serine Protease 2," *PLoS. ONE.* 2:e623 (2007)) MASP-2-generated thrombin is capable of promoting fibrin deposition in a defined reconstituted in vitro system, demonstrating the functional relevance of MASP-2 cleavage. (Krarup et al., 2007) As discussed in the examples herein below, the inventors have further corroborated the physiological significance of this discovery by documenting thrombin activation in normal rodent serum following lectin pathway activation, and demonstrated that this process is blocked by neutralizing MASP-2 monoclonal antibodies.

MASP-2 may represent a central branch point in the lectin pathway, capable of promoting activation of both complement and coagulation systems. Because lectin pathway activation is a physiologic response to many types of traumatic injury, the present inventors believe that concurrent systemic inflammation (mediated by complement components) and disseminated coagulation (mediated via the clotting pathway) can be explained by the capacity of MASP-2 to activate both pathways. These findings clearly suggest a role for MASP-2 in DIC generation and therapeutic benefit of MASP-2 inhibition in treating or preventing DIC. MASP-2 may provide the molecular link between complement and coagulation system, and activation of the lectin pathway as it occurs in settings of trauma can directly initiate activation of the clotting system via the MASP-2-thrombin axis, providing a mechanistic link between trauma and DIC. In accordance with an aspect of the present invention, inhibition of MASP-2 would inhibit lectin pathway activation and reduce the generation of both anaphylatoxins C3a and C5a. It is believed that prolonged elevation of C3 activation is necessary to generate DIC.

Therefore, an aspect of the invention thus provides a method for inhibiting MASP-2-dependent complement activation to treat disseminated intravascular coagulation or other complement mediated coagulation disorder by administering a composition comprising a therapeutically effective amount of a MASP-2 inhibitory agent (e.g., anti-MASP-2 antibody or fragment thereof, peptide inhibitors or small molecule inhibitors) in a pharmaceutical carrier to a subject suffering from or at risk for developing such a condition. In some embodiments, the MASP-2 inhibitory agents can block MASP-2 that has already been activated. The MASP-2 inhibitory composition is suitably administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled. The methods of this aspect of the present invention may be utilized for treatment of DIC secondary to sepsis, severe trauma, including neurological trauma (e.g., acute head injury, see Kumura, E., et al., *Acta Neurochirurgica* 85:23-28 (1987), infection (bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, accidental radiation exposure, and other causes. See e.g., Becker J. U. and Wira C. R. "Disseminated Intravascular Coagulation" emedicine.medscape.com/9/10/ 2009. For DIC secondary to trauma or other acute event, the MASP-2 inhibitory composition may be administered immediately following the traumatic injury or prophylactically prior to, during, immediately following, or within one to seven days or longer, such as within 24 hours to 72 hours, after trauma-inducing injury or situations such as surgery in patients deemed at risk of DIC. In some embodiments, the MASP-2 inhibitory composition may suitably be administered in a fast-acting dosage form, such as by intravenous or intra-arterial delivery of a bolus of a solution containing the MASP-2 inhibitory agent composition.

In another aspect, the present invention provides methods of treating a subject suffering from or at risk for developing thrombosis, microcirculatory coagulation or multi-organ failure subsequent to microcirculatory coagulation. Physiological thrombus (blood clot) forms in response to vascular insult to prevent leakage of blood from a damaged blood vessel. The lectin pathway may play a role in pathological thrombosis triggered by an underlying vascular inflammation linked to various etiologies. For example, a thrombus can form around atherosclerotic plaques, which is a known initiator of the lectin pathway. Thus, treatment with a MASP-2 inhibitor may be used to block thrombus formation in patients with underlying atherosceloris.

Figure 16A:
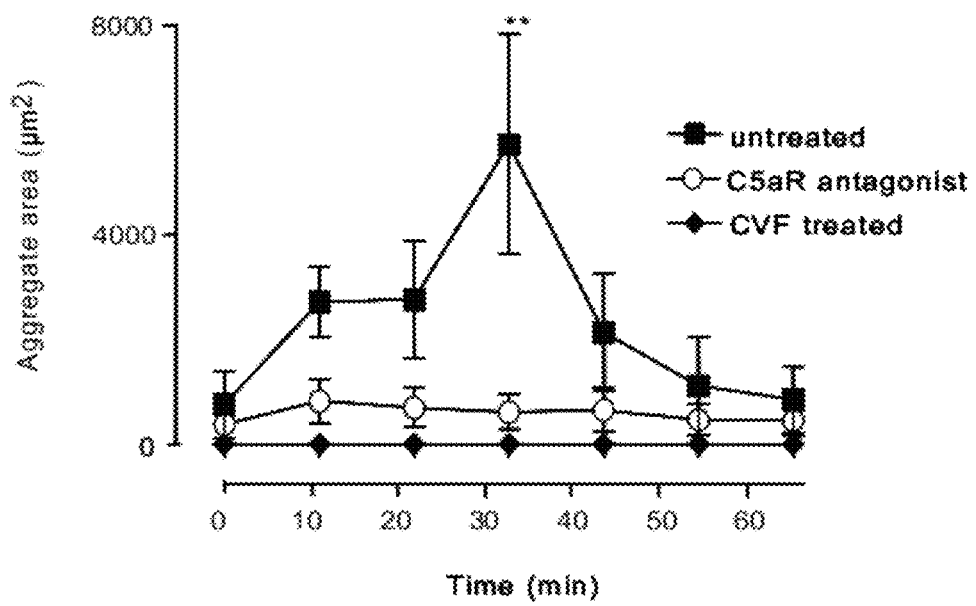
FIGS. 16A and 16B present measured platelet aggregation (expressed as aggregate area) in MASP-2 (−/−) mice (FIG. 16B) as compared to platelet aggregation in untreated wild type mice and wild type mice in which the complement pathway is inhibited by depletory agent cobra venom factor (CVF) and a terminal pathway inhibitor (C5aR antagonist) (FIG. 16A) in a localized Schwartzman reaction model of disseminated intravascular coagulation, as described in Example 15.
Figure 16B:
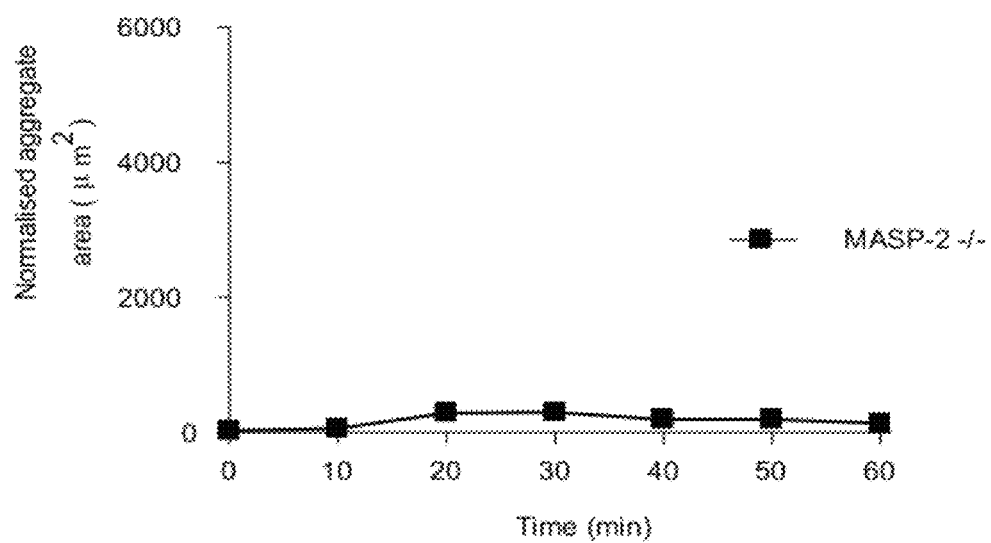

Microcirculatory coagulation (blot clots in capillaries and small blood vessels) occurs in settings such a septic shock. A role of the lectin pathway in septic shock is established, as evidenced by the protected phenotype of MASP-2 (−/−) mouse models of sepsis, described in Example 17 and FIGS. 18 and 19. Furthermore, as demonstrated in Example 15 and FIGS. 16A and 16B, MASP-2 (−/−) mice are protected in the localized Schwartzman reaction model of disseminated intravascular coagulation (DIC), a model of localized coagulation in microvessels.

Perichemotherapeutic Administration and Treatment of Malignancies

Activation of the complement system may also be implicated in the pathogenesis of malignancies. Recently, the neoantigens of the C5b-9 complement complex, IgG, C3, C4, S-protein/vitronectin, fibronectin, and macrophages were localized on 17 samples of breast cancer and on 6 samples of benign breast tumors using polyclonal or monoclonal antibodies and the streptavidin-biotin-peroxidase technique. All the tissue samples with carcinoma in each the TNM stages presented C5b-9 deposits on the membranes of tumor cells, thin granules on cell remnants, and diffuse deposits in the necrotic areas (Niculescu, F., et al., *Am. J. Pathol.* 140:1039-1043, 1992).

In addition, complement activation may be a consequence of chemotherapy or radiation therapy and thus inhibition of complement activation would be useful as an adjunct in the treatment of malignancies to reduce iatrogenic inflammation. When chemotherapy and radiation therapy preceded surgery, C5b-9 deposits were more intense and extended. The C5b-9 deposits were absent in all the samples with benign lesions. S-protein/vitronectin was present as fibrillar deposits in the connective tissue matrix and as diffuse deposits around the tumor cells, less intense and extended than fibronectin. IgG, C3, and C4 deposits were present only in carcinoma samples. The presence of C5b-9 deposits is indicative of complement activation and its subsequent pathogenetic effects in breast cancer (Niculescu, F., et al., *Am. J. Pathol.* 140:1039-1043, 1992).

Pulsed tunable dye laser (577 nm) (PTDL) therapy induces hemoglobin coagulation and tissue necrosis, which is mainly limited to blood vessels. In a PTDL-irradiated normal skin study, the main findings were as follows: 1) C3 fragments, C8, C9, and MAC were deposited in vessel walls; 2) these deposits were not due to denaturation of the proteins since they became apparent only 7 min after irradiation, contrary to immediate deposition of transferrin at the sites of erythrocyte coagulates; 3) the C3 deposits were shown to amplify complement activation by the alternative pathway, a reaction which was specific since tissue necrosis itself did not lead to such amplification; and 4) these reactions preceded the local accumulation of polymorphonuclear leucocytes. Tissue necrosis was more pronounced in the hemangiomas. The larger angiomatous vessels in the center of the necrosis did not fix complement significantly. By contrast, complement deposition in the vessels situated at the periphery was similar to that observed in normal skin with one exception: C8, C9, and MAC were detected in some blood vessels immediately after laser treatment, a finding consistent with assembly of the MAC occurring directly without the formation of a C5 convertase. These results indicate that complement is activated in PTDL-induced vascular necrosis, and might be responsible for the ensuing inflammatory response.

Photodynamic therapy (PDT) of tumors elicits a strong host immune response, and one of its manifestations is a pronounced neutrophilia. In addition to complement fragments (direct mediators) released as a consequence of PDT-induced complement activation, there are at least a dozen secondary mediators that all arise as a result of complement activity. The latter include cytokines IL-1beta, TNF-alpha, IL-6, IL-10, G-CSF and KC, thromboxane, prostaglandins, leukotrienes, histamine, and coagulation factors (Cecic, I., et al., *Cancer Lett.* 183:43-51, 2002).

Finally, the use of inhibitors of MASP-2-dependent complement activation may be envisioned in conjunction with the standard therapeutic regimen for the treatment of cancer. For example, treatment with rituximab, a chimeric anti-CD20 monoclonal antibody, can be associated with moderate to severe first-dose side-effects, notably in patients with high numbers of circulating tumor cells. Recent studies during the first infusion of rituximab measured complement activation products (C3b/c and C4b/c) and cytokines (tumour necrosis factor alpha (TNF-alpha), interleukin 6 (IL-6) and IL-8) in five relapsed low-grade non-Hodgkin's lymphoma (NHL) patients. Infusion of rituximab induced rapid complement activation, preceding the release of TNF-alpha, IL-6 and IL-8. Although the study group was small, the level of complement activation appeared to be correlated both with the number of circulating B cells prior to the infusion (r=0.85; P=0.07), and with the severity of the side-effects. The results indicated that complement plays a pivotal role in the pathogenesis of side-effects of rituximab treatment. As complement activation cannot be prevented by corticosteroids, it may be relevant to study the possible role of complement inhibitors during the first administration of rituximab (van der Kolk, L. E., et al., *Br. J. Haematol.* 115:807-811, 2001).

In another aspect of the invention, methods are provided for inhibiting MASP-2-dependent complement activation in a subject being treated with chemotherapeutics and/or radiation therapy, including without limitation for the treatment of cancerous conditions. This method includes administering a composition comprising a therapeutically effective amount of a MASP-2 inhibitor in a pharmaceutical carrier to a patient perichemotherapeutically, i.e., before and/or during and/or after the administration of chemotherapeutic(s) and/or radiation therapy. For example, administration of a MASP-2 inhibitor composition of the present invention may be commenced before or concurrently with the administration of chemo- or radiation therapy, and continued throughout the course of therapy, to reduce the detrimental effects of the chemo- and/or radiation therapy in the non-targeted, healthy tissues. In addition, the MASP-2 inhibitor composition can be administered following chemo- and/or radiation therapy. It is understood that chemo- and radiation therapy regimens often entail repeated treatments and, therefore, it is possible that administration of a MASP-2 inhibitor composition would also be repetitive and relatively coincident with the chemotherapeutic and radiation treatments. It is also believed that MASP-2 inhibitory agents may be used as chemotherapeutic agents, alone or in combination with other chemotherapeutic agents and/or radiation therapy, to treat patients suffering from malignancies. Administration may suitably be via oral (for non-peptidergic), intravenous, intramuscular or other parenteral route.

In another embodiment, MASP-2 inhibitory agents may be used to treat a subject for acute radiation syndrome (also known as radiation sickness or radiation poisoning) to reduce the detrimental effects of exposure to ionizing radiation (accidental or otherwise). Symptoms associated with acute radiation syndrome include nausea, vomiting, diarrhea, skin damage, hair loss, fatigue, fever, seizures and coma. For treatment of acute radiation syndrome, the MASP-2 inhibitory composition may be administered immediately following the radiation exposure or prophylactically prior to, during, immediately following, or within one to seven days or longer, such as within 24 hours to 72 hours, after exposure. In some embodiments, the methods may be used to treat a subject prior to or after exposure to a dosage of ionizing radiation sufficient to cause acute radiation syndrome (i.e. a whole body dosage of ionizing radiation of at least 1 Gy, or at least 2 Gy, or at least 3 Gy, or at least 4 Gy, or at least 5 Gy, or at least 6 Gy, or at least 7 Gy, or higher). In some embodiments, the MASP-2 inhibitory composition may suitably be administered in a fast-acting dosage form, such as by intravenous or intra-arterial delivery of a bolus of a solution containing the MASP-2 inhibitory agent composition.

Ophthalmologic Conditions

Age-related macular degeneration (AMD) is a blinding disease that afflicts millions of adults, yet the sequelae of biochemical, cellular, and/or molecular events leading to the development of AMD are poorly understood. AMD results in the progressive destruction of the macula which has been correlated with the formation of extracellular deposits called drusen located in and around the macula, behind the retina and between the retina pigment epithelium (RPE) and the choroid. Recent studies have revealed that proteins associated with inflammation and immune-mediated processes are prevalent among drusen-associated constituents. Transcripts that encode a number of these molecules have been detected in retinal, RPE, and choroidal cells. These data also demonstrate that dendritic cells, which are potent antigen-presenting cells, are intimately associated with drusen development, and that complement activation is a key pathway that is active both within drusen and along the RPE-choroid interface (Hageman, G. S., et al., *Prog. Retin. Eye Res.* 20:705-732, 2001).

Several independent studies have shown a strong association between AMD and a genetic polymorphism in the gene for complement factor H(CFH) in which the likelihood of AMD is increased by a factor of 7.4 in individuals homozygous for the risk allele (Klein, R. J. et al., *Science* 308:362-364, 2005; Haines et al., *Science* 308:362-364. 2005; Edwards et al., *Science* 308:263-264, 2005). The CFH gene has been mapped to chromosome 1q31 a region that had been implicated in AMD by six independent linkage scans (see, e.g., Schultz, D. W., et al., *Hum. Mol. Genet.* 12:3315, 2003). CFH is known to be a key regulator of the complement system. It has been shown that CFH on cells and in circulation regulates complement activity by inhibiting the activation of C3 to C3a and C3b, and by inactivating existing C3b. Deposition of C5b-9 has been observed in Brusch's membrane, the intercapillary pillars and within drusen in patients with AMD (Klein et al.). Immunofluorescence experiments suggest that in AMD, the polymorphism of CFH may give rise to complement deposition in chorodial capillaries and chorodial vessels (Klein et al.).

The membrane-associated complement inhibitor, complement receptor 1, is also localized in drusen, but it is not detected in RPE cells immunohistochemically. In contrast, a second membrane-associated complement inhibitor, membrane cofactor protein, is present in drusen-associated RPE cells, as well as in small, spherical substructural elements within drusen. These previously unidentified elements also show strong immunoreactivity for proteolytic fragments of complement component C3 that are characteristically deposited at sites of complement activation. It is proposed that these structures represent residual debris from degenerating RPE Cells that are the targets of complement attack (Johnson, L. V., et al., *Exp. Eye Res.* 73:887-896, 2001).

Identification and localization of these multiple complement regulators as well as complement activation products (C3a, C5a, C3b, C5b-9) have led investigators to conclude that chronic complement activation plays an important role in the process of drusen biogenesis and the etiology of AMD (Hageman et al., *Progress Retinal Eye Res.* 20:705-32, 2001). Identification of C3 and C5 activation products in drusen provides no insight into whether complement is activated via the classical pathway, the lectin pathway or the alternative amplification loop, as understood in accordance with the present invention, since both C3 and C5 are common to all three. However, two studies have looked for drusen immuno-labeling using antibodies specific to C1q, the essential recognition component for activation of the classical pathway (Mullins et al., *FASEB J.* 14:835-846, 2000; Johnson et al., *Exp. Eye Res.* 70:441-449, 2000). Both studies concluded that C1q immuno-labelling in drusen was not generally observed. These negative results with C1q suggest that complement activation in drusen does not occur via the classical pathway. In addition, immuno-labeling of drusen for immune-complex constituents (IgG light chains, IgM) is reported in the Mullins et al., 2000 study as being weak to variable, further indicating that the classical pathway plays a minor role in the complement activation that occurs in this disease process.

Two recent published studies have evaluated the role of complement in the development of laser-induced choroidal neovascularization (CNV) in mice, a model of human CNV. Using immunohistological methods, Bora and colleagues (2005) found significant deposition of the complement activation products C3b and C5b-9 (MAC) in the neovascular complex following laser treatment (Bora et al., *J. Immunol.* 174:491-7, 2005). Importantly, CNV did not develop in mice genetically deficient in C3 (C3−/− mice), the essential component required in all complement activation pathways. RNA message levels for VEGF, TGF-$\beta_2$, and β-FGF, three angiogenic factors implicated in CNV, were elevated in eye tissue from mice after laser-induced CNV. Significantly, complement depletion resulted in a marked reduction in the RNA levels of these angiogenic factors.

Using ELISA methods, Nozaki and colleagues demonstrated that the potent anaphylatoxins C3a and C5a are generated early in the course of laser-induced CNV (Nozaki et al., *Proc. Natl. Acad. Sci. U.S.A.* 103:2328-33, 2006). Furthermore, these two bioactive fragments of C3 and C5 induced VEGF expression following intravitreal injection in wild-type mice. Consistent with these results Nozaki and colleagues also showed that genetic ablation of receptors for C3a and C5a reduces VEGF expression and CNV formation after laser injury, and that antibody-mediated neutralization of C3a or C5a or pharmacologic blockade of their receptors also reduces CNV. Previous studies have established that recruitment of leukocytes, and macrophages in particular, plays a pivotal role in laser-induced CNV (Sakurai et al., *Invest. Opthomol. Vis. Sci.* 44:3578-85, 2003; Espinosa-Heidmann, et al., *Invest. Opthomol. Vis. Sci.* 44:3586-92, 2003). In their 2006 paper, Nozaki and colleagues report that leukocyte recruitment is markedly reduced in C3aR(−/−) and C5aR(−/−) mice after laser injury.

An aspect of the invention thus provides a method for inhibiting MASP-2-dependent complement activation to treat age-related macular degeneration or other complement mediated ophthalmologic condition by administering a composition comprising a therapeutically effective amount of a MASP-2 inhibitory agent in a pharmaceutical carrier to a subject suffering from such a condition or other complement-mediated ophthalmologic condition. The MASP-2 inhibitory composition may be administered locally to the eye, such as by irrigation or application of the composition in the form of a gel, salve or drops. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. The MASP-2 inhibitory agent composition may be combined with one or more additional therapeutic agents, such as are disclosed in U.S. Patent Application Publication No. 2004-0072809-A1. Administration may be repeated as determined by a physician until the condition has been resolved or is controlled.

In another aspect, the invention provides a method for inhibiting MASP-2-dependent complement activation to treat a subject suffering from or at risk for developing glaucoma. It has been shown that uncontrolled complement activation contributes to the progression of degenerative injury to retinal ganglion cells (RGCs), their synapses and axons in glaucoma. See Tezel G. et al., *Invest Ophihalmol Vis Sci* 51:5071-5082 (2010). For example, histopathologic studies of human tissues and in vivo studies using different animal models have demonstrated that complement components, including C1q and C3, are synthesized and terminal complement complex is formed in the glaucomatous retina (see Stasi K. et al., *Invest Ophthalmol Vis Sci* 47:1024-1029 (2006), Kuehn M. H. et al., *Exp Eye Res* 83:620-628 (2006)). As described in Tezel G. et al., it has been determined that in addition to the classical pathway, the lectin pathway is likely to be involved in complement activation during glaucomatous neurodegeneration, thereby facilitating the progression of neurodegenerative injury by collateral cell lysis, inflammation and autoimmunity. As described in Tezel G. et al., proteomic analysis of human retinal samples obtained from donor eyes with or without glaucoma detected the expression and differential regulation of several complement components. Notably, expression levels of complement components from the lectin pathway were higher, or only detected, in glaucomatous samples than controls, including MASP-1 and MASP-2, and C-type lectin. As further described in Kuehn M. H. et al., *Experimental Eye Research* 87:89-95 (2008), complement synthesis and deposition is induced by retinal I/R and the disruption of the complement cascade delays RGC degeneration. In this study, mice carrying a targeted disruption of the complement component C3 were found to exhibit delayed RGC degeneration after transient retinal I/R when compared to normal animals.

The findings of these studies suggest that alterations in the physiological balance between complement activation and intrinsic regulation under glaucomatous stress conditions may have an important impact on the progression of neurodegenerative injury, indicating that inhibition of complement activation, such as through the administration of anti-MASP-2 antibodies, can be used as a therapeutic for glaucoma patients.

An aspect of the invention thus provides a method for inhibiting MASP-2-dependent complement activation to treat glaucoma by administering a composition comprising a therapeutically effective amount of a MASP-2 inhibitory agent in a pharmaceutical carrier to a subject suffering from glaucoma. The MASP-2 inhibitory composition may be administered locally to the eye, such as by irrigation or application of the composition in the form of a gel, salve or drops.

Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

IV. MASP-2 INHIBITORY AGENTS

In one aspect, the present invention provides methods of inhibiting the adverse effects of MASP-2-dependent complement activation. MASP-2 inhibitory agents are administered in an amount effective to inhibit MASP-2-dependent complement activation in a living subject. In the practice of this aspect of the invention, representative MASP-2 inhibitory agents include: molecules that inhibit the biological activity of MASP-2 (such as small molecule inhibitors, anti-MASP-2 antibodies or blocking peptides which interact with MASP-2 or interfere with a protein-protein interaction), and molecules that decrease the expression of MASP-2 (such as MASP-2 antisense nucleic acid molecules, MASP-2 specific RNAi molecules and MASP-2 ribozymes), thereby preventing MASP-2 from activating the lectin complement pathway. The MASP-2 inhibitory agents can be used alone as a primary therapy or in combination with other therapeutics as an adjuvant therapy to enhance the therapeutic benefits of other medical treatments.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in Example 2), the reduction of complement activation assessed in a hemolytic assay using unsensitized rabbit or guinea pig red blood cells (measured, for example as described in Example 33), the reduction of C4 cleavage and C4b deposition (measured, for example as described in Example 2), or the reduction of C3 cleavage and C3b deposition (measured, for example as described in Example 2).

According to the present invention, MASP-2 inhibitory agents are utilized that are effective in inhibiting the MASP-2-dependent complement activation system. MASP-2 inhibitory agents useful in the practice of this aspect of the invention include, for example, anti-MASP-2 antibodies and fragments thereof, MASP-2 inhibitory peptides, small molecules, MASP-2 soluble receptors and expression inhibitors. MASP-2 inhibitory agents may inhibit the MASP-2-dependent complement activation system by blocking the biological function of MASP-2. For example, an inhibitory agent may effectively block MASP-2 protein-to-protein interactions, interfere with MASP-2 dimerization or assembly, block $Ca^{2+}$ binding, interfere with the MASP-2 serine protease active site, or may reduce MASP-2 protein expression.

In some embodiments, the MASP-2 inhibitory agents selectively inhibit MASP-2 complement activation, leaving the C1q-dependent complement activation system functionally intact.

In one embodiment, a MASP-2 inhibitory agent useful in the methods of the invention is a specific MASP-2 inhibitory agent that specifically binds to a polypeptide comprising SEQ ID NO:6 with an affinity of at least ten times greater than to other antigens in the complement system. In another embodiment, a MASP-2 inhibitory agent specifically binds to a polypeptide comprising SEQ ID NO:6 with a binding affinity of at least 100 times greater than to other antigens in the complement system. The binding affinity of the MASP-2 inhibitory agent can be determined using a suitable binding assay.

The MASP-2 polypeptide exhibits a molecular structure similar to MASP-1, MASP-3, and C1r and C1s, the proteases of the C1 complement system. The cDNA molecule set forth in SEQ ID NO:4 encodes a representative example of MASP-2 (consisting of the amino acid sequence set forth in SEQ ID NO:5) and provides the human MASP-2 polypeptide with a leader sequence (aa 1-15) that is cleaved after secretion, resulting in the mature form of human MASP-2 (SEQ ID NO:6). As shown in FIG. 2, the human MASP-2 gene encompasses twelve exons. The human MASP-2 cDNA is encoded by exons B, C, D, F, G, H, I, J, K AND L. An alternative splice results in a 20 kDa protein termed MBL-associated protein 19 ("MAp19", also referred to as "sMAP") (SEQ ID NO:2), encoded by (SEQ ID NO:1) arising from exons B, C, D and E as shown in FIG. 2. The cDNA molecule set forth in SEQ ID NO:50 encodes the murine MASP-2 (consisting of the amino acid sequence set forth in SEQ ID NO:51) and provides the murine MASP-2 polypeptide with a leader sequence that is cleaved after secretion, resulting in the mature form of murine MASP-2 (SEQ ID NO:52). The cDNA molecule set forth in SEQ ID NO:53 encodes the rat MASP-2 (consisting of the amino acid sequence set forth in SEQ ID NO:54) and provides the rat MASP-2 polypeptide with a leader sequence that is cleaved after secretion, resulting in the mature form of rat MASP-2 (SEQ ID NO:55).

Those skilled in the art will recognize that the sequences disclosed in SEQ ID NO:4, SEQ ID NO:50 and SEQ ID NO:53 represent single alleles of human, murine and rat MASP-2 respectively, and that allelic variation and alternative splicing are expected to occur. Allelic variants of the nucleotide sequences shown in SEQ ID NO:4, SEQ ID NO:50 and SEQ ID NO:53, including those containing silent mutations and those in which mutations result in amino acid sequence changes, are within the scope of the present invention. Allelic variants of the MASP-2 sequence can be cloned by probing cDNA or genomic libraries from different individuals according to standard procedures.

The domains of the human MASP-2 protein (SEQ ID NO:6) are shown in FIGS. 1 and 2A and include an N-terminal C1r/C1s/sea urchin Vegf/bone morphogenic protein (CUBI) domain (aa 1-121 of SEQ ID NO:6), an epidermal growth factor-like domain (aa 122-166), a second CUBI domain (aa 167-293), as well as a tandem of complement control protein domains and a serine protease domain. Alternative splicing of the MASP 2 gene results in MAp19 shown in FIG. 1. MAp19 is a nonenzymatic protein containing the N-terminal CUBI-EGF region of MASP-2 with four additional residues (EQSL) derived from exon E as shown in FIG. 1.

Several proteins have been shown to bind to, or interact with MASP-2 through protein-to-protein interactions. For example, MASP-2 is known to bind to, and form $Ca^{2+}$ dependent complexes with, the lectin proteins MBL, H-ficolin and L-ficolin. Each MASP-2/lectin complex has been shown to activate complement through the MASP-2-dependent cleavage of proteins C4 and C2 (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). Studies have shown that the CUBI-EGF domains of MASP-2 are essential for the association of MASP-2 with MBL (Thielens, N. M., et al., *J. Immunol.* 166:5068, 2001). It has also been shown that the CUBIEG-FCUBII domains mediate dimerization of MASP-2, which is required for formation of an active MBL complex (Wallis, R., et al., *J. Biol. Chem.* 275:30962-30969, 2000). Therefore, MASP-2 inhibitory agents can be identified that bind to or interfere with MASP-2 target regions known to be important for MASP-2-dependent complement activation.

Anti-MASP-2 Antibodies

In some embodiments of this aspect of the invention, the MASP-2 inhibitory agent comprises an anti-MASP-2 antibody that inhibits the MASP-2-dependent complement activation system. The anti-MASP-2 antibodies useful in this aspect of the invention include polyclonal, monoclonal or recombinant antibodies derived from any antibody producing mammal and may be multispecific, chimeric, humanized, anti-idiotype, and antibody fragments. Antibody fragments include Fab, Fab', F(ab)$_2$, F(ab')$_2$, Fv fragments, scFv fragments and single-chain antibodies as further described herein.

Several anti-MASP-2 antibodies have been described in the literature, some of which are listed below in TABLE 1. These previously described anti-MASP-2 antibodies can be screened for the ability to inhibit the MASP-2-dependent complement activation system using the assays described herein. For example, anti rat MASP-2 Fab2 antibodies have been identified that block MASP-2 dependent complement activation, as described in more detail in Examples 10 and 11 herein. Once an anti-MASP-2 antibody is identified that functions as a MASP-2 inhibitory agent, it can be used to produce anti-idiotype antibodies and used to identify other MASP-2 binding molecules as further described below.

TABLE 1

MASP-2 SPECIFIC ANTIBODIES FROM THE LITERATURE

| ANTIGEN | ANTIBODY TYPE | REFERENCE |
|---|---|---|
| Recombinant MASP-2 | Rat Polyclonal | Peterson, S.V., et al., Mol. Immunol. 37:803-811, 2000 |
| Recombinant human CCP1/ 2-SP fragment (MoAb 8B5) | Rat MoAb (subclass IgG1) | Moller-Kristensen, M., et al., J. of Immunol. Methods 282:159-167, 2003 |
| Recombinant human MAp19 (MoAb 6G12) (cross reacts with MASP-2) | Rat MoAb (subclass IgG1) | Moller-Kristensen, M., et al., J. of Immunol. Methods 282:159-167, 2003 |
| hMASP-2 | Mouse MoAb (S/P) Mouse MoAb (N-term) | Peterson, S.V., et al., Mol. Immunol. 35:409, April 1998 |
| hMASP-2 (CCP1-CCP2-SP domain | rat MoAb: Nimoab101, produced by hybridoma cell line 03050904 (ECACC) | WO 2004/106384 |
| hMASP-2 (full length-his tagged) | murine MoAbs: NimoAb104, produced by hybridoma cell line M0545YM035 (DSMZ) NimoAb108, produced by hybridoma cell line M0545YM029 (DSMZ) NimoAb109 produced by hybridoma cell line M0545YM046 (DSMZ) NimoAb110 produced by hybridoma cell line M0545YM048 (DSMZ) | WO 2004/106384 |

Anti-MASP-2 Antibodies with Reduced Effector Function

In some embodiments of this aspect of the invention, the anti-MASP-2 antibodies have reduced effector function in order to reduce inflammation that may arise from the activation of the classical complement pathway. The ability of IgG molecules to trigger the classical complement pathway has been shown to reside within the Fc portion of the molecule (Duncan, A. R., et al., Nature 332:738-740 1988). IgG molecules in which the Fc portion of the molecule has been removed by enzymatic cleavage are devoid of this effector function (see Harlow, Antibodies: A Laboratory Manual, Cold Spring Harbor Laboratory, New York, 1988). Accordingly, antibodies with reduced effector function can be generated as the result of lacking the Fc portion of the molecule by having a genetically engineered Fc sequence that minimizes effector function, or being of either the human IgG$_2$ or IgG$_4$ isotype.

Antibodies with reduced effector function can be produced by standard molecular biological manipulation of the Fc portion of the IgG heavy chains as described in Example 9 herein and also described in Jolliffe et al., Int'l Rev. Immunol. 10:241-250, 1993, and Rodrigues et al., J. Immunol. 151: 6954-6961, 1998. Antibodies with reduced effector function also include human IgG2 and IgG4 isotypes that have a reduced ability to activate complement and/or interact with Fc receptors (Ravetch, J. V., et al., Annu. Rev. Immunol. 9:457-492, 1991; Isaacs, J. D., et al., J. Immunol. 148:3062-3071, 1992; van de Winkel, J. G., et al., Immunol. Today 14:215-221, 1993). Humanized or fully human antibodies specific to human MASP-2 comprised of IgG2 or IgG4 isotypes can be produced by one of several methods known to one of ordinary skilled in the art, as described in Vaughan, T. J., et al., Nature Biotechnical 16:535-539, 1998.

Production of Anti-MASP-2 Antibodies

Anti-MASP-2 antibodies can be produced using MASP-2 polypeptides (e.g., full length MASP-2) or using antigenic MASP-2 epitope-bearing peptides (e.g., a portion of the MASP-2 polypeptide). Immunogenic peptides may be as small as five amino acid residues. For example, the MASP-2 polypeptide including the entire amino acid sequence of SEQ ID NO:6 may be used to induce anti-MASP-2 antibodies useful in the method of the invention. Particular MASP-2 domains known to be involved in protein-protein interactions, such as the CUBI, and CUBIEGF domains, as well as the region encompassing the serine-protease active site, may be expressed as recombinant polypeptides as described in Example 3 and used as antigens. In addition, peptides comprising a portion of at least 6 amino acids of the MASP-2 polypeptide (SEQ ID NO:6) are also useful to induce MASP-2 antibodies. Additional examples of MASP-2 derived antigens useful to induce MASP-2 antibodies are provided below in TABLE 2. The MASP-2 peptides and polypeptides used to raise antibodies may be isolated as natural polypeptides, or recombinant or synthetic peptides and catalytically inactive recombinant polypeptides, such as MASP-2A, as further described in Examples 5-7. In some embodiments of this aspect of the invention, anti-MASP-2 antibodies are obtained using a transgenic mouse strain as described in Examples 8 and 9 and further described below.

Antigens useful for producing anti-MASP-2 antibodies also include fusion polypeptides, such as fusions of MASP-2 or a portion thereof with an immunoglobulin polypeptide or with maltose-binding protein. The polypeptide immunogen may be a full-length molecule or a portion thereof. If the polypeptide portion is hapten-like, such portion may be advantageously joined or linked to a macromolecular carrier (such as keyhole limpet hemocyanin (KLH), bovine serum albumin (BSA) or tetanus toxoid) for immunization.

TABLE 2

MASP-2 DERIVED ANTIGENS

| SEQ ID NO: | Amino Acid Sequence |
|---|---|
| SEQ ID NO: 6 | Human MASP-2 protein |
| SEQ ID NO: 51 | Murine MASP-2 protein |
| SEQ ID NO: 8 | CUBI domain of human MASP-2 (aa 1-121 of SEQ ID NO: 6) |
| SEQ ID NO: 9 | CUBIEGF domains of human MASP-2 (aa 1-166 of SEQ ID NO: 6) |
| SEQ ID NO: 10 | CUBIEGFCUBII domains of human MASP-2 (aa 1-293 of SEQ ID NO: 6) |
| SEQ ID NO: 11 | EGF domain of human MASP-2 (aa 122-166 of SEQ ID NO: 6) |
| SEQ ID NO: 12 | Serine-Protease domain of human MASP-2 (aa 429-671 of SEQ ID NO: 6) |
| SEQ ID NO: 13 GKDSCRGDAGGALVFL | Serine-Protease inactivated mutant form (aa 610-625 of SEQ ID NO: 6 with mutated Ser 618) |
| SEQ ID NO: 14 TPLGPKWPEPVFGRL | Human CUBI peptide |
| SEQ ID NO: 15: TAPPGYRLRLYFTHFDLEL SHLCEYDFVKLSSGAKVL ATLCGQ | Human CUBI peptide |
| SEQ ID NO: 16: TFRSDYSN | MBL binding region in human CUBI domain |
| SEQ ID NO: 17: FYSLGSSLDITFRSDYSNEK PFTGF | MBL binding region in human CUBI domain |
| SEQ ID NO: 18 IDECQVAPG | EGF peptide |
| SEQ ID NO: 19 ANMLCAGLESGGKDSCRG DSGGALV | Peptide from serine-protease active site |

Polyclonal Antibodies

Polyclonal antibodies against MASP-2 can be prepared by immunizing an animal with MASP-2 polypeptide or an immunogenic portion thereof using methods well known to those of ordinary skill in the art. See, for example, Green et al., "Production of Polyclonal Antisera," in *Immunochemical Protocols* (Manson, ed.), page 105, and as further described in Example 6. The immunogenicity of a MASP-2 polypeptide can be increased through the use of an adjuvant, including mineral gels, such as aluminum hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as horses, cows, dogs, chicken, rats, mice, rabbits, guinea pigs, goats, or sheep. Alternatively, an anti-MASP-2 antibody useful in the present invention may also be derived from a subhuman primate. General techniques for raising diagnostically and therapeutically useful antibodies in baboons may be found, for example, in Goldenberg et al., International Patent Publication No. WO 91/11465, and in Losman, M. J., et al., *Int. J. Cancer* 46:310, 1990. Sera containing immunologically active antibodies are then produced from the blood of such immunized animals using standard procedures well known in the art.

Monoclonal Antibodies

In some embodiments, the MASP-2 inhibitory agent is an anti-MASP-2 monoclonal antibody. Anti-MASP-2 monoclonal antibodies are highly specific, being directed against a single MASP-2 epitope. As used herein, the modifier "monoclonal" indicates the character of the antibody as being obtained from a substantially homogenous population of antibodies, and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-2 polypeptide or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-2. An example further describing the production of anti-MASP-2 monoclonal antibodies is provided in Example 7. (See also *Current Protocols in Immunology*, Vol. 1., John Wiley & Sons, pages 2.5.1-2.6.7, 1991.)

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology as further described in Example 7. Transgenic mice with a human immunoglobulin genome are commercially available (e.g., from Abgenix, Inc., Fremont, Calif., and Medarex, Inc., Annandale, N.J.). Methods for obtaining human antibodies from transgenic mice are described, for example, by Green, L. L., et al., *Nature Genet.* 7:13, 1994; Lonberg, N., et al., *Nature* 368:856, 1994; and Taylor, L. D., et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, The Humana Press, Inc., Vol. 10, pages 79-104, 1992).

Once produced, polyclonal, monoclonal or phage-derived antibodies are first tested for specific MASP-2 binding. A variety of assays known to those skilled in the art may be utilized to detect antibodies which specifically bind to MASP-2. Exemplary assays include Western blot or immunoprecipitation analysis by standard methods (e.g., as described in Ausubel et al.), immunoelectrophoresis, enzyme-linked immuno-sorbent assays, dot blots, inhibition or competition assays and sandwich assays (as described in Harlow and Land, *Antibodies: A Laboratory Manual*, Cold Spring Harbor Laboratory Press, 1988). Once antibodies are identified that specifically bind to MASP-2, the anti-MASP-2 antibodies are tested for the ability to function as a MASP-2 inhibitory agent in one of several assays such as, for example, a lectin-specific C4 cleavage assay (described in Example 2), a C3b deposition assay (described in Example 2) or a C4b deposition assay (described in Example 2).

The affinity of anti-MASP-2 monoclonal antibodies can be readily determined by one of ordinary skill in the art (see, e.g., Scatchard, A., *NY Acad. Sci.* 51:660-672, 1949). In one embodiment, the anti-MASP-2 monoclonal antibodies useful for the methods of the invention bind to MASP-2 with a binding affinity of <100 nM, preferably <10 nM and most preferably <2 nM.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567, to Cabilly; and Morrison, S. L., et al., *Proc. Nat'l Acad. Sci. USA* 81:6851-6855, 1984).

One form of a chimeric antibody useful in the invention is a humanized monoclonal anti-MASP-2 antibody. Humanized forms of non-human (e.g., murine) antibodies are chimeric antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to further refine antibody performance. In general, the humanized antibody will comprise substantially all of at least one, and typically two variable domains, in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fe), typically that of a human immunoglobulin. For further details, see Jones, P. T., et al., *Nature* 321:522-525, 1986; Reichmann, L., et al., *Nature* 332:323-329, 1988; and Presta, *Curr. Op. Struct. Biol.* 2:593-596, 1992.

The humanized antibodies useful in the invention include human monoclonal antibodies including at least a MASP-2 binding CDR3 region. In addition, the Fc portions may be replaced so as to produce IgA or IgM as well as human IgG antibodies. Such humanized antibodies will have particular clinical utility because they will specifically recognize human MASP-2 but will not evoke an immune response in humans against the antibody itself. Consequently, they are better suited for in vivo administration in humans, especially when repeated or long-term administration is necessary.

An example of the generation of a humanized anti-MASP-2 antibody from a murine anti-MASP-2 monoclonal antibody is provided herein in Example 6. Techniques for producing humanized monoclonal antibodies are also described, for example, by Jones, P. T., et al., *Nature* 321:522, 1986; Carter, P., et al., *Proc. Nat'l. Acad. Sci. USA* 89:4285, 1992; Sandhu, J. S., *Crit. Rev. Biotech.* 12:437, 1992; Singer, I. I., et al., *J Immun.* 150:2844, 1993; Sudhir (ed.), *Antibody Engineering Protocols*, Humana Press, Inc., 1995; Kelley, "Engineering Therapeutic Antibodies," in *Protein Engineering: Principles and Practice*, Cleland et al. (eds.), John Wiley & Sons, Inc., pages 399-434, 1996; and by U.S. Pat. No. 5,693,762, to Queen, 1997. In addition, there are commercial entities that will synthesize humanized antibodies from specific murine antibody regions, such as Protein Design Labs (Mountain View, Calif.).

Recombinant Antibodies

Anti-MASP-2 antibodies can also be made using recombinant methods. For example, human antibodies can be made using human immunoglobulin expression libraries (available for example, from Stratagene, Corp., La Jolla, Calif.) to produce fragments of human antibodies ($V_H$, $V_L$, Fv, Fd, Fab or F(ab')$_2$). These fragments are then used to construct whole human antibodies using techniques similar to those for producing chimeric antibodies.

Anti-Idiotype Antibodies

Once anti-MASP-2 antibodies are identified with the desired inhibitory activity, these antibodies can be used to generate anti-idiotype antibodies that resemble a portion of MASP-2 using techniques that are well known in the art. See, e.g., Greenspan, N. S., et al., *FASEB J.* 7:437, 1993. For example, antibodies that bind to MASP-2 and competitively inhibit a MASP-2 protein interaction required for complement activation can be used to generate anti-idiotypes that resemble the MBL binding site on MASP-2 protein and therefore bind and neutralize a binding ligand of MASP-2 such as, for example, MBL.

Immunoglobulin Fragments

The MASP-2 inhibitory agents useful in the method of the invention encompass not only intact immunoglobulin molecules but also the well known fragments including Fab, Fab', F(ab)$_2$, F(ab')$_2$ and Fv fragments, scFv fragments, diabodies, linear antibodies, single-chain antibody molecules and multispecific antibodies formed from antibody fragments.

It is well known in the art that only a small portion of an antibody molecule, the paratope, is involved in the binding of the antibody to its epitope (see, e.g., Clark, W. R., *The Experimental Foundations of Modern Immunology*, Wiley & Sons, Inc., NY, 1986). The pFc' and Fc regions of the antibody are effectors of the classical complement pathway, but are not involved in antigen binding. An antibody from which the pFc' region has been enzymatically cleaved, or which has been produced without the pFc' region, is designated an F(ab')$_2$ fragment and retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331,647 to Goldenberg; Nisonoff, A., et al., *Arch. Biochem. Biophys.* 89:230, 1960; Porter, R. R., *Biochem. J.* 73:119, 1959; Edelman, et al., in *Methods in Enzymology* 1:422, Academic Press, 1967; and by Coligan at pages 2.8.1-2.8.10 and 2.10.-2.10.4.

In some embodiments, the use of antibody fragments lacking the Fc region are preferred to avoid activation of the classical complement pathway which is initiated upon binding Fc to the Fcγ receptor. There are several methods by which one can produce a MoAb that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or F(ab)$_2$ fragments (Mariani, M., et al., *Mol. Immunol.* 28:69-71, 1991). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for MASP-2 in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described for example, by Whitlow, et al., "Methods: A Companion to Methods in Enzymology" 2:97, 1991; Bird, et al., *Science* 242:423, 1988; U.S. Pat. No. 4,946, 778, to Ladner; Pack, P., et al., *Bio/Technology* 11:1271, 1993.

As an illustrative example, a MASP-2 specific scFv can be obtained by exposing lymphocytes to MASP-2 polypeptide in vitro and selecting antibody display libraries in phage or similar vectors (for example, through the use of immobilized or labeled MASP-2 protein or peptide). Genes encoding polypeptides having potential MASP-2 polypeptide binding domains can be obtained by screening random peptide libraries displayed on phage or on bacteria such as *E. coli*. These random peptide display libraries can be used to screen for peptides which interact with MASP-2. Techniques for creating and screening such random peptide display libraries are well known in the art (U.S. Pat. No. 5,223,409, to Lardner; U.S. Pat. No. 4,946,778, to Ladner; U.S. Pat. No. 5,403,484, to Lardner; U.S. Pat. No. 5,571,698, to Lardner; and Kay et al., *Phage Display of Peptides and Proteins* Academic Press, Inc., 1996) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.).

Another form of an anti-MASP-2 antibody fragment useful in this aspect of the invention is a peptide coding for a single complementarity-determining region (CDR) that binds to an epitope on a MASP-2 antigen and inhibits MASP-2-dependent complement activation. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166, Cambridge University Press, 1995; and Ward et al., "Genetic Manipulation and Expression of Antibodies," in *Monoclonal Antibodies: Principles and Applications*, Birch et al. (eds.), page 137, Wiley-Liss, Inc., 1995).

The MASP-2 antibodies described herein are administered to a subject in need thereof to inhibit MASP-2-dependent complement activation. In some embodiments, the MASP-2 inhibitory agent is a high-affinity human or humanized monoclonal anti-MASP-2 antibody with reduced effector function.

Peptide Inhibitors

In some embodiments of this aspect of the invention, the MASP-2 inhibitory agent comprises isolated MASP-2 peptide inhibitors, including isolated natural peptide inhibitors and synthetic peptide inhibitors that inhibit the MASP-2-dependent complement activation system. As used herein, the term "isolated MASP-2 peptide inhibitors" refers to peptides that inhibit MASP-2 dependent complement activation by binding to, competing with MASP-2 for binding to another recognition molecule (e.g., MBL, H-ficolin, M-ficolin, or L-ficolin) in the lectin pathway, and/or directly interacting with MASP-2 to inhibit MASP-2-dependent complement activation that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., European Heart J. 16:50-55, 1995). Short linear peptides (<30 amino acids) have been described that prevent or interfere with integrin-dependent adhesion (Murayama, O., et al., J. Biochem. 120:445-51, 1996). Longer peptides, ranging in length from 25 to 200 amino acid residues, have also been used successfully to block integrin-dependent adhesion (Zhang, L., et al., J. Biol. Chem. 271(47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D.Y., et al., J. Med. Chem. 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592, to Larson).

Synthetic MASP-2 Peptide Inhibitors

MASP-2 inhibitory peptides useful in the methods of this aspect of the invention are exemplified by amino acid sequences that mimic the target regions important for MASP-2 function. The inhibitory peptides useful in the practice of the methods of the invention range in size from about 5 amino acids to about 300 amino acids. TABLE 3 provides a list of exemplary inhibitory peptides that may be useful in the practice of this aspect of the present invention. A candidate MASP-2 inhibitory peptide may be tested for the ability to function as a MASP-2 inhibitory agent in one of several assays including, for example, a lectin specific C4 cleavage assay (described in Example 2), and a C3b deposition assay (described in Example 2).

In some embodiments, the MASP-2 inhibitory peptides are derived from MASP-2 polypeptides and are selected from the full length mature MASP-2 protein (SEQ ID NO:6), or from a particular domain of the MASP-2 protein such as, for example, the CUBI domain (SEQ ID NO:8), the CUBIEGF domain (SEQ ID NO:9), the EGF domain (SEQ ID NO:11), and the serine protease domain (SEQ ID NO:12). As previously described, the CUBEGFCUBII regions have been shown to be required for dimerization and binding with MBL (Thielens et al., supra). In particular, the peptide sequence TFRSDYN (SEQ ID NO:16) in the CUBI domain of MASP-2 has been shown to be involved in binding to MBL in a study that identified a human carrying a homozygous mutation at Asp105 to Gly105, resulting in the loss of MASP-2 from the MBL complex (Stengaard-Pedersen, K., et al., New England J. Med. 349:554-560, 2003).

In some embodiments, MASP-2 inhibitory peptides are derived from the lectin proteins that bind to MASP-2 and are involved in the lectin complement pathway. Several different lectins have been identified that are involved in this pathway, including mannan-binding lectin (MBL), L-ficolin, M-ficolin and H-ficolin. (Ikeda, K., et al., J. Biol. Chem. 262:7451-7454, 1987; Matsushita, M., et al., J. Exp. Med. 176:1497-2284, 2000; Matsushita, M., et al., J. Immunol. 168:3502-3506, 2002). These lectins are present in serum as oligomers of homotrimeric subunits, each having N-terminal collagen-like fibers with carbohydrate recognition domains. These different lectins have been shown to bind to MASP-2, and the lectin/MASP-2 complex activates complement through cleavage of proteins C4 and C2. H-ficolin has an amino-terminal region of 24 amino acids, a collagen-like domain with 11 Gly-Xaa-Yaa repeats, a neck domain of 12 amino acids, and a fibrinogen-like domain of 207 amino acids (Matsushita, M., et al., J. Immunol. 168:3502-3506, 2002). H-ficolin binds to GlcNAc and agglutinates human erythrocytes coated with LPS derived from S. typhimurium, S. minnesota and E. coli. H-ficolin has been shown to be associated with MASP-2 and MAp19 and activates the lectin pathway. Id. L-ficolin/P35 also binds to GlcNAc and has been shown to be associated with MASP-2 and MAp19 in human serum and this complex has been shown to activate the lectin pathway (Matsushita, M., et al., J. Immunol. 164:2281, 2000). Accordingly, MASA-2 inhibitory peptides useful in the present invention may comprise a region of at least 5 amino acids selected from the MBL protein (SEQ ID NO:21), the H-ficolin protein (Genbank accession number NM_173452), the M-ficolin protein (Genbank accession number O00602) and the L-ficolin protein (Genbank accession number NM_015838).

More specifically, scientists have identified the MASP-2 binding site on MBL to be within the 12 Gly-X-Y triplets "GKD GRD GTK GEK GEP GQG LRG LQG POG KLG POG NOG PSG SOG PKG QKG DOG KS" (SEQ ID NO:26) that lie between the hinge and the neck in the C-terminal portion of the collagen-like domain of MBP (Wallis, R., et al., J. Biol. Chem. 279:14065, 2004). This MASP-2 binding site region is also highly conserved in human H-ficolin and human L-ficolin. A consensus binding site has been described that is present in all three lectin proteins comprising the amino acid sequence "OGK-X-GP" (SEQ ID NO:22) where the letter "O" represents hydroxyproline and the letter "X" is a hydrophobic residue (Wallis et al., 2004, supra). Accordingly, in some embodiments, MASP-2 inhibitory peptides useful in this aspect of the invention are at least 6 amino acids in length and comprise SEQ ID NO:22. Peptides derived from MBL that include the amino acid sequence "GLR GLQ GPO GKL GPO G" (SEQ ID NO:24) have been shown to bind MASP-2 in vitro (Wallis, et al., 2004, supra). To enhance binding to MASP-2, peptides can be synthesized that are flanked by two GPO triplets at each end ("GPO GPO GLR GLQ GPO GKL GPO GGP OGP O" SEQ ID NO:25) to enhance the formation of triple helices as found in the native MBL protein (as further described in Wallis, R., et al., *J. Biol. Chem.* 279:14065, 2004).

MASP-2 inhibitory peptides may also be derived from human H-ficolin that include the sequence "GAO GSO GEK GAO GPQ GPO GPO GKM GPK GEO GDO" (SEQ ID NO:27) from the consensus MASP-2 binding region in H-ficolin. Also included are peptides derived from human L-ficolin that include the sequence "GCO GLO GAO GDK GEA GTN GKR GER GPO GPO GKA GPO GPN GAO GEO" (SEQ ID NO:28) from the consensus MASP-2 binding region in L-ficolin.

MASP-2 inhibitory peptides may also be derived from the C4 cleavage site such as "LQRALEILPNRVTIKANRP-FLVFI" (SEQ ID NO:29) which is the C4 cleavage site linked to the C-terminal portion of antithrombin III (Glover, G. I., et al., *Mol. Immunol.* 25:1261 (1988)).

TABLE 3

EXEMPLARY MASP-2 INHIBITORY PEPTIDES

| SEQ ID NO | Source |
| --- | --- |
| SEQ ID NO: 6 | Human MASP-2 protein |
| SEQ ID NO: 8 | CUBI domain of MASP-2 (aa 1-121 of SEQ ID NO: 6) |
| SEQ ID NO: 9 | CUBIEGF domains of MASP-2 (aa 1-166 of SEQ ID NO: 6) |
| SEQ ID NO: 10 | CUBIEGFCUBII domains of MASP-2 (aa 1-293 of SEQ ID NO: 6) |
| SEQ ID NO: 11 | EGF domain of MASP-2 (aa 122-166) |
| SEQ ID NO: 12 | Serine-protease domain of MASP-2 (aa 429-671) |
| SEQ ID NO: 16 | MBL binding region in MASP-2 |
| SEQ ID NO: 3 | Human MAp19 |
| SEQ ID NO: 21 | Human MBL protein |
| SEQ ID NO: 22<br>OGK-X-GP,<br>Where "O" = hydroxyproline and "X" is a hydrophobic amino acid residue | Synthetic peptide Consensus binding site from Human MBL and Human ficolins |
| SEQ ID NO: 23<br>OGKLG | Human MBL core binding site |
| SEQ ID NO: 24<br>GLR GLQ GPO GKL GPO G | Human MBP Triplets 6-10- demonstrated binding to MASP-2 |
| SEQ ID NO: 25<br>GPOGPOGLRGLQGPO GKLGPOGGPOGPO | Human MBP Triplets with GPO added to enhance formation of triple helices |
| SEQ ID NO: 26<br>GKDGRDGTKGEKGEP GQGLRGLQGPOGKLG POGNOGPSGSOGPKG QKGDOGKS | Human MBP Triplets 1-17 |
| SEQ ID NO: 27<br>GAOGSOGEKGAOGPQ GPOGPOGKMGPKGEO GDO | Human H-Ficolin (Hataka) |
| SEQ ID NO: 28<br>GCOGLOGAOGDKGE AGTNGKRGERGPOGP OGKAGPOGPNGAOGE O | Human L-Ficolin P35 |
| SEQ ID NO: 29<br>LQRALEILPNRVTIKA NRPFLVFI | Human C4 cleavage site |

Note:
The letter "O" represents hydroxyproline.
The letter "X" is a hydrophobic residue.

Peptides derived from the C4 cleavage site as well as other peptides that inhibit the MASP-2 serine protease site can be chemically modified so that they are irreversible protease inhibitors. For example, appropriate modifications may include, but are not necessarily limited to, halomethyl ketones (Br, Cl, I, F) at the C-terminus, Asp or Glu, or appended to functional side chains; haloacetyl (or other α-haloacetyl) groups on amino groups or other functional side chains; epoxide or imine-containing groups on the amino or carboxy termini or on functional side chains; or imidate esters on the amino or carboxy termini or on functional side chains. Such modifications would afford the advantage of permanently inhibiting the enzyme by covalent attachment of the peptide. This could result in lower effective doses and/or the need for less frequent administration of the peptide inhibitor.

In addition to the inhibitory peptides described above, MASP-2 inhibitory peptides useful in the method of the invention include peptides containing the MASP-2-binding CDR3 region of anti-MASP-2 MoAb obtained as described herein. The sequence of the CDR regions for use in synthesizing the peptides may be determined by methods known in the art. The heavy chain variable region is a peptide that generally ranges from 100 to 150 amino acids in length. The light chain variable region is a peptide that generally ranges from 80 to 130 amino acids in length. The CDR sequences within the heavy and light chain variable regions include only approximately 3-25 amino acid sequences that may be easily sequenced by one of ordinary skill in the art.

Those skilled in the art will recognize that substantially homologous variations of the MASP-2 inhibitory peptides described above will also exhibit MASP-2 inhibitory activity. Exemplary variations include, but are not necessarily limited to, peptides having insertions, deletions, replacements, and/or additional amino acids on the carboxy-terminus or amino-terminus portions of the subject peptides and mixtures thereof. Accordingly, those homologous peptides having MASP-2 inhibitory activity are considered to be useful in the methods of this invention. The peptides described may also include duplicating motifs and other modifications with conservative substitutions. Conservative variants are described elsewhere herein, and include the exchange of an amino acid for another of like charge, size or hydrophobicity and the like.

MASP-2 inhibitory peptides may be modified to increase solubility and/or to maximize the positive or negative charge in order to more closely resemble the segment in the intact protein. The derivative may or may not have the exact primary amino acid structure of a peptide disclosed herein so long as the derivative functionally retains the desired property of MASP-2 inhibition. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer, which mimics the natural conformation, charge distribution and function of the parent peptide. Peptides may also be modified by acetylation or amidation.

The synthesis of derivative inhibitory peptides can rely on known techniques of peptide biosynthesis, carbohydrate biosynthesis and the like. As a starting point, the artisan may rely on a suitable computer program to determine the conformation of a peptide of interest. Once the conformation of peptide disclosed herein is known, then the artisan can determine in a rational design fashion what sort of substitutions can be made at one or more sites to fashion a derivative that retains the basic conformation and charge distribution of the parent peptide but which may possess characteristics which are not present or are enhanced over those found in the parent peptide. Once candidate derivative molecules are identified, the derivatives can be tested to determine if they function as MASP-2 inhibitory agents using the assays described herein.

Screening for MASP-2 Inhibitory Peptides

One may also use molecular modeling and rational molecular design to generate and screen for peptides that mimic the molecular structures of key binding regions of MASP-2 and inhibit the complement activities of MASP-2. The molecular structures used for modeling include the CDR regions of anti-MA SP-2 monoclonal antibodies, as well as the target regions known to be important for MASP-2 function including the region required for dimerization, the region involved in binding to MBL, and the serine protease active site as previously described. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo synthesis of Macromolecular Binding and Catalytic Sties," *TRIP* 2(5) 1994.

As an illustrative example, one method of preparing mimics of MASP-2 binding peptides is as follows. Functional monomers of a known MASP-2 binding peptide or the binding region of an anti-MASP-2 antibody that exhibits MASP-2 inhibition (the template) are polymerized. The template is then removed, followed by polymerization of a second class of monomers in the void left by the template, to provide a new molecule that exhibits one or more desired properties that are similar to the template. In addition to preparing peptides in this manner, other MASP-2 binding molecules that are MASP-2 inhibitory agents such as polysaccharides, nucleosides, drugs, nucleoproteins, lipoproteins, carbohydrates, glycoproteins, steroid, lipids and other biologically active materials can also be prepared. This method is useful for designing a wide variety of biological mimics that are more stable than their natural counterparts because they are typically prepared by free radical polymerization of function monomers, resulting in a compound with a nonbiodegradable backbone.

Peptide Synthesis

The MASP-2 inhibitory peptides can be prepared using techniques well known in the art, such as the solid-phase synthetic technique initially described by Merrifield, in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein that can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

The MASP-2 inhibitory peptides that are useful in the method of the invention can also be produced in recombinant host cells following conventional techniques. To express a MASP-2 inhibitory peptide encoding sequence, a nucleic acid molecule encoding the peptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene, which are suitable for selection of cells that carry the expression vector.

Nucleic acid molecules that encode a MASP-2 inhibitory peptide can be synthesized with "gene machines" using protocols such as the phosphoramidite method. If chemically synthesized double-stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes, synthetic genes (double-stranded) are assembled in modular form from single-stranded fragments that are from 20 to 100 nucleotides in length. For reviews on polynucleotide synthesis, see, for example, Glick and Pasternak, "*Molecular Biotechnology, Principles and Applications of Recombinant DNA*", ASM Press, 1994; Itakura, K., et al., *Annu. Rev. Biochem.* 53:323, 1984; and Climie, S., et al., *Proc. Nat'l Acad. Sci. USA* 87:633, 1990.

Small Molecule Inhibitors

In some embodiments, MASP-2 inhibitory agents are small molecule inhibitors including natural and synthetic substances that have a low molecular weight, such as for example, peptides, peptidomimetics and nonpeptide inhibitors (including oligonucleotides and organic compounds). Small molecule inhibitors of MASP-2 can be generated based on the molecular structure of the variable regions of the anti-MASP-2 antibodies.

Small molecule inhibitors may also be designed and generated based on the MASP-2 crystal structure using computational drug design (Kuntz I. D., et al., *Science* 257:1078, 1992). The crystal structure of rat MASP-2 has been described (Feinberg, H., et al., *EMBO J.* 22:2348-2359, 2003). Using the method described by Kuntz et al., the MASP-2 crystal structure coordinates are used as an input for a computer program such as DOCK, which outputs a list of small molecule structures that are expected to bind to MASP-2. Use of such computer programs is well known to one of skill in the art. For example, the crystal structure of the HIV-1 protease inhibitor was used to identify unique nonpeptide ligands that are HIV-1 protease inhibitors by evaluating the fit of compounds found in the Cambridge Crystallographic database to the binding site of the enzyme using the program DOCK (Kuntz, I. D., et al., *J. Mol. Biol.* 161:269-288, 1982; DesJarlais, R. L., et al., *PNAS* 87:6644-6648, 1990).

The list of small molecule structures that are identified by a computational method as potential MASP-2 inhibitors are screened using a MASP-2 binding assay such as described in Example 10. The small molecules that are found to bind to MASP-2 are then assayed in a functional assay such as described in Example 2 to determine if they inhibit MASP-2-dependent complement activation.

MASP-2 Soluble Receptors

Other suitable MASP-2 inhibitory agents are believed to include MASP-2 soluble receptors, which may be produced using techniques known to those of ordinary skill in the art.

Expression Inhibitors of MASP-2

In another embodiment of this aspect of the invention, the MASP-2 inhibitory agent is a MASP-2 expression inhibitor capable of inhibiting MASP-2-dependent complement activation. In the practice of this aspect of the invention, representative MASP-2 expression inhibitors include MASP-2 antisense nucleic acid molecules (such as antisense mRNA, antisense DNA or antisense oligonucleotides), MASP-2 ribozymes and MASP-2 RNAi molecules.

Anti-sense RNA and DNA molecules act to directly block the translation of MASP-2 mRNA by hybridizing to MASP-2 mRNA and preventing translation of MASP-2 protein. An antisense nucleic acid molecule may be constructed in a number of different ways provided that it is capable of interfering with the expression of MASP-2. For example, an antisense nucleic acid molecule can be constructed by inverting the coding region (or a portion thereof) of MASP-2 cDNA (SEQ ID NO:4) relative to its normal orientation for transcription to allow for the transcription of its complement.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of MASP-2 is an antisense MASP-2 nucleic acid molecule which is at least ninety percent identical to the complement of the MASP-2 cDNA consisting of the nucleic acid sequence set forth in SEQ ID NO:4. The nucleic acid sequence set forth in SEQ ID NO:4 encodes the MASP-2 protein consisting of the amino acid sequence set forth in SEQ ID NO:5.

The targeting of antisense oligonucleotides to bind MASP-2 mRNA is another mechanism that may be used to reduce the level of MASP-2 protein synthesis. For example, the synthesis of polygalacturonase and the muscarine type 2 acetylcholine receptor is inhibited by antisense oligonucleotides directed to their respective mRNA sequences (U.S. Pat. No. 5,739,119, to Cheng, and U.S. Pat. No. 5,759,829, to Shewmaker). Furthermore, examples of antisense inhibition have been demonstrated with the nuclear protein cyclin, the multiple drug resistance gene (MDG1), ICAM-1, E-selectin, STK-1, striatal $GABA_A$ receptor and human EGF (see, e.g., U.S. Pat. No. 5,801,154, to Baracchini; U.S. Pat. No. 5,789,573, to Baker; U.S. Pat. No. 5,718,709, to Considine; and U.S. Pat. No. 5,610,288, to Reubenstein).

A system has been described that allows one of ordinary skill to determine which oligonucleotides are useful in the invention, which involves probing for suitable sites in the target mRNA using Rnase H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the MASP-2 transcript is added to cell extracts expressing MASP-2, such as hepatocytes, and hybridized in order to create an RNAseH vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, 1., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the MASP-2 mRNA are those that are at or near the AUG translation initiation codon, and those sequences that are substantially complementary to 5' regions of the mRNA, e.g., between the −10 and +10 regions of the MASP-2 gene nucleotide sequence (SEQ ID NO:4). Exemplary MASP-2 expression inhibitors are provided in TABLE 4.

(backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illustrative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent basepairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a sequence and its complement listed in TABLE 4. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:4 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif.).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods.

TABLE 4

EXEMPLARY EXPRESSION INHIBITORS OF MASP-2

| | |
|---|---|
| SEQ ID NO: 30 (nucleotides 22-680 of SEQ ID NO: 4) | Nucleic acid sequence of MASP-2 cDNA (SEQ ID NO: 4) encoding CUBIEGF |
| SEQ ID NO: 31<br>5'CGGGCACACCATGAGGCTGCTG ACCCTCCTGGGC3 | Nucleotides 12-45 of SEQ ID NO: 4 including the MASP-2 translation start site (sense) |
| SEQ ID NO: 32<br>5'GACATTACCTTCCGCTCCGACTC CAACGAGAAG3' | Nucleotides 361-396 of SEQ ID NO: 4 encoding a region comprising the MASP-2 MBL binding site (sense) |
| SEQ ID NO: 33<br>5'AGCAGCCCTGAATACCCACGGCC GTATCCCAAA3' | Nucleotides 610-642 of SEQ ID NO: 4 encoding a region comprising the CUBII domain |

As noted above, the term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. Such methods are taught in Ausubel et al., *Current Protocols in Molecular Biology*, John Wiley & Sons, Inc., 1993.

Ribozymes can also be utilized to decrease the amount and/or biological activity of MASP-2, such as ribozymes that target MASP-2 mRNA. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target MASP-2 mRNA, and a catalytic region that is adapted to cleave the target MASP-2 mRNA (see generally, EPA No. 0 321 201; WO88/04300; Haseloff, J., et al., *Nature* 339:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

V. PHARMACEUTICAL COMPOSITIONS AND DELIVERY METHODS DOSING

In another aspect, the invention provides compositions for inhibiting the adverse effects of MASP-2-dependent complement activation in a subject suffering from a disease or condition as disclosed herein, comprising administering to the subject a composition comprising a therapeutically effective amount of a MASP-2 inhibitory agent and a pharmaceutically acceptable carrier. The MASP-2 inhibitory agents can be administered to a subject in need thereof, at therapeutically effective doses to treat or ameliorate conditions associated with MASP-2-dependent complement activation. A therapeutically effective dose refers to the amount of the MASP-2 inhibitory agent sufficient to result in amelioration of symptoms associated with the disease or condition.

Toxicity and therapeutic efficacy of MASP-2 inhibitory agents can be determined by standard pharmaceutical procedures employing experimental animal models, such as the murine MASP-2-/- mouse model expressing the human MASP-2 transgene described in Example 1. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-2 inhibitory agents that exhibit large therapeutic ratios or indices are most preferred. The data obtained from the cell culture assays and animal studies can be used in formulating a range of dosages for use in humans. The dosage of the MASP-2 inhibitory agent preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration range that includes the MED. Quantitative levels of the MASP-2 inhibitory agent in plasma may also be measured, for example, by high performance liquid chromatography.

In addition to toxicity studies, effective dosage may also be estimated based on the amount of MASP-2 protein present in a living subject and the binding affinity of the MASP-2 inhibitory agent. It has been shown that MASP-2 levels in normal human subjects is present in serum in low levels in the range of 500 ng/ml, and MASP-2 levels in a particular subject can be determined using a quantitative assay for MASP-2 described in Moller-Kristensen M., et al., *J. Immunol. Methods* 282:159-167, 2003.

Generally, the dosage of administered compositions comprising MASP-2 inhibitory agents varies depending on such factors as the subject's age, weight, height, sex, general medical condition, and previous medical history. As an illustration, MASP-2 inhibitory agents, such as anti-MASP-2 antibodies, can be administered in dosage ranges from about 0.010 to 10.0 mg/kg, preferably 0.010 to 1.0 mg/kg, more preferably 0.010 to 0.1 mg/kg of the subject body weight. In some embodiments the composition comprises a combination of anti-MASP-2 antibodies and MASP-2 inhibitory peptides.

Therapeutic efficacy of MASP-2 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize monoclonal antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in measured, for example, as described in Example 2, the reduction of C4 cleavage and C4b deposition (measured, for example as described in Example 10), or the reduction of C3 cleavage and C3b deposition (measured, for example, as described in Example 10).

Additional Agents

The compositions and methods comprising MASP-2 inhibitory agents may optionally comprise one or more additional therapeutic agents, which may augment the activity of the MASP-2 inhibitory agent or that provide related therapeutic functions in an additive or synergistic fashion. For example, in the context of treating a subject suffering from TTP, wherein the subject is positive for an inhibitor of ADAM-TS13, one or more MASP-2 inhibitory agents may be administered in combination (including co-administration) with one or more immunosuppressive agents. Suitable immunosuppressive agents include: corticosteroids, rituxan, cyclosporine, and the like. In the context of treating a subject suffering from, or at risk for developing, HUS or aHUS, one or more MASP-2 inhibitory agents may be administered in combination (including co-administration) with a suitable antibiotic. In the context of treating a subject suffering from, or at risk for developing aHUS, one or more MASP-2 inhibitory agents may be administered in combination (including co-administration) with other complement inhibitory agents such as eculizumab (Soliris), TT-30, antibody to factor B, or other agents that inhibit terminal complement components or alternative pathway amplification.

The inclusion and selection of additional agent(s) will be determined to achieve a desired therapeutic result. In some embodiments, the MASP-2 inhibitory agent may be administered in combination with one or more anti-inflammatory and/or analgesic agents. Suitable anti-inflammatory and/or analgesic agents include: serotonin receptor antagonists; serotonin receptor agonists; histamine receptor antagonists; bradykinin receptor antagonists; kallikrein inhibitors; tachykinin receptor antagonists, including neurokinin, and neurokinin$_2$ receptor subtype antagonists; calcitonin gene-related peptide (CGRP) receptor antagonists; interleukin receptor antagonists; inhibitors of enzymes active in the synthetic pathway for arachidonic acid metabolites, including phospholipase inhibitors, including PLA$_2$ isoform inhibitors and PLC$_\gamma$ isoform inhibitors, cyclooxygenase (COX) inhibitors (which may be either COX-1, COX-2, or nonselective COX-1 and -2 inhibitors), lipooxygenase inhibitors; prostanoid receptor antagonists including eicosanoid EP-1 and EP-4 receptor subtype antagonists and thromboxane receptor subtype antagonists; leukotriene receptor antagonists including leukotriene B$_4$ receptor subtype antagonists and leukotriene D$_4$ receptor subtype antagonists; opioid receptor agonists, including μ-opioid, δ-opioid, and κ-opioid receptor subtype agonists; purinoceptor agonists and antagonists including P$_{2X}$ receptor antagonists and P$_{2Y}$ receptor agonists; adenosine triphosphate (ATP)-sensitive potassium channel openers; MAP kinase inhibitors; nicotinic acetylcholine inhibitors; and alpha adrenergic receptor agonists (including alpha-1, alpha-2, and nonselective alpha-1 and 2 agonists).

The MASP-2 inhibitory agents of the present invention may also be administered in combination with one or more other complement inhibitors, such as an inhibitor of C5. To date, Eculizumab (Solaris®), an antibody against C5, is the only complement-targeting drug that has been approved for human use. However some pharmacological agents have been shown to block complement in vivo. K76COOH and nafamstat mesilate are two agents that have shown some effectiveness in animal models of transplantation (Miyagawa, S., et al., *Transplant Proc.* 24:483-484, 1992). Low molecular weight heparins have also been shown to be effective in regulating complement activity (Edens, R. E., et al., *Complement Today*, pp. 96-120, Basel: Karger, 1993). It is believed that these small molecule inhibitors may be useful as agents to use in combination with the MASP-2 inhibitory agents of the present invention.

Other naturally occurring complement inhibitors may be useful in combination with the MASP-2 inhibitory agents of the present invention. Biological inhibitors of complement include soluble complement factor 1 (sCR1). This is a naturally-occurring inhibitor that can be found on the outer membrane of human cells. Other membrane inhibitors include DAF, MCP, and CD59. Recombinant forms have been tested for their anti-complement activity in vitro and in vivo. sCR1 has been shown to be effective in xenotransplantation, wherein the complement system (both alternative and classical) provides the trigger for a hyperactive rejection syndrome within minutes of perfusing blood through the newly transplanted organ (Platt, J. L., et al., *Immunol. Today* 11:450-6, 1990; Marino, I. R., et al., *Transplant Proc.* 1071:6, 1990; Johnstone, P. S., et al., *Transplantation* 54:573-6, 1992). The use of sCR1 protects and extends the survival time of the transplanted organ, implicating the complement pathway in the pathogenesis of organ survival (Leventhal, J. R., et al., *Transplantation* 55:857-66, 1993; Pruitt, S. K., et al., *Transplantation* 57:363-70, 1994).

Suitable additional complement inhibitors for use in combination with the compositions of the present invention also include, by way of example, MoAbs such as an anti-C5 antibody (e.g., eculizumab) being developed by Alexion Pharmaceuticals, Inc., New Haven, Conn., and anti-properdin MoAbs.

Pharmaceutical Carriers and Delivery Vehicles

In general, the MASP-2 inhibitory agent compositions of the present invention, combined with any other selected therapeutic agents, are suitably contained in a pharmaceutically acceptable carrier. The carrier is non-toxic, biocompatible and is selected so as not to detrimentally affect the biological activity of the MASP-2 inhibitory agent (and any other therapeutic agents combined therewith). Exemplary pharmaceutically acceptable carriers for peptides are described in U.S. Pat. No. 5,211,657 to Yamada. The anti-MASP-2 antibodies and inhibitory peptides useful in the invention may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO:PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular delivery, the MASP-2 inhibitory agent may be carried in above-described liquid or gel carriers that are injectable, above-described sustained-release delivery vehicles that are injectable, or a hyaluronic acid or hyaluronic acid derivative.

For oral administration of non-peptidergic agents, the MASP-2 inhibitory agent may be carried in an inert filler or diluent such as sucrose, cornstarch, or cellulose.

For topical administration, the MASP-2 inhibitory agent may be carried in ointment, lotion, cream, gel, drop, suppository, spray, liquid or powder, or in gel or microcapsular delivery systems via a transdermal patch.

Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavouring agents (for oral administration).

Pharmaceutical Carriers for Antibodies and Peptides

More specifically with respect to anti-MASP-2 antibodies and inhibitory peptides, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising anti-MASP-2 antibodies and inhibitory peptides. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-MASP-2 antibodies and inhibitory peptides can also be administered in the form of a depot injection or implant preparation that can be formulated in such a manner as to permit a sustained or pulsatile release of the active agents.

Pharmaceutically Acceptable Carriers for Expression Inhibitors

More specifically with respect to expression inhibitors useful in the methods of the invention, compositions are provided that comprise an expression inhibitor as described above and a pharmaceutically acceptable carrier or diluent. The composition may further comprise a colloidal dispersion system.

Pharmaceutical compositions that include expression inhibitors may include, but are not limited to, solutions, emulsions, and liposome-containing formulations. These compositions may be generated from a variety of components that include, but are not limited to, preformed liquids, self-emulsifying solids and self-emulsifying semisolids. The preparation of such compositions typically involves combining the expression inhibitor with one or more of the following: buffers, antioxidants, low molecular weight polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are examples of suitable diluents.

In some embodiments, the compositions may be prepared and formulated as emulsions which are typically heterogeneous systems of one liquid dispersed in another in the form of droplets (see, Idson, in *Pharmaceutical Dosage Forms*, Vol. 1, Rieger and Banker (eds.), Marcek Dekker, Inc., N.Y., 1988). Examples of naturally occurring emulsifiers used in emulsion formulations include acacia, beeswax, lanolin, lecithin and phosphatides.

In one embodiment, compositions including nucleic acids can be formulated as microemulsions. A microemulsion, as used herein refers to a system of water, oil, and amphiphile, which is a single optically isotropic and thermodynamically stable liquid solution (see Rosoff in *Pharmaceutical Dosage Forms*, Vol. 1). The method of the invention may also use liposomes for the transfer and delivery of antisense oligonucleotides to the desired site.

Pharmaceutical compositions and formulations of expression inhibitors for topical administration may include transdermal patches, ointments, lotions, creams, gels, drops, suppositories, sprays, liquids and powders. Conventional pharmaceutical carriers, as well as aqueous, powder or oily bases and thickeners and the like may be used.

Modes of Administration

The pharmaceutical compositions comprising MASP-2 inhibitory agents may be administered in a number of ways depending on whether a local or systemic mode of administration is most appropriate for the condition being treated. Additionally, as described herein above with respect to extracorporeal reperfusion procedures, MASP-2 inhibitory agents can be administered via introduction of the compositions of the present invention to recirculating blood or plasma. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

MASP-2 inhibitory antibodies and polypeptides can be delivered into a subject in need thereof by any suitable means. Methods of delivery of MASP-2 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-2 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-2 inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Mori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J. Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-2 inhibitory antibodies and polypeptides may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-2 inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-2 inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-2 inhibitory agent may be achieved in the context of surgical methods for treating a disease or condition, such as for example during procedures such as arterial bypass surgery, atherectomy, laser procedures, ultrasonic procedures, balloon angioplasty and stent placement. For example, a MASP-2 inhibitor can be administered to a subject in conjunction with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the vascular wall. As a result, the balloon surface is in contact with the layer of vascular endothelial cells on the surface of the blood vessel. The MASP-2 inhibitory agent may be attached to the balloon angioplasty catheter in a manner that permits release of the agent at the site of the atherosclerotic plaque. The agent may be attached to the balloon catheter in accordance with standard procedures known in the art. For example, the agent may be stored in a compartment of the balloon catheter until the balloon is inflated, at which point it is released into the local environment. Alternatively, the agent may be impregnated on the balloon surface, such that it contacts the cells of the arterial wall as the balloon is inflated. The agent may also be delivered in a perforated balloon catheter such as those disclosed in Flugelman, M. Y., et al., *Circulation* 85:1110-1117, 1992. See also published PCT Application WO 95/23161 for an exemplary procedure for attaching a therapeutic protein to a balloon angioplasty catheter. Likewise, the MASP-2 inhibitory agent may be included in a gel or polymeric coating applied to a stent, or may be incorporated into the material of the stent, such that the stent elutes the MASP-2 inhibitory agent after vascular placement.

MASP-2 inhibitory compositions used in the treatment of arthritides and other musculoskeletal disorders may be locally delivered by intra-articular injection. Such compositions may suitably include a sustained release delivery vehicle. As a further example of instances in which local delivery may be desired, MASP-2 inhibitory compositions used in the treatment of urogenital conditions may be suitably instilled intravesically or within another urogenital structure.

Coatings on a Medical Device

MASP-2 inhibitory agents such as antibodies and inhibitory peptides may be immobilized onto (or within) a surface of an implantable or attachable medical device. The modified surface will typically be in contact with living tissue after implantation into an animal body. By "implantable or attachable medical device" is intended any device that is implanted into, or attached to, tissue of an animal body, during the normal operation of the device (e.g., stents and implantable drug delivery devices). Such implantable or attachable medical devices can be made from, for example, nitrocellulose, diazocellulose, glass, polystyrene, polyvinylchloride, polypropylene, polyethylene, dextran, Sepharose, agar, starch, nylon, stainless steel, titanium and biodegradable and/or biocompatible polymers. Linkage of the protein to a device can be accomplished by any technique that does not destroy the biological activity of the linked protein, for example by attaching one or both of the N—C-terminal residues of the protein to the device. Attachment may also be made at one or more internal sites in the protein. Multiple attachments (both internal and at the ends of the protein) may also be used. A surface of an implantable or attachable medical device can be modified to include functional groups (e.g., carboxyl, amide, amino, ether, hydroxyl, cyano, nitrido, sulfanamido, acetylinic, epoxide, silanic, anhydric, succinimic, azido) for protein immobilization thereto. Coupling chemistries include, but are not limited to, the formation of esters, ethers, amides, azido and sulfanamido derivatives, cyanate and other linkages to the functional groups available on MASP-2 antibodies or inhibitory peptides. MASP-2 antibodies or inhibitory fragments can also be attached non-covalently by the addition of an affinity tag sequence to the protein, such as GST (D. B. Smith and K. S. Johnson, *Gene* 67:31, 1988), polyhistidines (E. Hochuli et al., *J. Chromatog.* 411:77, 1987), or biotin. Such affinity tags may be used for the reversible attachment of the protein to a device.

Proteins can also be covalently attached to the surface of a device body, for example, by covalent activation of the surface of the medical device. By way of representative example, matricellular protein(s) can be attached to the device body by any of the following pairs of reactive groups (one member of the pair being present on the surface of the device body, and the other member of the pair being present on the matricellular protein(s)): hydroxyl/carboxylic acid to yield an ester linkage; hydroxyl/anhydride to yield an ester linkage; hydroxyl/isocyanate to yield a urethane linkage. A surface of a device body that does not possess useful reactive groups can be treated with radio-frequency discharge plasma (RFGD) etching to generate reactive groups in order to allow deposition of matricellular protein(s) (e.g., treatment with oxygen plasma to introduce oxygen-containing groups; treatment with propyl amino plasma to introduce amine groups).

MASP-2 inhibitory agents comprising nucleic acid molecules such as antisense, RNAi- or DNA-encoding peptide inhibitors can be embedded in porous matrices attached to a device body. Representative porous matrices useful for making the surface layer are those prepared from tendon or dermal collagen, as may be obtained from a variety of commercial sources (e.g., Sigma and Collagen Corporation), or collagen matrices prepared as described in U.S. Pat. No. 4,394,370, to Jefferies, and U.S. Pat. No. 4,975,527, to Koezuka. One collagenous material is termed UltraFiber™ and is obtainable from Norian Corp. (Mountain View, Calif.).

Certain polymeric matrices may also be employed if desired, and include acrylic ester polymers and lactic acid polymers, as disclosed, for example, in U.S. Pat. Nos. 4,526,909 and 4,563,489, to Urist. Particular examples of useful polymers are those of orthoesters, anhydrides, propylene-cofumarates, or a polymer of one or more α-hydroxy carboxylic acid monomers, (e.g., α-hydroxy acetic acid (glycolic acid) and/or α-hydroxy propionic acid (lactic acid)).

Treatment Regimens

In prophylactic applications, the pharmaceutical compositions are administered to a subject susceptible to, or otherwise at risk of, a condition associated with MASP-2-dependent complement activation in an amount sufficient to eliminate or reduce the risk of developing symptoms of the condition. In therapeutic applications, the pharmaceutical compositions are administered to a subject suspected of, or already suffering from, a condition associated with MASP-2-dependent complement activation in a therapeutically effective amount sufficient to relieve, or at least partially reduce, the symptoms of the condition. In both prophylactic and therapeutic regimens, compositions comprising MASP-2 inhibitory agents may be administered in several dosages until a sufficient therapeutic outcome has been achieved in the subject. Application of the MASP-2 inhibitory compositions of the present invention may be carried out by a single administration of the composition, or a limited sequence of administrations, for treatment of an acute condition, e.g., reperfusion injury or other traumatic injury. Alternatively, the composition may be administered at periodic intervals over an extended period of time for treatment of chronic conditions, e.g., arthritides or psoriasis.

The methods and compositions of the present invention may be used to inhibit inflammation and related processes that typically result from diagnostic and therapeutic medical and surgical procedures. To inhibit such processes, the MASP-2 inhibitory composition of the present invention may be applied periprocedurally. As used herein "periprocedurally" refers to administration of the inhibitory composition preprocedurally and/or intraprocedurally and/or postprocedurally, i.e., before the procedure, before and during the procedure, before and after the procedure, before, during and after the procedure, during the procedure, during and after the procedure, or after the procedure. Periprocedural application may be carried out by local administration of the composition to the surgical or procedural site, such as by injection or continuous or intermittent irrigation of the site or by systemic administration. Suitable methods for local perioperative delivery of MASP-2 inhibitory agent solutions are disclosed in U.S. Pat. No. 6,420,432 to Demopulos and U.S. Pat. No. 6,645,168 to Demopulos. Suitable methods for local delivery of chondroprotective compositions including MASP-2 inhibitory agent(s) are disclosed in International PCT Patent Application WO 01/07067 A2. Suitable methods and compositions for targeted systemic delivery of chondroprotective compositions including MASP-2 inhibitory agent(s) are disclosed in International PCT Patent Application WO 03/063799 A2.

In one aspect of the invention, the pharmaceutical compositions are administered to a subject susceptible to, or otherwise at risk of, PNH in an amount sufficient to eliminate or reduce the risk of developing symptoms of the condition. In therapeutic applications, the pharmaceutical compositions are administered to a subject suspected of, or already suffering from, PNH in a therapeutically effective amount sufficient to relieve, or at least partially reduce, the symptoms of the condition.

In one embodiment, the subject's red blood cells are opsonized by fragments of C3 in the absence of the composition, and administration of the composition comprising a MASP-2 inhibitory agent to the subject increases the survival of red blood cells in the subject. In one embodiment, the subject exhibits one or more symptoms in the absence of the composition selected from the group consisting of (i) below normal levels of hemoglobin, (ii) below normal levels of platelets; (iii) above normal levels of reticulocytes, and (iv) above normal levels of bilirubin, and administration of the composition to the subject improves at least one or more of the symptoms, resulting in (i) increased, normal, or nearly normal levels of hemoglobin (ii) increased, normal or nearly normal levels of platelets, (iii) decreased, normal or nearly normal levels of reticulocytes, and/or (iv) decreased, normal or nearly normal levels of bilirubin.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of PNH. Alternatively, the composition may be administered at periodic intervals such as daily, biweekly, weekly, every other week, monthly or bimonthly over an extended period of time for treatment of PNH.

In some embodiments, the subject suffering from PNH has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject susceptible to, or otherwise at risk of, aHUS in an amount sufficient to eliminate or reduce the risk of developing symptoms of the condition. In therapeutic applications, the pharmaceutical compositions are administered to a subject suspected of, or already suffering from, aHUS in a therapeutically effective amount sufficient to relieve, or at least partially reduce, the symptoms of the condition. In one aspect of the invention, prior to administration, the subject may be examined to determine whether the subject exhibits one or more symptoms of aHUS, including (i) anemia, (ii) thrombocytopenia (iii) renal insufficiency and (iv) rising creatinine, and the composition of the present invention is then administered in an effective amount and for a sufficient time period to improve these symptom(s).

In another aspect of the invention, the MASP-2 inhibitory compositions of the present invention may be used to prophylactically treat a subject that has an elevated risk of developing aHUS and thereby reduce the likelihood that the subject will deliver aHUS. The presence of a genetic marker in the subject known to be associated with aHUS is first determined by performing a genetic screening test on a sample obtained from the subject and identifying the presence of at least one genetic marker associated with aHUS, complement factor H(CFH), factor I (CFI), factor B (CFB), membrane cofactor CD46, C3, complement factor H-related protein (CFHR1), anticoagulant protein thrombodulin (THBD), complement factor H-related protein 3 (CFHR3) or complement factor H-related protein 4 (CFHR4). The subject is then periodically monitored (e.g., monthly, quarterly, twice annually or annually) to determine the presence or absence of at least one symptom of aHUS, such as anemia, thrombocytopenia, renal insufficiency and rising creatinine. Upon the determination of the presence of at least one of these symptoms, the subject can be administered an amount of a MASP-2 inhibitory agent effective to inhibit MASP-2 dependent complement activation, in an effective amount and for a sufficient time period to improve said one or more symptoms. In a still further aspect of the present invention, a subject at increased risk of developing aHUS due to having been screened and determined to have one of the genetic markers associated with aHUS may be monitored for the occurrence of an event associated with triggering aHUS clinical symptoms, including drug exposure, infection (e.g., bacterial infection), malignancy, injury, organ or tissue transplant and pregnancy.

In a still further aspect of the present invention, a composition comprising an amount of a MASP-2 inhibitory agent effective to inhibit MASP-2 dependent complement activation can be administered to a suffering from or at risk of developing atypical hemolytic uremic syndrome (aHUS) secondary to an infection. For example, a patient suffering from or at risk of developing non-enteric aHUS associated with an *S. pneumonia* infection may be treated with the compositions of the present invention.

In a still further aspect of the present invention, a subject suffering from aHUS may initially be treated with a MASP-2 inhibitory composition of the present invention that is administered through a catheter line, such as an intravenous catheter line or a subcutaneous catheter line, for a first period of time such as one hour, twelve hours, one day, two days or three days. The subject may then be treated for a second period of time with the MASP-2 inhibitory composition administered through regular subcutaneous injections, such as daily, biweekly, weekly, every other week, monthly or bimonthly, injections.

In a still further aspect of the present invention, a MASP-2 inhibitory composition of the present invention may be administered to a subject suffering from aHUS in the absence of plasmapheresis (i.e., a subject whose aHUS symptoms have not been treated with plasmapheresis and are not treated with plasmapheresis at the time of treatment with the MASP-2 inhibitory composition), to avoid the potential complications of plasmapheresis including hemorrhage, infection, and exposure to disorders and/or allergies inherent in the plasma donor, or in a subject otherwise averse to plasmapheresis, or in a setting where plasmapheresis is unavailable.

In a still further aspect of the present invention, a MASP-2 inhibitory composition of the present invention may be administered to a subject suffering from aHUS coincident with treating the patient with plasmapheresis. For example, a subject receiving plasmapheresis treatment can then be administered the MASP-2 inhibitory composition following or alternating with plasma exchange.

In a still further aspect of the present invention, a subject suffering from or at risk of developing aHUS and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of aHUS. Alternatively, the composition may be administered at periodic intervals, such as daily, biweekly, weekly, every other week, monthly or bimonthly, over an extended period of time for treatment of aHUS.

In some embodiments, the subject suffering from aHUS has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject susceptible to, or otherwise at risk of, HUS in an amount sufficient to eliminate or reduce the risk of developing symptoms of the condition. In therapeutic applications, the pharmaceutical compositions are administered to a subject suspected of, or already suffering from, HUS in a therapeutically effective amount sufficient to relieve, or at least partially reduce, the symptoms of the condition.

In another aspect of the present invention, the likelihood of developing impaired renal function in a subject at risk for developing HUS can be reduced by administering to the subject a MASP-2 inhibitory composition of the present invention in an amount effective to inhibit MASP-2 dependent complement activation. For example, a subject at risk for developing HUS and to be treated with a MASP-2 inhibitory composition of the present invention may exhibit one or more symptoms associated with HUS, including diarrhea, a hematocrit level of less than 30% with smear evidence of intravascular erythrocyte destruction, thrombocytopenia and rising creatinine levels. As a further example, a subject at risk for developing HUS and to be treated with the MASP-2 inhibitory compositions of the present invention may be infected with *E. coli, shigella* or *salmonella*. Such subjects infected with *E. coli, shigella* or *salmonella* may be treated with a MASP-2 inhibitory composition of the present invention concurrent with antibiotic treatment, or alternately may be treated with a MASP-2 inhibitory composition without concurrent treatment with an antibiotic, particularly for enterogenic *E. coli* for which antibiotic treatment is contra-indicated. A subject infected with enterogenic *E. coli* that has been treated with an antibiotic may be at elevated risk of developing HUS, and may be suitably treated with a MASP-2 inhibitory composition of the present invention to reduce that risk. A subject infected with enterogenic *E. coli* may be treated for a first period of time with a MASP-2 inhibitory composition of the present invention in the absence of an antibiotic and then for a second period of time with both a MASP-2 inhibitory composition of the present invention and an antibiotic.

In a still further aspect of the present invention, a subject suffering from HUS may initially be treated with a MASP-2 inhibitory composition of the present invention that is administered through a catheter line, such as an intravenous catheter line or a subcutaneous catheter line, for a first period of time such as one hour, twelve hours, one day, two days or three days. The subject may then be treated for a second period of time with the MASP-2 inhibitory composition administered through regular subcutaneous injections, such as daily, biweekly, weekly, every other week, monthly or bimonthly, injections.

In a still further aspect of the present invention, a MASP-2 inhibitory composition of the present invention may be administered to a subject suffering from HUS in the absence of plasmapheresis (i.e., a subject whose HUS symptoms have not been treated with plasmapheresis and are not treated with plasmapheresis at the time of treatment with the MASP-2 inhibitory composition), to avoid the potential complications of plasmaphersis including hemorrhage, infection, and exposure to disorders and/or allergies inherent in the plasma donor, or in a subject otherwise averse to plasmapheresis, or in a setting where plasmapheresis is unavailable.

In a still further aspect of the present invention, a MASP-2 inhibitory composition of the present invention may be administered to a subject suffering from HUS coincident with treating the patient with plasmapheresis. For example, a subject receiving plasmapheresis treatment can then be administered the MASP-2 inhibitory composition following or alternating with plasma exchange.

In a still further aspect of the present invention, a subject suffering from or at risk of developing HUS and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of HUS. Alternatively, the composition may be administered at periodic intervals, such as daily, biweekly, weekly, every other week, monthly or bimonthly, over an extended period of time for treatment of HUS.

In some embodiments, the subject suffering from HUS has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject susceptible to, or otherwise at risk of, TTP in an amount sufficient to eliminate or reduce the risk of developing symptoms of the condition. In therapeutic applications, the pharmaceutical compositions are administered to a subject suspected of, or already suffering from, TTP in a therapeutically effective amount sufficient to relieve, or at least partially reduce, the symptoms of the condition.

In another aspect of the present invention, a subject exhibiting one or more of the symptoms of TTP, including central nervous system involvement, thrombocytopenia, severe cardiac involvement, severe pulmonary involvement, gastro-intestinal infarction and gangrene, may be treated with a MASP-2 inhibitory composition of the present invention. In another aspect of the present invention, a subject determined to have a depressed level of ADAMTS13 and also testing positive for the presence of an inhibitor of (i.e., an antibody) ADAMTS13 may be treated with a MASP-2 inhibitory composition of the present invention. In a still further aspect of the present invention, a subject testing positive for the presence of an inhibitor of ADAMTS13 may be treated with an immunosupressant (e.g., corticosteroids, rituxan, or cyclosporine) concurrently with treatment with a MASP-2 inhibitory composition of the present invention. In a still further aspect of the present invention, a subject determined to have a reduced level of ADAMTS13 and testing positive for the presence of an inhibitor of ADAMTS13 may be treated with ADAMTS13 concurrently with treatment with a MASP-2 inhibitory composition of the present invention.

In a still further aspect of the present invention, a subject suffering from TTP may initially be treated with a MASP-2 inhibitory composition of the present invention that is administered through a catheter line, such as an intravenous catheter line or a subcutaneous catheter line, for a first period of time such as one hour, twelve hours, one day, two days or three days. The subject may then be treated for a second period of time with the MASP-2 inhibitory composition administered through regular subcutaneous injections, such as daily, biweekly, weekly, every other week, monthly or bimonthly, injections.

In a still further aspect of the present invention, a MASP-2 inhibitory composition of the present invention may be administered to a subject suffering from HUS in the absence of plasmapheresis (i.e., a subject whose TTP symptoms have not been treated with plasmapheresis and are not treated with plasmapheresis at the time of treatment with the MASP-2 inhibitory composition), to avoid the potential complications of plasmaphersis including hemorrhage, infection, and exposure to disorders and/or allergies inherent in the plasma donor, or in a subject otherwise averse to plasmapheresis, or in a setting where plasmapheresis is unavailable.

In a still further aspect of the present invention, a MASP-2 inhibitory composition of the present invention may be administered to a subject suffering from TTP coincident with treating the patient with plasmapheresis. For example, a subject receiving plasmapheresis treatment can then be administered the MASP-2 inhibitory composition following or alternating with plasma exchange.

In a still further aspect of the present invention, a subject suffering from refractory TTP, i.e., symptoms of TTP that have not responded adequately to other treatment such as plasmapheresis, may be treated with a MASP-2 inhibitory composition of the present invention, with or without additional plasmapheresis.

In a still further aspect of the present invention, a subject suffering from or at risk of developing TTP and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of TTP. Alternatively, the composition may be administered at periodic intervals, such as daily, biweekly, weekly, every other week, monthly or bimonthly, over an extended period of time for treatment of TTP.

In some embodiments, the subject suffering from TTP has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject susceptible to, or otherwise at risk of, cold aggultinin disease or cryoglobulinemia in an amount sufficient to eliminate or reduce the risk of developing symptoms of the condition. In therapeutic applications, the pharmaceutical compositions are administered to a subject suspected of, or already suffering from, cold aggultinin disease or cryoglobulinemia in a therapeutically effective amount sufficient to relieve, or at least partially reduce, the symptoms of the condition.

In a still further aspect of the present invention, a subject suffering from or at risk of developing cold aggultinin disease or cryoglobulinemia and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of cold aggultinin disease or cryoglobulinemia. Alternatively, the composition may be administered at periodic intervals, such as daily, biweekly, weekly, every other week, monthly or bimonthly, over an extended period of time for treatment of cold aggultinin disease or cryoglobulinemia.

In some embodiments, the subject suffering from cold aggultinin disease or cryoglobulinemia has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject susceptible to, or otherwise at risk of, glaucoma in an amount sufficient to eliminate or reduce the risk of developing symptoms of the condition. In therapeutic applications, the pharmaceutical compositions are administered to a subject suspected of, or already suffering from, glaucoma in a therapeutically effective amount sufficient to relieve, or at least partially reduce, the symptoms of the condition.

In a still further aspect of the present invention, a subject suffering from or at risk of developing glaucoma and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of glaucoma. Alternatively, the composition may be administered at periodic intervals, such as daily, biweekly, weekly, every other week, monthly or bimonthly, over an extended period of time for treatment of cold aggultinin disease.

In some embodiments, the subject suffering from glaucoma has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

In one aspect of the invention, the pharmaceutical compositions are administered to a subject suffering from or at risk of developing acute radiation syndrome, in an amount sufficient to eliminate or reduce the risk of developing symptoms of the condition. In therapeutic applications, the pharmaceutical compositions are administered to a subject suspected of or already suffering from, acute radiation syndrome in a therapeutically effective amount sufficient to relieve, or at least partially reduce, the symptoms of the condition. A subject may be treated with a MASP-2 inhibitory composition of the present invention prior to or after exposure to radiation, such as radiation exposure for the treatment of cancerous conditions, while cleaning up a site contaminated with radiation, in working with radioactive materials in an energy generation plant or laboratory, or due to radiation exposure resulting from a nuclear accident, terrorist action or warfare. In one embodiment of the present invention, the MASP-2 inhibitory composition is administered within 24 to 48 hours after radiation exposure.

In a still further aspect of the present invention, a subject suffering from or at risk of developing acute radiation syndrome and being treated with a MASP-2 inhibitory composition of the present invention can be monitored by periodically determining, such as every twelve hours or on a daily basis, the level of at least one complement factor, wherein the determination of a reduced level of the at least one complement factor in comparison to a standard value or to a healthy subject is indicative of the need for continued treatment with the composition.

In both prophylactic and therapeutic regimens, compositions comprising MASP-2 inhibitory agents may be administered in several dosages until a sufficient therapeutic outcome has been achieved in the subject. In one embodiment of the invention, the MASP-2 inhibitory agent comprises an anti-MASP-2 antibody, which suitably may be administered to an adult patient (e.g., an average adult weight of 70 kg) in a dosage of from 0.1 mg to 10,000 mg, more suitably from 1.0 mg to 5,000 mg, more suitably 10.0 mg to 2,000 mg, more suitably 10.0 mg to 1,000 mg and still more suitably from 50.0 mg to 500 mg. For pediatric patients, dosage can be adjusted in proportion to the patient's weight. Application of the MASP-2 inhibitory compositions of the present invention may be carried out by a single administration of the composition, or a limited sequence of administrations, for treatment of glaucoma. Alternatively, the composition may be administered at periodic intervals, such as daily, biweekly, weekly, every other week, monthly or bimonthly, over an extended period of time for treatment of acute radiation syndrome.

In some embodiments, the subject suffering from acute radiation syndrome has previously undergone, or is currently undergoing treatment with a terminal complement inhibitor that inhibits cleavage of complement protein C5. In some embodiments, the method comprises administering to the subject a composition of the invention comprising a MASP-2 inhibitor and further administering to the subject a terminal complement inhibitor that inhibits cleavage of complement protein C5. In some embodiments, the terminal complement inhibitor is a humanized anti-C5 antibody or antigen-binding fragment thereof. In some embodiments, the terminal complement inhibitor is eculizumab.

VI. EXAMPLES

The following examples merely illustrate the best mode now contemplated for practicing the invention, but should not be construed to limit the invention. All literature citations herein are expressly incorporated by reference.

Example 1

This example describes the generation Of a mouse strain deficient in MASP-2 (MASP-2−/−) but sufficient of MAp19 (MAp19+/+).

Figure 3:
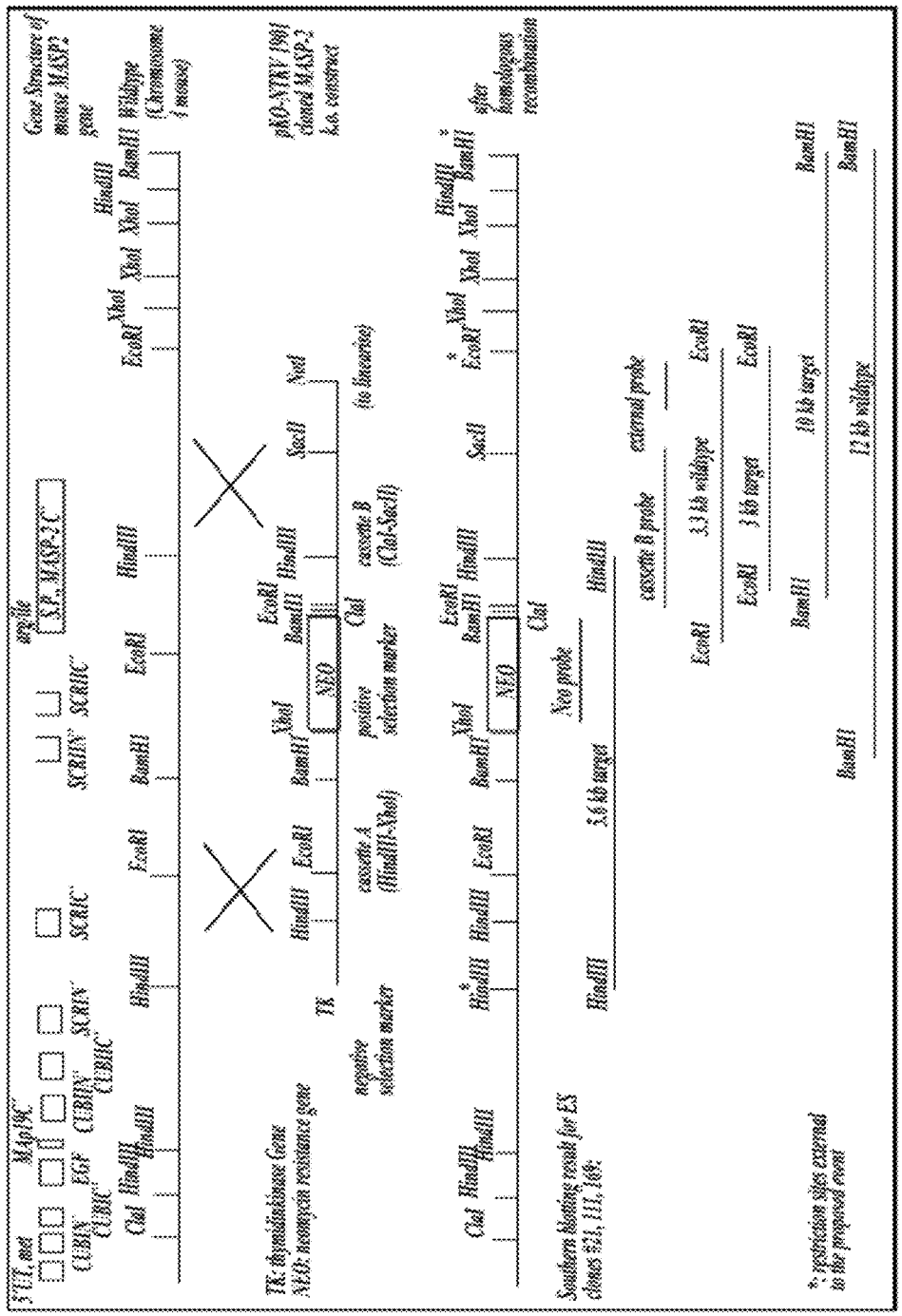
FIG. 3 is a diagram illustrating the murine MASP-2 knockout strategy.

Materials and Methods:

The targeting vector pKO-NTKV 1901 was designed to disrupt the three exons coding for the C-terminal end of murine MASP-2, including the exon that encodes the serine protease domain, as shown in FIG. 3. PKO-NTKV 1901 was used to transfect the murine ES cell line E14.1a (SV129 Ola). Neomycin-resistant and Thymidine Kinase-sensitive clones were selected. 600 ES clones were screened and, of these, four different clones were identified and verified by southern blot to contain the expected selective targeting and recombination event as shown in FIG. 3. Chimeras were generated from these four positive clones by embryo transfer. The chimeras were then backcrossed in the genetic background C57/BL6 to create transgenic males. The transgenic males were crossed with females to generate F1s with 50% of the offspring showing heterozygosity for the disrupted MASP-2 gene. The heterozygous mice were intercrossed to generate homozygous MASP-2 deficient offspring, resulting in heterozygous and wild-type mice in the ration of 1:2:1, respectively.

Results and Phenotype:

The resulting homozygous MASP-2−/− deficient mice were found to be viable and fertile and were verified to be MASP-2 deficient by southern blot to confirm the correct targeting event, by Northern blot to confirm the absence of MASP-2 mRNA, and by Western blot to confirm the absence of MASP-2 protein (data not shown). The presence of MAp19 mRNA and the absence of MASP-2 mRNA were further confirmed using time-resolved RT-PCR on a LightCycler machine. The MASP-2−/− mice do continue to express MAp19, MASP-1, and MASP-3 mRNA and protein as expected (data not shown). The presence and abundance of mRNA in the MASP-2−/− mice for Properdin, Factor B, Factor D, C4, C2, and C3 was assessed by LightCycler analysis and found to be identical to that of the wild-type littermate controls (data not shown). The plasma from homozygous MASP-2−/− mice is totally deficient of lectin-pathway-mediated complement activation as further described in Example 2.

Generation of a MASP-2−/− strain on a pure C57BL6 Background: The MASP-2−/− mice were back-crossed with a pure C57BL6 line for nine generations prior to use of the MASP-2−/− strain as an experimental animal model.

Figure 4:
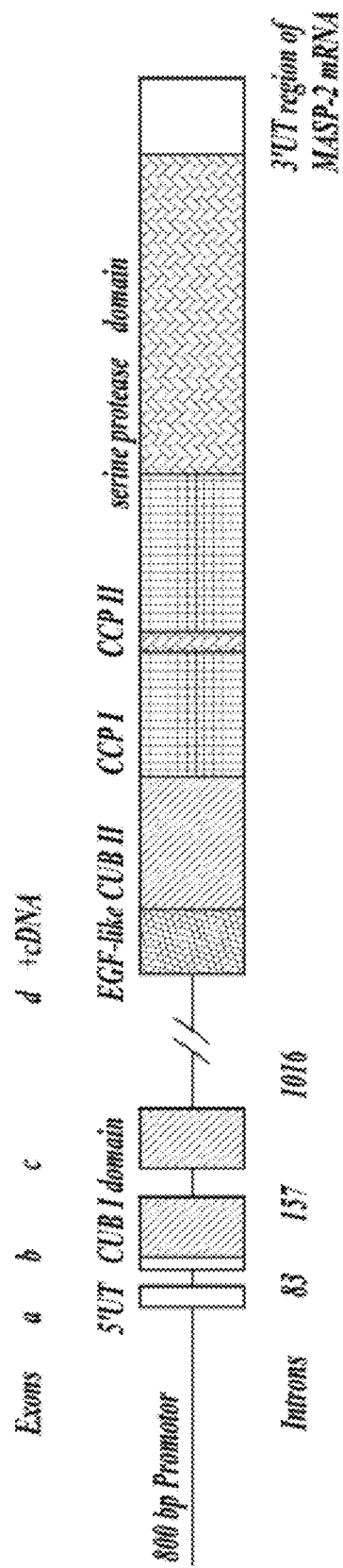
FIG. 4 is a diagram illustrating the human MASP-2 minigene construct.

A transgenic mouse strain that is murine MASP-2−/−, MAp19+/+ and that expresses a human MASP-2 transgene (a murine MASP-2 knock-out and a human MASP-2 knock-in) was also generated as follows:

Materials and Methods:

A minigene encoding human MASP-2 called "mini hMASP-2" (SEQ ID NO:49) as shown in FIG. 4 was constructed which includes the promoter region of the human MASP 2 gene, including the first 3 exons (exon I to exon 3) followed by the cDNA sequence that represents the coding sequence of the following 8 exons, thereby encoding the full-length MASP-2 protein driven by its endogenous promoter. The mini hMASP-2 construct was injected into fertilized eggs of MASP-2−/− in order to replace the deficient murine MASP 2 gene by transgenically expressed human MASP-2.

Example 2

This example demonstrates that MASP-2 is required for complement activation via the lectin pathway.

Methods and Materials:

Lectin Pathway Specific C4 Cleavage Assay:

A C4 cleavage assay has been described by Petersen, et al., *J. Immunol. Methods* 257:107 (2001) that measures lectin pathway activation resulting from lipoteichoic acid (LTA) from *S. aureus*, which binds L-ficolin. The assay described by Petersen et al., (2001) was adapted to measure lectin pathway activation via MBL by coating the plate with LPS and mannan or zymosan prior to adding serum from MASP-2−/− mice as described below. The assay was also modified to remove the possibility of C4 cleavage due to the classical pathway. This was achieved by using a sample dilution buffer containing 1 M NaCl, which permits high affinity binding of lectin pathway recognition components to their ligands but prevents activation of endogenous C4, thereby excluding the participation of the classical pathway by dissociating the C1 complex. Briefly described, in the modified assay serum samples (diluted in high salt (1 M NaCl) buffer) are added to ligand-coated plates, followed by the addition of a constant amount of purified C4 in a buffer with a physiological concentration of salt. Bound recognition complexes containing MASP-2 cleave the C4, resulting in C4b deposition.

Assay Methods:

1) Nunc Maxisorb microtiter plates (Maxisorb, Nunc, Cat. No. 442404, Fisher Scientific) were coated with 1 µg/ml mannan (M7504 Sigma) or any other ligand (e.g., such as those listed below) diluted in coating buffer (15 mM $Na_2CO_3$, 35 mM $NaHCO_3$, pH 9.6).

The following reagents were used in the assay:
a. mannan (1 µg/well mannan (M7504 Sigma) in 100 µl coating buffer):
b. zymosan (1 µg/well zymosan (Sigma) in 100 µl coating buffer);

c. LTA (1 µg/well in 100 µl coating buffer or 2 µg/well in 20 µl methanol)

d. 1 µg of the H-ficolin specific Mab 4H5 in coating buffer e. PSA from *Aerococcus viridans* (2 µg/well in 100 µl coating buffer)

f. 100 µl/well of formalin-fixed *S. aureus* DSM20233 ($OD_{550}$=0.5) in coating buffer.

2) The plates were incubated overnight at 4° C.

3) After overnight incubation, the residual protein binding sites were saturated by incubated the plates with 0.1% HSA-TBS blocking buffer (0.1% (w/v) HSA in 10 mM Tris-CL, 140 mM NaCl, 1.5 mM $NaN_3$, pH 7.4) for 1-3 hours, then washing the plates 3× with TBS/tween/$Ca^{2+}$ (TBS with 0.05% Tween 20 and 5 mM $CaCl_2$, 1 mM $MgCl_2$, pH 7.4).

4) Serum samples to be tested were diluted in MBL-binding buffer (1 M NaCl) and the diluted samples were added to the plates and incubated overnight at 4° C. Wells receiving buffer only were used as negative controls.

5) Following incubation overnight at 4° C., the plates were washed 3× with TBS/tween/Ca2+. Human C4 (100 µl/well of 1 µg/ml diluted in BBS (4 mM barbital, 145 mM NaCl, 2 mM $CaCl_2$, 1 mM $MgCl_2$, pH 7.4)) was then added to the plates and incubated for 90 minutes at 37° C. The plates were washed again 3× with TBS/tween/$Ca^{2+}$.

6) C4b deposition was detected with an alkaline phosphatase-conjugated chicken anti-human C4c (diluted 1:1000 in TBS/tween/$Ca^{2+}$), which was added to the plates and incubated for 90 minutes at room temperature. The plates were then washed again 3× with TBS/tween/$Ca^{2+}$.

7) Alkaline phosphatase was detected by adding 100 µl of p-nitrophenyl phosphate substrate solution, incubating at room temperature for 20 minutes, and reading the $OD_{405}$ in a microtiter plate reader.

Figure 5A:
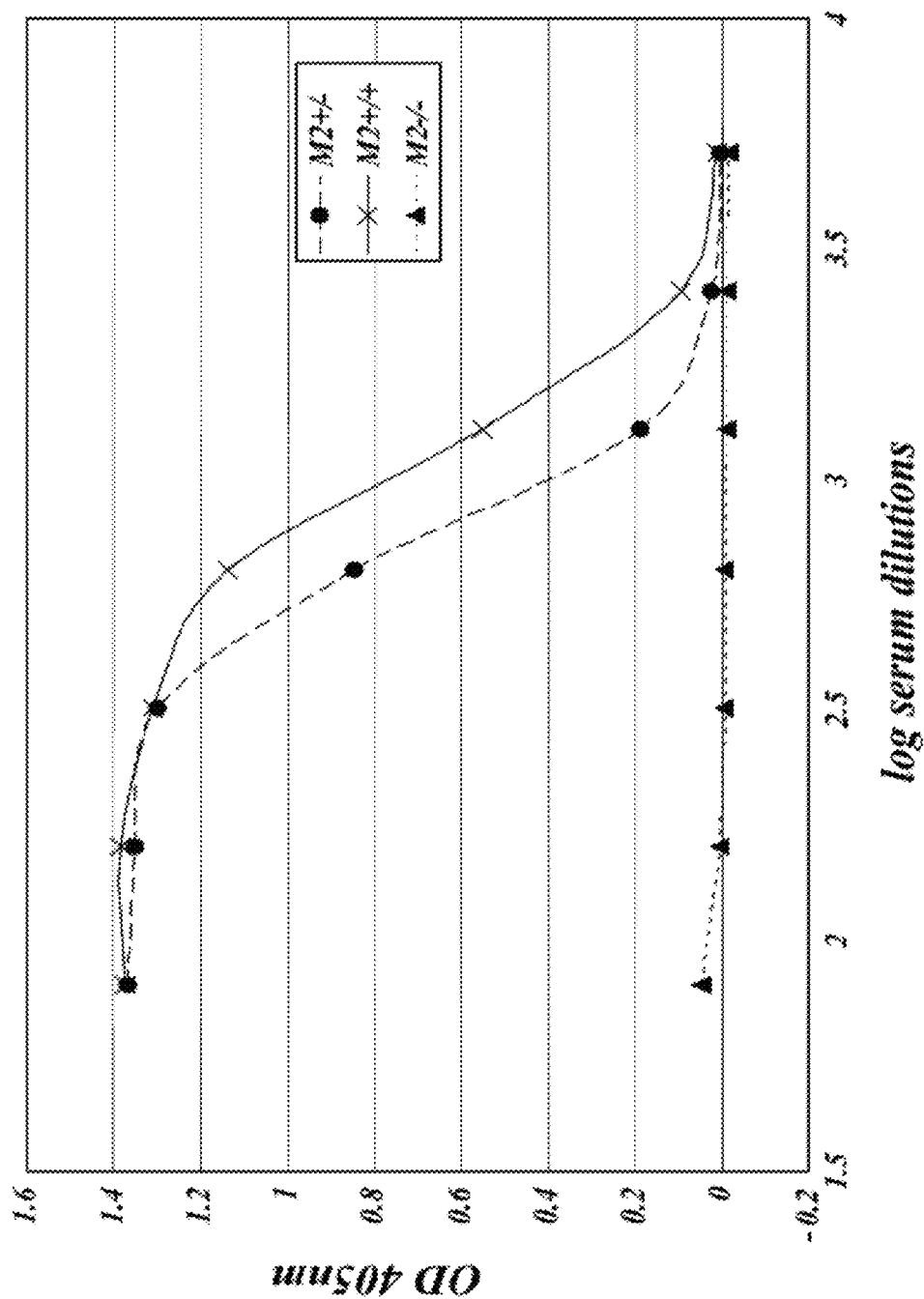
FIG. 5A presents results demonstrating that MASP-2-deficiency leads to the loss of lectin-pathway-mediated C4 activation as measured by lack of C4b deposition on mannan, as described in Example 2.
Figure 5B:
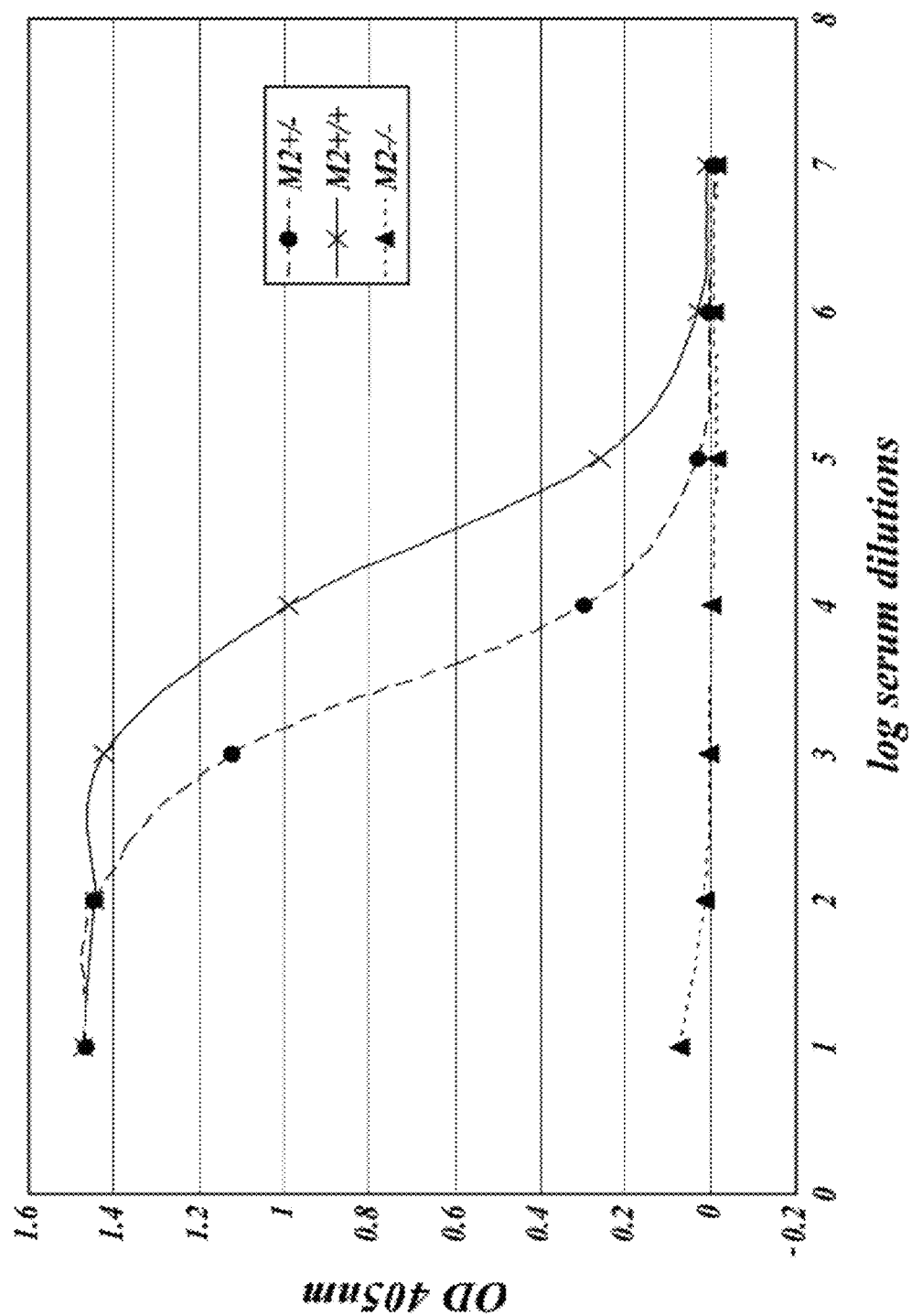
FIG. 5B presents results demonstrating that MASP-2-deficiency leads to the loss of lectin-pathway-mediated C4 activation as measured by lack of C4b deposition on zymosan, as described in Example 2.
Figure 5C:
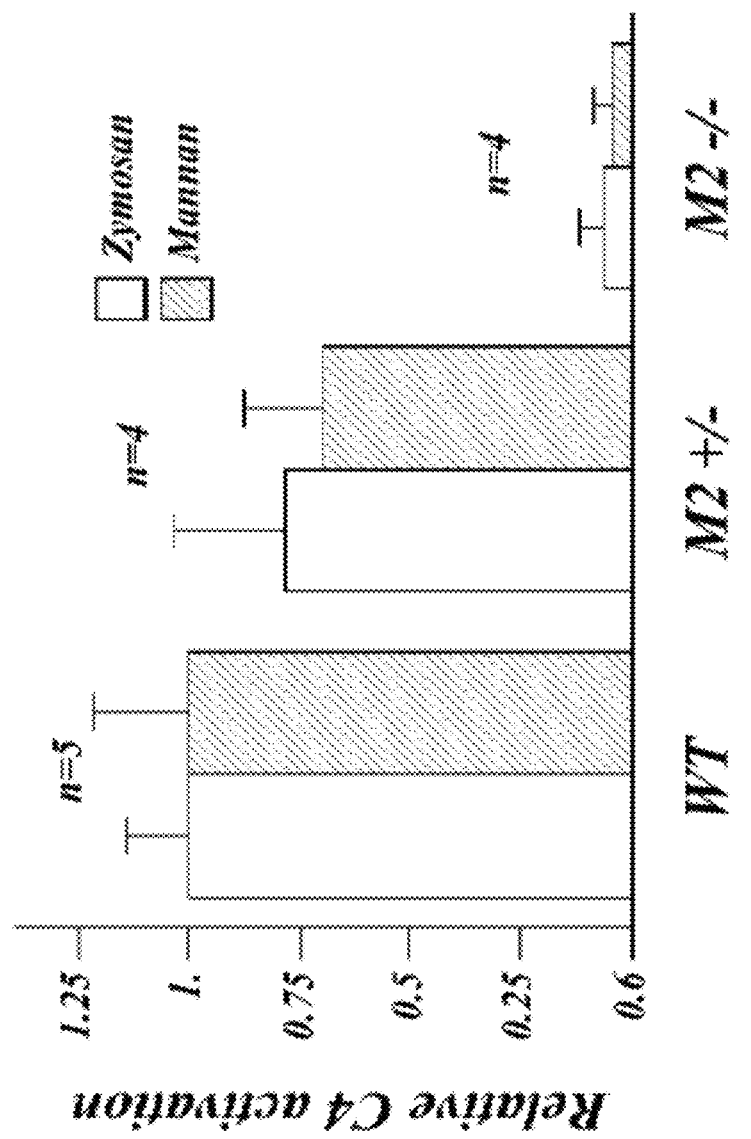
FIG. 5C presents results demonstrating the relative C4 activation levels of serum samples obtained from MASP-2+/−; MASP-2−/− and wild-type strains as measure by C4b deposition on mannan and on zymosan, as described in Example 2.

Results:

FIGS. 5A-B show the amount of C4b deposition on mannan (FIG. 5A) and zymosan (FIG. 5B) in serum dilutions from MASP-2+/+ (crosses), MASP-2+/− (closed circles) and MASP-2−/− (closed triangles). FIG. 5C shows the relative C4 convertase activity on plates coated with zymosan (white bars) or mannan (shaded bars) from MASP-2−/+ mice (n=5) and MASP-2−/− mice (n=4) relative to wild-type mice (n=5) based on measuring the amount of C4b deposition normalized to wild-type serum. The error bars represent the standard deviation. As shown in FIGS. 5A-C, plasma from MASP-2−/− mice is totally deficient in lectin-pathway-mediated complement activation on mannan and on zymosan coated plates. These results clearly demonstrate that MASP-2 is an effector component of the lectin pathway.

Recombinant MASP-2 Reconstitutes Lectin Pathway-Dependent C4 Activation in Serum from the MASP-2−/− Mice In order to establish that the absence of MASP-2 was the direct cause of the loss of lectin pathway-dependent C4 activation in the MASP-2−/− mice, the effect of adding recombinant MASP-2 protein to serum samples was examined in the C4 cleavage assay described above. Functionally active murine MASP-2 and catalytically inactive murine MASP-2A (in which the active-site serine residue in the serine protease domain was substituted for the alanine residue) recombinant proteins were produced and purified as described below in Example 3. Pooled serum from 4 MASP-2−/− mice was pre-incubated with increasing protein concentrations of recombinant murine MASP-2 or inactive recombinant murine MASP-2A and C4 convertase activity was assayed as described above.

Figure 6:
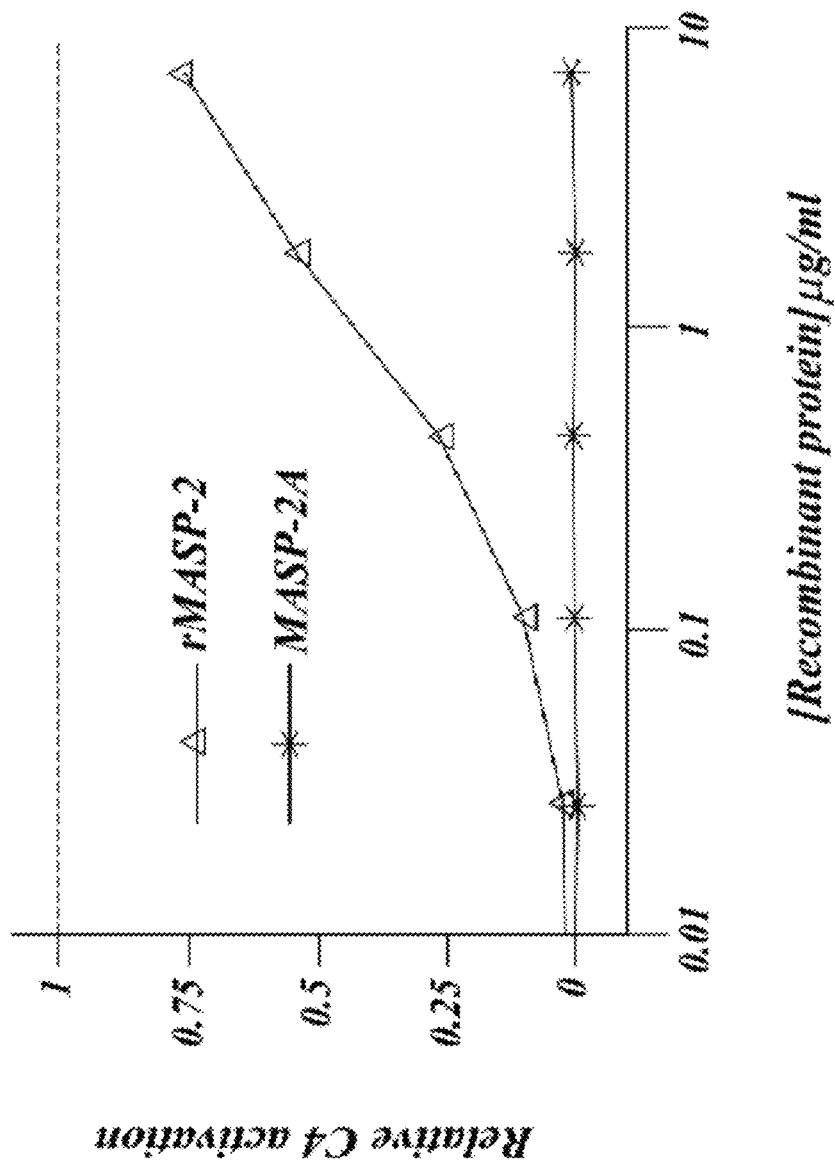
FIG. 6 presents results demonstrating that the addition of murine recombinant MASP-2 to MASP-2−/− serum samples recovers lectin-pathway-mediated C4 activation in a protein concentration dependant manner, as measured by C4b deposition on mannan, as described in Example 2.

Results:

As shown in FIG. 6, the addition of functionally active murine recombinant MASP-2 protein (shown as open triangles) to serum obtained from the MASA-2−/− mice restored lectin pathway-dependent C4 activation in a protein concentration dependent manner, whereas the catalytically inactive murine MASP-2A protein (shown as stars) did not restore C4 activation. The results shown in FIG. 6 are normalized to the C4 activation observed with pooled wild-type mouse scrum (shown as a dotted line).

Example 3

This example describes the recombinant expression and protein production of recombinant full-length human, rat and murine MASP-2, MASP-2 derived polypeptides, and catalytically inactivated mutant forms of MASP-2

Expression of Full-Length Human, Murine and Rat MASP-2:

The full length cDNA sequence of human MASP-2 (SEQ ID NO: 4) was also subcloned into the mammalian expression vector pCI-Neo (Promega), which drives eukaryotic expression under the control of the CMV enhancer/promoter region (described in Kaufman R. J. et al., *Nucleic Acids Research* 19:4485-90, 1991; Kaufman, *Methods in Enzymology*, 185: 537-66 (1991)). The full length mouse cDNA (SEQ ID NO:50) and rat MASP-2 cDNA (SEQ ID NO:53) were each subcloned into the pED expression vector. The MASP-2 expression vectors were then transfected into the adherent Chinese hamster ovary cell line DXB1 using the standard calcium phosphate transfection procedure described in Maniatis et al., 1989. Cells transfected with these constructs grew very slowly, implying that the encoded protease is cytotoxic.

In another approach, the minigene construct (SEQ ID NO:49) containing the human cDNA of MASP-2 driven by its endogenous promoter is transiently transfected into Chinese hamster ovary cells (CHO). The human MASP-2 protein is secreted into the culture media and isolated as described below.

Expression of Full-Length Catalytically Inactive MASP-2:

Rationale: MASP-2 is activated by autocatalytic cleavage after the recognition subcomponents MBL or ficolins (either L-ficolin, H-ficolin or M-ficolin) bind to their respective carbohydrate pattern. Autocatalytic cleavage resulting in activation of MASP-2 often occurs during the isolation procedure of MASP-2 from serum, or during the purification following recombinant expression. In order to obtain a more stable protein preparation for use as an antigen, a catalytically inactive form of MASP-2, designed as MASP-2A was created by replacing the serine residue that is present in the catalytic triad of the protease domain with an alanine residue in rat (SEQ ID NO:55 Ser617 to Ala617); in mouse (SEQ ID NO:52 Ser617 to Ala617); or in human (SEQ ID NO:3 Ser618 to Ala618).

In order to generate catalytically inactive human and murine MASP-2A proteins, site-directed mutagenesis was carried out using the oligonucleotides shown in TABLE 5. The oligonucleotides in TABLE 5 were designed to anneal to the region of the human and murine cDNA encoding the enzymatically active serine and oligonucleotide contain a mismatch in order to change the serine codon into an alanine codon. For example, PCR oligonucleotides SEQ ID NOS:56-59 were used in combination with human MASP-2 cDNA (SEQ ID NO:4) to amplify the region from the start codon to the enzymatically active serine and from the serine to the stop codon to generate the complete open reading from of the mutated MASP-2A containing the Ser618 to Ala618 mutation. The PCR products were purified after agarose gel electrophoresis and band preparation and single adenosine overlaps were generated using a standard tailing procedure. The adenosine tailed MASP-2A was then cloned into the pGEM-T easy vector, transformed into *E. coli*.

A catalytically inactive rat MASP-2A protein was generated by kinasing and annealing SEQ ID NO:64 and SEQ ID NO:65 by combining these two oligonucleotides in equal molar amounts, heating at 100° C. for 2 minutes and slowly cooling to room temperature. The resulting annealed fragment has PstI and XbaI compatible ends and was inserted in place of the PstI-XbaI fragment of the wild-type rat MASP-2 cDNA (SEQ ID NO:53) to generate rat MASP-2A.

```
                                            (SEQ ID NO: 64)
5'GAGGTGACGCAGGAGGGGCATTAGTGTTT 3'

(SEQ ID NO: 65)
5' CTAGAAACACTAATGCCCCTCCTGCGTCACCTCTGCA 3'
```

The human, murine and rat MASP-2A were each further subcloned into either of the mammalian expression vectors pED or pCI-Neo and transfected into the Chinese Hamster ovary cell line DXB1 as described below.

In another approach, a catalytically inactive form of MASP-2 is constructed using the method described in Chen et al., *J. Biol. Chem.*, 276(28):25894-25902, 2001. Briefly, the plasmid containing the full-length human MASP-2 cDNA (described in Thiel et al., *Nature* 386:506, 1997) is digested with XhoI and EcoRI and the MASP-2 cDNA (described herein as SEQ ID NO:4) is cloned into the corresponding restriction sites of the pFastBac1 baculovirus transfer vector (Life Technologies, N.Y.). The MASP-2 serine protease active site at Ser618 is then altered to Ala618 by substituting the double-stranded oligonucleotides encoding the peptide region amino acid 610-625 (SEQ ID NO:13) with the native region amino acids 610 to 625 to create a MASP-2 full length polypeptide with an inactive protease domain. Construction of Expression Plasmids Containing Polypeptide Regions Derived from Human Masp-2.

The following constructs are produced using the MASP-2 signal peptide (residues 1-15 of SEQ ID NO:5) to secrete various domains of MASP-2. A construct expressing the human MASP-2 CUBI domain (SEQ ID NO:8) is made by PCR amplifying the region encoding residues 1-121 of MASP-2 (SEQ ID NO:6) (corresponding to the N-terminal CUBI domain). A construct expressing the human MASP-2 CUBIEGF domain (SEQ ID NO:9) is made by PCR amplifying the region encoding residues 1-166 of MASP-2 (SEQ ID NO:6) (corresponding to the N-terminal CUBIEGF domain). A construct expressing the human MASP-2 CUBIEGFCUBII domain (SEQ ID NO:10) is made by PCR amplifying the region encoding residues 1-293 of MASP-2 (SEQ ID NO:6) (corresponding to the N-terminal CUBIEG-FCUBII domain). The above mentioned domains are amplified by PCR using Vent$_R$ polymerase and pBS-MASP-2 as a template, according to established PCR methods. The 5' primer sequence of the sense primer (5'-CG GGATCCATGAGGCTGCTGACCCTC-3' SEQ ID NO:34) introduces a BamHI restriction site (underlined) at the 5' end of the PCR products. Antisense primers for each of the MASP-2 domains, shown below in TABLE 5, are designed to introduce a stop codon (boldface) followed by an EcoRI site (underlined) at the end of each PCR product. Once amplified, the DNA fragments are digested with BamHI and EcoRI and cloned into the corresponding sites of the pFastBac1 vector. The resulting constructs are characterized by restriction mapping and confirmed by dsDNA sequencing.

TABLE 5

MASP-2 PCR PRIMERS

| MASP-2 domain | 5' PCR Primer | 3' PCR Primer |
|---|---|---|
| SEQ ID NO: 8 CUBI (aa 1-121 of SEQ ID NO: 6) | 5'CGGGATCCATGA GGCTGCTGACCCT C-3' (SEQ ID NO: 34) | 5'GGAATTCCTAGGCTGCAT A (SEQ ID NO: 35) |
| SEQ ID NO: 9 CUBIEGF (aa 1-166 of SEQ ID NO: 6) | 5'CGGGATCCATGA GGCTGCTGACCCT C-3' (SEQ ID NO: 34) | 5'GGAATTCCTACAGGGCGC T-3' (SEQ ID NO: 36) |
| SEQ ID NO:10 CUBIEGFCUBII (aa 1-293 of SEQ ID NO: 6) | 5'CGGGATCCATGA GGCTGCTGACCCT C-3' (SEQ ID NO: 34) | 5'GGAATTCCTAGTAGTGGA T3' (SEQ ID NO: 37) |
| SEQ ID NO: 4 human MASP-2 | 5'ATGAGGCTGCTG ACCCTCCTGGGCC TTC3' (SEQ ID NO: 56) hMASP-2_forward | 5'TAAAATCACTAATTATG TTCTCGATC 3' (SEQ ID NO: 59) hMASP-2_reverse |
| SEQ ID NO: 4 human MASP-2 | 5'CAGAGGTGACGC cDNA AGGAGGGGCAC 3' (SEQ ID NO: 58) hMASP-2_ala_forward | 5'GTGCCCCTCCTGCGTCAC CTCTG 3' (SEQ ID NO: 57) hMASP-2_ala_reverse |
| SEQ ID NO: 50 Murine MASP-2 | 5'ATGAGGCTACTC cDNA ATCTTCCTGG3' (SEQ ID NO: 60) mMASP-2_forward | 5'TTAGAAATTACTTATTAT GTTCTCAATCC3' (SEQ ID NO: 63) mMASP-2_reverse |
| SEQ ID NO: 50 Murine MASP-2 | 5'CCCCCCCTGCGT cDNACACCTCTGCAG3' (SEQ ID NO: 62) mMASP-2_ala_forward | 5'CTGCAGAGGTGACGCAG GGGGGG 3' (SEQ ID NO: 61) mMASP-2_ala_reverse |

Recombinant Eukaryotic Expression of MASP-2 and Protein Production of Enzymatically Inactive Mouse, Rat, and Human MASP-2A.

The MASP-2 and MASP-2A expression constructs described above were transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium for each of the three 10 species.

MASP-2A Protein Purification:

The MASP-2A (Ser-Ala mutant described above) was purified by affinity chromatography on MBP-A-agarose columns. This strategy enabled rapid purification without the use of extraneous tags. MASP-2A (100-200 ml of medium diluted with an equal volume of loading buffer (50 mM Tris-Cl, pH 7.5, containing 150 mM NaCl and 25 mM $CaCl_2$) was loaded onto an MBP-agarose affinity column (4 ml) pre-equilibrated with 10 ml of loading buffer. Following washing with a further 10 ml of loading buffer, protein was eluted in 1 ml fractions with 50 mM Tris-Cl, pH 7.5, containing 1.25 M NaCl and 10 mM EDTA. Fractions containing the MASP-2A were identified by SDS-polyacrylamide gel electrophoresis. Where necessary, MASP-2A was purified further by ion-exchange chromatography on a MonoQ column (HR. 5/5). Protein was dialysed with 50 mM Tris-Cl pH 7.5, containing 50 mM NaCl and loaded onto the column equilibrated in the same buffer. Following washing, bound MASP-2A was eluted with a 0.05-1 M NaCl gradient over 10 ml.

Results:

Yields of 0.25-0.5 mg of MASP-2A protein were obtained from 200 ml of medium. The molecular mass of 77.5 kDa determined by MALDI-MS is greater than the calculated value of the unmodified polypeptide (73.5 kDa) due to glycosylation. Attachment of glycans at each of the N-glycosylation sites accounts for the observed mass. MASP-2A migrates as a single band on SDS-polyacrylamide gels, demonstrating that it is not proteolytically processed during biosynthesis. The weight-average molecular mass determined by equilibrium ultracentrifugation is in agreement with the calculated value for homodimers of the glycosylated polypeptide.

Production of Recombinant Human MASP-2 Polypeptides

Another method for producing recombinant MASP-2 and MASP2A derived polypeptides is described in Thielens, N. M., et al., *J. Immunol.* 166:5068-5077, 2001. Briefly, the *Spodoptera frugiperda* insect cells (Ready-Plaque Sf9 cells obtained from Novagen, Madison, Wis.) are grown and maintained in Sf900II serum-free medium (Life Technologies) supplemented with 50 IU/ml penicillin and 50 mg/ml streptomycin (Life Technologies). The *Trichoplusia ni* (High Five) insect cells (provided by Jadwiga Chroboczek, Institut de Biologie Structurale, Grenoble, France) are maintained in TC100 medium (Life Technologies) containing 10% FCS (Dominique Dutscher, Brumath, France) supplemented with 50 IU/ml penicillin and 50 mg/ml streptomycin. Recombinant baculoviruses are generated using the Bac-to-Bac system (Life Technologies). The bacmid DNA is purified using the Qiagen midiprep purification system (Qiagen) and is used to transfect Sf9 insect cells using cellfectin in Sf900 II SFM medium (Life Technologies) as described in the manufacturer's protocol. Recombinant virus particles are collected 4 days later, titrated by virus plaque assay, and amplified as described by King and Possee, in *The Baculovirus Expression System: A Laboratory Guide*, Chapman and Hall Ltd., London, pp. 111-114, 1992.

High Five cells ($1.75 \times 10^7$ cells/175-$cm^2$ tissue culture flask) are infected with the recombinant viruses containing MASP-2 polypeptides at a multiplicity of infection of 2 in Sf900 II SFM medium at 28° C. for 96 h. The supernatants are collected by centrifugation and diisopropyl phosphorofluoridate is added to a final concentration of 1 mM.

The MASP-2 polypeptides are secreted in the culture medium. The culture supernatants are dialyzed against 50 mM NaCl, 1 mM $CaCl_2$, 50 mM triethanolamine hydrochloride, pH 8.1, and loaded at 1.5 ml/min onto a Q-Sepharose Fast Flow column (Amersham Pharmacia Biotech) (2.8×12 cm) equilibrated in the same buffer. Elution is conducted by applying a 1.2 liter linear gradient to 350 mM NaCl in the same buffer. Fractions containing the recombinant MASP-2 polypeptides are identified by Western blot analysis, precipitated by addition of $(NH_4)_2SO_4$ to 60% (w/v), and left overnight at 4° C. The pellets are resuspended in 145 mM NaCl, 1 mM $CaCl_2$, 50 mM triethanolamine hydrochloride, pH 7.4, and applied onto a TSK G3000 SWG column (7.5×600 mm) (Tosohaas, Montgomeryville, Pa.) equilibrated in the same buffer. The purified polypeptides are then concentrated to 0.3 mg/ml by ultrafiltration on Microsep microconcentrators (m.w. cut-off=10,000) (Filtron, Karlstein, Germany).

Example 4

This example describes a method of producing polyclonal antibodies against MASP-2 polypeptides.

Materials and Methods:

MASP-2 Antigens:

Polyclonal anti-human MASP-2 antiserum is produced by immunizing rabbits with the following isolated MASP-2 polypeptides: human MASP-2 (SEQ ID NO:6) isolated from serum; recombinant human MASP-2 (SEQ ID NO:6), MASP-2A containing the inactive protease domain (SEQ ID NO:13), as described in Example 3; and recombinant CUBI (SEQ ID NO:8), CUBEGFI (SEQ ID NO:9), and CUBEGFCUBII (SEQ ID NO:10) expressed as described above in Example 3.

Polyclonal Antibodies:

Six-week old Rabbits, primed with BCG (bacillus Calmette-Guerin vaccine) are immunized by injecting 100 µg of MASP-2 polypeptide at 100 µg/ml in sterile saline solution. Injections are done every 4 weeks, with antibody titer monitored by ELISA assay as described in Example 5. Culture supernatants are collected for antibody purification by protein A affinity chromatography.

Example 5

This example describes a method for producing murine monoclonal antibodies against rat or human MASP-2 polypeptides.

Materials and Methods:

Male A/J mice (Harlan, Houston, Tex.), 8-12 weeks old, are injected subcutaneously with 100 µg human or rat rMASP-2 or rMASP-2A polypeptides (made as described in Example 3) in complete Freund's adjuvant (Difco Laboratories, Detroit, Mich.) in 200 µl of phosphate buffered saline (PBS) pH 7.4. At two-week intervals the mice are twice injected subcutaneously with 50 µg of human or rat rMASP-2 or rMASP-2A polypeptide in incomplete Freund's adjuvant. On the fourth week the mice are injected with 50 μg of human or rat rMASP-2 or rMASP-2A polypeptide in PBS and are fused 4 days later.

For each fusion, single cell suspensions are prepared from the spleen of an immunized mouse and used for fusion with the Sp2/0 myeloma cells. $5 \times 10^8$ of the Sp2/0 and $5 \times 10^8$ spleen cells are fused in a medium containing 50% polyethylene glycol (M.W. 1450) (Kodak, Rochester, N.Y.) and 5% dimethylsulfoxide (Sigma Chemical Co., St. Louis, Mo.). The cells are then adjusted to a concentration of $1.5 \times 10^5$ spleen cells per 200 μl of the suspension in Iscove medium (Gibco, Grand Island, N.Y.), supplemented with 10% fetal bovine serum, 100 units/ml of penicillin, 100 μg/ml of streptomycin, 0.1 mM hypoxanthine, 0.4 μM aminopterin and 16 μM thymidine. Two hundred microliters of the cell suspension are added to each well of about twenty 96-well microculture plates. After about ten days culture supernatants are withdrawn for screening for reactivity with purified factor MASP-2 in an ELISA assay.

ELISA Assay:

Wells of Immulon 2 (Dynatech Laboratories, Chantilly, Va.) microtest plates are coated by adding 50 μl of purified hMASP-2 at 50 ng/ml or rat rMASP-2 (or rMASP-2A) overnight at room temperature. The low concentration of MASP-2 for coating enables the selection of high-affinity antibodies. After the coating solution is removed by flicking the plate, 200 μl of BLOTTO (non-fat dry milk) in PBS is added to each well for one hour to block the non-specific sites. An hour later, the wells are then washed with a buffer PBST (PBS containing 0.05% Tween 20). Fifty microliters of culture supernatants from each fusion well is collected and mixed with 50 μl of BLOTTO and then added to the individual wells of the microtest plates. After one hour of incubation, the wells are washed with PBST. The bound murine antibodies are then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma, St. Louis, Mo.) and 0.0003% hydrogen peroxide (Sigma) is added to the wells for color development for 30 minutes. The reaction is terminated by addition of 50 μl of 2M $H_2SO_4$ per well. The Optical Density at 450 nm of the reaction mixture is read with a BioTek ELISA Reader (BioTek Instruments, Winooski, Vt.).

MASP-2 Binding Assay:

Culture supernatants that test positive in the MASP-2 ELISA assay described above can be tested in a binding assay to determine the binding affinity the MASP-2 inhibitory agents have for MASP-2. A similar assay can also be used to determine if the inhibitory agents bind to other antigens in the complement system.

Polystyrene microtiter plate wells (96-well medium binding plates, Corning Costar, Cambridge, Mass.) are coated with MASP-2 (20 ng/100 μl/well, Advanced Research Technology, San Diego, Calif.) in phosphate-buffered saline (PBS) pH 7.4 overnight at 4° C. After aspirating the MASP-2 solution, wells are blocked with PBS containing 1% bovine serum albumin (BSA; Sigma Chemical) for 2 h at room temperature. Wells without MASP-2 coating serve as the background controls. Aliquots of hybridoma supernatants or purified anti-MASP-2 MoAbs, at varying concentrations in blocking solution, are added to the wells. Following a 2 h incubation at room temperature, the wells are extensively rinsed with PBS. MASP-2-bound anti-MASP-2 MoAb is detected by the addition of peroxidase-conjugated goat anti-mouse IgG (Sigma Chemical) in blocking solution, which is allowed to incubate for 1 h at room temperature. The plate is rinsed again thoroughly with PBS, and 100 μl of 3,3',5,5'-tetramethyl benzidine (TMB) substrate (Kirkegaard and Perry Laboratories, Gaithersburg, Md.) is added. The reaction of TMB is quenched by the addition of 100 μl of 1M phosphoric acid, and the plate is read at 450 nm in a microplate reader (SPECTRA MAX 250, Molecular Devices, Sunnyvale, Calif.).

The culture supernatants from the positive wells are then tested for the ability to inhibit complement activation in a functional assay such as the C4 cleavage assay as described in Example 2. The cells in positive wells are then cloned by limiting dilution. The MoAbs are tested again for reactivity with hMASP-2 in an ELISA assay as described above. The selected hybridomas are grown in spinner flasks and the spent culture supernatant collected for antibody purification by protein A affinity chromatography.

Example 6

This example describes the generation and production of humanized murine anti-MASP-2 antibodies and antibody fragments.

A murine anti-MASP-2 monoclonal antibody is generated in Male A/J mice as described in Example 5. The murine antibody is then humanized as described below to reduce its immunogenicity by replacing the murine constant regions with their human counterparts to generate a chimeric IgG and Fab fragment of the antibody, which is useful for inhibiting the adverse effects of MASP-2-dependent complement activation in human subjects in accordance with the present invention.

1. Cloning of Anti-MASP-2 Variable Region Genes from Murine Hybridoma Cells.

Total RNA is isolated from the hybridoma cells secreting anti-MASP-2 MoAb (obtained as described in Example 7) using RNAzol following the manufacturer's protocol (Biotech, Houston, Tex.). First strand cDNA is synthesized from the total RNA using oligo dT as the primer. PCR is performed using the immunoglobulin constant C region-derived 3' primers and degenerate primer sets derived from the leader peptide or the first framework region of murine $V_H$ or $V_K$ genes as the 5' primers. Anchored PCR is carried out as described by Chen and Platsucas (Chen, P. F., Scand. J. Immunol. 35:539-549, 1992). For cloning the $V_K$ gene, double-stranded cDNA is prepared using a NotI-MAK1 primer (5'-TGCGGCCGCTG-TAGGTGCTGTCTTT-3' SEQ ID NO:38). Annealed adaptors AD1 (5'-GGAATTCACTCGTTATTCTCGGA-3' SEQ ID NO:39) and AD2 (5'-TCCGAGAATAACGAGTG-3' SEQ ID NO:40) are ligated to both 5' and 3' termini of the double-stranded cDNA. Adaptors at the 3' ends are removed by NotI digestion. The digested product is then used as the template in PCR with the AD1 oligonucleotide as the 5' primer and MAK2 (5'-CATTGAAAGCTTTGGGGTAGAAGTTGTTC-3' SEQ ID NO:41) as the 3' primer. DNA fragments of approximately 500 bp are cloned into pUC19. Several clones are selected for sequence analysis to verify that the cloned sequence encompasses the expected murine immunoglobulin constant region. The NotI-MAK1 and MAK2 oligonucleotides are derived from the $V_K$ region and are 182 and 84 bp, respectively, downstream from the first base pair of the C kappa gene. Clones are chosen that include the complete $V_K$ and leader peptide.

For cloning the $V_H$ gene, double-stranded cDNA is prepared using the NotI MAG1 primer (5'-CGCGGCCG-CAGCTGCTCAGAGTGTAGA-3' SEQ ID NO:42). Annealed adaptors AD1 and AD2 are ligated to both 5' and 3' termini of the double-stranded cDNA. Adaptors at the 3' ends are removed by NotI digestion. The digested product are used as the template in PCR with the AD1 oligonucleotide and MAG2 (5'-CGGTAAGCTTCACTGGCTCAGGGAAATA-3' SEQ ID NO:43) as primers. DNA fragments of 500 to 600 bp in length are cloned into pUC19. The NotI-MAG1 and MAG2 oligonucleotides are derived from the murine Cγ.7.1 region, and are 180 and 93 bp, respectively, downstream from the first by of the murine Cγ.7.1 gene. Clones are chosen that encompass the complete $V_H$ and leader peptide.

2. Construction of Expression Vectors for Chimeric MASP-2 IgG and Fab.

The cloned $V_H$ and $V_K$ genes described above are used as templates in a PCR reaction to add the Kozak consensus sequence to the 5' end and the splice donor to the 3' end of the nucleotide sequence. After the sequences are analyzed to confirm the absence of PCR errors, the $V_H$ and $V_K$ genes are inserted into expression vector cassettes containing human C.γ1 and C. kappa respectively, to give pSV2neo$V_H$-huCγ1 and pSV2neoV-huCγ. CsCl gradient-purified plasmid DNAs of the heavy- and light-chain vectors are used to transfect COS cells by electroporation. After 48 hours, the culture supernatant is tested by ELISA to confirm the presence of approximately 200 ng/ml of chimeric IgG. The cells are harvested and total RNA is prepared. First strand cDNA is synthesized from the total RNA using oligo dT as the primer. This cDNA is used as the template in PCR to generate the Fd and kappa DNA fragments. For the Fd gene, PCR is carried out using 5'-AAGAAGCTTGCCGCCACCATGGATTG-GCTGTGGAACT-3' (SEQ ID NO:44) as the 5' primer and a CH1-derived 3' primer (5'-CGGGATCCTCAAACTTTCT-TGTCCACCTTGG-3' SEQ ID NO:45). The DNA sequence is confirmed to contain the complete $V_H$ and the CH1 domain of human IgG1. After digestion with the proper enzymes, the Fd DNA fragments are inserted at the HindIII and BamHI restriction sites of the expression vector cassette pSV2dhfr-TUS to give pSV2dhfrFd. The pSV2 plasmid is commercially available and consists of DNA segments from various sources: pBR322 DNA (thin line) contains the pBR322 origin of DNA replication (pBR ori) and the lactamase ampicillin resistance gene (Amp); SV40 DNA, represented by wider hatching and marked, contains the SV40 origin of DNA replication (SV40 ori), early promoter (5' to the dhfr and neo genes), and polyadenylation signal (3' to the dhfr and neo genes). The SV40-derived polyadenylation signal (pA) is also placed at the 3' end of the Fd gene.

For the kappa gene, PCR is carried out using 5'-AA-GAAAGCTTGCCGCCACCATGTTCTCACTAGCTCT-3' (SEQ ID NO:46) as the 5' primer and a $C_K$-derived 3' primer (5'-CGGGATCCTTCTCCCTCTAACACTCT-3' SEQ ID NO:47). DNA sequence is confirmed to contain the complete $V_K$ and human $C_K$ regions. After digestion with proper restriction enzymes, the kappa DNA fragments are inserted at the HindIII and BamHI restriction sites of the expression vector cassette pSV2neo-TUS to give pSV2neoK. The expression of both Fd and .kappa genes are driven by the HCMV-derived enhancer and promoter elements. Since the Fd gene does not include the cysteine amino acid residue involved in the inter-chain disulfide bond, this recombinant chimeric Fab contains non-covalently linked heavy- and light-chains. This chimeric Fab is designated as cFab.

To obtain recombinant Fab with an inter-heavy and light chain disulfide bond, the above Fd gene may be extended to include the coding sequence for additional 9 amino acids (EPKSCDKTH SEQ ID NO:48) from the hinge region of human IgG1. The BstEII-BamHI DNA segment encoding 30 amino acids at the 3' end of the Fd gene may be replaced with DNA segments encoding the extended Fd, resulting in pSV2dhfrFd/9aa.

3. Expression and Purification of Chimeric Anti-MASP-2 IgG

To generate cell lines secreting chimeric anti-MASP-2 IgG, NSO cells are transfected with purified plasmid DNAs of pSV2neo$V_H$-huC.γ1 and pSV2neoV-huC kappa by electroporation. Transfected cells are selected in the presence of 0.7 mg/ml G418. Cells are grown in a 250 ml spinner flask using serum-containing medium.

Culture supernatant of 100 ml spinner culture is loaded on a 10-ml PROSEP-A column (Bioprocessing, Inc., Princeton, N.J.). The column is washed with 10 bed volumes of PBS. The bound antibody is eluted with 50 mM citrate buffer, pH 3.0. Equal volume of 1 M Hepes, pH 8.0 is added to the fraction containing the purified antibody to adjust the pH to 7.0. Residual salts are removed by buffer exchange with PBS by Millipore membrane ultrafiltration (M.W. cut-off: 3,000). The protein concentration of the purified antibody is determined by the BCA method (Pierce).

4. Expression and Purification of Chimeric Anti-MASP-2 Fab

To generate cell lines secreting chimeric anti-MASP-2 Fab, CHO cells are transfected with purified plasmid DNAs of pSV2dhfrFd (or pSV2dhfrFd/9aa) and pSV2neokappa, by electroporation. Transfected cells are selected in the presence of G418 and methotrexate. Selected cell lines are amplified in increasing concentrations of methotrexate. Cells are single-cell subcloned by limiting dilution. High-producing single-cell subcloned cell lines are then grown in 100 ml spinner culture using serum-free medium.

Chimeric anti-MASP-2 Fab is purified by affinity chromatography using a mouse anti-idiotypic MoAb to the MASP-2 MoAb. An anti-idiotypic MASP-2 MoAb can be made by immunizing mice with a murine anti-MASP-2 MoAb conjugated with keyhole limpet hemocyanin (KLH) and screening for specific MoAb binding that can be competed with human MASP-2. For purification, 100 ml of supernatant from spinner cultures of CHO cells producing cFab or cFab/9aa are loaded onto the affinity column coupled with an anti-idiotype MASP-2 MoAb. The column is then washed thoroughly with PBS before the bound Fab is eluted with 50 mM diethylamine, pH 11.5. Residual salts are removed by buffer exchange as described above. The protein concentration of the purified Fab is determined by the BCA method (Pierce).

The ability of the chimeric MASP-2 IgG, cFab, and cFAb/9aa to inhibit MASP-2-dependent complement pathways may be determined by using the inhibitory assays described in Example 2 or Example 7.

Example 7

This example describes an in vitro C4 cleavage assay used as a functional screen to identify MASP-2 inhibitory agents capable of blocking MASP-2-dependent complement activation via L-ficolin/P35, H-ficolin, M-ficolin or mannan.

C4 Cleavage Assay:

A C4 cleavage assay has been described by Petersen, S. V., et al., *J. Immunol. Methods* 257:107, 2001, which measures lectin pathway activation resulting from lipoteichoic acid (LTA) from *S. aureus* which binds L-ficolin.

Reagents:

Formalin-fixed *S. aureous* (DSM20233) is prepared as follows: bacteria is grown overnight at 37° C. in tryptic soy blood medium, washed three times with PBS, then fixed for 1 h at room temperature in PBS/0.5% formalin, and washed a further three times with PBS, before being resuspended in coating buffer (15 mM $Na_2Co_3$, 35 mM $NaHCO_3$, pH 9.6).

Assay:

The wells of a Nunc MaxiSorb microtiter plate (Nalgene Nunc International, Rochester, N.Y.) are coated with: 100 µl of formalin-fixed *S. aureus* DSM20233 ($OD_{550}$=0.5) in coating buffer with 1 ug of L-ficolin in coating buffer. After overnight incubation, wells are blocked with 0.1% human serum albumin (HSA) in TBS (10 mM Tris-HCl, 140 mM NaCl, pH 7.4), then are washed with TBS containing 0.05% Tween 20 and 5 mM $CaCl_2$ (wash buffer). Human serum samples are diluted in 20 mM 1 M NaCl, 10 mM $CaCl_2$, 0.05% Triton X-100, 0.1% HSA, pH 7.4, which prevents activation of endogenous C4 and dissociates the C1 complex (composed of C1q, C1r and C1s). MASP-2 inhibitory agents, including anti-MASP-2 MoAbs and inhibitory peptides are added to the serum samples in varying concentrations. The diluted samples are added to the plate and incubated overnight at 4° C. After 24 hours, the plates are washed thoroughly with wash buffer, then 0.1 µg of purified human C4 (obtained as described in Dodds, A. W., *Methods Enzymol.* 223:46, 1993) in 100 µl of 4 mM barbital, 145 mM NaCl, 2 mM $CaCl_2$, 1 mM $MgCl_2$, pH 7.4 is added to each well. After 1.5 h at 37° C., the plates are washed again and C4b deposition is detected using alkaline phosphatase-conjugated chicken anti-human C4c (obtained from Immunsystem, Uppsala, Sweden) and measured using the colorimetric substrate p-nitrophenyl phosphate.

C4 Assay on Mannan:

The assay described above is adapted to measure lectin pathway activation via MBL by coating the plate with LSP and mannan prior to adding serum mixed with various MASP-2 inhibitory agents.

C4 Assay on H-Ficolin (Hakata Ag):

The assay described above is adapted to measure lectin pathway activation via H-ficolin by coating the plate with LPS and H-ficolin prior to adding serum mixed with various MASP-2 inhibitory agents.

Example 8

The following assay demonstrates the presence of classical pathway activation in wild-type and MASP-2-/- mice.

Methods:

Immune complexes were generated in situ by coating microtiter plates (Maxisorb, Nunc, cat. No. 442404, Fisher Scientific) with 0.1% human serum albumin in 10 mM Tris, 140 mM NaCl, pH 7.4 for 1 hours at room temperature followed by overnight incubation at 4° C. with sheep anti whole serum antiserum (Scottish Antibody Production Unit, Carluke, Scotland) diluted 1:1000 in TBS/tween/$Ca^{2+}$. Serum samples were obtained from wild-type and MASP-2-/- mice and added to the coated plates. Control samples were prepared in which C1q was depleted from wild-type and MASP-2-/- serum samples. C1q-depleted mouse serum was prepared using protein-A-coupled Dynabeads (Dynal Biotech, Oslo, Norway) coated with rabbit anti-human C1q IgG (Dako, Glostrup, Denmark), according to the supplier's instructions. The plates were incubated for 90 minutes at 37° C. Bound C3b was detected with a polyclonal anti-human-C3c Antibody (Dako A 062) diluted in TBS/tw/$Ca^{++}$ at 1:1000. The secondary antibody is goat anti-rabbit IgG.

Figure 7:
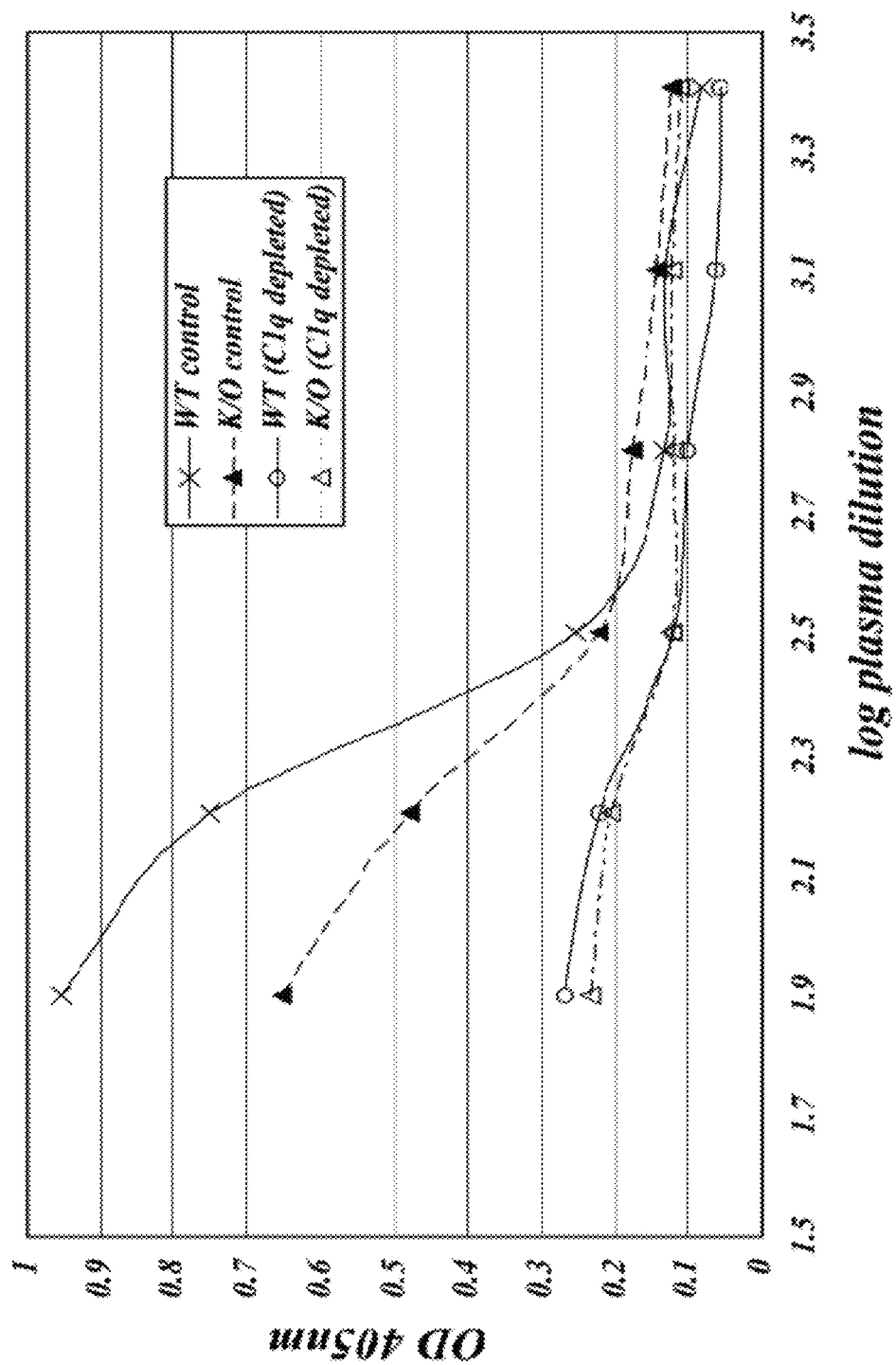
FIG. 7 presents results demonstrating that the classical pathway is functional in the MASP-2−/− strain, as described in Example 8.

Results:

FIG. 7 shows the relative C3b deposition levels on plates coated with IgG in wild-type serum, MASP-2-/- serum, C1q-depleted wild-type and C1q-depleted MASP-2-/- serum. These results demonstrate that the classical pathway is intact in the MASP-2-/- mouse strain.

Example 9

The following assay is used to test whether a MASP-2 inhibitory agent blocks the classical pathway by analyzing the effect of a MASP-2 inhibitory agent under conditions in which the classical pathway is initiated by immune complexes.

Methods:

To test the effect of a MASP-2 inhibitory agent on conditions of complement activation where the classical pathway is initiated by immune complexes, triplicate 50 µl samples containing 90% NHS are incubated at 37° C. in the presence of 10 µg/ml immune complex (IC) or PBS, and parallel triplicate samples (+/-IC) are also included which contain 200 nM anti-properdin monoclonal antibody during the 37° C. incubation. After a two hour incubation at 37° C., 13 mM EDTA is added to all samples to stop further complement activation and the samples are immediately cooled to 5° C. The samples are then stored at -70° C. prior to being assayed for complement activation products (C3a and sC5b-9) using ELISA kits (Quidel, Catalog Nos. A015 and A009) following the manufacturer's instructions.

Example 10

This example describes the identification of high affinity anti-MASP-2 Fab2 antibody fragments that block MASP-2 activity.

Background and Rationale:

MASP-2 is a complex protein with many separate functional domains, including: binding site(s) for MBL and ficolins, a serine protease catalytic site, a binding site for proteolytic substrate C2, a binding site for proteolytic substrate C4, a MASP-2 cleavage site for autoactivation of MASP-2 zymogen, and two $Ca^{++}$ binding sites. Fab2 antibody fragments were identified that bind with high affinity to MASP-2, and the identified Fab2 fragments were tested in a functional assay to determine if they were able to block MASP-2 functional activity.

To block MASP-2 functional activity, an antibody or Fab2 antibody fragment must bind and interfere with a structural epitope on MASP-2 that is required for MASP-2 functional activity. Therefore, many or all of the high affinity binding anti-MASP-2 Fab2s may not inhibit MASP-2 functional activity unless they bind to structural epitopes on MASP-2 that are directly involved in MASP-2 functional activity.

A functional assay that measures inhibition of lectin pathway C3 convertase formation was used to evaluate the "blocking activity" of anti-MASP-2 Fab2s. It is known that the primary physiological role of MASP-2 in the lectin pathway is to generate the next functional component of the lectin-mediated complement pathway, namely the lectin pathway C3 convertase. The lectin pathway C3 convertase is a critical enzymatic complex (C4bC2a) that proteolytically cleaves C3 into C3a and C3b. MASP-2 is not a structural component of the lectin pathway C3 convertase (C4bC2a); however, MASP-2 functional activity is required in order to generate the two protein components (C4b, C2a) that comprise the lectin pathway C3 convertase. Furthermore, all of the separate functional activities of MASP-2 listed above appear to be required in order for MASP-2 to generate the lectin pathway C3 convertase. For these reasons, a preferred assay to use in evaluating the "blocking activity" of anti-MASP-2 Fab2s is believed to be a functional assay that measures inhibition of lectin pathway C3 convertase formation.

Generation of High Affinity Fab2s:

A phage display library of human variable light and heavy chain antibody sequences and automated antibody selection technology for identifying Fab2s that react with selected ligands of interest was used to create high affinity Fab2s to rat MASP-2 protein (SEQ ID NO:55). A known amount of rat MASP-2 (~1 mg, >85% pure) protein was utilized for antibody screening. Three rounds of amplification were utilized for selection of the antibodies with the best affinity. Approximately 250 different hits expressing antibody fragments were picked for ELISA screening. High affinity hits were subsequently sequenced to determine uniqueness of the different antibodies.

Fifty unique anti-MASP-2 antibodies were purified and 250 μg of each purified Fab2 antibody was used for characterization of MASP-2 binding affinity and complement pathway functional testing, as described in more detail below.

Assays Used to Evaluate the Inhibitory (Blocking) Activity of Anti-MASP-2 Fab2s

1. Assay to Measure Inhibition of Formation of Lectin Pathway C3 Convertase:

Background: The lectin pathway C3 convertase is the enzymatic complex (C4bC2a) that proteolytically cleaves C3 into the two potent proinflammatory fragments, anaphylatoxin C3a and opsonic C3b. Formation of C3 convertase appears to a key step in the lectin pathway in terms of mediating inflammation. MASP-2 is not a structural component of the lectin pathway C3 convertase (C4bC2a); therefore anti-MASP-2 antibodies (or Fab2) will not directly inhibit activity of pre-existing C3 convertase. However, MASP-2 serine protease activity is required in order to generate the two protein components (C4b, C2a) that comprise the lectin pathway C3 convertase. Therefore, anti-MASP-2 Fab2 which inhibit MASP-2 functional activity (i.e., blocking anti-MASP-2 Fab2) will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated for 30 min at 37° C. with diluted rat serum to activate the lectin pathway. The wells were then washed and assayed for C3b immobilized onto the wells using standard ELISA methods. The amount of C3b generated in this assay is a direct reflection of the de novo formation of lectin pathway C3 convertase. Anti-MASP-2 Fab2s at selected concentrations were tested in this assay for their ability to inhibit C3 convertase formation and consequent C3b generation.

Methods:

96-well Costar Medium Binding plates were incubated overnight at 5° C. with mannan diluted in 50 mM carbonate buffer, pH 9.5 at 1 ug/50 Tl/well. After overnight incubation, each well was washed three times with 200 Tl PBS. The wells were then blocked with 100 Tl/well of 1% bovine serum albumin in PBS and incubated for one hour at room temperature with gentle mixing. Each well was then washed three times with 200 Tl of PBS. The anti-MASP-2 Fab2 samples were diluted to selected concentrations in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) at 5 C. A 0.5% rat serum was added to the above samples at 5 C and 100 Tl was transferred to each well. Plates were covered and incubated for 30 minutes in a 37 C waterbath to allow complement activation. The reaction was stopped by transferring the plates from the 37 C waterbath to a container containing an ice-water mix. Each well was washed five times with 200 Tl with PBS-Tween 20 (0.05% Tween 20 in PBS), then washed two times with 200 Tl PBS. A 100 Tl/well of 1:10,000 dilution of the primary antibody (rabbit anti-human C3c, DAKO A0062) was added in PBS containing 2.0 mg/ml bovine serum albumin and incubated 1 hr at room temperature with gentle mixing. Each well was washed 5×200 Tl PBS. 100 Tl/well of 1:10,000 dilution of the secondary antibody (peroxidase-conjugated goat anti-rabbit IgG, American Qualex A102PU) was added in PBS containing 2.0 mg/ml bovine serum albumin and incubated for one hour at room temperature on a shaker with gentle mixing. Each well was washed five times with 200 Tl with PBS. 100 Tl/well of the peroxidase substrate TMB (Kirkegaard & Perry Laboratories) was added and incubated at room temperature for 10 min. The peroxidase reaction was stopped by adding 100 Tl/well of 1.0 M $H_3PO_4$ and the $OD_{450}$ was measured.

2. Assay to Measure Inhibition of MASP-2-dependent C4 Cleavage

Background: The serine protease activity of MASP-2 is highly specific and only two protein substrates for MASP-2 have been identified; C2 and C4. Cleavage of C4 generates C4a and C4b. Anti-MASP-2 Fab2 may bind to structural epitopes on MASP-2 that are directly involved in C4 cleavage (e.g., MASP-2 binding site for C4; MASP-2 serine protease catalytic site) and thereby inhibit the C4 cleavage functional activity of MASP-2.

Yeast mannan is a known activator of the lectin pathway. In the following method to measure the C4 cleavage activity of MASP-2, plastic wells coated with mannan were incubated for 30 minutes at 37 C with diluted rat serum to activate the lectin pathway. Since the primary antibody used in this ELISA assay only recognizes human C4, the diluted rat serum was also supplemented with human C4 (1.0 Tg/ml). The wells were then washed and assayed for human C4b immobilized onto the wells using standard ELISA methods. The amount of C4b generated in this assay is a measure of MASP-2 dependent C4 cleavage activity. Anti-MASP-2 Fab2 at selected concentrations were tested in this assay for their ability to inhibit C4 cleavage.

Methods:

96-well Costar Medium Binding plates were incubated overnight at 5 C with mannan diluted in 50 mM carbonate buffer, pH 9.5 at 1.0 Tg/50 Tl/well. Each well was washed 3× with 200 Tl PBS. The wells were then blocked with 100 Tl/well of 1% bovine serum albumin in PBS and incubated for one hour at room temperature with gentle mixing. Each well was washed 3× with 200 Tl of PBS. Anti-MASP-2 Fab2 samples were diluted to selected concentrations in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) at 5 C. 1.0 Tg/ml human C4 (Quidel) was also included in these samples. 0.5% rat serum was added to the above samples at 5 C and 100 Tl was transferred to each well. The plates were covered and incubated for 30 min in a 37 C waterbath to allow complement activation. The reaction was stopped by transferring the plates from the 37 C waterbath to a container containing an ice-water mix. Each well was washed 5×200 Tl with PBS-Tween 20 (0.05% Tween 20 in PBS), then each well was washed with 2× with 200 TI PBS. 100 Tl/well of 1:700 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 Tl PBS. 100 Tl/well of 0.1 Tg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 Tl with PBS. 100 Tl/well of the peroxidase substrate TMB (Kirkegaard & Perry Laboratories) was added and incubated at room temperature for 16 min. The peroxidase reaction was stopped by adding 100 Tl/well of 1.0 M $H_3PO_4$ and the $OD_{450}$ was measured.

3. Binding Assay of Anti-Rat MASP-2 Fab2 to 'Native' Rat MASP-2

Background: MASP-2 is usually present in plasma as a MASP-2 dimer complex that also includes specific lectin molecules (mannose-binding protein (MBL) and ficolins). Therefore, if one is interested in studying the binding of anti-MASP-2 Fab2 to the physiologically relevant form of MASP-2, it is important to develop a binding assay in which the interaction between the Fab2 and 'native' MASP-2 in plasma is used, rather than purified recombinant MASP-2. In this binding assay the 'native' MASP-2-MBL complex from 10% rat serum was first immobilized onto mannan-coated wells. The binding affinity of various anti-MASP-2 Fab2s to the immobilized 'native' MASP-2 was then studied using a standard ELISA methodology.

Methods:

96-well Costar High Binding plates were incubated overnight at 5° C. with mannan diluted in 50 mM carbonate buffer, pH 9.5 at 1 Tg/50 Tl/well. Each well was washed 3× with 200 Tl PBS. The wells were blocked with 100 Tl/well of 0.5% nonfat dry milk in PBST (PBS with 0.05% Tween 20) and incubated for one hour at room temperature with gentle mixing. Each well was washed 3× with 200 Tl of TBS/Tween/$Ca^{++}$ Wash Buffer (Tris-buffered saline, 0.05% Tween 20, containing 5.0 mM $CaCl_2$, pH 7.4.10% rat serum in High Salt Binding Buffer (20 mM Tris, 1.0 M NaCl, 10 mM $CaCl_2$, 0.05% Triton-X100, 0.1% (w/v) bovine serum albumin, pH 7.4) was prepared on ice. 100 Tl/well was added and incubated overnight at 5° C. Wells were washed 3× with 200 Tl of TBS/Tween/$Ca^{++}$ Wash Buffer. Wells were then washed 2× with 200 Tl PBS. 100 Tl/well of selected concentration of anti-MASP-2 Fab2 diluted in $Ca^{++}$ and $Mg^{++}$ containing GVB Buffer (4.0 mM barbital, 141 mM NaCl, 1.0 mM $MgCl_2$, 2.0 mM $CaCl_2$, 0.1% gelatin, pH 7.4) was added and incubated for one hour at room temperature with gentle mixing. Each well was washed 5×200 Tl PBS. 100 Tl/well of HRP-conjugated goat anti-Fab2 (Biogenesis Cat No 0500-0099) diluted 1:5000 in 2.0 mg/ml bovine serum albumin in PBS was added and incubated for one hour at room temperature with gentle mixing. Each well was washed 5×200 Tl PBS. 100 Tl/well of the peroxidase substrate TMB (Kirkegaard & Perry Laboratories) was added and incubated at room temperature for 70 min. The peroxidase reaction was stopped by adding 100 Tl/well of 1.0 M $H_3PO_4$ and $OD_{450}$ was measured.

Results:

Approximately 250 different Fab2s that reacted with high affinity to the rat MASP-2 protein were picked for ELISA screening. These high affinity Fab2s were sequenced to determine the uniqueness of the different antibodies, and 50 unique anti-MASP-2 antibodies were purified for further analysis. 250 ug of each purified Fab2 antibody was used for characterization of MASP-2 binding affinity and complement pathway functional testing. The results of this analysis is shown below in TABLE 6.

TABLE 6

ANTI-MASP-2 FAB2 THAT BLOCK LECTIN PATHWAY COMPLEMENT ACTIVATION

| Fab2 antibody # | C3 Convertase ($IC_{50}$ (nM)) | $K_d$ | C4 Cleavage $IC_{50}$ (nM) |
|---|---|---|---|
| 88 | 0.32 | 4.1 | ND |
| 41 | 0.35 | 0.30 | 0.81 |
| 11 | 0.46 | 0.86 | <2 nM |
| 86 | 0.53 | 1.4 | ND |
| 81 | 0.54 | 2.0 | ND |
| 66 | 0.92 | 4.5 | ND |
| 57 | 0.95 | 3.6 | <2 nM |
| 40 | 1.1 | 7.2 | 0.68 |
| 58 | 1.3 | 2.6 | ND |
| 60 | 1.6 | 3.1 | ND |
| 52 | 1.6 | 5.8 | <2 nM |
| 63 | 2.0 | 6.6 | ND |
| 49 | 2.8 | 8.5 | <2 nM |
| 89 | 3.0 | 2.5 | ND |
| 71 | 3.0 | 10.5 | ND |
| 87 | 6.0 | 2.5 | ND |
| 67 | 10.0 | 7.7 | ND |

Figure 8A:
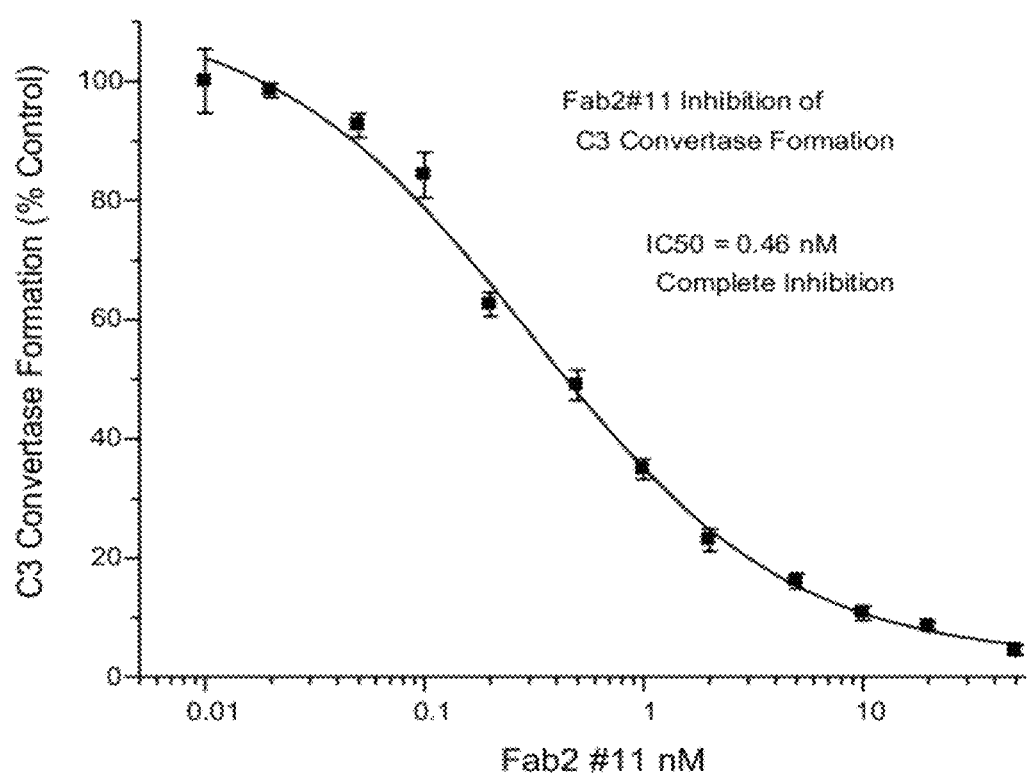
FIG. 8A presents results demonstrating that anti-MASP-2 Fab2 antibody #11 inhibits C3 convertase formation, as described in Example 10.

As shown above in TABLE 6, of the 50 anti-MASP-2 Fab2s tested, seventeen Fab2s were identified as MASP-2 blocking Fab2 that potently inhibit C3 convertase formation with $IC_{50}$ equal to or less than 10 nM Fab2s (a 34% positive hit rate). Eight of the seventeen Fab2s identified have $IC_{50}$s in the subnanomolar range. Furthermore, all seventeen of the MASP-2 blocking Fab2s shown in TABLE 6 gave essentially complete inhibition of C3 convertase formation in the lectin pathway C3 convertase assay. FIG. 8A graphically illustrates the results of the C3 convertase formation assay for Fab2 antibody #11, which is representative of the other Fab2 antibodies tested, the results of which are shown in TABLE 6. This is an important consideration, since it is theoretically possible that a "blocking" Fab2 may only fractionally inhibit MASP-2 function even when each MASP-2 molecule is bound by the Fab2.

Although mannan is a known activator of the lectin pathway, it is theoretically possible that the presence of anti-mannan antibodies in the rat serum might also activate the classical pathway and generate C3b via the classical pathway C3 convertase. However, each of the seventeen blocking anti-MASP-2 Fab2s listed in this example potently inhibits C3b generation (>95%), thus demonstrating the specificity of this assay for lectin pathway C3 convertase.

Figure 8B:
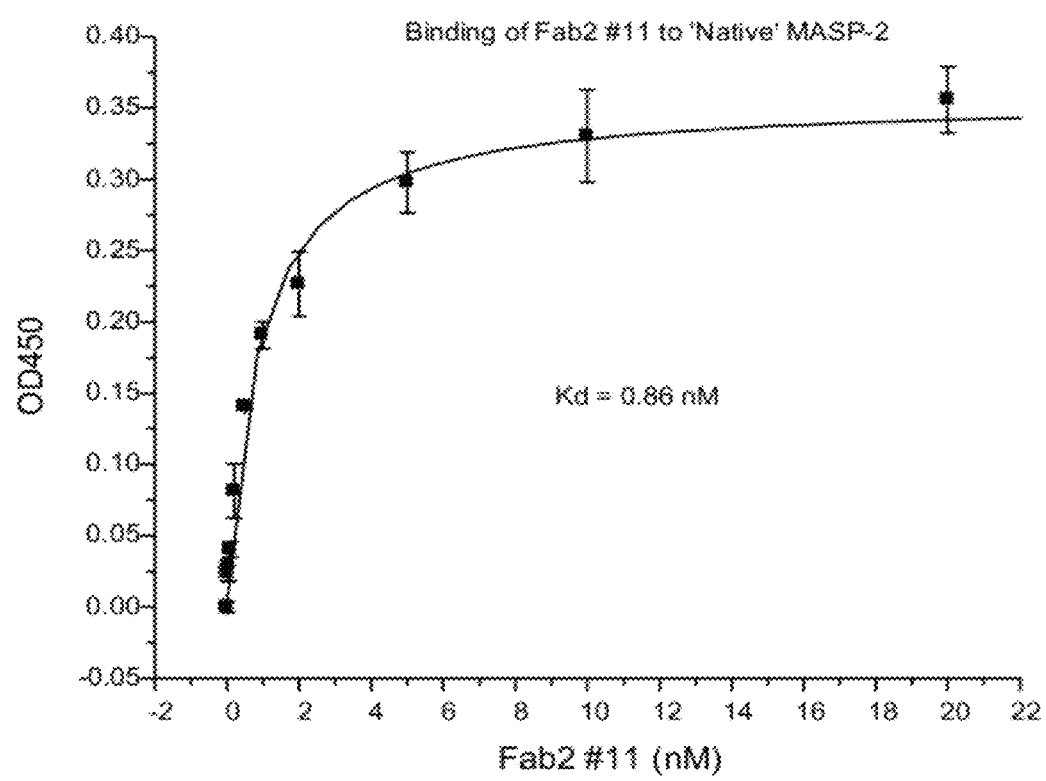
FIG. 8B presents results demonstrating that anti-MASP-2 Fab2 antibody #11 binds to native rat MASP-2, as described in Example 10.

Binding assays were also performed with all seventeen of the blocking Fab2s in order to calculate an apparent $K_d$ for each. The results of the binding assays of anti-rat MASP-2 Fab2s to native rat MASP-2 for six of the blocking Fab2s are also shown in TABLE 6. FIG. 8B graphically illustrates the results of a binding assay with the Fab2 antibody #11. Similar binding assays were also carried out for the other Fab2s, the results of which are shown in TABLE 6. In general, the apparent $K_d$s obtained for binding of each of the six Fab2s to 'native' MASP-2 corresponds reasonably well with the $IC_{50}$ for the Fab2 in the C3 convertase functional assay. There is evidence that MASP-2 undergoes a conformational change from an 'inactive' to an 'active' form upon activation of its protease activity (Feinberg et al., *EMBO J* 22:2348-59 (2003); Gal et al., *J. Biol. Chem.* 280:33435-44 (2005)). In the normal rat plasma used in the C3 convertase formation assay, MASP-2 is present primarily in the 'inactive' zymogen conformation. In contrast, in the binding assay, MASP-2 is present as part of a complex with MBL bound to immobilized mannan; therefore, the MASP-2 would be in the 'active' conformation (Petersen et al., *J. Immunol Methods* 257:107-

16, 2001). Consequently, one would not necessarily expect an exact correspondence between the $IC_{50}$ and $K_d$ for each of the seventeen blocking Fab2 tested in these two functional assays since in each assay the Fab2 would be binding a different conformational form of MASP-2. Never-the-less, with the exception of Fab2 #88, there appears to be a reasonably close correspondence between the $IC_{50}$ and apparent Kd for each of the other sixteen Fab2 tested in the two assays (see TABLE 6).

Figure 8C:
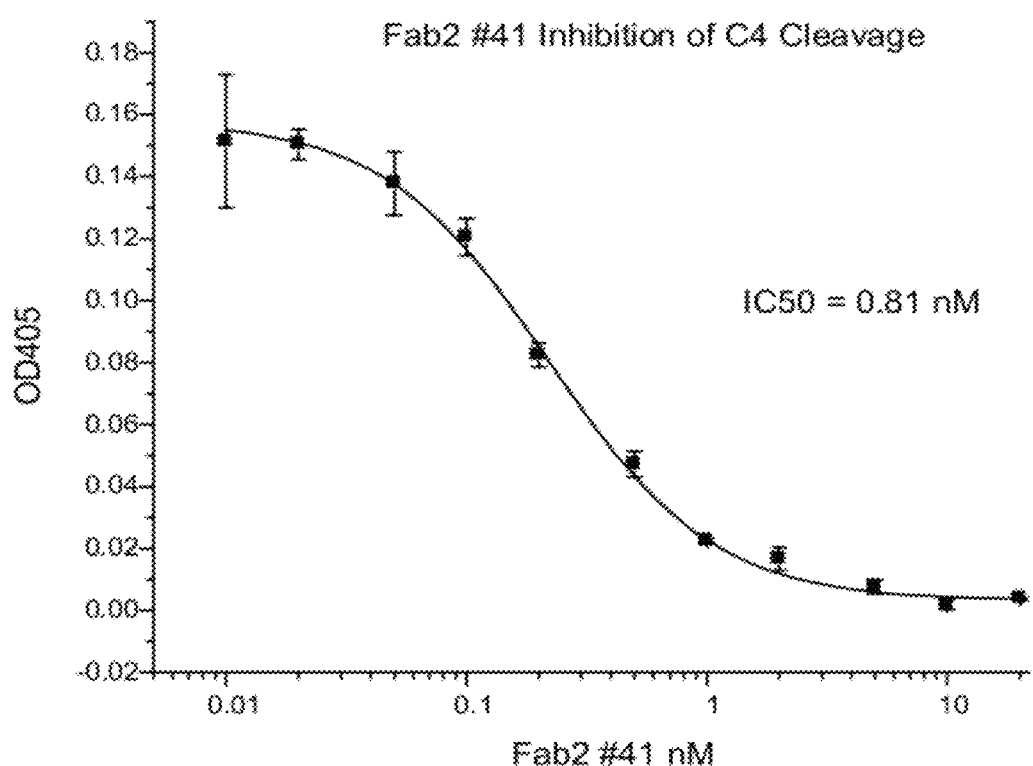
FIG. 8C presents results demonstrating that anti-MASP-2 Fab2 antibody #41 inhibits C4 cleavage, as described in Example 10.
Figure 9:
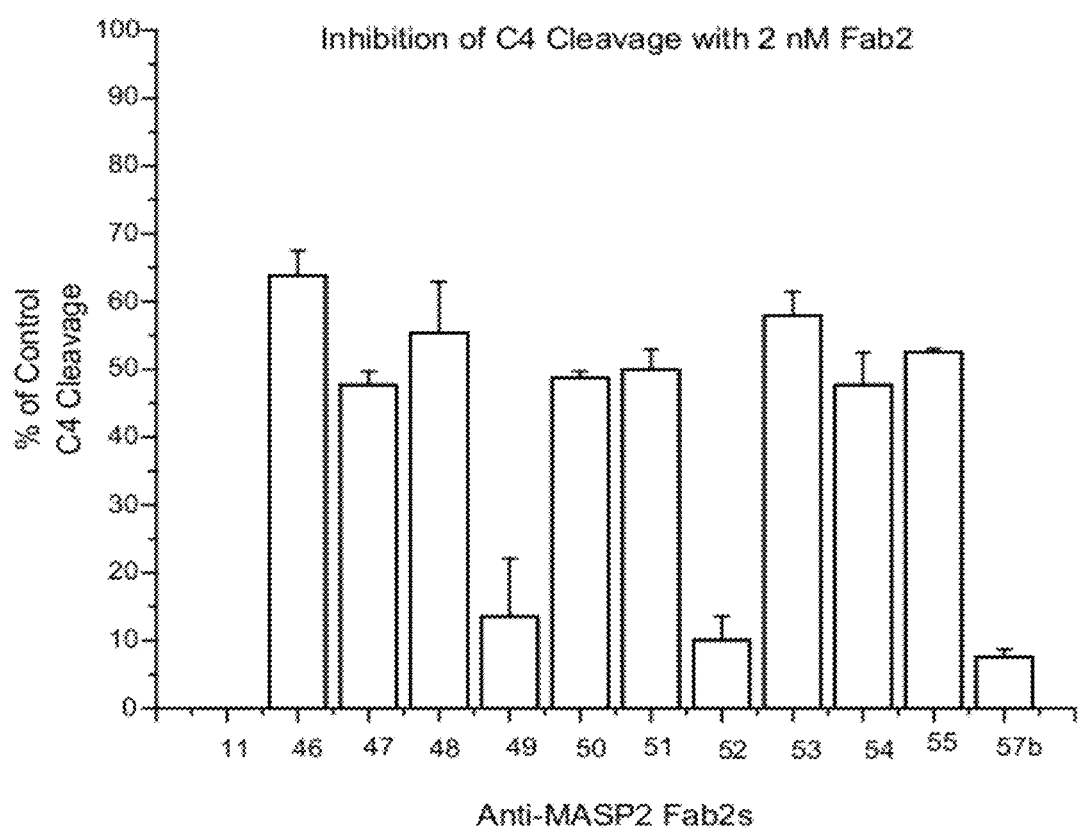
FIG. 9 presents results demonstrating that all of the anti-MASP-2 Fab2 antibodies tested that inhibited C3 convertase formation also were found to inhibit C4 cleavage, as described in Example 10.

Several of the blocking Fab2s were evaluated for inhibition of MASP-2 mediated cleavage of C4. FIG. 8C graphically illustrates the results of a C4 cleavage assay, showing inhibition with Fab2 #41, with an $IC_{50}$=0.81 nM (see TABLE 6). As shown in FIG. 9, all of the Fab2s tested were found to inhibit C4 cleavage with $IC_{50}$s similar to those obtained in the C3 convertase assay (see TABLE 6).

Although mannan is a known activator of the lectin pathway, it is theoretically possible that the presence of anti-mannan antibodies in the rat serum might also activate the classical pathway and thereby generate C4b by C1s-mediated cleavage of C4. However, several anti-MASP-2 Fab2s have been identified which potently inhibit C4b generation (>95%), thus demonstrating the specificity of this assay for MASP-2 mediated C4 cleavage. C4, like C3, contains an unusual and highly reactive thioester group as part of its structure. Upon cleavage of C4 by MASP-2 in this assay, the thioester group on C4b can form a covalent bond with hydroxyl or amino groups on macromolecules immobilized on the bottom of the plastic wells via ester or amide linkages, thus facilitating detection of C4b in the ELISA assay.

These studies clearly demonstrate the creation of high affinity FAB2s to rat MASP-2 protein that functionally block both C4 and C3 convertase activity, thereby preventing lectin pathway activation.

Example 11

This Example describes the epitope mapping for several of the blocking anti-rat MASP-2 Fab2 antibodies that were generated as described in Example 10.

Figure 10:
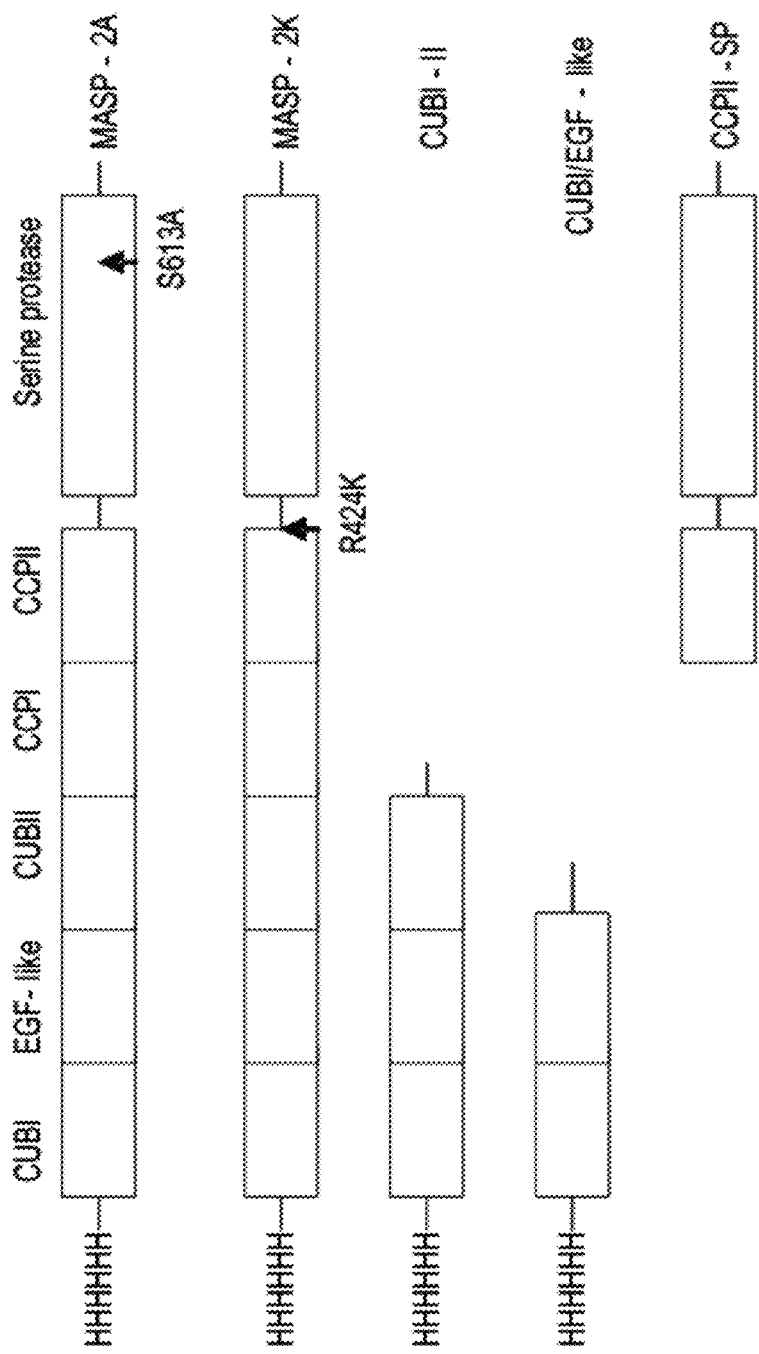
FIG. 10 is a diagram illustrating the recombinant polypeptides derived from rat MASP-2 that were used for epitope mapping of the anti-MASP-2 blocking Fab2 antibodies, as described in Example 11.

Methods:

As shown in FIG. 10, the following proteins, all with N-terminal 6xHis tags were expressed in CHO cells using the pED4 vector:

rat MASP-2A, a full length MASP-2 protein, inactivated by altering the serine at the active center to alanine (S613A);

rat MASP-2K, a full-length MASP-2 protein altered to reduce autoactivation (R424K);

CUBI-II, an N-terminal fragment of rat MASP-2 that contains the CUBI, EGF-like and CUBII domains only; and CUBI/EGF-like, an N-terminal fragment of rat MASP-2 that contains the CUBI and EGF-like domains only.

These proteins were purified from culture supernatants by nickel-affinity chromatography, as previously described (Chen et al., *J. Biol. Chem.* 276:25894-02 (2001)).

A C-terminal polypeptide (CCPII-SP), containing CCPII and the serine protease domain of rat MASP-2, was expressed in *E. coli* as a thioredoxin fusion protein using pTrxFus (Invitrogen). Protein was purified from cell lysates using Thiobond affinity resin. The thioredoxin fusion partner was expressed from empty pTrxFus as a negative control.

All recombinant proteins were dialyzed into TBS buffer and their concentrations determined by measuring the OD at 280 nm.

Dot Blot Analysis:

Serial dilutions of the five recombinant MASP-2 polypeptides described above and shown in FIG. 10 (and the thioredoxin polypeptide as a negative control for CCPII-serine protease polypeptide) were spotted onto a nitrocellulose membrane. The amount of protein spotted ranged from 100 ng to 6.4 pg, in five-fold steps. In later experiments, the amount of protein spotted ranged from 50 ng down to 16 pg, again in five-fold steps. Membranes were blocked with 5% skimmed milk powder in TBS (blocking buffer) then incubated with 1.0 µg/ml anti-MASP-2 Fab2s in blocking buffer (containing 5.0 mM $Ca^{2+}$). Bound Fab2s were detected using HRP-conjugated anti-human Fab (AbD/Serotec; diluted 1/10,000) and an ECL detection kit (Amersham). One membrane was incubated with polyclonal rabbit-anti human MASP-2 Ab (described in Stover et al., *J Immunol* 163:6848-59 (1999)) as a positive control. In this case, bound Ab was detected using HRP-conjugated goat anti-rabbit IgG (Dako; diluted 1/2,000).

MASP-2 Binding Assay

ELISA plates were coated with 1.0 µg/well of recombinant MASP-2A or CUBI-II polypeptide in carbonate buffer (pH 9.0) overnight at 4° C. Wells were blocked with 1% BSA in TBS, then serial dilutions of the anti-MASP-2 Fab2s were added in TBS containing 5.0 mM $Ca^{2+}$. The plates were incubated for one hour at RT. After washing three times with TBS/tween/$Ca^{2+}$, HRP-conjugated anti-human Fab (AbD/Serotec) diluted 1/10,000 in TBS/$Ca^{2+}$ was added and the plates incubated for a further one hour at RT. Bound antibody was detected using a TMB peroxidase substrate kit (Biorad).

Results:

Results of the dot blot analysis demonstrating the reactivity of the Fab2s with various MASP-2 polypeptides are provided below in TABLE 7. The numerical values provided in TABLE 7 indicate the amount of spotted protein required to give approximately half-maximal signal strength. As shown, all of the polypeptides (with the exception of the thioredoxin fusion partner alone) were recognized by the positive control Ab (polyclonal anti-human MASP-2 sera, raised in rabbits).

TABLE 7

REACTIVITY WITH VARIOUS RECOMBINANT RAT MASP-2 POLYPEPTIDES ON DOT BLOTS

| Fab2 Antibody # | MASP-2A | CUBI-II | CUBI/EGF-like | CCPII-SP | Thioredoxin |
|---|---|---|---|---|---|
| 40 | 0.16 ng | NR | NR | 0.8 ng | NR |
| 41 | 0.16 ng | NR | NR | 0.8 ng | NR |
| 11 | 0.16 ng | NR | NR | 0.8 ng | NR |
| 49 | 0.16 ng | NR | NR | >20 ng | NR |
| 52 | 0.16 ng | NR | NR | 0.8 ng | NR |
| 57 | 0.032 ng | NR | NR | NR | NR |
| 58 | 0.4 ng | NR | NR | 2.0 ng | NR |
| 60 | 0.4 ng | 0.4 ng | NR | NR | NR |
| 63 | 0.4 ng | NR | NR | 2.0 ng | NR |
| 66 | 0.4 ng | NR | NR | 2.0 ng | NR |

TABLE 7-continued

REACTIVITY WITH VARIOUS RECOMBINANT RAT MASP-2
POLYPEPTIDES ON DOT BLOTS

| Fab2Antibody # | MASP-2A | CUBI-II | CUBI/EGF-like | CCPII-SP | Thioredoxin |
|---|---|---|---|---|---|
| 67 | 0.4 ng | NR | NR | 2.0 ng | NR |
| 71 | 0.4 ng | NR | NR | 2.0 ng | NR |
| 81 | 0.4 ng | NR | NR | 2.0 ng | NR |
| 86 | 0.4 ng | NR | NR | 10 ng | NR |
| 87 | 0.4 ng | NR | NR | 2.0 ng | NR |
| Positive Control | <0.032 ng | 0.16 ng | 0.16 ng | <0.032 ng | NR |

NR = No reaction.
The positive control antibody is polyclonal anti-human MASP-2 sera, raised in rabbits.

Figure 11:
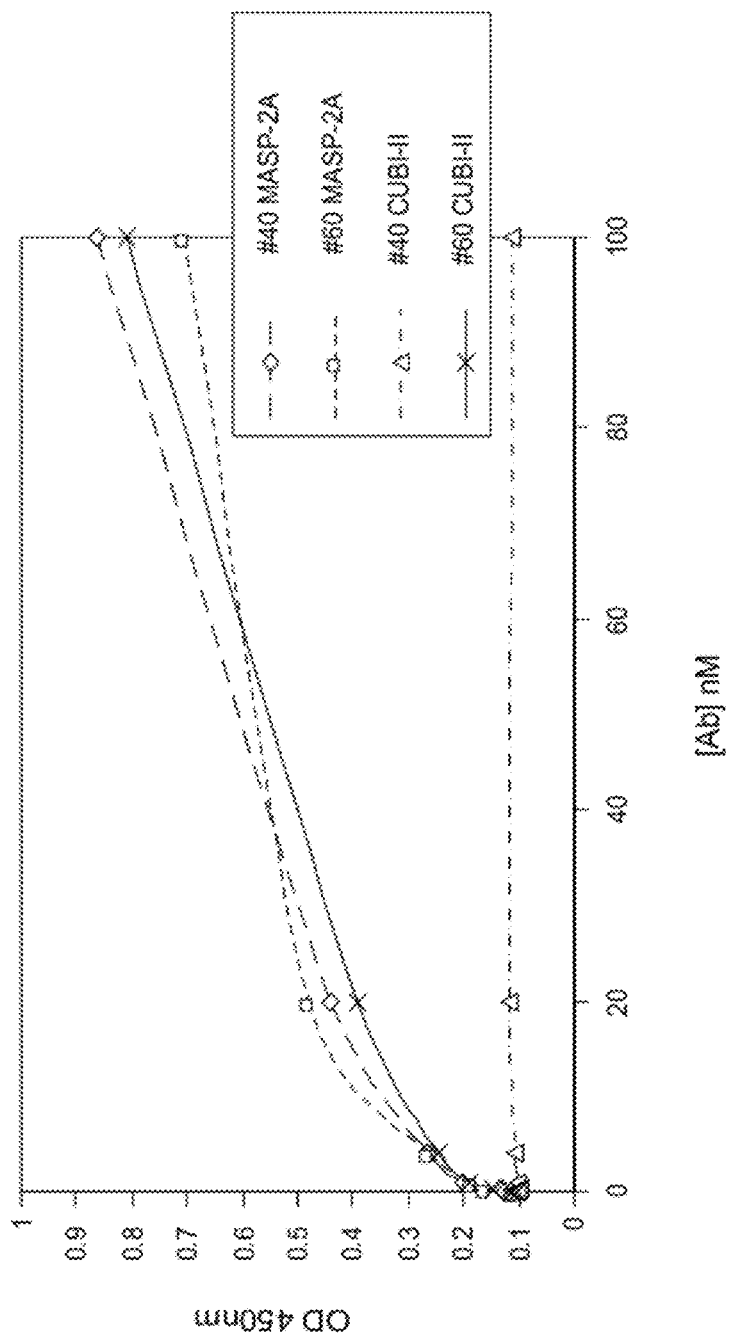
FIG. 11 presents results demonstrating the binding of anti-MASP-2 Fab2 #40 and #60 to rat MASP-2 polypeptides, as described in Example 11.

All of the Fab2s reacted with MASP-2A as well as MASP-2K (data not shown). The majority of the Fab2s recognized the CCPII-SP polypeptide but not the N-terminal fragments. The two exceptions are Fab2 #60 and Fab2 #57. Fab2 #60 recognizes MASP-2A and the CUBI-II fragment, but not the CUBI/EGF-like polypeptide or the CCPII-SP polypeptide, suggesting it binds to an epitope in CUBII, or spanning the CUBII and the EGF-like domain. Fab2 #57 recognizes MASP-2A but not any of the MASP-2 fragments tested, indicating that this Fab2 recognizes an epitope in CCP1. Fab2 #40 and #49 bound only to complete MASP-2A. In the ELISA binding assay shown in FIG. 11, Fab2 #60 also bound to the CUBI-II polypeptide, albeit with a slightly lower apparent affinity.

These finding demonstrate the identification of unique blocking Fab2s to multiple regions of the MASP-2 protein Example 12

This Example describes the analysis of MASP-2-/- mice in a Murine Renal Ischemia/Reperfusion Model.

Background/Rationale:

Ischemia-Reperfusion (I/R) injury in kidney at body temperature has relevance in a number of clinical conditions, including hypovolaemic shock, renal artery occlusion and cross-clamping procedures.

Kidney ischemia-reperfusion (I/R) is an important cause of acute renal failure, associated with a mortality rate of up to 50% (Levy et al., *JAMA* 275:1489-94, 1996; Thadhani et al., *N. Engl. J. Med.* 334:1448-60, 1996). Post-transplant renal failure is a common and threatening complication after renal transplantation (Nicholson et al., *Kidney Int.* 58:2585-91, 2000). Effective treatment for renal I/R injury is currently not available and hemodialysis is the only treatment available. The pathophysiology of renal I/R injury is complicated. Recent studies have shown that the lectin pathway of complement activation may have an important role in the pathogenesis of renal I/R injury (deVries et al., *Am. J. Path.* 165:1677-88, 2004).

Methods:

A MASP-2(-/-) mouse was generated as described in Example 1 and backcrossed for at least 10 generations with C57Bl/6. Six male MASP-2(-/-) and six wildtype (+/+) mice weighing between 22-25 g were administered an intraperitoneal injection of Hypnovel (6.64 mg/kg; Roche products Ltd. Welwyn Garden City, UK), and subsequently anaesthetized by inhalation of isoflurane (Abbott Laboratories Ltd., Kent, UK). Isoflurane was chosen because it is a mild inhalation anaesthetic with minimal liver toxicity; the concentrations are produced accurately and the animal recovers rapidly, even after prolonged anaesthesia. Hypnovel was administered because it produces a condition of neuroleptanalgesia in the animal and means that less isoflurane needs to be administered. A warm pad was placed beneath the animal in order to maintain a constant body temperature. Next, a midline abdominal incision was performed and the body cavity held open using a pair of retractors. Connective tissue was cleared above and below the renal vein and artery of both right and left kidneys, and the renal pedicle was clamped via the application of microaneurysm clamps for a period of 55 minutes. This period of ischemia was based initially on a previous study performed in this laboratory (Zhou et al., *J. Clin. Invest.* 105:1363-71 (2000)). In addition, a standard ischemic time of 55 minutes was chosen following ischemic titration and it was found that 55 minutes gave consistent injury that was also reversible, with low mortality, less than 5%. After occlusion, 0.4 ml of warm saline (37° C.) was placed in the abdominal cavity and then the abdomen was closed for the period of ischemia. Following removal of the microaneurysm clamps, the kidneys were observed until color change, an indication of blood re-flow to the kidneys. A further 0.4 ml of warm saline was placed in the abdominal cavity and the opening was sutured, whereupon animals were returned to their cages. Tail blood samples were taken at 24 hours after removing the clamps, and at 48 hours the mice were sacrificed and an additional blood sample was collected.

Figure 12:
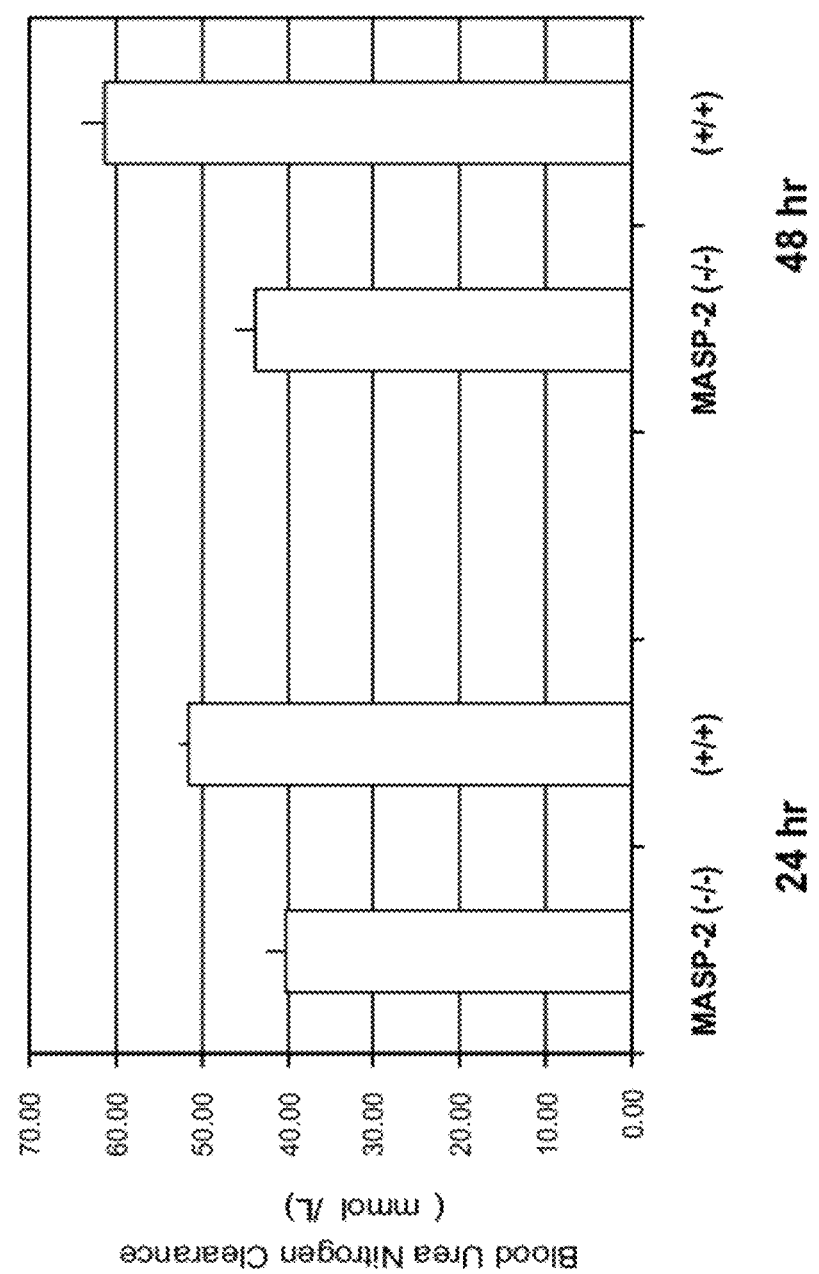
FIG. 12 presents results demonstrating the blood urea nitrogen clearance for wild type (+/+) and MASP-2 (−/−) mice at 24 and 48 hours after reperfusion in a renal ischemia/reperfusion injury model, as described in Example 12.

Assessment of Renal Injury:

Renal function was assessed at 24 and 48 hours after reperfusion in six male MASP-2(-/-) and six WT (+/+) mice. Blood creatinine measurement was determined by mass spectrometry, which provides a reproducible index of renal function (sensitivity <1.0 μmol/L). FIG. 12 graphically illustrates the blood urea nitrogen clearance for wildtype C57Bl/6 controls and MASP-2 (-/-) at 24 hours and 48 hours after reperfusion. As shown in FIG. 12, MASP-2(-/-) mice displayed a significant reduction in the amount of blood urea at 24 and 48 hours, in comparison to wildtype control mice, indicating a protective functional effect from renal damage in the ischemia reperfusion injury model.

Overall, increased blood urea was seen in both the WT (+/+) and MASP-2 (-/-) mice at 24 and 48 hours following the surgical procedure and ischemic insult. Levels of blood urea in a non-ischemic WT (+/+) surgery animal was separately determined to be 5.8 mmol/L. In addition to the data presented in FIG. 12, one MASP-2 (-/-) animal showed nearly complete protection from the ischemic insult, with values of 6.8 and 9.6 mmol/L at 24 and 48 hours, respectively. This animal was excluded from the group analysis as a potential outlier, wherein no ischemic injury may have been present. Therefore, the final analysis shown in FIG. 12 included 5 MASP-2(-/-) mice and 6 WT (+/+) mice and a statistically significant reduction in blood urea was seen at 24 and 48 hours in the MASP-2 (-/-) mice (Student t-test p<0.05). These findings indicate inhibition of MASP-2 activ-

Example 13

This Example describes the results of MASP-2–/– in a Murine Macular Degeneration Model.

Background/Rationale:

Age-related macular degeneration (AMD) is the leading cause of blindness after age 55 in the industrialized world. AMD occurs in two major forms: neovascular (wet) AMD and atrophic (dry) AMD. The neovascular (wet) form accounts for 90% of severe visual loss associated with AMD, even though only ~20% of individuals with AMD develop the wet form. Clinical hallmarks of AMD include multiple drusen, geographic atrophy, and choroidal neovascularization (CNV). In December, 2004, the FDA approved Macugen (pegaptanib), a new class of ophthalmic drugs to specifically target and block the effects of vascular endothelial growth factor (VEGF), for treatment of the wet (neovascular) form of AMD (Ng et al., *Nat Rev. Drug Discov* 5:123-32 (2006)). Although Macugen represents a promising new therapeutic option for a subgroup of AMD patients, there remains a pressing need to develop additional treatments for this complex disease. Multiple, independent lines of investigation implicate a central role for complement activation in the pathogenesis of AMD. The pathogenesis of choroidal neovascularization (CNV), the most serious form of AMD, may involve activation of complement pathways.

Over twenty-five years ago, Ryan described a laser-induced injury model of CNV in animals (Ryan, S. J., *Tr. Am. Opth. Soc. LXXVII*:707-745, 1979). The model was initially developed using rhesus monkeys, however, the same technology has since been used to develop similar models of CNV in a variety of research animals, including the mouse (Tobe et al., *Am. J. Pathol,* 153:1641-46, 1998). In this model, laser photocoagulation is used to break Bruch's membrane, an act which results in the formation of CNV-like membranes. The laser-induced model captures many of the important features of the human condition (for a recent review, sec Ambati et al., *Survey Ophthalmology* 48:257-293, 2003). The laser-induced mouse model is now well established, and is used as an experimental basis in a large, and ever increasing, number of research projects. It is generally accepted that the laser-induced model shares enough biological similarity with CNV in humans that preclinical studies of pathogenesis and drug inhibition using this model are relevant to CNV in humans.

Methods:

A MASP-2–/– mouse was generated as described in Example 1 and backcrossed for 10 generations with C57Bl/6. The current study compared the results when MASP-2 (–/–) and MASP-2 (+/+) male mice were evaluated in the course of laser-induced CNV, an accelerated model of neovascular AMD focusing on the volume of laser-induced CNV by scanning laser confocal microscopy as a measure of tissue injury and determination of levels of VEGF, a potent angiogenic factor implicated in CNV, in the retinal pigment epithelium (RPE)/choroids by ELISA after laser injury.

Induction of Choroidal Neovascularization (CNV):

Laser photocoagulation (532 nm, 200 mW, 100 ms, 75 μm; Oculight GL, Iridex, Mountain View, Calif.) was performed on both eyes of each animal on day zero by a single individual masked to drug group assignment. Laser spots were applied in a standardized fashion around the optic nerve, using a slit lamp delivery system and a coverslip as a contact lens. The morphologic end point of the laser injury was the appearance of a cavitation bubble, a sign thought to correlate with the disruption of Bruch's membrane. The detailed methods and endpoints that were evaluated are as follows.

Fluorescein Angiography:

Fluorescein angiography was performed with a camera and imaging system (TRC 50 1A camera; ImageNet 2.01 system; Topcon, Paramus, N.J.) at 1 week after laser photocoagulation. The photographs were captured with a 20-D lens in contact with the fundus camera lens after intraperitoneal injection of 0.1 ml of 2.5% fluorescein sodium. A retina expert not involved in the laser photocoagulation or angiography evaluated the fluorescein angiograms at a single sitting in masked fashion.

Volume of Choroidal Neovascularization (CNV):

One week after laser injury, eyes were enucleated and fixed with 4% paraformaldehyde for 30 min at 4° C. Eye cups were obtained by removing anterior segments and were washed three times in PBS, followed by dehydration and rehydration through a methanol series. After blocking twice with buffer (PBS containing 1% bovine serumalbumin and 0.5% Triton X-100) for 30 minutes at room temperature, eye cups were incubated overnight at 4° C. with 0.5% FITC-isolectin B4 (Vector laboratories, Burlingame, Calif.), diluted with PBS containing 0.2% BSA and 0.1% Triton X-100, which binds terminal β-D-galactose residues on the surface of endothelial cells and selectively labels the murine vasculature. After two washings with PBS containing 0.1% Triton X-100, the neurosensory retina was gently detached and severed from the optic nerve. Four relaxing radial incisions were made, and the remaining RPE-choroid-sclera complex was flatmounted in antifade medium (Immu-Mount Vectashield Mounting Medium; Vector Laboratories) and cover-slipped.

Flatmounts were examined with a scanning laser confocal microscope (TCS SP; Leica, Heidelberg, Germany). Vessels were visualized by exciting with blue argon wavelength (488 nm) and capturing emission between 515 and 545 nm. A 40× oil-immersion objective was used for all imaging studies. Horizontal optical sections (1 μm step) were obtained from the surface of the RPE-choroid-sclera complex. The deepest focal plane in which the surrounding choroidal vascular network connecting to the lesion could be identified was judged to be the floor of the lesion. Any vessel in the laser-targeted area and superficial to this reference plane was judged as CNV. Images of each section were digitally stored. The area of CNV-related fluorescence was measured by computerized image analysis with the microscope software (TCS SP; Leica). The summation of whole fluorescent area in each horizontal section was used as an index for the volume of CNV. Imaging was performed by an operator masked to treatment group assignment.

Because the probability of each laser lesion developing CNV is influenced by the group to which it belongs (mouse, eye, and laser spot), the mean lesion volumes were compared using a linear mixed model with a split plot repeated-measures design. The whole plot factor was the genetic group to which the animal belongs, whereas the split plot factor was the eye. Statistical significance was determined at the 0.05 level. Post hoc comparisons of means were constructed with a Bonferroni adjustment for multiple comparisons.

VEGF ELISA.

At three days after injury by 12 laser spots, the RPE-choroid complex was sonicated in lysis buffer (20 mM imidazole HCl, 10 mM KCl, 1 mM $MgCL_2$, 10 mM EGTA, 1% Triton X-100, 10 mM NaF, 1 mM Na molybdate, and 1 mM EDTA with protease inhibitor) on ice for 15 min. VEGF protein levels in the supernatant were determined by an ELISA kit (R&D Systems, Minneapolis, Minn.) that recognizes all splice variants, at 450 to 570 nm (Emax; Molecular Devices, Sunnyvale, Calif.), and normalized to total protein. Duplicate measurements were performed in a masked fashion by an operator not involved in photocoagulation, imaging, or angiography. VEGF numbers were represented as the mean+/−SEM of at least three independent experiments and compared using the Mann-Whitney U test. The null hypothesis was rejected at P<0.05.

Figure 13A:
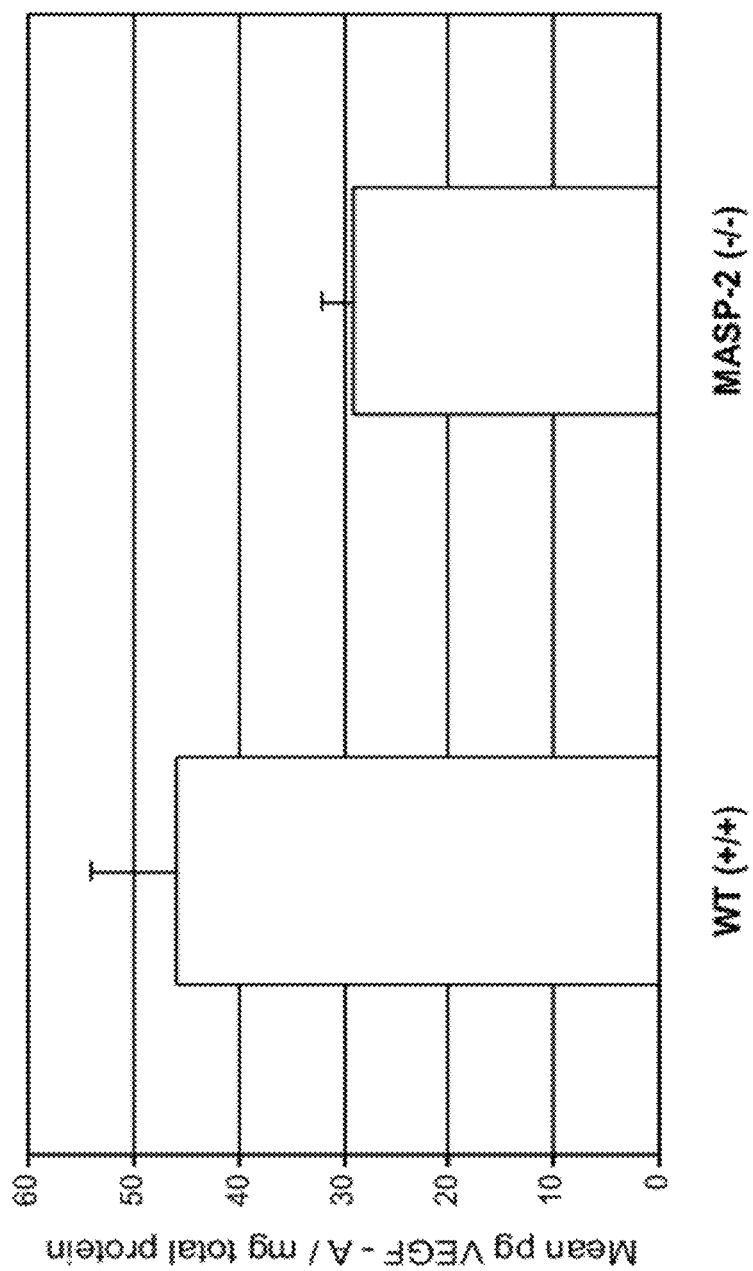
FIG. 13A presents results showing the baseline VEGF protein levels in RPE-choroid complex isolated from wild type (+/+) and MASP-2 (−/−) mice, as described in Example 13.
Figure 13B:
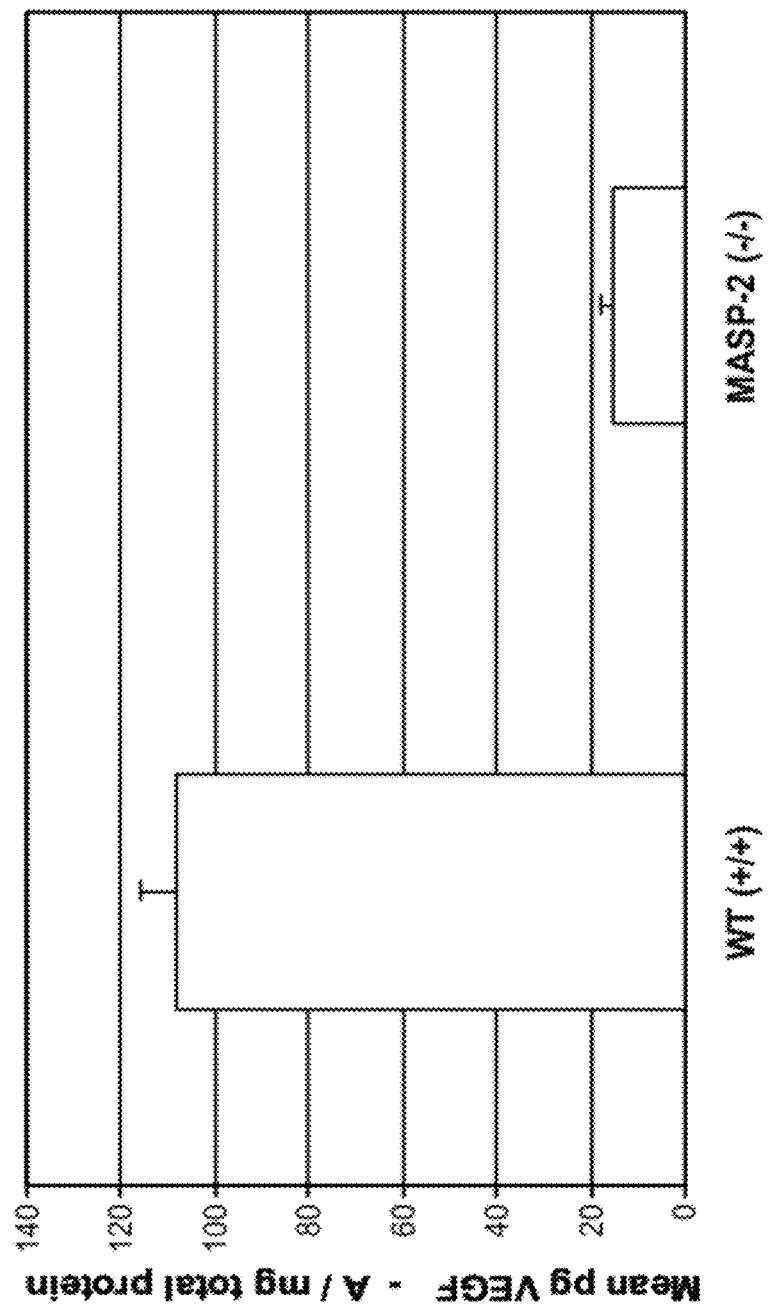
FIG. 13B presents results showing the VEGF protein levels in RPE-choroid complex at day 3 in wild type (+/+) and MASP-2 (−/−) mice following laser induced injury in a macular degeneration model, as described in Example 13.

Results:

Assessment of VEGF Levels:

FIG. 13A graphically illustrates the VEGF protein levels in RPE-choroid complex isolated from C57Bl6 wildtype and MASP-2(−/−) mice at day zero. As shown in FIG. 13A, the assessment of VEGF levels indicate a decrease in baseline levels for VEGF in the MASP-2 (−/−) mice versus the C57bl wildtype control mice. FIG. 13B graphically illustrates VEGF protein levels measured at day three following laser induced injury. As shown in FIG. 13B VEGF levels were significantly increased in the wildtype (+/+) mice three days following laser induced injury, consistent with published studies (Nozaki et al., *Proc. Natl. Acad. Sci. USA* 103:2328-33 (2006)). However, surprisingly very low levels of VEGF were seen in the MASP-2 (−/−) mice.

Figure 14:
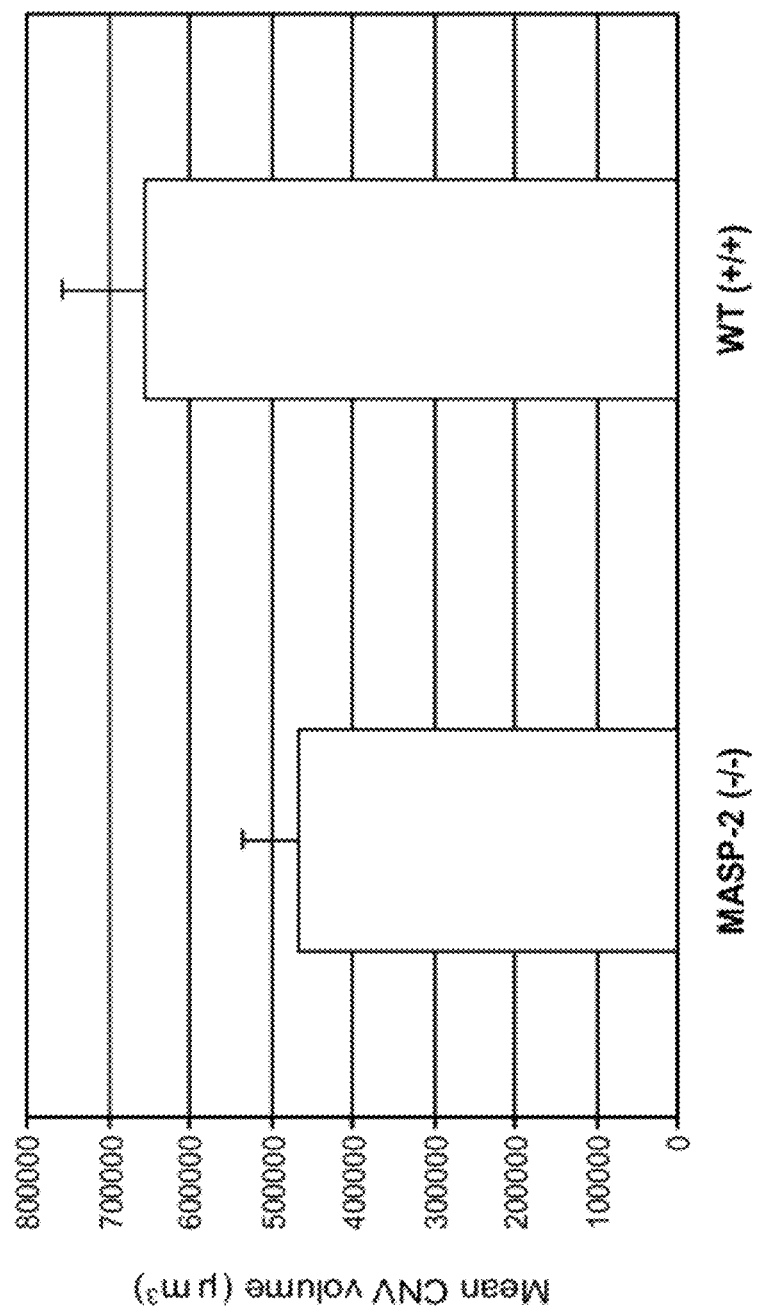
FIG. 14 presents results showing the mean choroidal neovascularization (CNV) volume at day seven following laser induced injury in wild type (+/+) and MASP-2 (−/−) mice, as described in Example 13.

Assessment of Choroidal Neovascularization (CNV):

In addition to the reduction in VEGF levels following laser induced macular degeneration, CNV area was determined before and after laser injury. FIG. 14 graphically illustrates the CNV volume measured in C57bl wildtype mice and MASP-2(−/−) mice at day seven following laser induced injury. As shown in FIG. 14, the MASP-2 (−/−) mice displayed about a 30% reduction in the CNV area following laser induced damage at day seven in comparison to the wildtype control mice.

These findings indicate a reduction in VEGF and CNV as seen in the MASP (−/−) mice versus the wildtype (+/+) control and that blockade of MASP-2 with an inhibitor would have a preventive or therapeutic effect in the treatment of macular degeneration.

Example 14

Figure 15A:
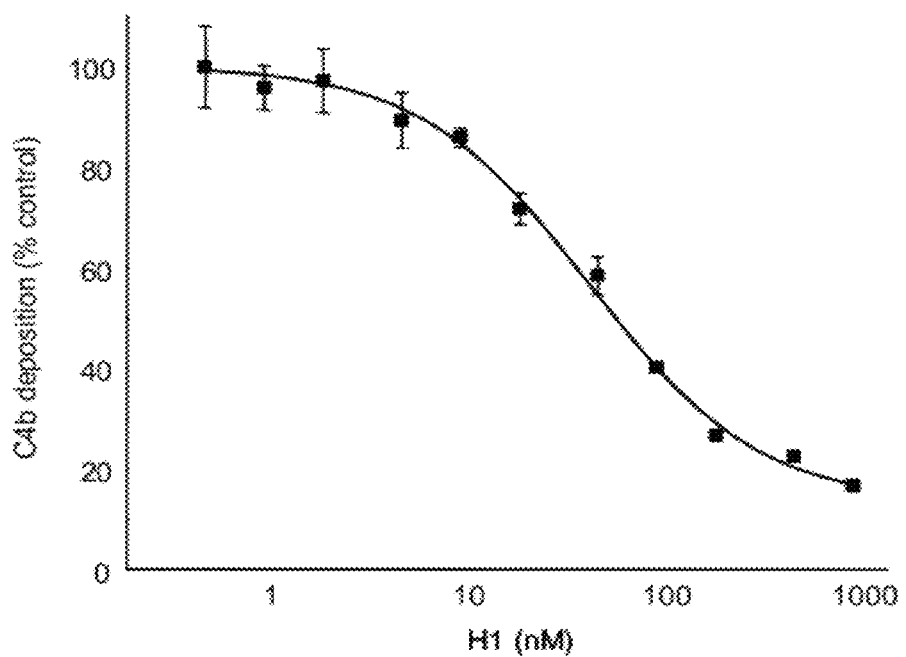
FIGS. 15A and 15B present dose response curves for the inhibition of C4b deposition (FIG. 15A) and the inhibition of thrombin activation (FIG. 15B) following the administration of a MASP-2 Fab2 antibody in normal rat serum, as described in Example 14.
Figure 15B:
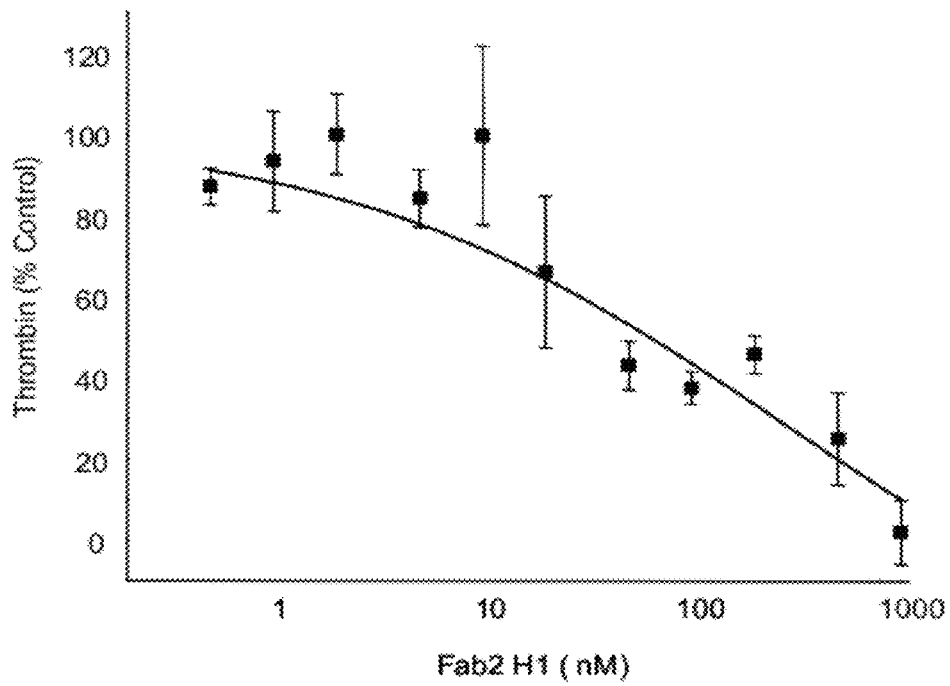

This Example demonstrates that thrombin activation can occur following lectin pathway activation under physiological conditions, and demonstrates the extent of MASP-2 involvement. In normal rat serum, activation of the lectin pathway leads to thrombin activation (assessed as thrombin deposition) concurrent with complement activation (assessed as C4 deposition). As can be seen in FIGS. 15A and 15B, thrombin activation in this system is inhibited by a MASP-2 blocking antibody (Fab2 format), exhibiting an inhibition concentration-response curve (FIG. 15B) that parallels that for complement activation (FIG. 15A). These data suggest that activation of the lectin pathway as it occurs in trauma will lead to activation of both complement and coagulation systems in a process that is entirely dependent on MASP-2. By inference, MASP2 blocking antibodies may prove efficacious in mitigating cases of excessive systemic coagulation, e.g., disseminated intravascular coagulation, which is one of the hallmarks leading to mortality in major trauma cases.

Example 15

This Example provides results generated using a localized Schwartzman reaction model of disseminated intravascular coagulation ("DIC") in MASP-2−/− deficient and MASP-2+/+ sufficient mice to evaluate the role of lectin pathway in DIC.

Background/Rationale:

As described supra, blockade of MASP-2 inhibits lectin pathway activation and reduces the generation of both anaphylatoxins C3a and C5a. C3a anaphylatoxins can be shown to be potent platelet aggregators in vitro, but their involvement in vivo is less well defined and the release of platelet substances and plasmin in wound repair may only secondarily involve complement C3. In this Example, the role of the lectin pathway was analyzed in MASP-2 (−/−) and WT (+/+) mice in order to address whether prolonged elevation of C3 activation is necessary to generate disseminated intravascular coagulation.

Methods:

The MASP-2 (−/−) mice used in this study were generated as described in Example 1 and backcrossed for at least 10 generations with C57Bl/6.

The localized Schwartzman reaction model was used in this experiment. The localized Schwartzman reaction (LSR) is a lipopolysaccharide (LPS)-induced response with well-characterized contributions from cellular and humoral elements of the innate immune system. Dependent of the LSR on complement is well established (Polak, L., et al., *Nature* 223:738-739 (1969); Fong J. S. et al., *J Exp Med* 134:642-655 (1971)). In the LSR model, the mice were primed for 4 hours with TNF alpha (500 ng, intrascrotal), then the mice were anaesthetized and prepared for intravital microscopy of the cremaster muscle. Networks of post-capillary venules (15-60 μm diameter) with good blood flow (1-4 mm/s) were selected for observation. Animals were treated with fluorescent antibodies to selectively label neutrophils, or platelets. The network of vessels was sequentially scanned and images of all vessels were digitally recorded of later analysis. After recording the basal state of the microcirculation, mice received a single intravenous injection of LPS (100 μg), either alone or with the agents listed below. The same network of vessels was then scanned every 10 minutes for 1 hour. Specific accumulation of fluorophores was identified by subtraction of background fluorescence and enhanced by thresholding the image. The magnitude of reactions was measured from recorded images. The primary measure of Schwartzman reactions was aggregate data.

The studies compared the MASP-2+/+ sufficient, or wild type, mice exposed to either a known complement pathway depletory agent, cobra venom factor (CV F), or a terminal pathway inhibitor (C5aR antagonist). The results (FIG. 16A) demonstrate that CVF as well as a C5aR antagonist both prevented the appearance of aggregates in the vasculature. In addition, the MASP-2−/− deficient mice (FIG. 16B) also demonstrated complete inhibition of the localized Schwartzman reaction, supporting lectin pathway involvement. These results clearly demonstrate the role of MASP-2 in DIC generation and support the use of MASP-2 inhibitors for the treatment and prevention of DIC.

Example 16

This Example describes the analysis of MASP-2 (−/−) mice in a Murine Renal Transplantation Model.

Background/Rationale:

The role of MASP-2 in the functional outcome of kidney transplantation was assessed using a mouse model.

Methods:

The functional outcome of kidney transplantation was assessed using a single kidney isograft into uninephrecomized recipient mice, with six WT (+/+) transplant recipients (B6), and six MASP-2 (−/−) transplant recipients. To assess the function of the transplanted kidney, the remaining native kidney was removed from the recipient 5 days after transplantation, and renal function was assessed 24 hours later by measurement of blood urea nitrogen (BUN) levels.

Figure 17:
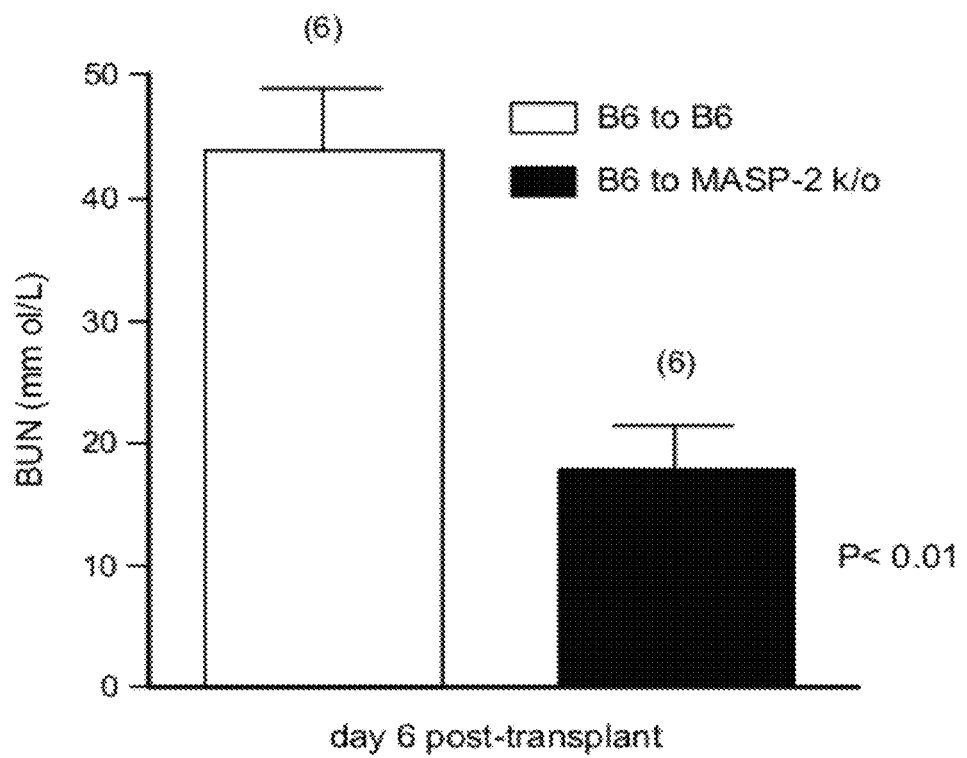
FIG. 17 graphically illustrates the blood urea nitrogen (BUN) levels measured in either WT (+/+) (B6) or MASP-2 (−/−) transplant recipient mice of WT (+/+) donor kidneys, as described in Example 16.

Results:

FIG. 17 graphically illustrates the blood urea nitrogen (BUN) levels of the kidney at 6 days post kidney transplant in the WT (+/+) recipients and the MASP-2 (−/−) recipients. As shown in FIG. 17, strongly elevated BUN levels were observed in the WT (+/+) (B6) transplant recipients (normal BUN levels in mice are <5 mM), indicating renal failure. In contrast, MASP-2 (−/−) isograft recipient mice showed substantially lower BUN levels, suggesting improved renal function. It is noted that these results were obtained using grafts from WT (+/+) kidney donors, suggesting that the absence of a functional lectin pathway in the transplant recipient alone is sufficient to achieve a therapeutic benefit.

Taken together, these results indicate that transient inhibition of the lectin pathway via MASP-2 inhibition provides a method of reducing morbidity and delayed graft function in renal transplantation, and that this approach is likely to be useful in other transplant settings.

Example 17

This Example demonstrates that MASP-2 (−/−) mice are resistant to septic shock in a Murine Polymicrobial Septic Peritonitis Model.

Background/Rationale:

To evaluate the potential effects of MASP-2 (−/−) in infection, the cecal ligation and puncture (CLP) model, a model of polymicrobial septic peritonitis was evaluated. This model is thought to most accurately mimic the course of human septic peritonitis. The cecal ligation and puncture (CLP) model is a model in which the cecum is ligated and punctured by a needle, leading to continuous leakage of the bacteria into the abdominal cavity which reach the blood through the lymph drainage and are then distributed into all the abdominal organs, leading to multi-organ failure and septic shock (Eskandari et al., *J Immunol* 148(9):2724-2730 (1992)). The CLP model mimics the course of sepsis observed in patients and induces an early hyper-inflammatory response followed by a pronounced hypo-inflammatory phase. During this phase, the animals are highly sensitive to bacterial challenges (Wichterman et al., *J. Surg. Res.* 29(2):189-201 (1980)).

Methods:

The mortality of polymicrobial infection using the cecal ligation and puncture (CLP) model was measured in WT (+/+) (n=18) and MASP-2 (−/−) (n=16) mice. Briefly described, MASP-2 deficient mice and their wild-type littermates were anaesthetized and the cecum was exteriorized and ligated 30% above the distal end. After that, the cecum was punctured once with a needle of 0.4 mm diameter. The cecum was then replaced into the abdominal cavity and the skin was closed with clamps. The survival of the mice subjected to CLP was monitored over a period of 14 days after CLP. A peritoneal lavage was collected in mice 16 hours post CLP to measure bacterial load. Serial dilutions of the peritoneal lavage were prepared in PBS and inoculated in Mueller Hinton plates with subsequent incubation at 37° C. under anaerobic conditions for 24 hours after which bacterial load was determined.

The TNF-alpha cytokine response to the bacterial infection was also measured in the WT (+/+) and MASP-2 (−/−) mice 16 hours after CLP in lungs and spleens via quantitative real time polymerase chain reaction (qRT-PCR). The serum level of TNF-alpha 16 hours after CLP in the WT (+/+) and MASP-2 (−/−) mice was also quantified by sandwich ELISA.

Figure 18:
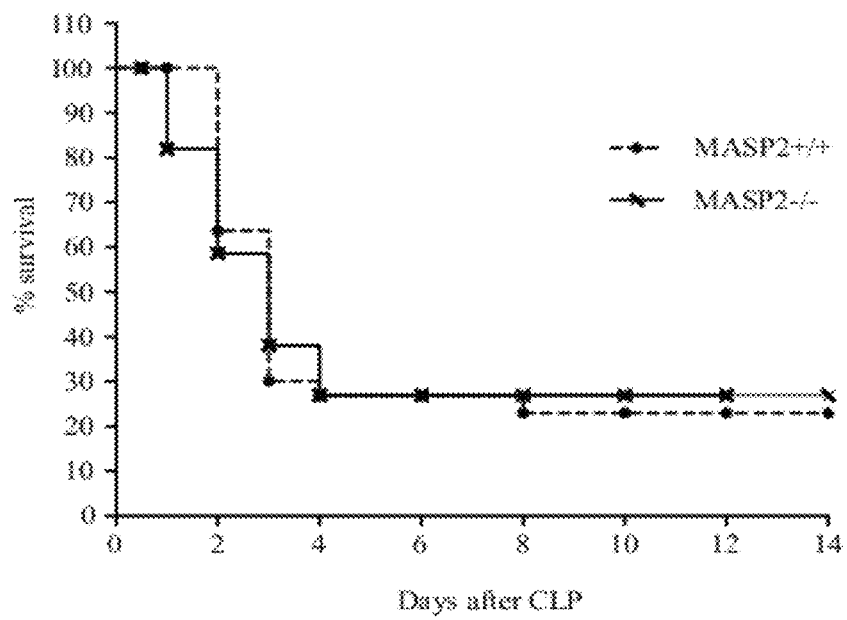
FIG. 18 graphically illustrates the percentage survival of WT (+/+) and MASP-2 (−/−) mice as a function of the number of days after microbial infection in the cecal ligation and puncture (CLP) model, as described in Example 17.
Figure 19:
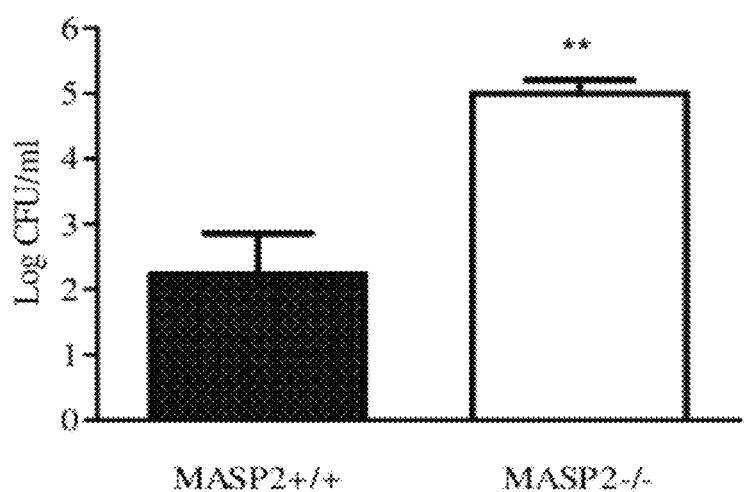
FIG. 19 graphically illustrates the number of bacteria measured in WT (+/+) and MASP-2 (−/−) after microbial infection in the cecal ligation and puncture (CLP) model, as described in Example 17.

Results:

FIG. 18 graphically illustrates the percentage survival of the CLP treated animals as a function of the days after the CLP procedure. As shown in FIG. 18, the lectin pathway deficiency in the MASP-2 (−/−) mice does not increase the mortality of mice after polymicrobial infection using the cecal ligation and puncture model as compared to WT (+1+) mice. However, as shown in FIG. 19, MASP-2 (−/−) mice showed a significantly higher bacterial load (approximately a 1000-fold increase in bacterial numbers) in peritoneal lavage after CLP when compared to their WT (+/+) littermates. These results indicate that MASP-2 (−/−) deficient mice are resistant to septic shock. The reduced bacterial clearance in MASP-2 deficient mice in this model may be due to an impaired C3b mediated phagocytosis, as it was demonstrated that C3 deposition is MASP-2 dependent.

It was determined that the TNF-alpha cytokine response to the bacterial infection was not elevated in the MASP-2 (−/−) mice as compared to the WT (+/+) controls (data not shown). It was also determined that there was a significantly higher serum concentration of TNF-alpha in WT (+/+) mice 16 hours after CLP in contrast to MASP-2 (−/−) mice, where the serum level of TNF-alpha remained nearly unaltered. These results suggest that the intense inflammatory response to the septic condition was tempered in MASP-2 (−/−) mice and allowed the animals to survive in the presence of higher bacterial counts.

Taken together, these results demonstrate the potential deleterious effects of lectin pathway complement activation in the case of septicemia and the increased mortality in patients with overwhelming sepsis. These results further demonstrate that MASP-2 deficiency modulates the inflammatory immune response and reduces the expression levels of inflammatory mediators during sepsis. Therefore, it is believed that inhibition of MASP-2 (−/−) by administration of inhibitory monoclonal antibodies against MASP-2 would be effective to reduce the inflammatory response in a subject suffering from septic shock.

Example 18

This Example describes analysis of MASP-2 (−/−) mice in a Murine Intranasal Infectivity Model.

Background/Rationale:

*Pseudomonas aeruginosa* is a Gram negative opportunistic human bacterial pathogen that causes a wide range of infections, particularly in immune-compromised individuals. It is a major source of acquired nosocomial infections, in particular hospital-acquired pneumonia. It is also responsible for significant morbidity and mortality in cystic fibrosis (CF) patients. *P. aeruginosa* pulmonary infection is characterized by strong neutrophil recruitment and significant lung inflammation resulting in extensive tissue damage (Palanki M. S. et al., *J. Med. Chem.* 51:1546-1559 (2008)).

In this Example, a study was undertaken to determine whether the removal of the lectin pathway in MASP-2 (−/−) mice increases the susceptibility of the mice to bacterial infections.

Methods:

Twenty-two WT (+/+) mice, twenty-two MASP-2 (−/−) mice, and eleven C3 (−/−) mice were challenged with intranasal administration of *P. aeruginosa* bacterial strain. The mice were monitored over the six days post-infection and Kaplan-Mayer plots were constructed showing percent survival.

Figure 20:
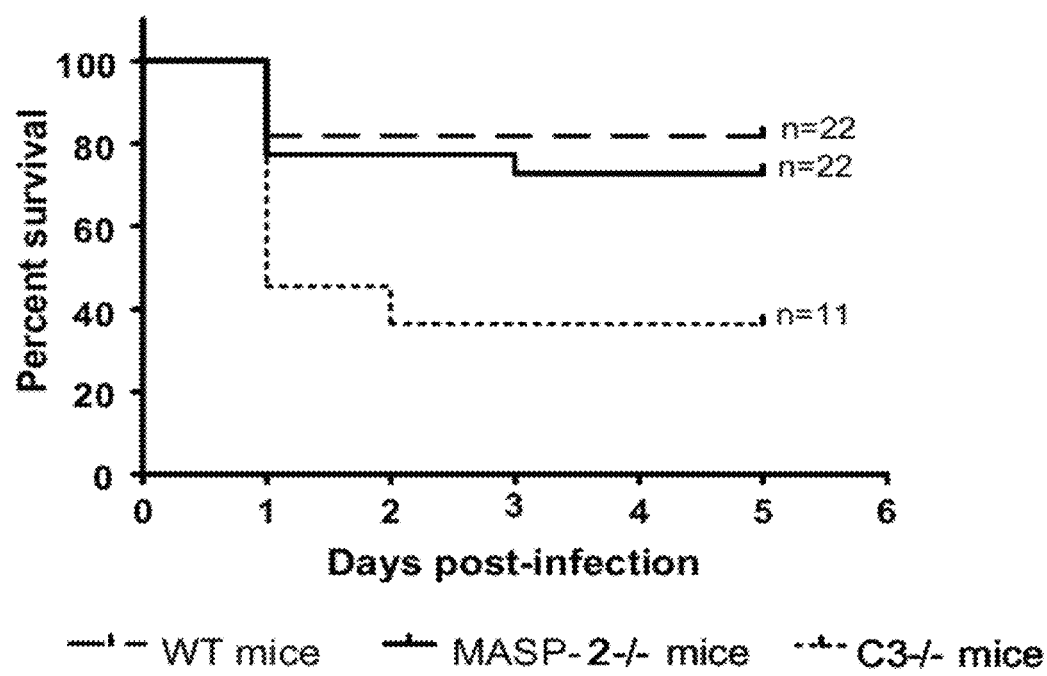
FIG. 20 is a Kaplan-Mayer plot illustrating the percent survival of WT (+/+), MASP-2 (−/−) and C3 (−/−) mice six days after challenge with intranasal administration of *Pseudomonas aeruginosa*, as described in Example 18.

Results:

FIG. 20 is a Kaplan-Mayer plot of the percent survival of WT (+/+), MASP-2 (−/−) or C3 (−/−) mice six days postinfection. As shown in FIG. 20, no differences were observed in the MASP-2 (−/−) mice versus the WT (+/+) mice. However, removal of the classical (C1q) pathway in the C3 (−/−) mice resulted in a severe susceptibility to bacterial infection. These results demonstrate that MASP-2 inhibition does not increase susceptibility to bacterial infection, indicating that it is possible to reduce undesirable inflammatory complications in trauma patients by inhibiting MASP-2 without compromising the patient's ability to fight infections using the classical complement pathway.

Example 19

This Example describes the pharmacodynamic analysis of representative high affinity anti-MASP-2 Fab2 antibodies that were identified as described in Example 10.

Background/Rationale:

As described in Example 10, in order to identify highaffinity antibodies that block the rat lectin pathway, rat MASP-2 protein was utilized to pan a phage display library. This library was designed to provide for high immunological diversity and was constructed using entirely human immunoglobin gene sequences. As described in Example 10, approximately 250 individual phage clones were identified that bound with high affinity to the rat MASP-2 protein by ELISA screening. Sequencing of these clones identified 50 unique MASP-2 antibody encoding phage. Fab2 protein was expressed from these clones, purified and analyzed for MASP-2 binding affinity and lectin complement pathway functional inhibition.

As shown in TABLE 6 of Example 10, 17 anti-MASP-2 Fab2s with functional blocking activity were identified as a result of this analysis (a 34% hit rate for blocking antibodies). Functional inhibition of the lectin complement pathway by Fab2s was apparent at the level of C4 deposition, which is a direct measure of C4 cleavage by MASP-2. Importantly, inhibition was equally evident when C3 convertase activity was assessed, demonstrating functional blockade of the lectin complement pathway. The 17 MASP-2 blocking Fab2s identified as described in Example 10 potently inhibit C3 convertase formation with $IC_{50}$ values equal to or less than 10 nM. Eight of the 17 Fab2s identified have $IC_{50}$ values in the subnanomolar range. Furthermore, all 17 of the MASP-2 blocking Fab2s gave essentially complete inhibition of the C3 convertase formation in the lectin pathway C3 convertase assay, as shown in FIGS. 8A-C, and summarized in TABLE 6 of Example 10. Moreover, each of the 17 blocking anti-MASP-2 Fab2s shown in TABLE 6 potently inhibit C3b generation (>95%), thus demonstrating the specificity of this assay for lectin pathway C3 convertase.

Rat IgG2c and mouse IgG2a full-length antibody isotype variants were derived from Fab2 #11. This Example describes the in vivo characterization of these isotypes for pharmacodynamic parameters.

Methods:

As described in Example 10, rat MASP-2 protein was utilized to pan a Fab phage display library, from which Fab2#11 was identified. Rat IgG2c and mouse IgG2a fulllength antibody isotype variants were derived from Fab2 #11. Both rat IgG2c and mouse IgG2a full length antibody isotypes were characterized in vivo for pharmacodynamic parameters as follows.

In Vivo Study in Mice:

A pharmacodynamic study was carried out in mice to investigate the effect of anti-MASP-2 antibody dosing on the plasma lectin pathway activity in vivo. In this study, C4 deposition was measured ex vivo in a lectin pathway assay at various time points following subcutaneous (sc) and intraperitoneal (ip) administration of 0.3 mg/kg or 1.0 mg/kg of the mouse anti-MASP-2 MoAb (mouse IgG2a full-length antibody isotype derived from Fab2#11).

Figure 21:
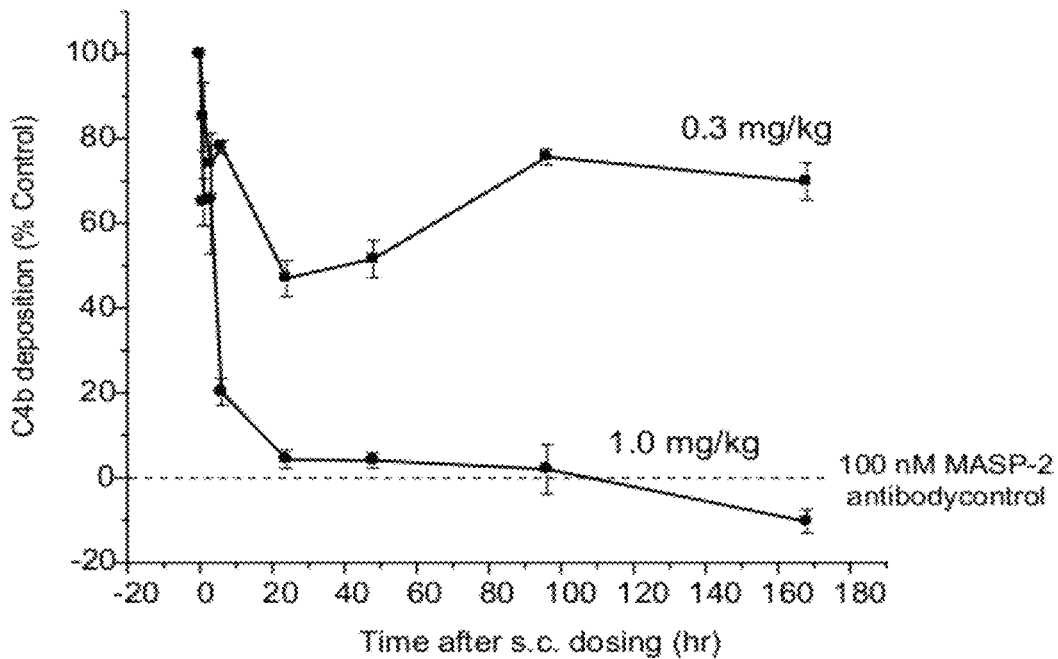
FIG. 21 graphically illustrates the level of C4b deposition, measured as % of control, in samples taken at various time points after subcutaneous dosing of either 0.3 mg/kg or 1.0 mg/kg of mouse anti-MASP-2 monoclonal antibody in WT mice, as described in Example 19.

FIG. 21 graphically illustrates lectin pathway specific C4b deposition, measured ex vivo in undiluted serum samples taken from mice (n=3 mice/group) at various time points after subcutaneous dosing of either 0.3 mg/kg or 1.0 mg/kg of the mouse anti-MASP-2 MoAb. Serum samples from mice collected prior to antibody dosing served as negative controls (100% activity), while serum supplemented in vitro with 100 nM of the same blocking anti-MASP-2 antibody was used as a positive control (0% activity).

The results shown in FIG. 21 demonstrate a rapid and complete inhibition of C4b deposition following subcutaneous administration of 1.0 mg/kg dose of mouse anti-MASP-2 MoAb. A partial inhibition of C4b deposition was seen following subcutaneous administration of 0.3 mg/kg dose of mouse anti-MASP-2 MoAb.

Figure 22:
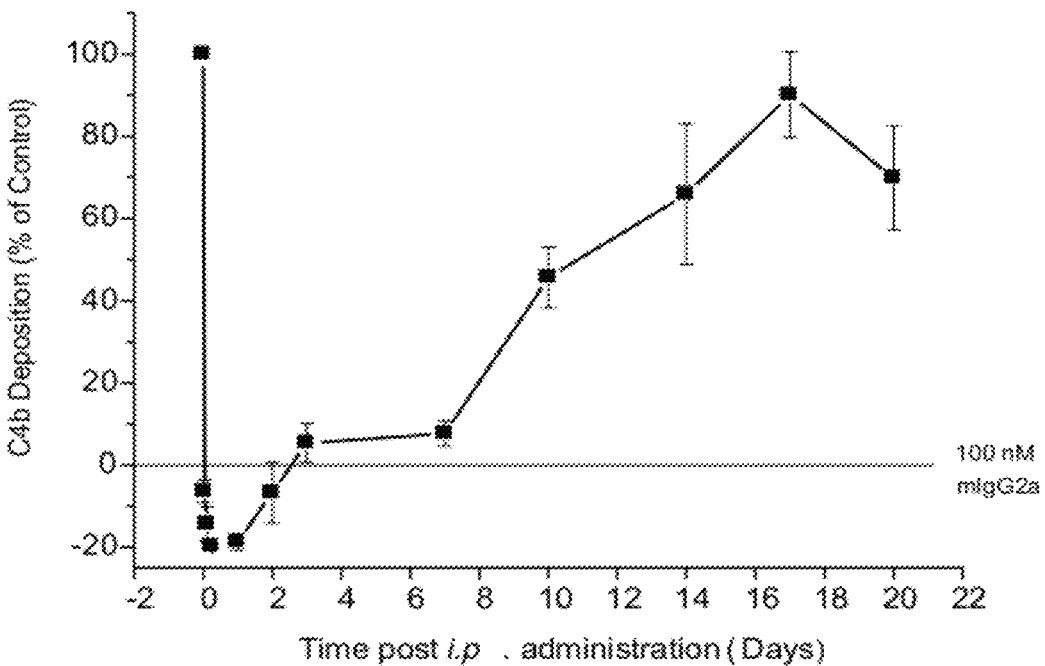
FIG. 22 graphically illustrates the level of C4b deposition, measured as % of control, in samples taken at various time points after ip dosing of 0.6 mg/kg of mouse anti-MASP-2 monoclonal antibody in WT mice, as described in Example 19.

The time course of lectin pathway recovery was followed for three weeks following a single ip administration of mouse anti-MASP-2 MoAb at 0.6 mg/kg in mice. As shown in FIG. 22, a precipitous drop in lectin pathway activity occurred post antibody dosing followed by complete lectin pathway inhibition that lasted for about 7 days after ip administration. Slow restoration of lectin pathway activity was observed over the second and third weeks, with complete lectin pathway restoration in the mice by 17 days post anti-MASP-2 MoAb administration.

These results demonstrate that the mouse anti-MASP-2 Moab derived from Fab2 #11 inhibits the lectin pathway of mice in a dose-responsive manner when delivered systemically.

Example 20

This Example describes analysis of the mouse antiMASP-2 Moab derived from Fab2 #11 for efficacy in a mouse model for age-related macular degeneration.

Background/Rationale:

As described in Example 10, rat MASP-2 protein was utilized to pan a Fab phage display library, from which Fab2#11 was identified as a functionally active antibody. Full length antibodies of the rat IgG2c and mouse IgG2a isotypes were generated from Fab2 #11. The full length anti-MASP-2 antibody of the mouse IgG2a isotype was characterized for pharmacodynamic parameters as described in Example 19. In this Example, the mouse anti-MASP-2 full-length antibody derived from Fab2 #11 was analyzed in the mouse model of age-related macular degeneration (AMD), described by Bora P. S. et al, *J Immunol* 174:491-497 (2005).

Methods:

The mouse IgG2a full-length anti-MASP-2 antibody isotype derived from Fab2 #11 as described in Example 19, was tested in the mouse model of age-related macular degeneration (AMD) as described in Example 13 with the following modifications.

Administration of Mouse-Anti-MASP-2 MoAbs

Two different doses (0.3 mg/kg and 1.0 mg/kg) of mouse anti-MASP-2 MoAb along with an isotype control MoAb treatment were injected ip into WT (+/+) mice (n=8 mice per group) 16 hours prior to CNV induction Induction of Choroidal Neovascularization (CNV)

The induction of choroidal neovascularization (CNV) and measurement of the volume of CNV was carried out using laser photocoagulation as described in Example 13.

Figure 23:
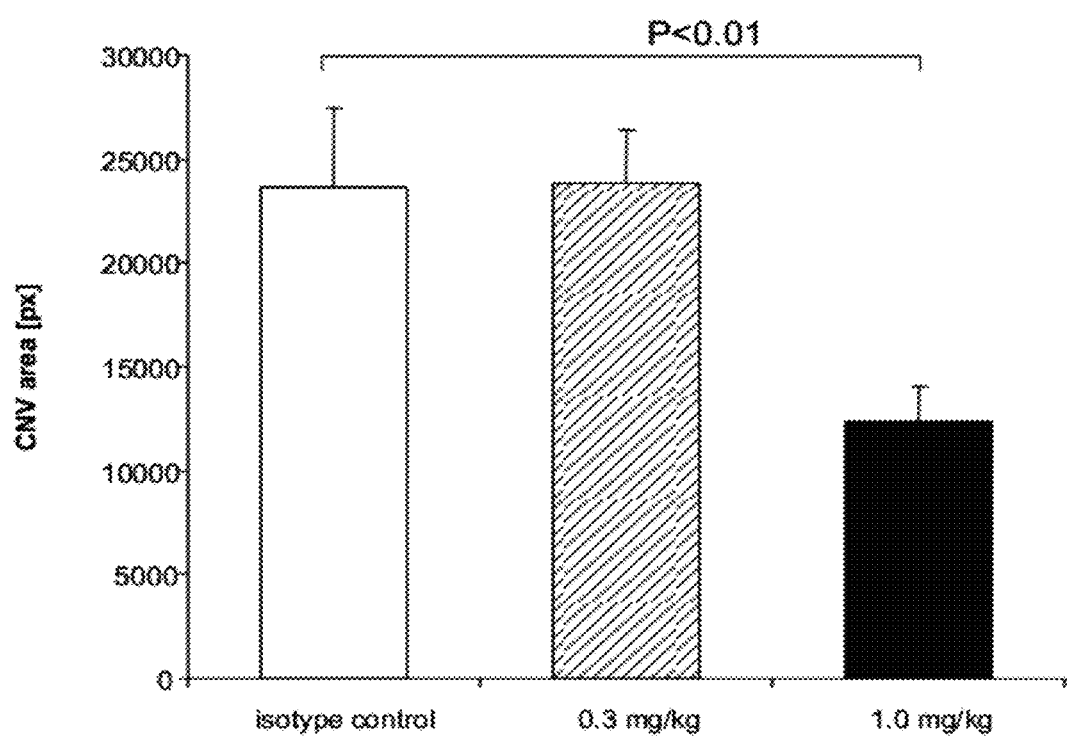
FIG. 23 graphically illustrates the mean choroidal neovascularization (CNV) volume at day seven following laser induced injury in WT (+/+) mice pre-treated with a single ip injection of 0.3 mg/kg or 1.0 mg/kg mouse anti-MASP-2 monoclonal antibody; as described in Example 20.

Results:

FIG. 23 graphically illustrates the CNV area measured at 7 days post laser injury in mice treated with either isotype control MoAb, or mouse anti-MASP-2 MoAb (0.3 mg/kg and 1.0 mg/kg). As shown in FIG. 23, in the mice pre-treated with 1.0 mg/kg anti-MASP-2 MoAb, a statistically significant ($p<0.01$) approximately 50% reduction in CNV was observed seven days post-laser treatment. As further shown in FIG. 23, it was observed that a 0.3 mg/kg dose of anti-MASP-2 MoAb was not efficacious in reducing CNV. It is noted that the 0.3 mg/kg dose of anti-MASP-2 MoAb was shown to have a partial and transient inhibition of C4b deposition following subcutaneous administration, as described in Example 19 and shown in FIG. 21.

The results described in this Example demonstrate that blockade of MASP-2 with an inhibitor, such as anti-MASP-2 MoAb, has a preventative and/or therapeutic effect in the treatment of macular degeneration. It is noted that these results are consistent with the results observed in the study carried out in the MASP-2 (−/−) mice, described in Example 13, in which a 30% reduction in the CNV 7 days post-laser treatment was observed in MASP-2 (−/−) mice in comparison to the wild-type control mice. Moreover, the results in this Example further demonstrate that systemically delivered anti-MASP-2 antibody provides local therapeutic benefit in the eye, thereby highlighting the potential for a systemic route of administration to treat AMD patients. In summary, these results provide evidence supporting the use of MASP-2 MoAb in the treatment of AMD.

Example 21

This Example demonstrates that MASP-2 deficient mice are protected from *Neisseria meningitidis* induced mortality after infection with *N. meningitidis* and have enhanced clearance of bacteraemia as compared to wild type control mice.

Rationale:

*Neisseria meningitidis* is a heterotrophic gram-negative diplococcal bacterium known for its role in meningitis and other forms of meningococcal disease such as meningococcemia. *N. meningitidis* is a major cause of morbidity and mortality during childhood. Severe complications include septicaemia, Waterhouse-Friderichsen syndrome, adrenal insufficiency and disseminated intravascular coagulation (DIC). See e.g., Rintala E. et al., *Critical Care Medicine* 28(7):2373-2378 (2000). In this Example, the role of the lectin pathway was analyzed in MASP-2 (−/−) and WT (+/+) mice in order to address whether MASP-2 deficient mice would be susceptible to *N. meningitidis* induced mortality.

Methods:

MASP-2 knockout mice were generated as described in Example 1 and backcrossed for at least 10 generations with C57Bl/6. 10 week old MASP-2 KO mice (n=10) and wild type C57/B6 mice (n=10) were innoculated by intravenous injection with either a dosage of $5\times10^8$ cfu/100 µl, $2\times10^8$ cfu/100 µl or $3\times10^7$ cfu/100 µl of *Neisseria meningitidis* Serogroup A Z2491 in 400 mg/kg iron dextran. Survival of the mice after infection was monitored over a 72 hour time period. Blood samples were taken from the mice at hourly intervals after infection and analyzed to determine the serum level (log cfu/ml of *N. meningitidis* in order to verify infection and determine the rate of clearance of the bacteria from the serum.

Figure 24A:
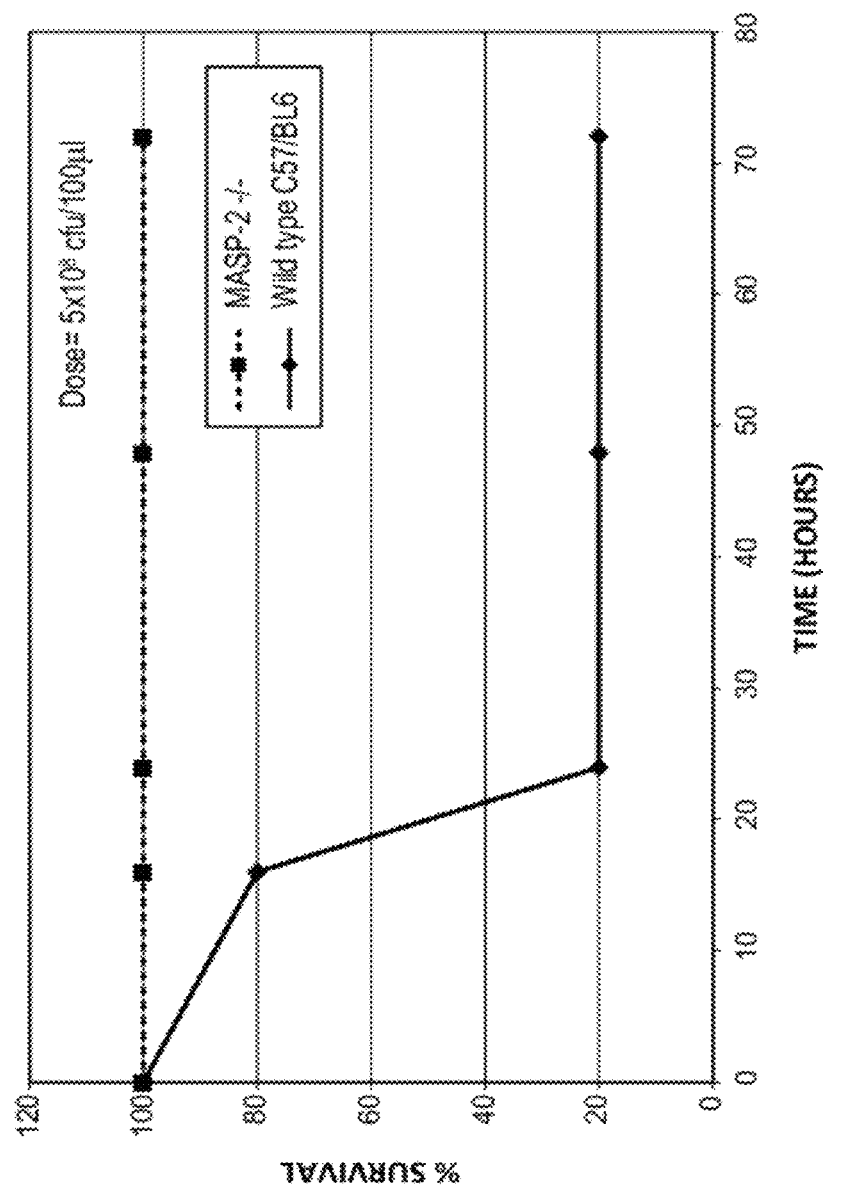
FIG. 24A graphically illustrates the percent survival of MASP-2 (−/−) and WT (+/+) mice after infection with $5 \times 10^8 / 100$ μl cfu *N. meningitidis*, as described in Example 21.

Results:

FIG. 24A graphically illustrates the percent survival of MASP-2 KO and WT mice after administration of an infective dose of $5\times10^8/100$ µl cfu *N. meningitidis*. As shown in FIG. 24A, after infection with the highest dose of $5\times10^8/100$ µl cfu *N. meningitidis*, 100% of the MASP-2 KO mice survived throughout the 72 hour period after infection. In contrast, only 20% of the WT mice were still alive 24 hours after infection. These results demonstrate that MASP-2 deficient mice are protected from *N. meningitidis* induced mortality.

Figure 24B:
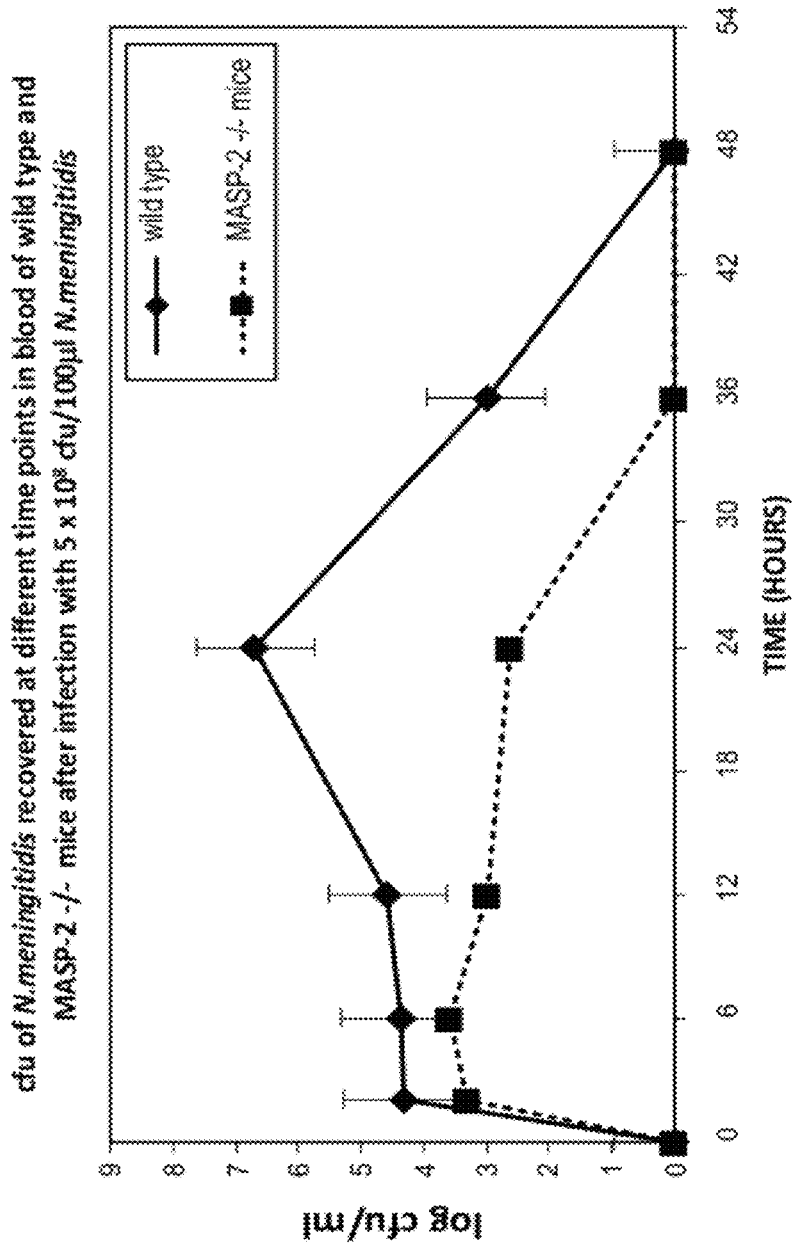
FIG. 24B graphically illustrates the log cfu/ml of *N. meningitidis* recovered at different time points in blood samples taken from the MASP-2 KO (−/−) and WT (+/+) mice infected with 5×10⁸ cfu/100 µl *N. meningitidis*, as described in Example 21.

FIG. 24B graphically illustrates the log cfu/ml of *N. meningitidis* recovered at different time points in blood samples taken from the MASP-2 KO and WT mice infected with $5\times10^8$ cfu/100 µl *N. meningitidis*. As shown in FIG. 24B, in WT mice the level of *N. meningitidis* in the blood reached a peak of about 6.5 log cfu/ml at 24 hours after infection and dropped to zero by 48 hours after infection. In contrast, in the MASP-2 KO mice, the level of *N. meningitidis* reached a peak of about 3.5 log cfu/ml at 6 hours after infection and dropped to zero by 36 hours after infection.

Figure 25A:
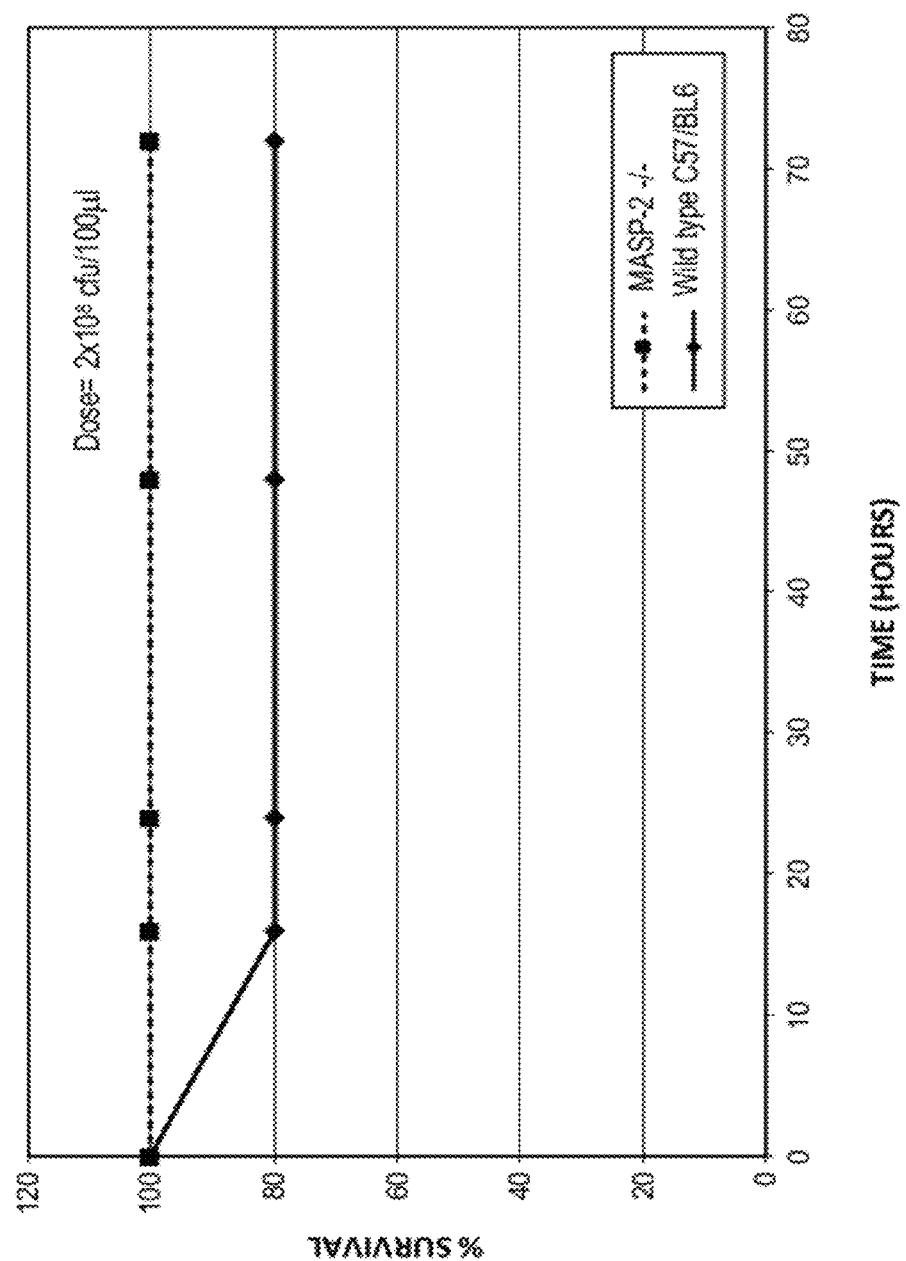
FIG. 25A graphically illustrates the percent survival of MASP-2 KO (−/−) and WT (+/+) mice after infection with 2×10⁸ cfu/100 µl *N. meningitidis*, as described in Example 21.

FIG. 25A graphically illustrates the percent survival of MASP-2 KO and WT mice after infection with $2\times10^8$ cfu/100 µl *N. meningitidis*. As shown in FIG. 25A, after infection with the dose of $2\times10^8$ cfu/100 µl *N. meningitidis*, 100% of the MASP-2 KO mice survived throughout the 72 hour period after infection. In contrast, only 80% of the WT mice were still alive 24 hours after infection. Consistent with the results shown in FIG. 24A, these results further demonstrate that MASP-2 deficient mice are protected from *N. meningitidis* induced mortality.

Figure 25B:
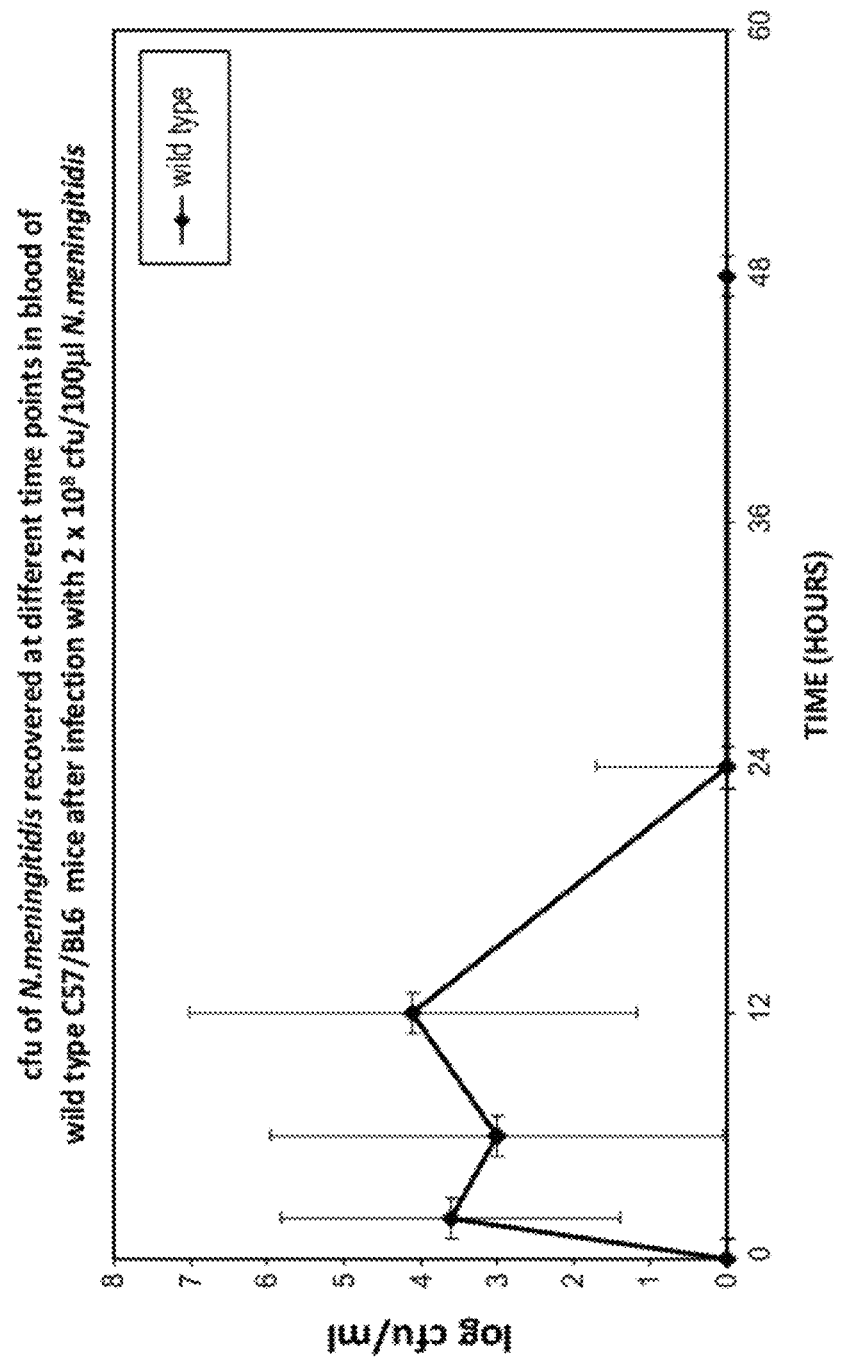
FIG. 25B graphically illustrates the log cfu/ml of *N. meningitidis* recovered at different time points in blood samples taken from the WI (+/+) mice infected with 2×10⁸ cfu/100 µl *N. meningitidis*, as described in Example 21.
Figure 25C:
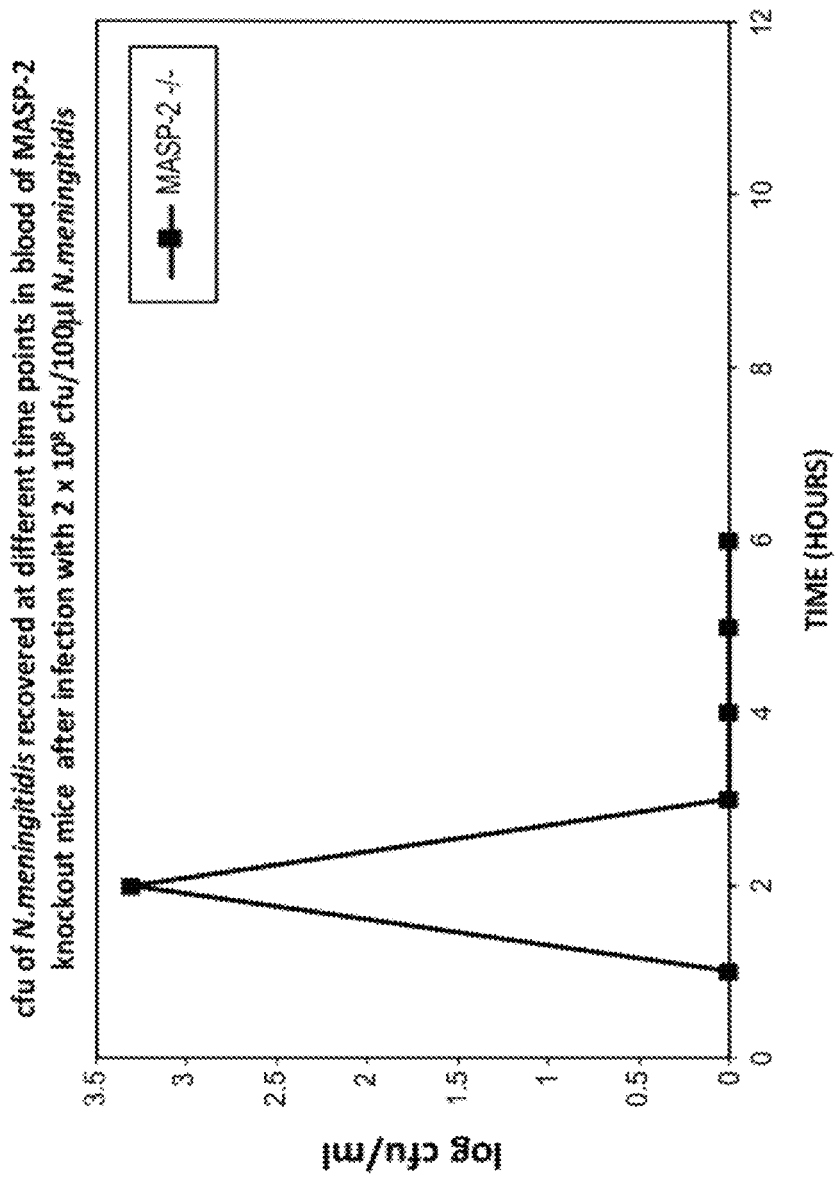
FIG. 25C graphically illustrates the log cfu/ml of *N. meningitidis* recovered at different time points in blood samples taken from the MASP-2 (−/−) mice infected with 2×10⁸ cfu/100 µl *N. meningitidis*, as described in Example 21.

FIG. 25B graphically illustrates the log cfu/ml of *N. meningitidis* recovered at different time points in blood samples taken from the WT mice infected with $2\times10^8$ cfu/100 µl *N. meningitidis*. As shown in FIG. 25B, the level of *N. meningitidis* in the blood of WT mice infected with $2\times10^8$ cfu reached a peak of about 4 log cfu/ml at 12 hours after infection and dropped to zero by 24 hours after infection. FIG. 25C graphically illustrates the log cfu/ml of *N. meningitidis* recovered at different time points in blood samples taken from the MASP-2 KO mice infected with $2\times10^8$ cfu/100 µl *N. meningitidis*. As shown in FIG. 25C, the level of *N. meningitidis* in the blood of MASP-2 KO mice infected with $2\times10^8$ cfu reached a peak level of about 3.5 log cfu/ml at 2 hours after infection and dropped to zero at 3 hours after infection. Consistent with the results shown in FIG. 24B, these results demonstrate that although the MASP-2 KO mice were infected with the same dose of *N. meningitidis* as the WT mice, the MASP-2 KO mice have enhanced clearance of bacteraemia as compared to WT.

The percent survival of MASP-2 KO and WT mice after infection with the lowest dose of $3\times10^7$ cfu/100 µl *N. meningitidis* was 100% at the 72 hour time period (data not shown).

Discussion

These results show that MASP-2 deficient mice are protected from *N. meningitidis* induced mortality and have enhanced clearance of bacteraemia as compared to the WT mice. Therefore, in view of these results, it is expected that therapeutic application of MASP-2 inhibitors, such as MASP-2 MoAb, would be expected to be efficacious to treat, prevent or mitigate the effects of infection with *N. meningitidis* bacteria (i.e., sepsis and DIC). Further, these results indicate that therapeutic application of MASP-2 inhibitors, such as MASP-2 MoAb would not predispose a subject to an increased risk to contract *N. meningitidis* infections.

Example 22

This Example describes the discovery of novel lectin pathway mediated and MASP-2 dependent C4-bypass activation of complement C3.

Rationale:

The principal therapeutic benefit of utilizing inhibitors of complement activation to limit myocardial ischemia/reperfusion injury (MIRI) was convincingly demonstrated in an experimental rat model of myocardial infarction two decades ago: Recombinant sCR1, a soluble truncated derivative of the cell surface complement receptor type-I (CR1), was given intravenously and its effect assessed in a rat in vivo model of MIRI. Treatment with sCR1 reduced infarct volume by more than 40% (Weisman, H. F., et al., *Science* 249:146-151 (1990)). The therapeutic potential of this recombinant inhibitor was subsequently demonstrated in a clinical trial showing that the administration of sCR1 in patients with MI prevented contractile failure in the post-ischemic heart (Shandelya, S., et al., *Circulation* 87:536-546 (1993)). The primary mechanism leading to the activation of complement in ischemic tissue, however, has not been ultimately defined, mainly due to the lack of appropriate experimental models, the limited understanding of the molecular processes that lead to complement activation of oxygen-deprived cells, and the cross-talk and synergisms between the different complement activation pathways.

As a fundamental component of the immune response, the complement system provides protection against invading microorganisms through both antibody-dependent and -independent mechanisms. It orchestrates many cellular and humoral interactions within the immune response, including chemotaxis, phagocytosis, cell adhesion, and B-cell differentiation. Three different pathways initiate the complement cascade: the classical pathway, the alternative pathway, and the lectin pathway. The classical pathway recognition subcomponent C1q binds to a variety of targets—most prominently immune complexes—to initiate the step-wise activation of associated serine proteases, C1r and C1s, providing a major mechanism for pathogen and immune complex clearance following engagement by the adaptive immune system. Binding of C1q to immune complexes converts the C1r zymogen dimer into its active form to cleave and thereby activate C1s. C1s translates C1q binding into complement activation in two cleavage steps: It first converts C4 into C4a and C4b and then cleaves C4b-bound C2 to form the C3 convertase C4b2a. This complex converts the abundant plasma component C3 into C3a and C3b. Accumulation of C3b in close proximity of the C4b2a complex shifts the substrate specificity for C3 to C5 to form the C5 convertase $C4b2a(C3b)_n$. The C3 and C5 convertase complexes generated via classical pathway activation are identical to those generated through the lectin pathway activation route. In the alternative pathway, spontaneous low-level hydrolysis of component C3 results in deposition of protein fragments onto cell surfaces, triggering complement activation on foreign cells, while cell-associated regulatory proteins on host tissues avert activation, thus preventing self-damage. Like the alternative pathway, the lectin pathway may be activated in the absence of immune complexes. Activation is initiated by the binding of a multi-molecular lectin pathway activation complex to Pathogen-Associated Molecular Patterns (PAMPs), mainly carbohydrate structures present on bacterial, fungal or viral pathogens or aberrant glycosylation patterns on apoptotic, necrotic, malignant or oxygen-deprived cells (Collard, C. D., et al., *Am. J. Pathol.* 156:1549-1556 (2000); Walport, M. J., *N. Engl. J. Med.* 344:1058-1066 (2001); Schwaeble, W., et al., *Immunobiology* 205:455-466 (2002); and Fujita, T., *Nat. Rev. Immunol.* 2:346-353 (2002)).

Mannan-binding lectin (MBL) was the first carbohydrate recognition subcomponent shown to form complexes with a group of novel serine proteases, named MBL-associated Serine Proteases (MASPs) and numbered according to the sequence of their discovery (i.e., MASP-1, MASP-2 and MASP-3). In man, lectin pathway activation complexes can be formed with four alternative carbohydrate recognition subcomponents with different carbohydrate binding specificities, i.e., MBL 2, and three different members of the ficolin family, namely L-Ficolin, H-ficolin and M-ficolin and MASPs. Two forms of MBL, MBL A and MBL C, and ficolin-A form lectin activation pathway complexes with MASPs in mouse and rat plasma. We have previously cloned and characterised MASP-2 and an additional truncated MASP-2 gene product of 19 kDa, termed MAp 19 or sMAP, in human, mouse and rat (Thiel, S., et al., *Nature* 386:506-510 (1997); Stover, C. M., et al., *J. Immunol.* 162:3481-3490 (1999); Takahashi, M., et al., *Int. Immunol.* 11:859-863 (1999); and Stover, C. M., et al., *J. Immunol.* 163:6848-6859 (1999)). MAp19/sMAP is devoid of protease activity, but may regulate lectin pathway activation by competing for the binding of MASPs to carbohydrate recognition complexes (Iwaki, D. et al., *J. Immunol.* 177:8626-8632 (2006)).

There is evidence suggesting that of the three MASPs, only MASP-2 is required to translate binding of the lectin pathway recognition complexes into complement activation (Thiel, S., et al. (1997); Vorup-Jensen, T., et al., *J. Immunol.* 165:2093-2100 (2000); Thiel, S., et al., *J. Immunol.* 165:878-887 (2000); Rossi, V., et al., *J. Biol. Chem.* 276:40880-40887 (2001)). This conclusion is underlined by the phenotype of a most recently described mouse strain deficient in MASP-1 and MASP-3. Apart from a delay in the onset of lectin pathway mediated complement activation in vitro—MASP-1/3 deficient mice retain lectin pathway functional activity. Reconstitution of MASP-1 and MASP-3 deficient serum with recombinant MASP-1 overcomes this delay in lectin pathway activation implying that MASP-1 may facilitate MASP-2 activation (Takahashi, M., et al., *J. Immunol.* 180:6132-6138 (2008)). A most recent study has shown that MASP-1 (and probably also MASP-3) are required to convert the alternative pathway activation enzyme Factor D from its zymogen form into its enzymatically active form (Takahashi, M., et al., *J. Exp. Med.* 207:29-37 (2010)). The physiological importance of this process is underlined by the absence of alternative pathway functional activity in plasma of MASP-1/3 deficient mice.

The recently generated mouse strains with combined targeted deficiencies of the lectin pathway carbohydrate recognition subcomponents MBL A and MBL C may still initiate lectin pathway activation via the remaining murine lectin pathway recognition subcomponent ficolin A (Takahashi, K., et al., *Microbes Infect.* 4:773-784 (2002)). The absence of any residual lectin pathway functional activity in MASP-2 deficient mice delivers a conclusive model to study the role of this effector arm of innate humoral immunity in health and disease.

The availability of C4 and MASP-2 deficient mouse strains allowed us to define a novel lectin pathway specific, but MASP-2 dependent, C4-bypass activation route of complement C3. The essential contribution of this novel lectin pathway mediated C4-bypass activation route towards post-ischemic tissue loss is underlined by the prominent protective phenotype of MASP-2 deficiency in MIRI while C4-deficient mice tested in the same model show no protection.

In this Example, we describe a novel lectin pathway mediated and MASP-2 dependent C4-bypass activation of complement C3. The physiological relevance of this new activation route is established by the protective phenotype of MASP-2 deficiency in an experimental model of myocardial ischemia/reperfusion injury (MIRI), where C4 deficient animals were not protected.

Methods:

MASP-2 Deficient Mice Show No Gross Abnormalities.

MASP-2 deficient mice were generated as described in Example 1. Both heterozygous ($^{+/-}$) and homozygous ($^{-/-}$) MASP-2 deficient mice are healthy and fertile, and show no gross abnormalities. Their life expectancy is similar to that of their WT littermates (>18 months). Prior to studying the phenotype of these mice in experimental models of disease, our MASP-2$^{-/-}$ line was backcrossed for eleven generations onto a C57BL/6 background. The total absence of MASP-2 mRNA was confirmed by Northern blotting of poly A+ selected liver RNA preparations, while the 1.2 kb mRNA encoding MAp19 or sMAP (a truncated alternative splicing product of the MASP2 gene) is abundantly expressed.

qRT-PCR analysis using primer pairs specific for either the coding sequence for the serine protease domain of MASP-2 (B chain) or the remainder of the coding sequence for the A-chain showed that no B chain encoding mRNA is detectable in MASP-2$^{-/-}$ mice while the abundance of the disrupted A chain mRNA transcript was significantly increased. Likewise, the abundance of MAp19/sMAP encoding mRNA is increased in MASP-2$^{-/-}$ and MASP-2$^{-/-}$ mice. Plasma MASP-2 levels, determined by ELISA for 5 animals of each genotype, were 300 ng/ml for WT controls (range 260-330 ng/ml), 360 ng/ml for heterozygous mice (range 330-395 ng/ml) and undetectable in MASP-2$^{-/-}$ mice. Using qRT-PCR, mRNA expression profiles were established demonstrating that MASP-2$^{-/-}$ mice express mRNA for MBL A, MBL C, ficolin A, MASP-1, MASP-3, C1q, C1rA, C1 sA, Factor B, Factor D, C4, and C3 at an abundance similar to that of their MASP-2 sufficient littermates (data not shown).

Plasma C3 levels of MASP-2$^{-/-}$ (n=8) and MASP-2$^{+/+}$ (n=7) littermates were measured using a commercially available mouse C3 ELISA kit (Kamiya, Biomedical, Seattle, Wash.). C3 levels of MASP-2 deficient mice (average 0.84 mg/ml, +/−0.34) were similar to those of the WT controls (average 0.92, +/−0.37).

Results:

MASP-2 is Essential for Lectin Pathway Functional Activity.

As described in Example 2 and shown in FIG. 5, the in vitro analyses of MASP-2$^{-/-}$ plasma showed a total absence of lectin pathway functional activity on activating Mannan- and Zymosan-coated surfaces for the activation of C4. Likewise, neither lectin pathway-dependent C4 nor C3 cleavage was detectable in MASP-2$^{-/-}$ plasma on surfaces coated with N-acetyl glucosamine, which binds and triggers activation via MBL A, MBL C and ficolin A (data not shown).

Figure 26A:
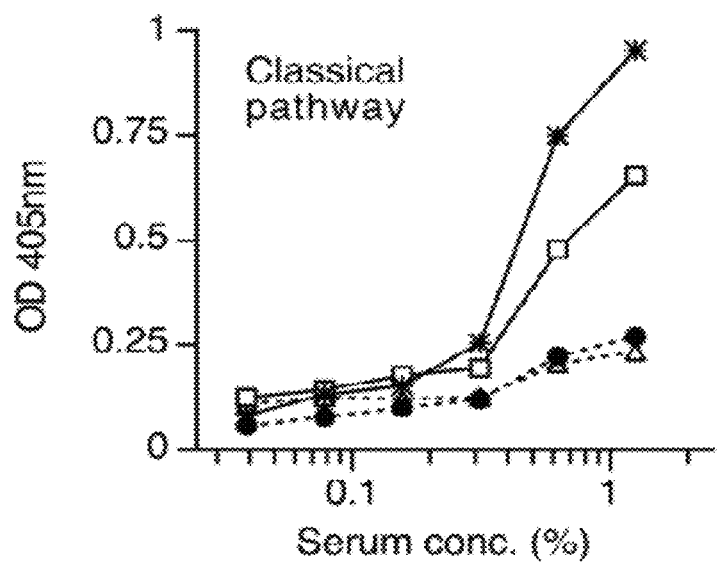
FIG. 26A graphically illustrates the results of a C3b deposition assay demonstrating that MASP-2 (−/−) mice retain a functional classical pathway, as described in Example 22.
Figure 26B:
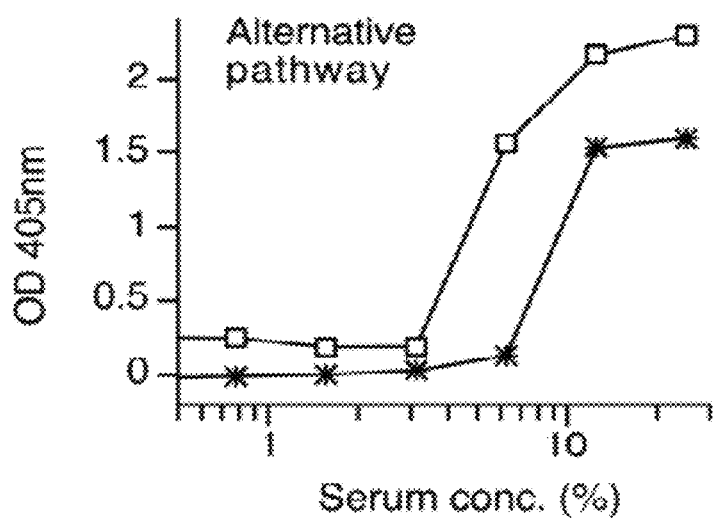
FIG. 26B graphically illustrates the results of a C3b deposition assay on zymosan coated plates, demonstrating that MASP-2 (−/−) mice retain a functional alternative pathway, as described in Example 22.

The analyses of sera and plasma of MASP-2−/− mice clearly demonstrated that MASP-2 is essentially required to activate complement via the lectin pathway. The total deficiency of lectin pathway functional activity, however, leaves the other complement activation pathways intact: MASP-2−/− plasma can still activate complement via the classical (FIG. 26A) and the alternative pathway (FIG. 26B). In FIGS. 26A and 26B, the symbol "*" symbol indicates serum from WT (MASP-2 (+/+)); the symbol "●" indicates serum from WT (C1q depleted); the symbol "□" indicates serum from MASP-2 (−/−); and the symbol "Δ" indicates serum from MASP-2 (−/−) (C1q depleted).

FIG. 26A graphically illustrates that MASP-2−/− mice retain a functional classical pathway: C3b deposition was assayed on microtiter plates coated with immune complexes (generated in situ by coating with BSA then adding goat anti-BSA IgG). FIG. 26B graphically illustrates MASP-2 deficient mice retain a functional alternative pathway: C3b deposition was assayed on Zymosan coated microtiter plates under conditions that permit only alternative pathway activation (buffer containing Mg$^{2+}$ and EGTA). Results shown in FIG. 26A and FIG. 26B are means of duplicates and are typical of three independent experiments. Same symbols for plasma sources were used throughout. These results show that a functional alternative pathway is present in MASP-2 deficient mice, as evidenced in the results shown in FIG. 26B under experimental conditions designed to directly trigger the alternative pathway, while inactivating both the classical pathway and lectin pathway.

The Lectin Pathway of Complement Activation Critically Contributes to Inflammatory Tissue Loss in Myocardial Ischemia/Reperfusion Injury (MIRI).

Figure 27A:
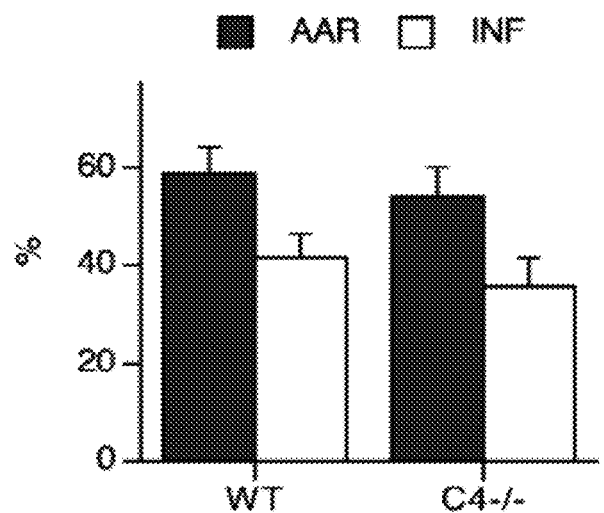
FIG. 27A graphically illustrates myocardial ischemia/reperfusion injury (MIRI)-induced tissue loss following ligation of the left anterior descending branch of the coronary artery (LAD) and reperfusion in C4 (−/−) mice (n=6) and matching WT littermate controls (n=7), showing area at risk (AAR) and infarct size (INF) as described in Example 22.
Figure 27B:
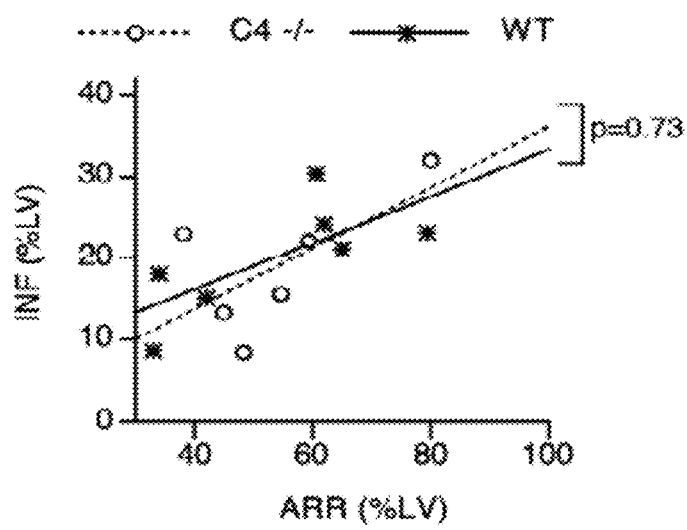
FIG. 27B graphically illustrates infarct size (INF) as a function of area at risk (AAR) in C4 (−/−) and WT mice treated as describe in FIG. 42A, demonstrating that C4 (−/−) mice are as susceptible to MIRI as WT controls (dashed line), as described in Example 22.

In order to study the contribution of lectin pathway functional activity to MIRI, we compared MASP-2$^{-/-}$ mice and WT littermate controls in a model of MIRI following transient ligation and reperfusion of the left anterior descending branch of the coronary artery (LAD). The presence or absence of complement C4 has no impact on the degree of ischemic tissue loss in MIRI. We assessed the impact of C4 deficiency on infarct sizes following experimental MIRI. As shown in FIG. 27A and FIG. 27B, identical infarct sizes were observed in both C4-deficient mice and their WT littermates. FIG. 27A graphically illustrates MIRI-induced tissue loss following LAD ligation and reperfusion in C4−/− mice (n=6) and matching WT littermate controls (n=7). FIG. 27B graphically illustrates INF as a function of AAR, clearly demonstrating that C4−/− mice are as susceptible to MIRI as their WI controls (dashed line).

These results demonstrate that C4 deficient mice are not protected from MIRI. This result was unexpected, as it is in conflict with the widely accepted view that the major C4 activation fragment, C4b, is an essential component of the classical and the lectin pathway C3 convertase C4b2a. We therefore assessed whether a residual lectin pathway specific activation of complement C3 can be detected in C4-deficient mouse and human plasma.

The Lectin Pathway can Activate Complement C3 in Absence of C4 Via a Novel MASP-2 Dependent C4-Bypass Activation Route.

Encouraged by historical reports indicating the existence of a C4-bypass activation route in C4-deficient guinea pig serum (May, J. E., and M. Frank, *J. Immunol.* 111:1671-1677 (1973)), we analyzed whether C4-deficient mice may have residual classical or lectin pathway functional activity and monitored activation of C3 under pathway-specific assay conditions that exclude contributions of the alternative pathway.

Figure 28A:
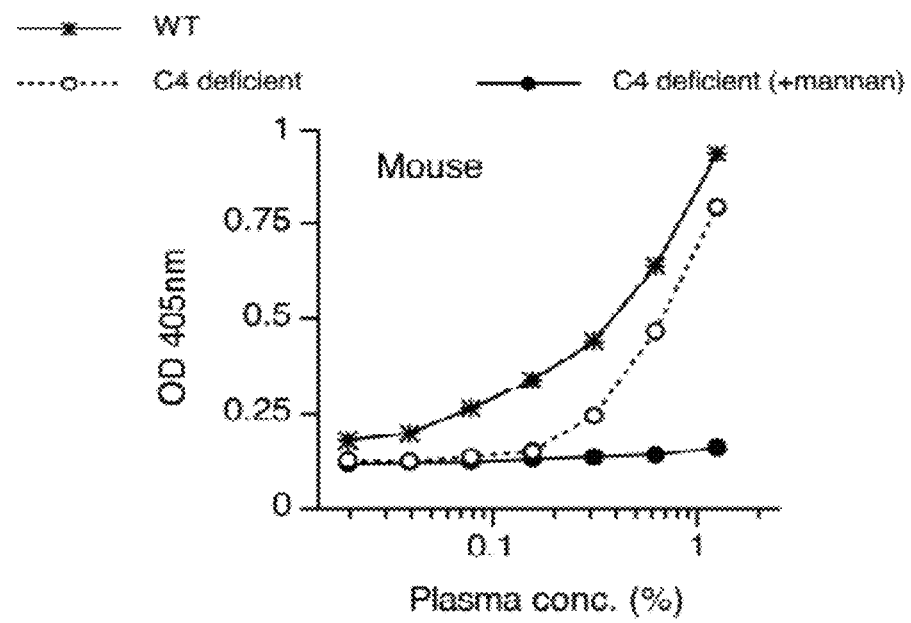
FIG. 28A graphically illustrates the results of a C3b deposition assay using serum from WT mice, C4 (−/−) mice and serum from C4 (−/−) mice pre-incubated with mannan, as described in Example 22.
Figure 28B:
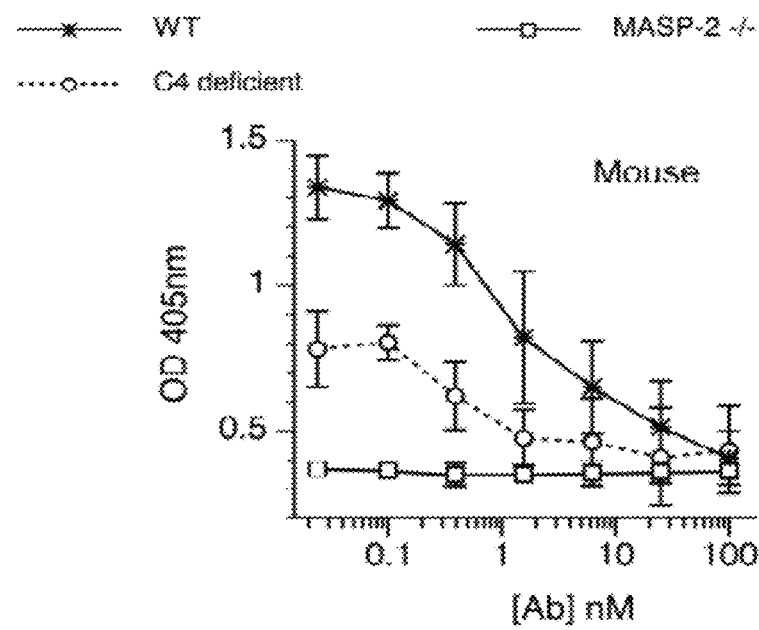
FIG. 28B graphically illustrates the results of a C3b deposition assay on serum from WT, C4 (−/−), and MASP-2 (−/−) mice mixed with various concentrations of an anti-murine MASP-2 mAb (mAbM11), as described in Example 22.
Figure 28C:
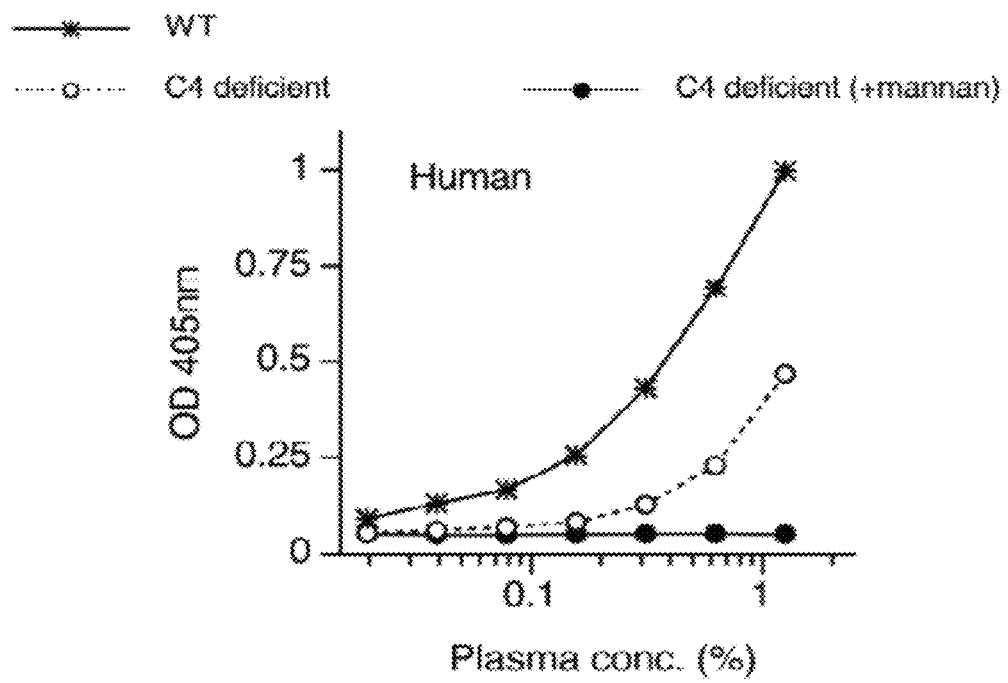
FIG. 28C graphically illustrates the results of a C3b deposition assay on human serum from WT (C4 sufficient) and C4 deficient serum, and serum from C4 deficient subjects pre-incubated with mannan, as described in Example 22.
Figure 28D:
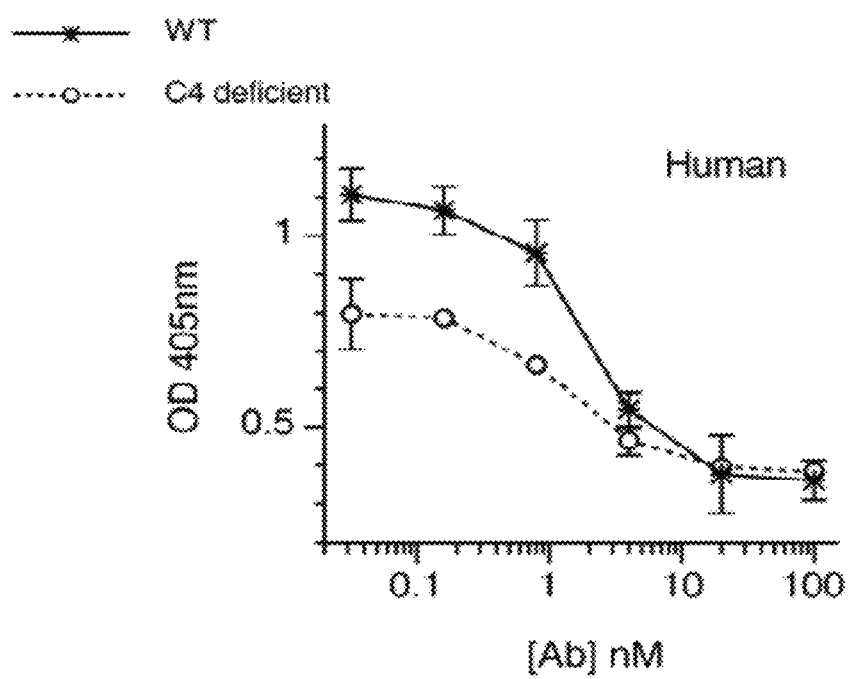
FIG. 28D graphically illustrates the results of a C3b deposition assay on human serum from WT (C4 sufficient) and C4 deficient subjects mixed with anti-human MASP-2 mAb (mAbH3), as described in Example 22.

C3b deposition was assayed on Mannan-coated microtiter plates using re-calcified plasma at plasma concentrations prohibitive for alternative pathway activation (1.25% and below). While no cleavage of C3 was detectable in C4-deficient plasma tested for classical pathway activation (data not shown), a strong residual C3 cleavage activity was observed in C4-deficient mouse plasma when initiating complement activation via the lectin pathway. The lectin pathway dependence is demonstrated by competitive inhibition of C3 cleavage following preincubation of C4-deficient plasma dilutions with soluble Mannan (see FIG. 28A). As shown in FIG. 28A-D, MASP-2 dependent activation of C3 was observed in the absence of C4. FIG. 28A graphically illustrates C3b deposition by C4+/+ (crosses) and C4−/− (open circles) mouse plasma. Pre-incubating the C4−/− plasma with excess (1 µg/ml) fluid-phase Mannan prior to the assay completely inhibits C3 deposition (filled circles). Results are typical of 3 independent experiments. FIG. 28B graphically illustrates the results of an experiment in which wild-type, MASP-2 deficient (open squares) and C4−/− mouse plasma (1%) was mixed with various concentrations of anti-rat MASP-2 mAbM11 (abscissa) and C3b deposition assayed on Mannan-coated plates. Results are means (±SD) of 4 assays (duplicates of 2 of each type of plasma). FIG. 28C graphically illustrates the results of an experiment in which Human plasma: pooled NHS (crosses), C4−/− plasma (open circles) and C4−/− plasma pre-incubated with 1 µg/ml Mannan (filled circles). Results are representative of three independent experiments. FIG. 28D graphically illustrates that inhibition of C3b deposition in C4 sufficient and C4 deficient human plasma. (1%) by anti-human MASP-2 mAbH3 (Means±SD of triplicates). As shown in FIG. 28B, no lectin pathway-dependent C3 activation was detected in MASP-2−/− plasma assayed in parallel, implying that this C4-bypass activation route of C3 is MASP-2 dependent.

To further corroborate these findings, we established a series of recombinant inhibitory mAbs isolated from phage display antibody libraries by affinity screening against recombinant human and rat MASP-2A (where the serine residue of the active protease domain was replaced by an alanine residue by site-directed mutagenesis to prevent autolytic degradation of the antigen). Recombinant antibodies against MASP-2 (AbH3 and AbM11) were isolated from Combinatorial Antibody Libraries (Knappik, A., et al., *J. Mol. Biol.* 296:57-86 (2000)), using recombinant human and rat MASP-2A as antigens (Chen, C. B. and Wallis, *J. Biol. Chem.* 276:25894-25902 (2001)). An anti-rat Fab2 fragment that potently inhibited lectin pathway-mediated activation of C4 and C3 in mouse plasma (IC50~1 nM) was converted to a full-length IgG2a antibody. Polyclonal anti-murine MASP-2A antiserum was raised in rats. These tools allowed us to confirm MASP-2 dependency of this novel lectin pathway specific C4-bypass activation route of C3, as further described below.

As shown in FIG. 28B, M211, an inhibitory monoclonal antibody which selectively binds to mouse and rat MASP-2 inhibited the C4-bypass activation of C3 in C4-deficient mouse as well as C3 activation of WT mouse plasma via the lectin pathway in a concentration dependent fashion with similar $IC_{50}$ values. All assays were carried out at high plasma dilutions rendering the alternative pathway activation route dysfunctional (with the highest plasma concentration being 1.25%).

In order to investigate the presence of an analogous lectin pathway specific C4-bypass activation of C3 in humans, we analyzed the plasma of a donor with an inherited deficiency of both human C4 genes (i.e., C4A and C4B), resulting in total absence of C4 (Yang, Y., et al., *J. Immunol.* 173:2803-2814 (2004)). FIG. 28C shows that this patient's plasma efficiently activates C3 in high plasma dilutions (rendering the alternative activation pathway dysfunctional). The lectin pathway specific mode of C3 activation on Mannan-coated plates is demonstrated in murine C4-deficient plasma (FIG. 28A) and human C4 deficient plasma (FIG. 28C) by adding excess concentrations of fluid-phase Mannan. The MASP-2 dependence of this activation mechanism of C3 in human C4-deficient plasma was assessed using AbH3, a monoclonal antibody that specifically binds to human MASP-2 and ablates MASP-2 functional activity. As shown in FIG. 28D, AbH3 inhibited the deposition of C3b (and C3dg) in both C4-sufficient and C4-deficient human plasma with comparable potency.

In order to assess a possible role of other complement components in the C4-bypass activation of C3, we tested plasma of MASP-1/3−/− and Bf/C2−/− mice alongside MASP-2−/−, C4−/− and C1q−/− plasma (as controls) under both lectin pathway specific and classical pathway specific assay conditions. The relative amount of C3 cleavage was plotted against the amount of C3 deposited when using WT plasma.

Figure 29A:
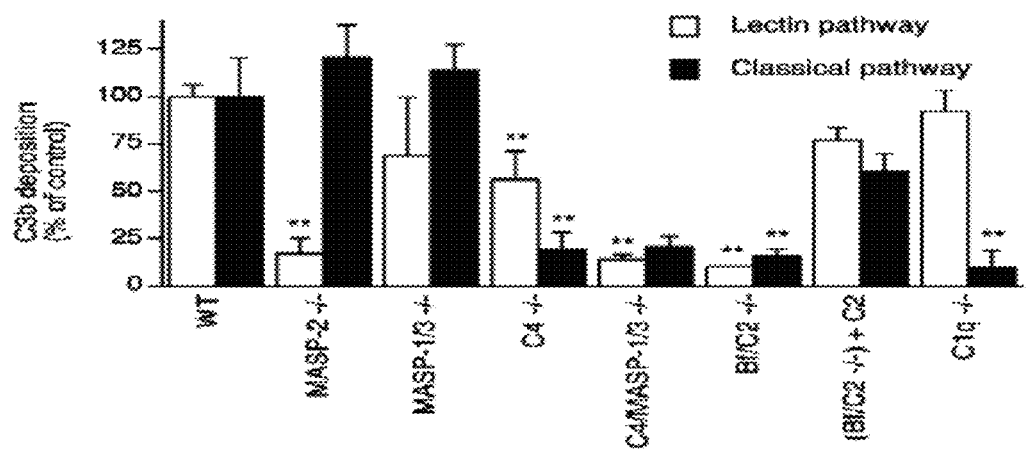
FIG. 29A graphically illustrates a comparative analysis of C3 convertase activity in plasma from various complement deficient mouse strains tested either under lectin activation pathway specific assay conditions, or under classical activation pathway specific assay conditions, as described in Example 22.

FIG. 29A graphically illustrates a comparative analysis of C3 convertase activity in plasma from various complement deficient mouse strains tested either under lectin activation pathway or classical activation pathway specific assay conditions. Diluted plasma samples (1%) of WT mice (n=6), MASP-2−/− mice (n=4), MASP-1/3−/− mice (n=2), C4−/− mice (n=8), C4/MASP-1/3−/− mice (n=8), Bf/C2−/− (n=2) and C1q−/− mice (n=2) were tested in parallel. Reconstitution of Bf/C2−/− plasma with 2.5 µg/ml recombinant rat C2 (Bf/C2−/−+C2) restored C3b deposition. Results are means (±SD).

p<0.01 (compared to WT plasma). As shown in FIG. 29A**, substantial C3 deposition is seen in C4−/− plasma tested under lectin pathway specific assay conditions, but not under classical pathway specific conditions. Again, no C3 deposition was seen in MASP-2 deficient plasma via the lectin pathway activation route, while the same plasma deposited C3 via the classical pathway. In MASP-1/3−/− plasma, C3 deposition occurred in both lectin and classical pathway specific assay conditions. No C3 deposition was seen in plasma with a combined deficiency of C4 and MASP-1/3, either using lectin pathway or classical pathway specific conditions. No C3 deposition is detectable in C2/Bf−/− plasma, either via the lectin pathway, or via the classical pathway. Reconstitution of C2/Bf−/− mouse plasma with recombinant C2, however, restored both lectin pathway and classical pathway-mediated C3 cleavage. The assay conditions were validated using C1q−/− plasma.

Figure 29B:
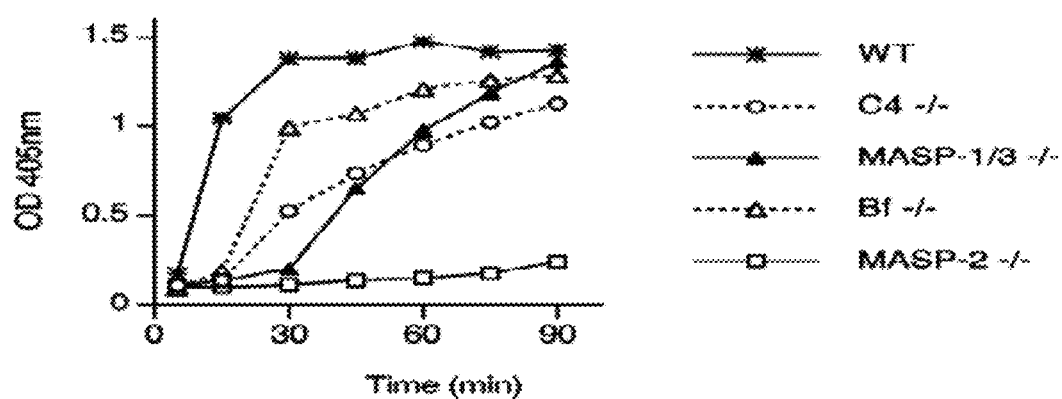
FIG. 29B graphically illustrates the time-resolved kinetics of C3 convertase activity in plasma from various complement deficient mouse strains tested under lectin activation pathway specific conditions, as described in Example 22.

FIG. 29B graphically illustrates time-resolved kinetics of C3 convertase activity in plasma from various complement deficient mouse strains WT, fB−/−, C4−/−, MASP-1/3−/−, and MASP-2−/− plasma, tested under lectin activation pathway specific assay conditions (1% plasma, results are typical of three independent experiments). As shown in FIG. 29B, while no C3 cleavage was seen in MASP-2−/− plasma, fB−/− plasma cleaved C3 with similar kinetics to the WT plasma. A significant delay in the lectin pathway-dependent conversion of C3 to C3b (and C3dg) was seen in C4−/− as well as in MASP-1/3 deficient plasma. This delay of C3 activation in MASP-1/3−/− plasma was recently shown to be MASP-1, rather than MASP-3 dependent (Takahashi, M., et al., *J. Immunol.* 180:6132-6138 (2008)).

Discussion:

The results described in this Example strongly suggest that MASP-2 functional activity is essential for the activation of C3 via the lectin pathway both in presence and absence of C4. Furthermore, C2 and MASP-1 are required for this novel lectin pathway specific C4-bypass activation route of C3 to work. The comparative analysis of lectin pathway functional activity in MASP-2−/− as well as C4−/− plasma revealed the existence of a previously unrecognized C4-independent, but MASP-2-dependent activation route of complement C3 and showed that C3 can be activated in a lectin pathway-dependent mode in total absence of C4. While the detailed molecular composition and the sequence of activation events of this novel MASP-2 dependent C3 convertase remains to be elucidated, our results imply that this C4-bypass activation route additionally requires the presence of complement C2 as well as MASP-1. The loss of lectin pathway-mediated C3 cleavage activity in plasma of mice with combined C4 and MASP-1/3 deficiency may be explained by a most recently described role of MASP-1 to enhance MASP-2 dependent complement activation through direct cleavage and activation of MASP-2

(Takahashi, M., et al., *J. Immunol.* 180:6132-6138 (2008)). Likewise, MASP-1 may aid MASP-2-functional activity through its ability to cleave C2 (Moller-Kristensen, et al., *Int. Immunol.* 19:141-149 (2007)). Both activities may explain the reduced rate by which MASP-1/3 deficient plasma cleaves C3 via the lectin activation pathway and why MASP-1 may be required to sustain C3 conversion via the C4-bypass activation route.

The inability of C2/fB−/− plasma to activate C3 via the lectin pathway was shown to be C2-dependent as the addition of recombinant rat C2 to C2/fB−/− plasma restored the ability of the reconstituted plasma to activate C3 on Mannan-coated plates.

The finding that C4 deficiency specifically disrupts the classical complement activation pathway while the lectin pathway retains a physiologically critical level of C3 convertase activity via a MASP-2 dependent C4-bypass activation route calls for a re-assessment of the role of the lectin pathway in various disease models, including experimental *S. pneumoniae* infection (Brown, J. S., et al., *Proc. Natl. Acad. Sci. U.S.A.* 99:16969-16974 (2002); Experimental Allergic Encephalomyelitis (Boos, L. A., et al., *Glia* 49:158-160 (2005); and models of C3 dependent murine liver regeneration (Clark, A., et al., *Mol. Immunol.* 45:3125-3132 (2008)). The latter group demonstrated that C4-deficient mice can activate C3 in an alternative pathway independent fashion as in vivo inhibition of the alternative pathway by an antibody-mediated depletion of factor B functional activity did not effect C3 cleavage-dependent liver regeneration in C4−/− mice (Clark, A., et al. (2008)). This lectin pathway mediated C4-bypass activation route of C3 may also explain the lack of a protective phenotype of C4 deficiency in our model of MIRI as well as in a previously described model of renal allograft rejection (Lin, T., et al., *Am. J. Pathol.* 168:1241-1248 (2006)). In contrast, our recent results have independently demonstrated a significant protective phenotype of MASP-2−/− mice in models of renal transplantation (Farrar, C. A., et al., *Mol. Immunol.* 46:2832 (2009)).

In summary, the results of this Example support the view that MASP-2 dependent C4-bypass activation of C3 is a physiologically relevant mechanism that may be important under conditions where availability of C4 is limiting C3 activation.

Example 23

This Example describes activation of C3 by thrombin substrates and C3 deposition on mannan in WT (+/+), MASP-2 (−/−), F11 (−/−), F11/C4 (−/−) and C4 (−/−) mice.

Rationale:

As described in Example 14, it was determined that thrombin activation can occur following lectin pathway activation under physiological conditions, and demonstrates the extent of MASP-2 involvement. C3 plays a central role in the activation of complement system. C3 activation is required for both classical and alternative complement activation pathways. An experiment was carried out to determine whether C3 is activated by thrombin substrates.

Methods:

C3 Activation by Thrombin Substrates

Activation of C3 was measured in the presence of the following activated forms of thrombin substrates; human FCXIa, human FVIIa, bovine FXa, human FXa, human activated protein C, and human thrombin. C3 was incubated with the various thrombin substrates, then separated under reducing conditions on 10% SDS-polyacrylamide gels. After electrophoretic transfer using cellulose membrane, the membrane was incubated with monoclonal biotin-coupled rat anti-mouse C3, detected with a streptavidin-HRP kit and developed using ECL reagent.

Results:

Activation of C3 involves cleavage of the intact a-chain into the truncated a chain and soluble C3a (not shown in FIG. 30). FIG. 30 shows the results of a Western blot analysis on the activation of human C3 by thrombin substrates, wherein the uncleaved C3 alpha chain, and the activation product a' chain are shown by arrows. As shown in FIG. 30, incubation of C3 with the activated forms of human clotting factor XI and factor X, as well as activated bovine clotting factor X, can cleave C3 in vitro in the absence of any complement proteases.

C3 Deposition on Mannan

C3 deposition assays were carried out on serum samples obtained from WT, MASP-2 (−/−), F11(−/−), F11(−/−)/C4 (−/−) and C4(−/−). F11 is the gene encoding coagulation factor XI. To measure C3 activation, microtiter plates were coated with mannan (1 μg/well), then adding sheep anti-HSA serum (2 μg/ml) in TBS/tween/$Ca^{2+}$. Plates were blocked with 0.1% HSA in TBS and washed as above. Plasma samples were diluted in 4 mM barbital, 145 mM NaCl, 2 mM $CaCl_2$, 1 mM $MgCl_2$, 7.4, added to the plates and incubated for 1.5 h at 37° C. After washing, bound C3b was detected using rabbit anti-human C3c (Dako), followed by alkaline phosphatase-conjugated goat anti-rabbit IgG and pNPP.

Figure 31:
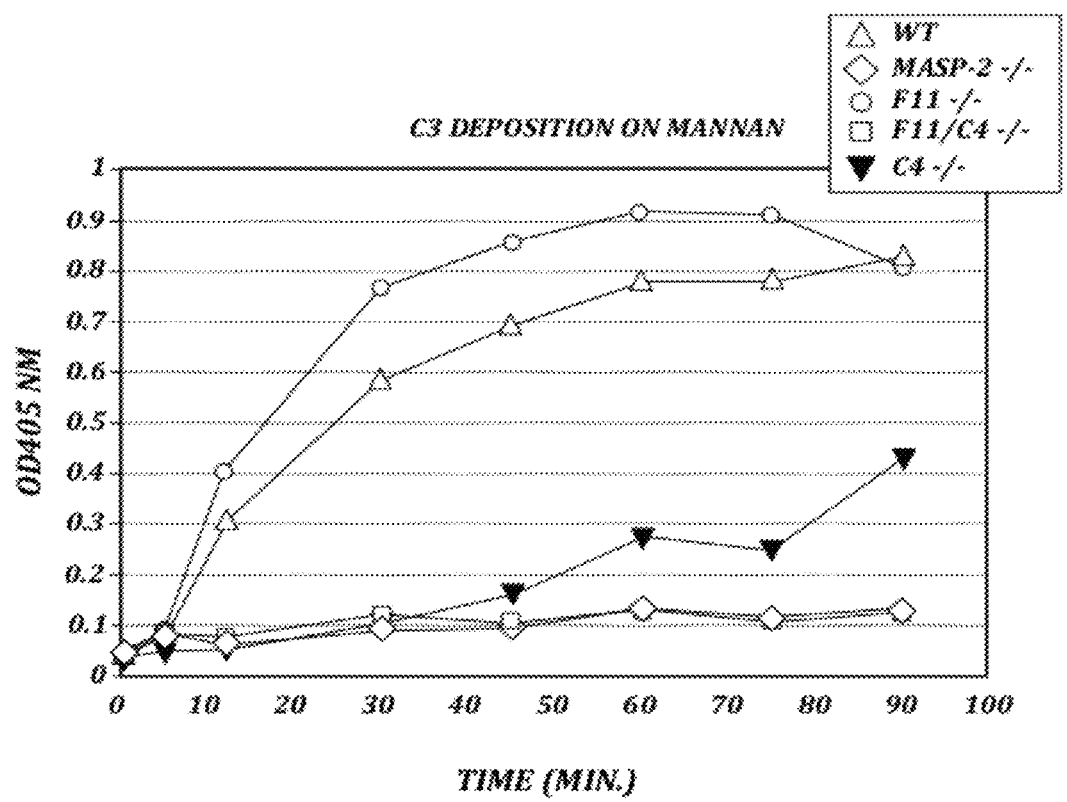
FIG. 31 shows the results of the C3 deposition assay on serum samples obtained from WT, MASP-2 (−/−), F11(−/−), F11(−/−)/C4 (−/−) and C4 (−/−), as described in Example 23.

Results:

FIG. 31 shows the results of the C3 deposition assay on serum samples obtained from WT, MASP-2 (−/−), F11(−/−), F11(−/−)/C4 (−/−) and C4 (−/−). As shown in FIG. 31, there is a functional lectin pathway even in the complete absence of C4. As further shown in FIG. 31, this novel lectin pathway dependent complement activation requires coagulation factor XI.

Discussion:

Prior to the results obtained in this experiment, it was believed by those in the art that the lectin pathway of complement required C4 for activity. Hence, data from C4 knockout mice (and C4 deficient humans) were interpreted with the assumption that such organisms were lectin pathway deficient (in addition to classical pathway deficiency). The present results demonstrate that this notion is false. Thus, conclusions of past studies suggesting that the lectin pathway was not important in certain disease settings based on the phenotype of C4 deficient animals may be false. The data described in this Example also show that in the physiological context of whole serum the lectin pathway can activate components of the coagulation cascade. Thus, it is demonstrated that there is cross-talk between complement and coagulation involving MASP-2.

Example 24

This Example describes methods to assess the effect of an anti-MASP-2 antibody on lysis of red blood cells from blood samples obtained from Paroxysmal nocturnal hemoglobinuria (PNH) patients.

Background/Rationale:

Paroxysmal nocturnal hemoglobinuria (PNH), also referred to as Marchiafava-Micheli syndrome, is an acquired, potentially life-threatening disease of the blood, characterized by complement-induced intravascular hemolytic anemia. The hallmark of PNH is chronic intravascular hemolysis that is a consequence of unregulated activation of the alternative pathway of complement. Lindorfer, M. A., et al., *Blood* 115(11) (2010). Anemia in PNH is due to destruction of red blood cells in the bloodstream. Symptoms of PNH include red urine, due to appearance of hemoglobin in the urine, and thrombosis. PNH may develop on its own, referred to as "primary PNH" or in the context of other bone marrow disorders such as aplastic anemia, referred to as "secondary PNH". Treatment for PNH includes blood transfusion for anemia, anticoagulation for thrombosis and the use of the monoclonal antibody eculizumab (Soliris), which protects blood cells against immune destruction by inhibiting the complement system (Hillmen P. et al., *N. Engl. J. Med.* 350 (6):552-9 (2004)). However, a significant portion of PNH patients treated with eculizumab are left with clinically significant immune-mediated hemolytic anemia because the antibody does not block activation of the alternative pathway of complement.

This Example describes methods to assess the effect of an anti-MASP-2 antibody on lysis of red blood cells from blood samples obtained from PNH patients (not treated with Soliris) that are incubated with ABO-matched acidified normal human serum.

Methods:

Reagents:

Erythrocytes from normal donors and from patients suffering from PNH (not treated with Soliris) are obtained by venipuncture, and prepared as described in Wilcox, L. A., et al., *Blood* 78:820-829 (1991), hereby incorporated herein by reference. Anti MASP-2 antibodies with functional blocking activity of the lectin pathway may be generated as described in Example 10.

Hemolysis Analysis:

The method for determining the effect of anti-MASP-2 antibodies on the ability to block hemolysis of erythrocytes from PNH patients is carried out using the methods described in Lindorfer, M. A., et al., *Blood* 15(11):2283-91 (2010) and Wilcox, L. A., et al., *Blood* 78:820-829 (1991), both references hereby incorporated herein by reference. As described in Lindorfer et al., erythrocytes from PNH patient samples are centrifuged, the buffy coat is aspirated and the cells are washed in gelatin veronal buffer (GVB) before each experiment. The erythrocytes are tested for susceptibility to APC-mediated lysis as follows. ABO-matched normal human sera are diluted with GVB containing 0.15 mM $CaCl_2$ and 0.5 mM $MgCl_2$ ($GVB^{+2}$) and acidified to pH 6.4 (acidified NHS, aNHS) and used to reconstitute the erythrocytes to a hematocrit of 1.6% in 50% aNHS. The mixtures are then incubated at 37° C., and after 1 hour, the erythrocytes are pelleted by centrifugation. The optical density of an aliquot of the recovered supernate is measured at 405 nM and used to calculate the percent lysis. Samples reconstituted in acidified serum-EDTA are processed similarly and used to define background noncomplement-mediated lysis (typically less than 3%). Complete lysis (100%) is determined after incubating the erythrocytes in distilled water.

In order to determine the effect of anti-MASP-2 antibodies on hemolysis of PNH erythrocytes, erythrocytes from PNH patients are incubated in aNHS in the presence of incremental concentrations of the anti-MASP-2 antibodies, and the presence/amount of hemolysis is subsequently quantified.

In view of the fact that anti-MASP-2 antibodies have been shown to block subsequent activation of the alternative complement pathway, it is expected that anti-MASP-2 antibodies will be effective in blocking alternative pathway-mediated hemolysis of PNH erythrocytes, and will be useful as a therapeutic to treat patients suffering from PNH.

Example 25

This Example describes methods to assess the effect of an anti-MASP-2 blocking antibody on complement activation by cryoglobulins in blood samples obtained from patients suffering from cryoglobulinemia.

Background/Rationale:

Cryoglobulinemia is characterized by the presence of cryoglobulins in the serum. Cryoglobulins are single or mixed immunoglobulins (typically IgM antibodies) that undergo reversible aggregation at low temperatures. Aggregation leads to classical pathway complement activation and inflammation in vascular beds, particularly in the periphery. Clinical presentations of cryoglobulinemia include vasculitis and glomerulonephritis.

Cryoglobulinemia may be classified as follows based on cryoglobulin composition: Type I cryoglobulinemia, or simple cryoglobulinemia, is the result of a monoclonal immunoglobulin, usually immunoglobulin M (IgM); Types II and III cryoglobulinemia (mixed cryoglobulinemia) contain rheumatoid factors (RFs), which are usually IgM in complexes with the Fc portion of polyclonal IgG.

Conditions associated with cryoglobulinemia include hepatitis C infection, lymphoproliferative disorders and other autoimmune diseases. Cryoglobulin-containing immune complexes result in a clinical syndrome of systemic inflammation, possibly due to their ability to activate complement. While IgG immune complexes normally activate the classical pathway of complement, IgM containing complexes can also activate complement via the lectin pathway (Zhang, M., et al., *Mol Immunol* 44(1-3):103-110 (2007) and Zhang. M., et al., *J. Immunol.* 177(7):4727-34 (2006)).

Immunohistochemical studies have further demonstrated the cryoglobulin immune complexes contain components of the lectin pathway, and biopsies from patients with cryoglobulinemic glomerulonephritis showed immunohistochemical evidence of lectin pathway activation in situ (Ohsawa, I., et al, *Clin Immunol* 101(1):59-66 (2001)). These results suggest that the lectin pathway may contribute to inflammation and adverse outcomes in cryoglobulemic diseases.

Methods:

The method for determining the effect of anti-MASP-2 antibodies on the ability to block the adverse effects of Cryoglobulinemia is carried out using the assay for fluid phase C3 conversion as described in Ng Y. C. et al., *Arthritis and Rheumatism* 31(1):99-107 (1988), hereby incorporated herein by reference. As described in Ng et al., in essential mixed cryoglobulinemia (EMC), monoclonal rheumatoid factor (mRF), usually IgM, complexes with polyclonal IgG to form the characteristic cryoprecipitate immune complexes (IC) (type II cryoglobulin). Immunoglobulins and C3 have been demonstrated in vessel walls in affected tissues such as skin, nerve and kidney. As described in Ng et al., $^{125}$I-labeled mRF is added to serum (normal human serum and serum obtained from patients suffering from cryoglobulinemia), incubated at 37° C., and binding to erythrocytes is measured.

Fluid phase C3 conversion is determined in serum (normal human serum and serum obtained from patients suffering from cryoglobulinemia) in the presence or absence of the following IC: BSA-anti BSA, mRF, mRF plus IgG, or cryoglobulins, in the presence or absence of anti-MASP-2 antibodies. The fixation of C3 and C4 to IC is measured using a coprecipitation assay with F(ab')2 anti-C3 and F(ab')2 anti-C4.

In view of the fact that anti-MASP-2 antibodies have been shown to block activation of the lectin pathway it is expected that anti-MASP-2 antibodies will be effective in blocking complement mediated adverse effects associated with cryoglobulinemia, and will be useful as a therapeutic to treat patients suffering from cryoglobulinemia.

Example 26

This Example describes methods to assess the effect of an anti-MASP-2 antibody on blood samples obtained from patients with Cold Agglutinin Disease, which manifests as anemia.

Background/Rationale:

Cold Agglutinin Disease (CAD), is a type of autoimmune hemolytic anemia. Cold agglutinins antibodies (usually IgM) are activated by cold temperatures and bind to and aggregate red blood cells. The cold agglutinin antibodies combine with complement and attack the antigen on the surface of red blood cells. This leads to opsoniation of red blood cells (hemolysis) which triggers their clearance by the reticuloendothelial system. The temperature at which the agglutination takes place varies from patient to patient.

CAD manifests as anemia. When the rate of destruction of red blood cell destruction exceeds the capacity of the bone marrow to produce an adequate number of oxygen-carrying cells, then anemia occurs. CAD can be caused by an underlying disease or disorder, referred to as "Secondary CAD", such as an infectious disease (mycoplasma pneumonia, mumps, mononucleosis), lymphoproliferative disease (lymphoma, chronic lymphocytic leukemia), or connective tissue disorder. Primary CAD patients are considered to have a low grade lymphoproliferative bone marrow disorder. Both primary and secondary CAD are acquired conditions.

Methods:

Reagents:

Erythrocytes from normal donors and from patients suffering from CAD are obtained by venipuncture. Anti-MASP-2 antibodies with functional blocking activity of the lectin pathway may be generated as described in Example 10.

The effect of anti-MASP-2 antibodies to block cold agglutinin-mediated activation of the lectin pathway may be determined as follows: Erythrocytes from blood group 1 positive patients are sensitized with cold aggultinins (i.e., IgM antibodies), in the presence or absence of anti-MASP-2 antibodies. The erythrocytes are then tested for the ability to activate the lectin pathway by measuring C3 binding.

In view of the fact that anti-MASP-2 antibodies have been shown to block activation of the lectin pathway, it is expected that anti-MASP-2 antibodies will be effective in blocking complement mediated adverse effects associated with Cold Agglutinin Disease, and will be useful as a therapeutic to treat patients suffering from Cold Agglutinin Disease.

Example 27

This Example describes methods to assess the effect of an anti-MASP-2 antibody on lysis of red blood cells in blood samples obtained from mice with atypical hemolytic uremic syndrome (aHUS).

Background/Rationale:

Atypical hemolytic uremic syndrome (aHUS) is characterized by hemolytic anemia, thrombocytopenia, and renal failure caused by platelet thrombi in the microcirculation of the kidney and other organs. aHUS is associated with defective complement regulation and can be either sporadic or familial. aHUS is associated with mutations in genes coding for complement activation, including complement factor H, membrane cofactor B and factor I, and well as complement factor H-related 1 (CFHR1) and complement factor H-related 3 (CFI-1R3). Zipfel, P. F., et al., *PLoS Genetics* 3(3):e41 (2007). This Example describes methods to assess the effect of an anti-MASP-2 antibody on lysis of red blood cells from blood samples obtained from aHUS mice.

Methods:

The effect of anti-MASP-2 antibodies to treat aHUS may be determined in a mouse model of this disease in which the endogenouse mouse fH gene has been replaced with a human homologue encoding a mutant form of fH frequently found in aHUS patients. Sec Pickering M. C. et al., *J. Exp. Med.* 204(6):1249-1256 (2007), hereby incorporated herein by reference. As described in Pickering et al., such mice develop an aHUS like pathology. In order to assess the effect of an anti-MASP-2 antibody for the treatment of aHUS, anti-MASP-2 antibodies are administered to the mutant aHUS mice and lysis of red blood cells obtained from anti-MASP-2 ab treated and untreated controls is compared. In view of the fact that anti-MASP-2 antibodies have been shown to block activation of the lectin pathway it is expected that anti-MASP-2 antibodies will be effective in blocking lysis of red blood cells in mammalian subjects suffering from aHUS.

Example 28

This Example describes methods to assess the effect of an anti-MASP-2 antibody for the treatment of glaucoma.

Rationale/Background:

It has been shown that uncontrolled complement activation contributes to the progression of degenerative injury to retinal ganglion cells (RGCs), their synapses and axons in glaucoma. See Tezel G. et al., *Invest Ophthalmol Vis Sci* 51:5071-5082 (2010). For example, histopathologic studies of human tissues and in vivo studies using different animal models have demonstrated that complement components, including C1q and C3, are synthesized and terminal complement complex is formed in the glaucomatous retina (see Stasi K. et al., *Invest Ophthalmol Vis Sci* 47:1024-1029 (2006), Kuehn M. H. et al., *Exp Eye Res* 83:620-628 (2006)). As further described in Kuehn M. H. et al., *Experimental Eye Research* 87:89-95 (2008), complement synthesis and deposition is induced by retinal I/R and the disruption of the complement cascade delays RGC degeneration. In this study, mice carrying a targeted disruption of the complement component C3 were found to exhibit delayed RGC degeneration after transient retinal I/R when compared to normal animals.

Methods:

The method for determining the effect of anti-MASP-2 antibodies on RGC degeneration is carried out in an animal model of retinal 1/R as described in Kuehn M. H. et al., *Experimental Eye Research* 87:89-95 (2008), hereby incorporated herein by reference. As described in Kuehn et al., retinal ischemia is induced by anesthetizing the animals, then inserting a 30-gauge needle connected to a reservoir containing phosphate buffered saline through the cornea into the anterior chamber of the eye. The saline reservoir is then elevated to yield an intraocular pressure of 104 mmHg, sufficient to completely prevent circulation through the retinal vasculature. Elevated intraocular ischemia is confirmed by blanching of the iris and retina and ischemia is maintained for 45 minutes in the left eye only; the right eye serves as a control and does not receive cannulation. Mice are then euthanized either 1 or 3 weeks after the ischemic insult. Anti-MASP-2 antibodies are administered to the mice either locally to the eye or systemically to assess the effect of an anti-MASP antibody administered prior to ischemic insult.

Immunohistochemistry of the eyes is carried out using antibodies against C1q and C3 to detect complement deposition. Optic nerve damage can also be assessed using standard electron microscopy methods. Quantitation of surviving retinal RGCs is performed using gamma synuclein labeling.

Results:

As described in Kuehn et al., in normal control mice, transient retinal ischemia results in degenerative changes of the optic nerve and retinal deposits of C1q and C3 detectable by immunohistochemistry. In contrast, C3 deficient mice displayed a marked reduction in axonal degeneration, exhibiting only minor levels of optic nerve damage 1 week after induction. Based on these results, it is expected that similar results would be observed when this assay is carried out in a MASP-2 knockout mouse, and when anti-MASP-2 antibodies are administered to a normal mouse prior to ischemic insult.

Example 29

This Example demonstrates that a MASP-2 inhibitor, such as an anti-MASP-2 antibody, is effective for the treatment of radiation exposure and/or for the treatment, amelioration or prevention of acute radiation syndrome.

Rationale:

Exposure to high doses of ionizing radiation causes mortality by two main mechanisms: toxicity to the bone marrow and gastrointestinal syndrome. Bone marrow toxicity results in a drop in all hematologic cells, predisposing the organism to death by infection and hemorrhage. The gastrointestinal syndrome is more severe and is driven by a loss of intestinal barrier function due to disintegration of the gut epithelial layer and a loss of intestinal endocrine function. This leads to sepsis and associated systemic inflammatory response syndrome which can result in death.

The lectin pathway of complement is an innate immune mechanism that initiates inflammation in response to tissue injury and exposure to foreign surfaces (i.e., bacteria). Blockade of this pathway leads to better outcomes in mouse models of ischemic intestinal tissue injury or septic shock. It is hypothesized that the lectin pathway may trigger excessive and harmful inflammation in response to radiation-induced tissue injury. Blockade of the lectin pathway may thus reduce secondary injury and increase survival following acute radiation exposure.

The objective of the study carried out as described in this Example was to assess the effect of lectin pathway blockade on survival in a mouse model of radiation injury by administering anti-murine MASP-2 antibodies.

Methods and Materials:

Materials.

The test articles used in this study were (i) a high affinity anti-murine MASP-2 antibody (mAbM11) and (ii) a high affinity anti-human MASP-2 antibody (mAbH6) that block the MASP-2 protein component of the lectin complement pathway which were produced in transfected mammalian cells. Dosing concentrations were 1 mg/kg of anti-murine MASP-2 antibody (mAbM11), 5 mg/kg of anti-human MASP-2 antibody (mAbH6), or sterile saline. For each dosing session, an adequate volume of fresh dosing solutions were prepared.

Animals.

Young adult male Swiss-Webster mice were obtained from Harlan Laboratories (Houston, Tex.). Animals were housed in solid-bottom cages with Alpha-Dri bedding and provided certified PMI 5002 Rodent Diet (Animal Specialties, Inc., Hubbard Oreg.) and water ad libitum. Temperature was monitored and the animal holding room operated with a 12 hour light/12 hour dark light cycle.

Irradiation.

After a 2-week acclimation in the facility, mice were irradiated at 6.5 and 7.0 Gy by whole-body exposure in groups of 10 at a dose rate of 0.78 Gy/min using a Therapax X-RAD 320 system equipped with a 320-kV high stability X-ray generator, metal ceramic X-ray tube, variable x-ray beam collimator and filter (Precision X-ray Incorporated, East Haven, Conn.). Dose levels were selected based on prior studies conducted with the same strain of mice indicating the $LD_{50/30}$ was between 6.5 and 7.0 Gy (data not shown).

Drug Formulation and Administration.

The appropriate volume of concentrated stock solutions were diluted with ice cold saline to prepare dosing solutions of 0.2 mg/ml anti-murine MASP-2 antibody (mAbM11) or 0.5 mg/ml anti-human MASP-2 antibody (mAbH6) according to protocol. Administration of anti-MASP-2 antibody mAbM11 and mAbH6 was via IP injection using a 25-gauge needle base on animal weight to deliver 1 mg/kg mAbM11, 5 mg/kg mAbH6, or saline vehicle.

Study Design.

Mice were randomly assigned to the groups as described in Table 8. Body weight and temperature were measured and recorded daily. Mice in Groups 7, 11 and 13 were sacrificed at post-irradiation day 7 and blood collected by cardiac puncture under deep anesthesia. Surviving animals at post-irradiation day 30 were sacrificed in the same manner and blood collected. Plasma was prepared from collected blood samples according to protocol and returned to Sponsor for analysis.

TABLE 8

Study Groups

| Group ID | N | Irradiation Level (Gy) | Treatment | Dose Schedule |
|---|---|---|---|---|
| 1 | 20 | 6.5 | Vehicle | 18 hr prior to irradiation, 2 hr post irradiation, weekly booster |
| 2 | 20 | 6.5 | anti-murine MASP-2 ab (mAbM11) | 18 hr prior to irradiation only |
| 3 | 20 | 6.5 | anti-murine MASP-2 ab (mAbM11) | 18 hr prior to irradiation, 2 hr post irradiation, weekly booster |
| 4 | 20 | 6.5 | anti-murine MASP-2 ab (mAbM11) | 2 hr post irradiation, weekly booster |
| 5 | 20 | 6.5 | anti-human MASP-2 ab (mAbH6) | 18 hr prior to irradiation, 2 hr post irradiation, weekly booster |
| 6 | 20 | 7.0 | Vehicle | 18 hr prior to irradiation, 2 hr post irradiation, weekly booster |
| 7 | 5 | 7.0 | Vehicle | 2 hr post irradiation only |
| 8 | 20 | 7.0 | anti-murine MASP-2 ab (mAbM11) | 18 hr prior to irradiation only |
| 9 | 20 | 7.0 | anti-murine MASP-2 ab (mAbM11) | 18 hr prior to irradiation, 2 hr post irradiation, weekly booster |
| 10 | 20 | 7.0 | anti-murine MASP-2 ab (mAbM11) | 2 hr post irradiation, weekly booster |
| 11 | 5 | 7.0 | anti-murine MASP-2 ab (mAbM11) | 2 hr post irradiation only |
| 12 | 20 | 7.0 | anti-human MASP-2 ab (mAbH6) | 18 hr prior to irradiation, 2 hr post irradiation, weekly booster |
| 13 | 5 | None | None | None |

Statistical Analysis.

Kaplan-Meier survival curves were generated and used to compare mean survival time between treatment groups using log-Rank and Wilcoxon methods. Averages with standard deviations, or means with standard error of the mean are reported. Statistical comparisons were made using a two-tailed unpaired t-test between controlled irradiated animals and individual treatment groups.

Results

Figure 32A:
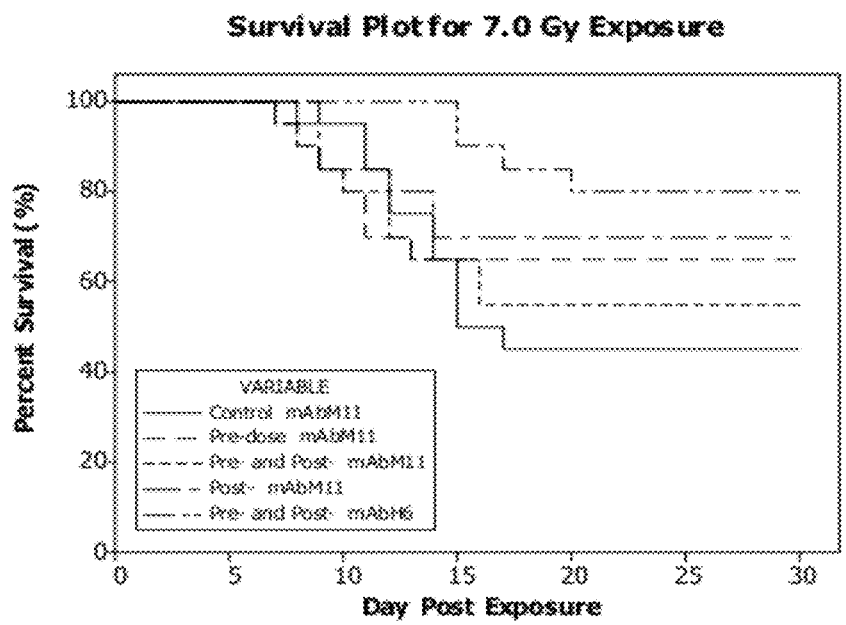
FIG. 32A is a Kaplain-Mcier survival plot showing the percent survival over time after exposure to 7.0 Gy radiation in control mice and in mice treated with anti-murine MASP-2 antibody (mAbM11) or anti-human MASP-2 antibody (mAbH6) as described in Example 29.
Figure 32B:
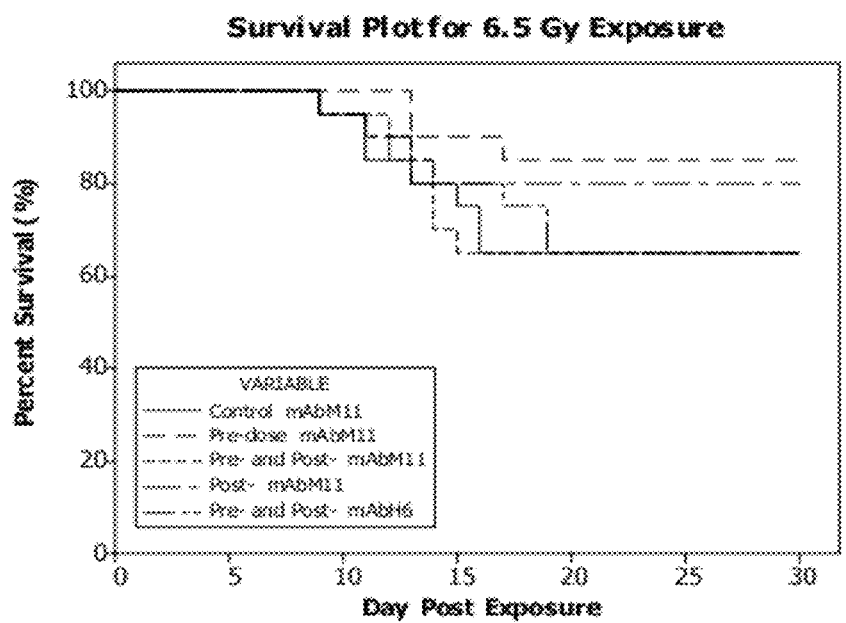
FIG. 32B is a Kaplain-Meier survival plot showing the percent survival over time after exposure to 6.5 Gy radiation in control mice and in mice treated with anti-murine MASP-2 antibody (mAbM11) or anti-human MASP-2 antibody (mAbH6), as described in Example 29.

Kaplan-Meier survival plots for 7.0 and 6.5 Gy exposure groups are provided in FIGS. 32A and 32B, respectively, and summarized below in Table 9. Overall, treatment with anti-murine MASP-2 ab (mAbM11) pre-irradiation increased the survival of irradiated mice compared to vehicle treated irradiated control animals at both 6.5 (20% increase) and 7.0 Gy (30% increase) exposure levels. At the 6.5 Gy exposure level, post-irradiation treatment with anti-murine MASP-2 ab resulted in a modest increase in survival (15%) compared to vehicle control irradiated animals.

In comparison, all treated animals at the 7.0 Gy exposure level showed an increase in survival compared to vehicle treated irradiated control animals. The greatest change in survival occurred in animals receiving mAbH6, with a 45% increase compared to control animals. Further, at the 7.0 Gy exposure level, mortalities in the mAbH6 treated group first occurred at post-irradiation day 15 compared to post-irradiation day 8 for vehicle treated irradiated control animals, an increase of 7 days over control animals. Mean time to mortality for mice receiving mAbH6 (27.3±1.3 days) was significantly increased (p=0.0087) compared to control animals (20.7±2.0 days) at the 7.0 Gy exposure level.

The percent change in body weight compared to pre-irradiation day (day −1) was recorded throughout the study. A transient weight loss occurred in all irradiated animals, with no evidence of differential changes due to mAbM11 or mAbH6 treatment compared to controls (data not shown). At study termination, all surviving animals showed an increase in body weight from starting (day −1) body weight.

TABLE 9

Survival rates of test animals exposed to radiation

| Test Group | Exposure Level | Survival (%) | Time to Death (Mean ± SEM, Day) | First/Last Death (Day) |
|---|---|---|---|---|
| Control Irradiation | 6.5 Gy | 65% | 24.0 ± 2.0 | 9/16 |
| mAbM11 pre-exposure | 6.5 Gy | 85% | 27.7 ± 1.5 | 13/17 |
| mAbM11 pre + post-exposure | 6.5 Gy | 65% | 24.0 ± 2.0 | 9/15 |
| mAbM11 post-exposure | 6.5 Gy | 80% | 26.3 ± 1.9 | 9/13 |
| mAbH6 pre + post-exposure | 6.5 Gy | 65% | 24.6 ± 1.9 | 9/19 |
| Control irradiation | 7.0 Gy | 35% | 20.7 ± 2.0 | 8/17 |
| mAbM11 pre-exposure | 7.0 Gy | 65% | 23.0 ± 2.3 | 7/13 |
| mAbM11 pre + post-exposure | 7.0 Gy | 55% | 21.6 ± 2.2 | 7/16 |
| mAbM11 post-exposure | 7.0 Gy | 70% | 24.3 ± 2.1 | 9/14 |
| mAbH6 pre + post-exposure | 7.0 Gy | 80% | 27.3 ± 1.3* | 15/20 |

*p = 0.0087 by two-tailed unpaired t-test between controlled irradiated animals and treatment group at the same irradiation exposure level.

Discussion

Acute radiation syndrome consists of three defined subsyndromes: hematopoietic, gastrointestinal, and cerebrovascular. The syndrome observed depends on the radiation dose, with the hematopoietic effects observed in humans with significant partial or whole-body radiation exposures exceeding 1 Gy. The hematopoietic syndrome is characterized by severe depression of bone-marrow function leading to pancytopenia with changes in blood counts, red and white blood cells, and platelets occurring concomitant with damage to the immune system. As nadir occurs, with few neutrophils and platelets present in peripheral blood, neutropenia, fever, complications of sepsis and uncontrollable hemorrhage lead to death.

In the present study, administration of mAbH6 was found to increase survivability of whole-body x-ray irradiation in Swiss-Webster male mice irradiated at 7.0 Gy. Notably, at the 7.0 Gy exposure level, 80% of the animals receiving mAbH6 survived to 30 days compared to 35% of vehicle treated control irradiated animals. Importantly, the first day of death in this treated group did not occur until post-irradiation day 15, a 7-day increase over that observed in vehicle treated control irradiated animals. Curiously, at the lower X-ray exposure (6.5 Gy), administration of mAbH6 did not appear to impact survivability or delay in mortality compared to vehicle treated control irradiated animals. There could be multiple reasons for this difference in response between exposure levels, although verification of any hypothesis may require additional studies, including interim sample collection for microbiological culture and hematological parameters. One explanation may simply be that the number of animals assigned to groups may have precluded seeing any subtle treatment-related differences. For example, with groups sizes of n=20, the difference in survival between 65% (mAbH6 at 6.5 Gy exposure) and 80% (mAbH6 at 7.0 Gy exposure) is 3 animals. On the other hand, the difference between 35% (vehicle control at 7.0 Gy exposure) and 80% (mAbH6 at 7.0 Gy exposure) is 9 animals, and provides sound evidence of a treatment-related difference.

These results demonstrate that anti-MASP-2 antibodies are effective in treating a mammalian subject at risk for, or suffering from the detrimental effects of acute radiation syndrome.

Example 30

This Example demonstrates that MASP-2 deficient mice are protected from *Neisseria meningitidis* induced mortality after infection with either *N. meningitidis* serogroup A or *Neisseria meningitidis* serogroup B.

Methods:

MASP-2 knockout mice (MASP-2 KO mice) were generated as described in Example 1. 10-week-old MASP-2 KO mice (n=10) and wild-type (WT) C57/BL6 mice (n=10) were inoculated by intraperitoneal (i.p.) injection with a dosage of $2.6 \times 10^7$ CFU of *Neisseria meningitidis* serogroup A Z2491 in a volume of 100 μl. The infective dose was administered to mice in conjunction with iron dextran at a final concentration of 400 mg/kg. Survival of the mice after infection was monitored over a 72-hour time period.

In a separate experiment, 10-week-old MASP-2 KO mice (n=10) and wild-type C57/BL6 mice (n=10) were inoculated by i.p. injection with a dosage of $6 \times 10^6$ CFU of *Neisseria meningitidis* serogroup B strain MC58 in a volume of 100 μl. The infective dose was administered to mice in conjunction with iron dextran at a final dose of 400 mg/kg. Survival of the mice after infection was monitored over a 72-hour time period. An illness score was also determined for the WT and MASP-2 KO mice during the 72-hour time period after infection, based on the illness scoring parameters described below in TABLE 10, which is based on the scheme of Fransen et al. (2010) with slight modifications.

TABLE 10

Illness Scoring associated with clinical signs in infected mice

| Signs | Score |
| --- | --- |
| Normal | 0 |
| Slightly ruffled fur | 1 |
| Ruffled fur, slow and sticky eyes | 2 |
| Ruffled fur, lethargic and eyes shut | 3 |
| Very sick and no movement after stimulation | 4 |
| Dead | 5 |

Blood samples were taken from the mice at hourly intervals after infection and analyzed to determine the scrum level (log cfu/mL) of N. meningitidis in order to verify infection and determine the rate of clearance of the bacteria from the serum.

Results:

FIG. 33 is a Kaplan-Meyer plot graphically illustrating the percent survival of MASP-2 KO and WT mice after administration of an infective dose of $2.6 \times 10^7$ cfu of N. meningitidis serogroup A Z2491. As shown in FIG. 33, 100% of the MASP-2 KO mice survived throughout the 72-hour period after infection. In contrast, only 80% of the WT mice (p=0.012) were still alive 24 hours after infection, and only 50% of the WT mice were still alive at 72 hours after infection. These results demonstrate that MASP-2-deficient mice are protected from N. meningitidis serogroup A Z2491-induced mortality.

FIG. 34 is a Kaplan-Meyer plot graphically illustrating the percent survival of MASP-2 KO and WT mice after administration of an infective dose of $6 \times 10^6$ cfu of N. meningitidis serogroup B strain MC58. As shown in FIG. 34, 90% of the MASP-2 KO mice survived throughout the 72-hour period after infection. In contrast, only 20% of the WT mice (p=0.0022) were still alive 24 hours after infection. These results demonstrate that MASP-2-deficient mice are protected from N. meningitidis serogroup B strain MC58-induced mortality.

FIG. 35 graphically illustrates the log cfu/mL of N. meningitidis serogroup B strain MC58 recovered at different time points in blood samples taken from the MASP-2 KO and WT mice after i.p. infection with $6 \times 10^6$ cfu of N. meningitidis serogroup B strain MC58 (n=3 at different time points for both groups of mice). The results are expressed as Means±SEM. As shown in FIG. 35, in WT mice the level of N. meningitidis in the blood reached a peak of about 6.0 log cfu/mL at 24 hours after infection and dropped to about 4.0 log cfu/mL by 36 hours after infection. In contrast, in the MASP-2 KO mice, the level of N. meningitidis reached a peak of about 4.0 log cfu/mL at 12 hours after infection and dropped to about 1.0 log cfu/mL by 36 hours after infection (the symbol "*" indicates p<0.05; the symbol "**" indicates p=0.0043). These results demonstrate that although the MASP-2 KO mice were infected with the same dose of N. meningitidis serogroup B strain MC58 as the WT mice, the MASP-2 KO mice have enhanced clearance of bacteraemia as compared to WT.

Figure 36:
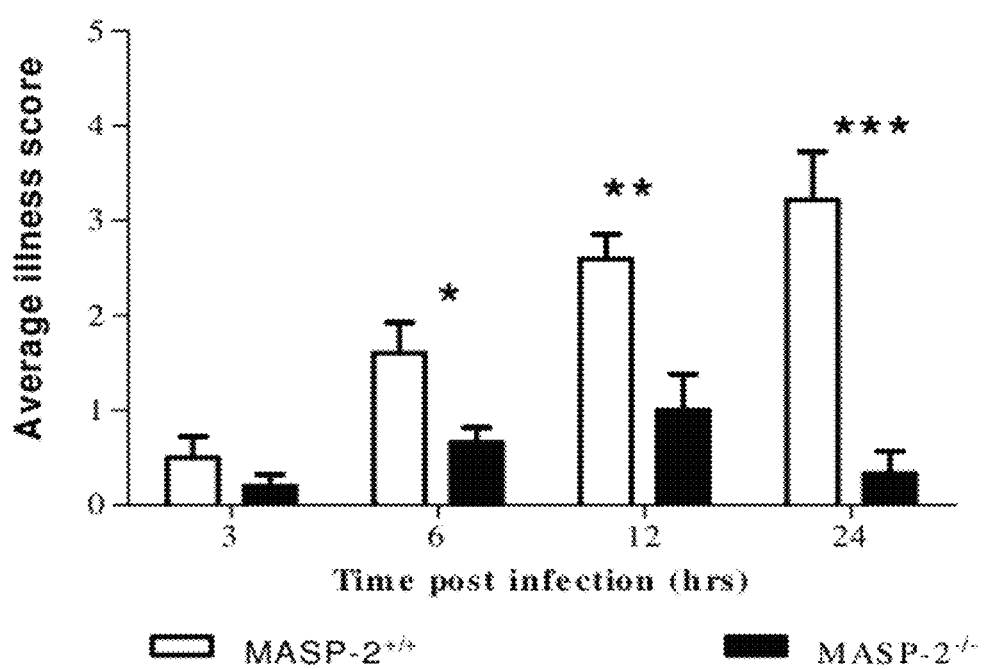
FIG. 36 graphically illustrates the average illness score of MASP-2 and WT mice at 3, 6, 12 and 24 hours after infection with 6×10⁶ cfu/100 µl *N. meningitidis* Serogroup Serogroup B strain MC58, demonstrating that the MASP-2 deficient mice showed high resistance to the infection, with much lower illness scores at 6 hours, as described in Example 30.

FIG. 36 graphically illustrates the average illness score of MASP-2 KO and WT mice at 3, 6, 12 and 24 hours after infection with $6 \times 10^6$ cfu of N. meningitidis serogroup B strain MC58. As shown in FIG. 36, the MASP-2-deficient mice showed high resistance to the infection, with much lower illness scores at 6 hours (symbol "*" indicates p=0.0411), 12 hours (symbol "*" indicates p=0.0049) and 24 hours (symbol "***" indicates p=0.0049) after infection, as compared to WT mice. The results in FIG. 36 are expressed as means±SEM.

In summary, the results in this Example demonstrate that MASP-2-deficient mice are protected from Neisseria meningitides-induced mortality after infection with either N. meningitidis serogroup A or N. meningitidis serogroup B.

Example 31

This Example demonstrates that the administration of anti-MASP-2 antibody after infection with N. meningitidis increases the survival of mice infected with N. meningitidis.

Background/Rationale:

As described in Example 10, rat MASP-2 protein was utilized to pan a Fab phage display library, from which Fab2 #11 was identified as a functionally active antibody. Full-length antibodies of the rat IgG2c and mouse IgG2a isotypes were generated from Fab2 #11. The full-length anti-MASP-2 antibody of the mouse IgG2a isotype was characterized for pharmacodynamic parameters (as described in Example 19).

In this Example, the mouse anti-MASP-2 full-length antibody derived from Fab2 #11 was analyzed in the mouse model of N. meningitidis infection.

Methods:

The mouse IgG2a full-length anti-MASP-2 antibody isotype derived from Fab2 #11, generated as described above, was tested in the mouse model of N. meningitidis infection as follows.

Administration of Mouse-Anti-MASP-2 Monoclonal Antibodies (MoAb) after Infection 9-week-old C57/BL6 Charles River mice were treated with inhibitory mouse anti-MASP-2 antibody (1.0 mg/kg) (n=12) or control isotype antibody (n=10) at 3 hours after i.p. injection with a high dose ($4 \times 10^6$ cfu) of N. meningitidis serogroup B strain MC58.

Figure 37:
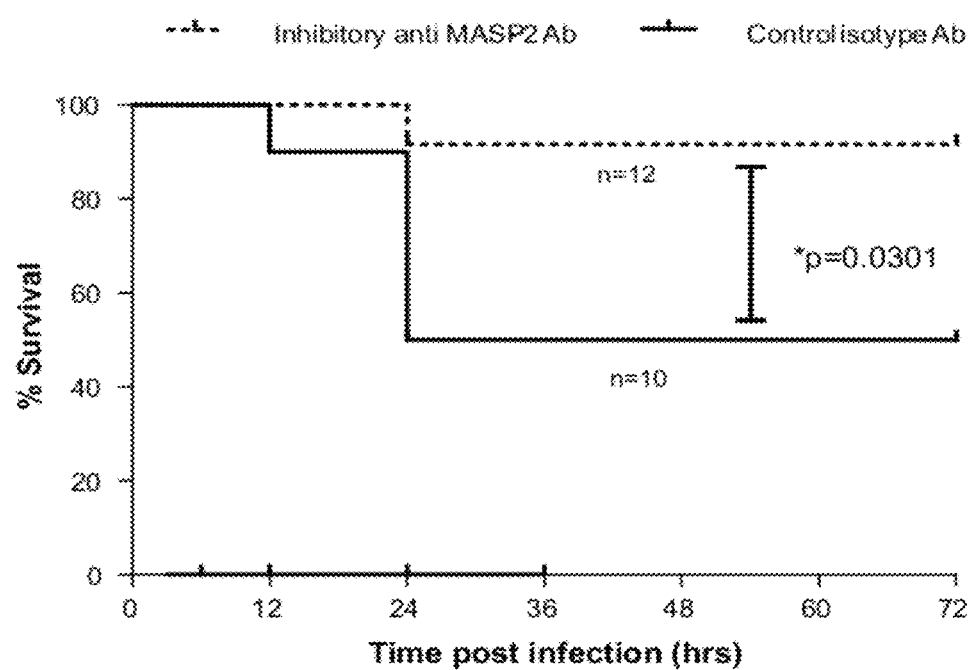
FIG. 37 is a Kaplan-Meyer plot graphically illustrating the percent survival of mice after administration of an infective dose of 4×10⁶/100 µl cfu *N. meningitidis* Serogroup B strain MC58, followed by administration 3 hours post infection of either inhibitory anti-MASP-2 antibody (1 mg/kg) or control isotype antibody, demonstrating that anti-MASP-2 antibody is effective to treat and improve survival in subjects infected with *N. meningitidis*, as described in Example 31.
Figure 38:
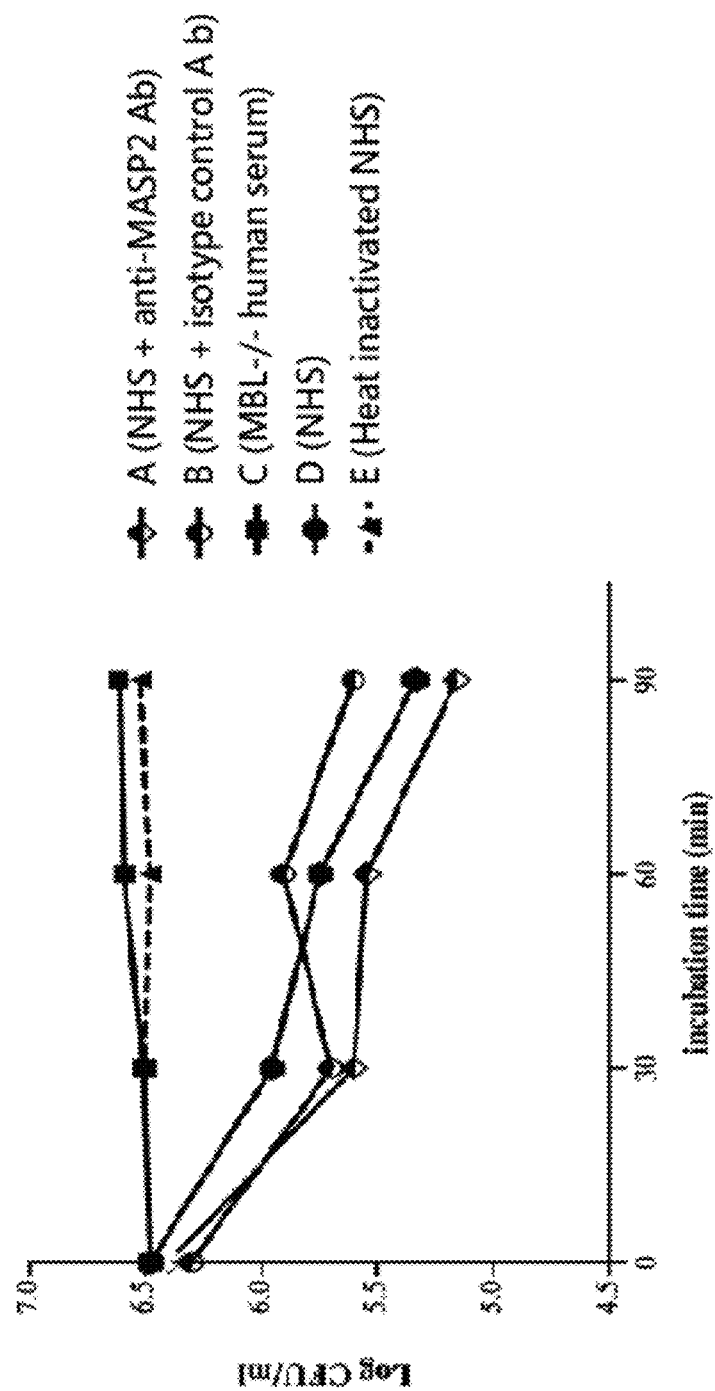
FIG. 38 graphically illustrates the log cfu/ml of viable counts of *N. meningitidis* serogroup B-MC58 recovered at different time points in 20% human serum concentration after i.p. infection with 6.5×10⁶ cfu/100 µl *N. meningitidis* serogroup B strain MC58 at 0, 30, 60 and 90 minutes after incubation in the presence of (A) normal human serum (NHS) plus human anti-MASP-2 antibody; (B) normal human serum (NHS) plus isotype control antibody; (C) MBL−/− human serum; (D) normal human serum (NHS) and (E) heat inactivated normal human serum (NHS), showing that complement dependent killing of *N. meningitidis* in human serum was significantly enhanced by the addition of the human anti-MASP-2 antibody, as described in Example 32.
Figure 39:
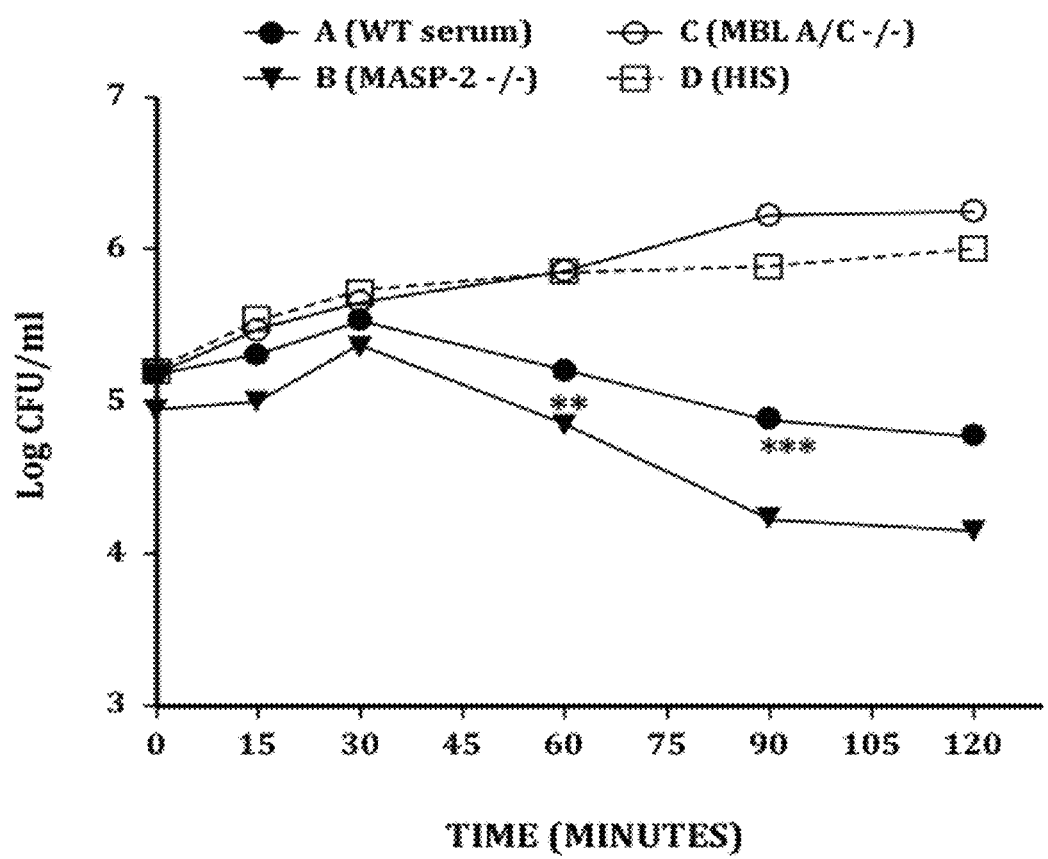
FIG. 39 graphically illustrates the log cfu/ml of viable counts of *N. meningitidis* serogroup B-MC58 recovered at different time points in the mouse sera samples, demonstrating MASP-2−/− mouse sera has a higher level of bactericidal activity for *N. meningitidis* than WT mouse sera, as described in Example 32.

Results:

FIG. 37 is a Kaplan-Meyer plot graphically illustrating the percent survival of mice after administration of an infective dose of $4 \times 10^6$ cfu of N. meningitidis serogroup B strain MC58, followed by administration 3 hours post-infection of either inhibitory anti-MASP-2 antibody (1.0 mg/kg) or control isotype antibody. As shown in FIG. 37, 90% of the mice treated with anti-MASP-2 antibody survived throughout the 72-hour period after infection. In contrast, only 50% of the mice treated with isotype control antibody survived throughout the 72-hour period after infection. The symbol "*" indicates p=0.0301, as determined by comparison of the two survival curves.

These results demonstrate that administration of anti-MASP-2 antibody is effective to treat and improve survival in subjects infected with N. meningitidis.

As demonstrated herein, the use of anti-MASP-2 antibody in the treatment of a subject infected with N. meningitidis is effective when administered within 3 hours post-infection, and is expected to be effective within 24 hours to 48 hours after infection. Meningococcal disease (either meningococcemia or meningitis) is a medical emergency, and therapy will typically be initiated immediately if meningococcal disease is suspected (i.e., before N. meningitidis is positively identified as the etiological agent).

In view of the results in the MASP-2 KO mouse demonstrated in EXAMPLE 30, it is believed that administration of anti-MASP-2 antibody prior to infection with N. meningitidis would also be effective to prevent or ameliorate the severity of infection.

Example 32

This Example demonstrates that administration of anti-MASP-2 antibody is effective to treat N. meningitidis infection in human serum:

Rationale:

Patients with decreased serum levels of functional MBL display increased susceptibility to recurrent bacterial and fungal infections (Kilpatrick et al., *Biochim Biophys Acta* 1572: 401-413 (2002)). It is known that *N. meningitidis* is recognized by MBL, and it has been shown that MBL-deficient sera do not lyse *Neisseria*.

In view of the results described in Examples 30 and 31, a series of experiments were carried out to determine the efficacy of administration of anti-MASP-2 antibody to treat *N. meningitidis* infection in complement-deficient and control human sera. Experiments were carried out in a high concentration of serum (20%) in order to preserve the complement pathway.

Methods:

1. Serum Bactericidal Activity in Various Complement-Deficient Human Sera and in Human Sera Treated with Human Anti-MASP-2 Antibody The following complement-deficient human sera and control human sera were used in this experiment:

TABLE 11

Human sera samples tested (as shown in FIG. 38)

| Sample | Serum type |
|---|---|
| A | Normal human sera (NHS) + human anti-MASP-2 Ab |
| B | NHS + isotype control Ab |
| C | MBL −/− human serum |
| D | NHS |
| E | Heat-Inactivated (HI) NHS |

A recombinant antibody against human MASP-2 was isolated from a Combinatorial Antibody Library (Knappik, A., et al., *J. Mol. Biol.* 296:57-86 (2000)), using recombinant human MASP-2A as an antigen (Chen, C. B. and Wallis, *J. Biol. Chem.* 276:25894-25902 (2001)). An anti-human scFv fragment that potently inhibited lectin pathway-mediated activation of C4 and C3 in human plasma (IC50~20 nM) was identified and converted to a full-length human IgG4 antibody.

*N. meningitidis* serogroup B-MC58 was incubated with the different sera show in TABLE 11, each at a serum concentration of 20%, with or without the addition of inhibitory human anti-MASP-2 antibody (3 μg in 100 μl total volume) at 37° C. with shaking. Samples were taken at the following time points: 0-, 30-, 60- and 90-minute intervals, plated out and then viable counts were determined. Heat-inactivated human serum was used as a negative control.

Results:

FIG. 38 graphically illustrates the log cfu/mL of viable counts of *N. meningitidis* serogroup B-MC58 recovered at different time points in the human sera samples shown in TABLE 11. TABLE 12 provides the Student's t-test results for FIG. 38.

TABLE 12

Student's t-test Results for FIG. 38 (time point 60 minutes)

| | Mean Diff. (Log) | Significant? P < 0.05? | P value summary |
|---|---|---|---|
| A vs B | −0.3678 | Yes | ***(0.0002) |
| A vs C | −1.1053 | Yes | ***(p < 0.0001) |
| A vs D | −0.2111 | Yes | **(0.0012) |
| C vs D | 1.9 | Yes | ***(p < 0.0001) |

As shown in FIG. 38 and TABLE 12, complement-dependent killing of *N. meningitidis* in human 20% serum was significantly enhanced by the addition of the human anti-MASP-2 inhibitory antibody.

2. Complement-Dependent Killing of *N. meningitidis* in 20% (v/v) Mouse Sera Deficient of MASP-2.

The following complement-deficient mouse sera and control mouse sera were used in this experiment:

TABLE 13

Mouse sera samples tested (as shown in FIG. 39)

| Sample | Serum Type |
|---|---|
| A | WT |
| B | MASP-2 −/− |
| C | MBL A/C −/− |
| D | WT heat-inactivated (HIS) |

*N. meningitidis* serogroup B-MC58 was incubated with different complement-deficient mouse sera, each at a serum concentration of 20%, at 37° C. with shaking. Samples were taken at the following time points: 0-, 15-, 30-, 60-, 90- and 120-minute intervals, plated out and then viable counts were determined. Heat-inactivated human serum was used as a negative control.

Results:

FIG. 39 graphically illustrates the log cfu/mL of viable counts of *N. meningitidis* serogroup B-MC58 recovered at different time points in the mouse sera samples shown in TABLE 13. As shown in FIG. 39, the MASP-2−/− mouse sera have a higher level of bactericidal activity for *N. meningitidis* than WT mouse sera. The symbol "*" indicates p=0.0058, the symbol "*" indicates p=0.001. TABLE 14 provides the Student's t-test results for FIG. 39**.

TABLE 14

Student's t-test Results for FIG. 39

| Comparison | Time point | Mean Diff. (LOG) | Significant? (p < 0.05)? | P value summary |
|---|---|---|---|---|
| A vs. B | 60 min. | 0.39 | yes | ** (0.0058) |
| A vs. B | 90 min. | 0.6741 | yes | *** (0.001) |

In summary, the results in this Example demonstrate that MASP-2−/− sera has a higher level of bactericidal activity for *N. meningitidis* than WT sera.

Example 33

This Example demonstrates the inhibitory effect of MASP-2 deficiency on lysis of red blood cells from blood samples obtained from a mouse model of paroxysmal nocturnal hemoglobinuria (PNH).

Background/Rationale:

Paroxysmal nocturnal hemoglobinuria (PNH), also referred to as Marchiafava-Micheli syndrome, is an acquired, potentially life-threatening disease of the blood, characterized by complement-induced intravascular hemolytic anemia. The hallmark of PNH is the chronic complement-mediated intravascular hemolysis that is a consequence of unregulated activation of the alternative pathway of complement due to the absence of the complement regulators CD55 and CD59 on PNH erythrocytes, with subsequent hemoglobinuria and anemia. Lindorfer, M. A., et al., *Blood* 115(11) (2010), Risitano, A. M, *Mini-Reviews in Medicinal Chemis-* try, 11:528-535 (2011). Anemia in PNH is due to destruction of red blood cells in the bloodstream. Symptoms of PNH include red urine, due to appearance of hemoglobin in the urine, back pain, fatigue, shortness of breath and thrombosis. PNH may develop on its own, referred to as "primary PNH" or in the context of other bone marrow disorders such as aplastic anemia, referred to as "secondary PNH". Treatment for PNH includes blood transfusion for anemia, anticoagulation for thrombosis and the use of the monoclonal antibody eculizumab (Soliris®), which protects blood cells against immune destruction by inhibiting the complement system (Hillmen P. et al., *N. Engl. J. Med.* 350(6):552-9 (2004)). Eculizumab (Soliris®) is a humanized monoclonal antibody that targets the complement component C5, blocking its cleavage by C5 convertases, thereby preventing the production of C5a and the assembly of the MAC. Treatment of PNH patients with eculizumab has resulted in a reduction of intravascular hemolysis, as measured by lactate dehydrogenase (LDH), leading to hemoglobin stabilization and transfusion independence in about half of the patients (Hillmen P, et al., Mini-Reviews in Medicinal Chemistry, vol 11(6) (2011)). While nearly all patients undergoing therapy with eculizumab achieve normal or almost normal LDH levels (due to control of intravascular hemolysis), only about one third of the patients reach a hemoglobin value above 11 gr/dL, and the remaining patients on eculizumab continue to exhibit moderate to severe (i.e., transfusion-dependent) anemia, in about equal proportions (Risitano A. M. et al., *Blood* 113:4094-100 (2009)). As described in Risitano et al., Mini-Reviews in *Medicinal Chemistry* 11:528-535 (2011), it was demonstrated that PNH patients on eculizumab contained C3 fragments bound to a substantial portion of their PNH erythrocytes (while untreated patients did not), leading to the conclusion that membrane-bound C3 fragments work as opsonins on PNH erythrocytes, resulting in their entrapment in the reticuloendothelial cells through specific C3 receptors and subsequent extravascular hemolysis. Therefore, therapeutic strategies in addition to the use of eculizumab are needed for those patients developing C3 fragment-mediated extravascular hemolysis because they continue to require red cell transfusions.

This Example describes methods to assess the effect of MASP-2-deficient serum and serum treated with MASP-2 inhibitory agent on lysis of red blood cells from blood samples obtained from a mouse model of PNH and demonstrates the efficacy of MASP-2 inhibition to treat subjects suffering from PNH, and also supports the use of inhibitors of MASP-2 to ameliorate the effects of C3 fragment-mediated extravascular hemolysis in PNH subjects undergoing therapy with a C5 inhibitor such as eculizumab.

Methods:

PNH Animal Model:

Blood samples were obtained from gene-targeted mice with deficiencies of Crry and C3 (Crry/C3−/−) and CD55/CD59-deficient mice. These mice are missing the respective surface complement regulators and their erythrocytes are, therefore, susceptible to spontaneous complement autolysis as are PNH human blood cells.

In order to sensitize these erythrocytes even more, these cells were used with and without coating by mannan and then tested for hemolysis in WT C56/BL6 plasma, MBL null plasma, MASP-2−/− plasma, human NHS, human MBL−/− plasma, and NHS treated with human anti-MASP-2 antibody.

1. Hemolysis Assay of Crry/C3 and CD55/CD59 Double-Deficient Murine Erythrocytes in MASP-2-Deficient/Depleted Sera and Controls Day 1. Preparation of murine RBC (±mannan coating)

Materials Included:

fresh mouse blood, BBS/Mg$^{2+}$/Ca$^{2+}$ (4.4 mM barbituric acid, 1.8 mM sodium barbitone, 145 mM NaCl, pH7.4, 5 mM Mg$^{2+}$, 5 mM Ca$^{2+}$), chromium chloride, CrCl$_3$.6H$_2$O (0.5 mg/mL in BBS/Mg2+/Ca2+) and mannan, 100 µg/mL in BBS/Mg2+/Ca2+.

Whole blood (2 mL) was spun down for 1-2 min at 2000×g in a refrigerated centrifuge at 4° C. The plasma and buffy coat were aspirated off. The sample was then washed three times by re-suspending the RBC pellet in 2 mL ice-cold BBS/gelatin/Mg2+/Ca2+ and repeating centrifugation step. After the third wash, the pellet was re-suspended in 4 mL BBS/Mg2+/Ca2+. A 2 mL aliquot of the RBC was set aside as an uncoated control. To the remaining 2 mL, 2 mL CrCl3 and 2 mL mannan were added and the sample was incubated with gentle mixing at room temperature for 5 minutes. The reaction was terminated by adding 7.5 mL BBS/gelatin/Mg2+/Ca2+. The sample Was spun down as above, re-suspended in 2 mL BBS/gelatin/Mg2+/Ca2+ and washed a further two times as above, then stored at 4° C.

Day 2. Hemolysis assay

Materials included BBS/gelatin/Mg$^{2+}$/Ca$^{2+}$ (as above), test sera, 96-well round-bottomed and flat-bottomed plates and a spectrophotometer that reads 96-well plates at 410-414 nm.

The concentration of the RBC was first determined and the cells were adjusted to $10^9$/mL, and stored at this concentration. Before use, the assay buffer was diluted to $10^8$/mL, and then 100 µl per well was used. Hemolysis was measured at 410-414 nm (allowing for greater sensitivity then 541 nm). Dilutions of test sera were prepared in ice-cold BBS/gelatin/Mg2+/Ca2+. 100 µl of each serum dilution was pipetted into round-bottomed plate (see plate layout). 100 µl of appropriately diluted RBC preparation was added (i.e., $10^8$/mL) (see plate layout), incubated at 37° C. for about 1 hour, and observed for lysis. (The plates may be photographed at this point.) The plate was then spun down at maximum speed for 5 minutes. 100 µl was aspirated of the fluid-phase, transferred to flat-bottom plates, and the OD was recorded at 410-414 nm. The RBC pellets were retained (these can be subsequently lysed with water to obtain an inverse result).

Experiment #1:

Fresh blood was obtained from CD55/CD59 double-deficient mice and blood of Crry/C3 double-deficient mice and erythrocytes were prepared as described in detail in the above protocol. The cells were split and half of the cells were coated with mannan and the other half were left untreated, adjusting the final concentration to 1×$10^8$ per mL, of which 100 µl was used in the hemolysis assay, which was carried out as described above.

Results of Experiment #1: The Lectin Pathway is Involved in Erythrocyte Lysis in the PM Animal Model In an initial experiment, it was determined that non-coated WT mouse erythrocytes were not lysed in any mouse serum. It was further determined that mannan-coated Crry−/− mouse erythrocytes were slowly lysed (more than 3 hours at 37 degrees) in WT mouse serum, but they were not lysed in MBL null serum. (Data not shown).

It was determined that mannan-coated Crry−/− mouse erythrocytes were rapidly lysed in human serum but not in heat-inactivated NHS. Importantly, mannan-coated Crry−/− mouse erythrocytes were lysed in NHS diluted down to 1/640 (i.e., 1/40, 1/80, 1/160, 1/320 and 1/640 dilutions all lysed). (Data not shown). In this dilution, the alternative pathway does not work (AP functional activity is significantly reduced below 8% serum concentration).

Conclusions from Experiment #1

Mannan-coated Crry–/– mouse erythrocytes are very well lysed in highly diluted human serum with MBL but not in that without MBL. The efficient lysis in every serum concentration tested implies that the alternative pathway is not involved or needed for this lysis. The inability of MBL-deficient mouse serum and human serum to lyse the mannan-coated Crry–/– mouse erythrocytes indicates that the classical pathway also has nothing to do with the lysis observed. As lectin pathway recognition molecules are required (i.e., MBL), this lysis is mediated by the lectin pathway.

Experiment #2:

Fresh blood was obtained from the Crry/C3 and CD55/CD59 double-deficient mice and mannan-coated Crry–/– mouse erythrocytes were analyzed in the haemolysis assay as described above in the presence of the following human serum: MBL null; WT; NHS pretreated with human anti-MASP-2 antibody; and heat-inactivated NHS as a control.

Results of Experiment #2: MASP-2 Inhibitors Prevent Erythrocyte Lysis in the PNH Animal Model With the Mannan-coated Crry–/– mouse erythrocytes, NHS was incubated in the dilutions diluted down to 1/640 (i.e., 1/40, 1/80, 1/160, 1/320 and 1/640), human MBL–/– serum, NHS pretreated with anti-MASP-2 mAb, and heat-inactivated NHS as a control.

The ELISA microtiter plate was spun down and the non-lysed erythrocytes were collected on the bottom of the round-well plate. The supernatant of each well was collected and the amount of hemoglobin released from the lysed erythrocytes was measured by reading the OD415 nm in an ELISA reader.

In the control heat-inactivated NHS (negative control), as expected, no lysis was observed. MBL–/– human serum lysed mannan-coated mouse erythrocytes at 1/8 and 1/16 dilutions. Anti-MASP-2-antibody-pretreated NHS lysed mannan-coated mouse erythrocytes at 1/8 and 1/16 dilutions while WT human serum lysed mannan-coated mouse erythrocytes down to dilutions of 1/32.

FIG. 40 graphically illustrates hemolysis (as measured by hemoglobin release of lysed mouse erythrocytes (Cryy/C3–/–) into the supernatant measured by photometry) of mannan-coated murine erythrocytes by human serum over a range of serum concentrations in serum from heat-inactivated (HI) NHS, MBL–/–, NHS pretreated with anti-MASP-2 antibody, and NHS control.

From the results shown in FIG. 40, it is demonstrated that MASP-2 inhibition with anti-MASP-2 antibody significantly shifted the $CH_{50}$ and inhibited complement-mediated lysis of sensitized erythrocytes with deficient protection from autologous complement activation.

Experiment #3

Fresh blood obtained from the Crry/C3 and CD55/CD59 double-deficient mice in non-coated Crry–/– mouse erythrocytes was analyzed in the hemolysis assay as described above in the presence of the following serum: MBL–/–; WT sera; NHS pretreated with human anti-MASP-2 antibody and heat-inactivated NHS as a control.

Figure 41:
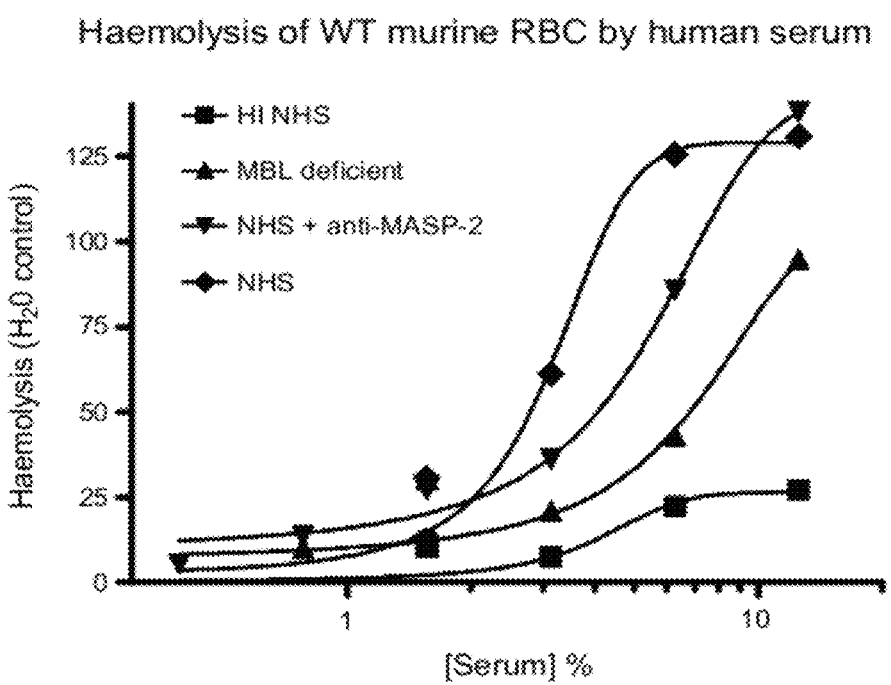
FIG. 41 graphically illustrates hemolysis (as measured by hemoglobin release of lysed WT mouse erythrocytes into the supernatant measured by photometry) of non-coated murine erythrocytes by human serum over a range of serum concentrations. The sera tested included heat-inactivated (HI) NHS, MBL−/−, NHS +anti-MASP-2 antibody and NHS control, demonstrating that inhibiting MASP-2 inhibits complement-mediated lysis of non-sensitized WT mouse erythrocytes, as described in Example 33.

Results:

FIG. 41 graphically illustrates hemolysis (as measured by hemoglobin release of lysed WT mouse erythrocytes into the supernatant measured by photometry) of non-coated murine erythrocytes by human serum over a range of serum concentrations in serum from heat inactivated (HI) NHS, MBL–/–, NHS pretreated with anti-MASP-2 antibody, and NHS control. As shown in FIG. 41, it is demonstrated that inhibiting MASP-2 inhibits complement-mediated lysis of non-sensitized WT mouse erythrocytes.

FIG. 42 graphically illustrates hemolysis (as measured by hemoglobin release of lysed mouse erythrocytes (CD55/59–/–) into the supernatant measured by photometry) of non-coated murine erythrocytes by human serum over a range of serum concentration in serum from heat-inactivated (HI) NHS, MBL–/–, NHS pretreated with anti-MASP-2 antibody, and NHS control.

TABLE 12

$CH_{50}$ values expressed as serum concentrations

| Serum | WT | CD55/59 –/– |
|---|---|---|
| Heat-inactivated NHS | No lysis | No lysis |
| MBL AO/XX donor (MBL deficient) | 7.2% | 2.1% |
| NHS + anti-MASP-2 antibody | 5.4% | 1.5% |
| NHS | 3.1% | 0.73% |

Note:
"$CH_{50}$" is the point at which complement mediated hemolysis reaches 50%.

In summary, the results in this Example demonstrate that inhibiting MASP-2 inhibits complement-mediated lysis of sensitized and non-sensitized erythrocytes with deficient protection from autologous complement activation. Therefore, MASP-2 inhibitors may be used to treat subjects suffering from PNFI, and may also be used to ameliorate (i.e., inhibit, prevent or reduce the severity of) extravascular hemolysis in PNH patients undergoing treatment with a C5 inhibitor such as eculizumab (Soliris®).

Example 34

This Example describes a follow on study to the study described above in Example 29, providing further evidence confirming that a MASP-2 inhibitor, such as a MASP-2 antibody, is effective for the treatment of radiation exposure and/or for the treatment, amelioration or prevention of acute radiation syndrome.

Rationale:

In the initial study described in Example 29, it was demonstrated that pre-irradiation treatment with an anti-MASP-2 antibody in mice increased the survival of irradiated mice as compared to vehicle treated irradiated control animals at both 6.5 Gy and 7.0 Gy exposure levels. It was further demonstrated in Example 29 that at the 6.5 Gy exposure level, post-irradiation treatment with anti-MASP-2 antibody resulted in a modest increase in survival as compared to vehicle control irradiated animals. This Example describes a second radiation study that was carried out to confirm the results of the first study.

Methods:

Design of Study A:

Swiss Webster mice (n=50) were exposed to ionizing radiation (8.0 Gy). The effect of anti-MASP-2 antibody therapy (mAbH6 5 mg/kg), administered 18 hours before and 2 hours after radiation exposure, and weekly thereafter, on mortality was assessed.

Figure 43:
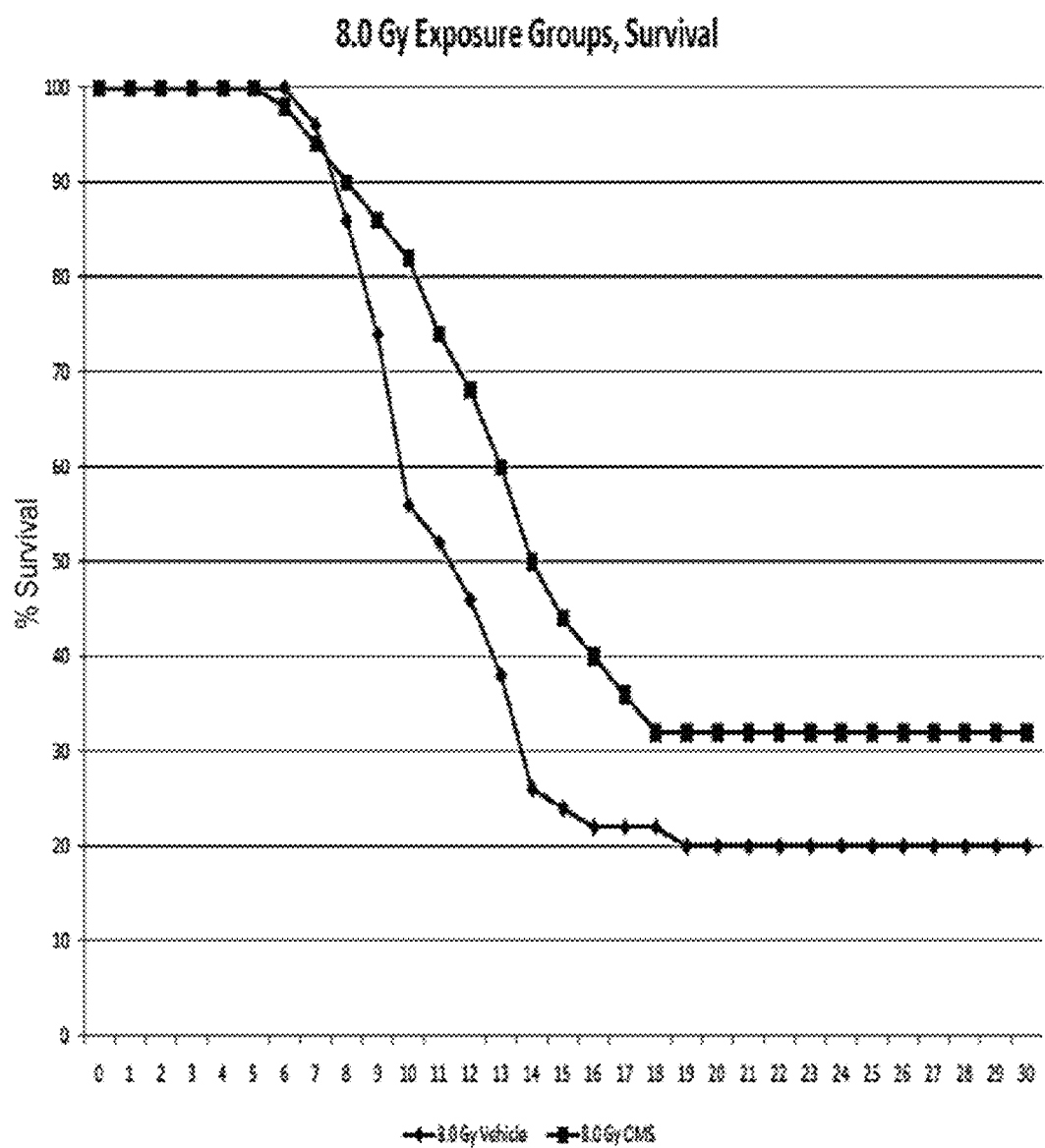
FIG. 43 graphically illustrates the percent survival over time (days) after exposure to 8.0 Gy radiation in control mice and in mice treated with anti-human MASP-2 antibody (mAbH6), as described in Example 34.

Results of Study A:

As shown in FIG. 43, it was determined that administration of the anti-MASP-2 antibody mAbH6 increased survival in mice exposed to 8.0 Gy, with an adjusted median survival rate increased from 4 to 6 days as compared to mice that received vehicle control, and a mortality reduced by 12% when compared to mice that received vehicle control (log-rank test, p=0.040).

Design of Study B:

Swiss Webster mice (n=50) were exposed to ionizing radiation (8.0 Gy) in the following groups (1: vehicle) saline control; (II: low) anti-MASP-2 antibody mAbH6 (5 mg/kg) administered 18 hours before irradiation and 2 hours after irradiation; (III: high) mAbH6 (10 mg/kg) administered 18 hours before irradiation and 2 hours post irradiation; and (IV: high post) mAbH6 (10 mg/kg) administered 2 hours post irradiation only.

Results of Study B:

Administration of anti-MASP-2 antibody pre- and post-irradiation adjusted the mean survival from 4 to 5 days in comparison to animals that received vehicle control. Mortality in the anti-MASP-2 antibody-treated mice was reduced by 6-12% in comparison to vehicle control mice. It is further noted that no significant detrimental treatment effects were observed (data not shown).

In summary, the results shown in this Example are consistent with the results shown in Example 29 and further demonstrate that anti-MASP-2 antibodies are effective in treating a mammalian subject at risk for, or suffering from the detrimental effects of acute radiation syndrome.

Example 35

This study investigates the effect of MASP-2-deficiency in a mouse model of LPS (lipopolysaccharide)-induced thrombosis.

Rationale:

Hemolytic uremic syndrome (HUS), which is caused by Shiga toxin-producing *E. coli* infection, is the leading cause of acute renal failure in children. In this Example, a Schwartzman model of LPS-induced thrombosis (microvascular coagulation) was carried out in MASP-2−/− (KO) mice to determine whether MASP-2 inhibition is effective to inhibit or prevent the formation of intravascular thrombi.

Methods:

MASP-2−/− (n=9) and WI (n=10) mice were analyzed in a Schwarztman model of LPS-induced thrombosis (microvascular coagulation). Mice were administered *Serratia* LPS and thrombus formation was monitored over time. A comparison of the incidence of microthromi and LPS-induced microvascular coagulation was carried out.

Figure 44:
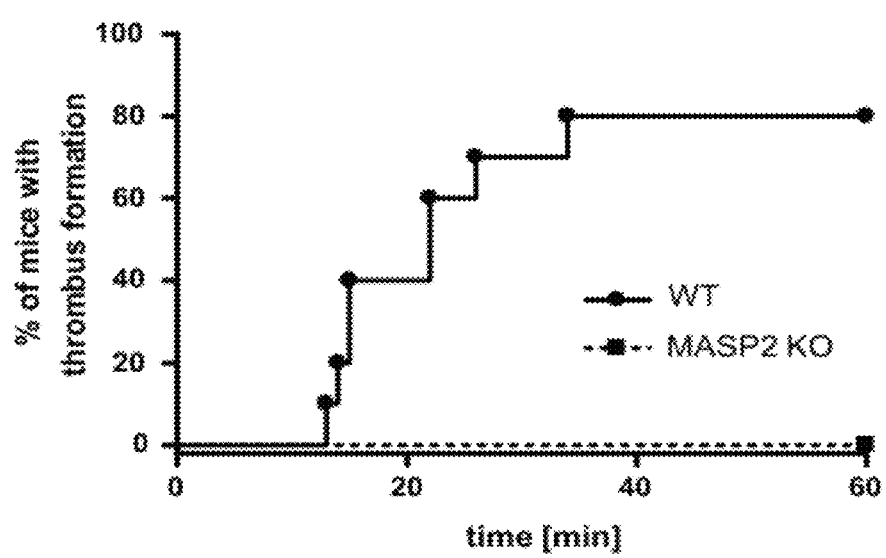
FIG. 44 graphically illustrates the time to onset of microvascular occlusion following LPS injection in MASP-2−/− and WT mice, showing the percentage of mice with thrombus formation measured over 60 minutes, demonstrating that thrombus formation is detected after 15 minutes in WT mice, with up to 80% of the WT mice demonstrated thrombus formation at 60 minutes; in contrast, none of the MASP-2−/− mice showed any thrombus formation during the 60 minute period (log rank: p=0.0005), as described in Example 35.

Results:

Notably, all MASP-2−/− mice tested (9/9) did not form intravascular thrombi after *Serratia* LPS administration. In contrast, microthrombi were detected in 7 of 10 of the WT mice tested in parallel (p=0.0031, Fischer's exact). As shown in FIG. 44, the time to onset of microvascular occlusion following LPS infection was measured in MASP-2−/− and WT mice, showing the percentage of WT mice with thrombus formation measured over 60 minutes, with thrombus formation detected as early as about 15 minutes. Up to 80% of the WT mice demonstrated thrombus formation at 60 minutes. In contrast, as shown in FIG. 44, none of the MASP-2−/− had thrombus formation at 60 minutes (log rank: p=0.0005).

These results demonstrate that MASP-2 inhibition is protective against the development of intravascular thrombi in an HUS model.

Example 36

This Example describes the effect of anti-MASP-2 antibodies in a mouse model of HUS using intraperitoneal co-injection of purified Shiga toxin 2 (STX2) plus LPS.

Background:

A mouse model of HUS was developed using intraperitoneal co-injection of purified Shiga toxin 2 (STX2) plus LPS. Biochemical and microarray analysis of mouse kidneys revealed the STX2 plus LPS challenge to be distinct from the effects of either agent alone. Blood and scrum analysis of these mice showed neutrophilia, thrombocytopenia, red cell hemolysis, and increased serum creatinine and blood urea nitrogen. In addition, histologic analysis and electron microscopy of mouse kidneys demonstrated glomerular fibrin deposition, red cell congestion, microthrombi formation, and glomerular ultrastructural changes. It was established that this model of HUS induces all clinical symptoms of human HUS pathology in C57BL/6 mice including thrombocytopenia, hemolytic anemia, and renal failure that define the human disease. (J. Immunol 187(1):172-80 (2011))

Methods:

C57BL/6 female mice that weighed between 18 to 20 g were purchased from Charles River Laboratories and divided in to 2 groups (5 mice in each group). One group of mice was pretreated by intraperitoneal (i.p.) injection with the recombinant anti-MASP-2 antibody mAbM11 (100 µg per mouse; corresponding to a final concentration of 5 mg/kg body weight) diluted in a total volume of 150 µl saline. The control group received saline without any antibody. Six hours after i.p injection of anti-MASP-2 antibody mAbM11, all mice received a combined i.p. injection of a sublethal dose (3 ng/animal; corresponding to 150 µg/kg body weight) of LPS of *Serratia marcescens* (L6136; Sigma-Aldrich, St. Louis, Mo.) and a dose of 4.5 ng/animal (corresponding to 225 ng/kg) of STX2 (two times the LD50 dose) in a total volume of 150 µl. Saline injection was used for control.

Survival of the mice was monitored every 6 hours after dosing. Mice were culled as soon as they reached the lethargic stage of HUS pathology. After 36 hours, all mice were culled and both kidneys were removed for immunohistochemistry and scanning electron microscopy. Blood samples were taken at the end of the experiment by cardiac puncture. Serum was separated and kept frozen at −80° C. for measuring BUN and serum Creatinine levels in both treated and control groups.

Immunohistochemistry

One-third of each mouse kidney was fixed in 4% paraformaldehyde for 24 h, processed, and embedded in paraffin. Three-micron-thick sections were cut and placed onto charged slides for subsequent staining with H & E stain.

Electron Microscopy

The middle section of the kidneys was cut into blocks of approximately 1 to 2 mm$^3$, and fixed overnight at 4° C. in 2.5% glutaraldehyde in 1×PBS. The fixed tissue subsequently was processed by the University of Leicester Electron Microscopy Facility Cryostat Sections The other third of the kidneys was, cut into blocks approximately 1 to 2 mm$^3$ and snap frozen in liquid nitrogen and kept at −80° C. for cryostat sections and mRNA analysis.

Figure 45:
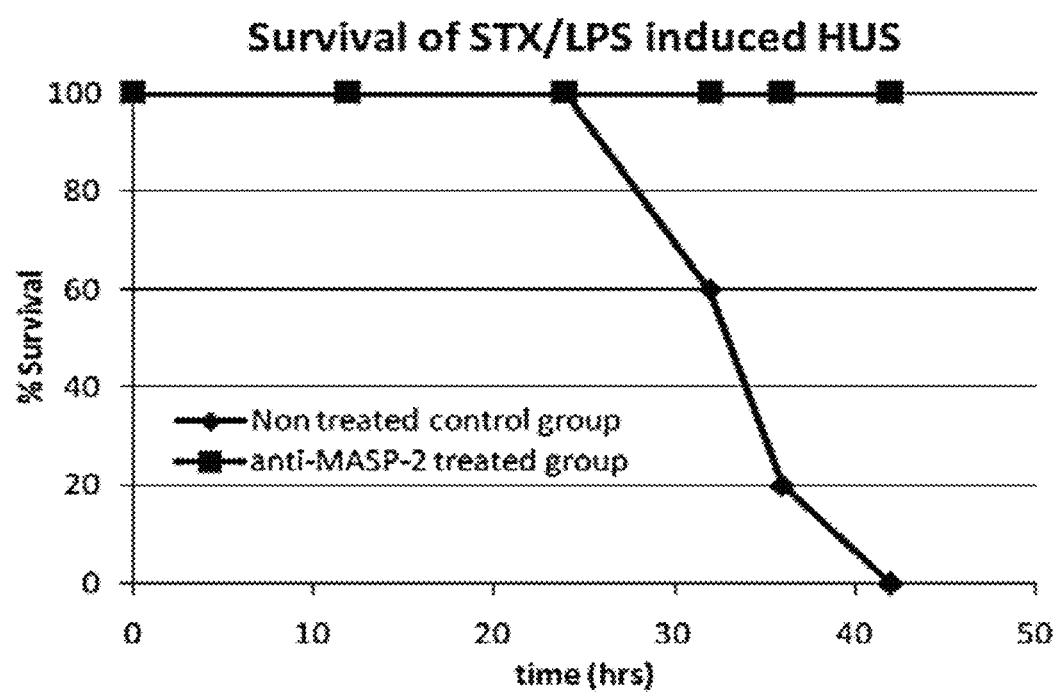
FIG. 45 graphically illustrates the percent survival of saline treated control mice (n=5) and anti-MASP-2 antibody treated mice (n=5) in the STX/LPS-induced model of HUS over time (hours), demonstrating that all of the control mice died by 42 hours, whereas, in contrast, 100% of the anti-MASP-2 antibody-treated mice survived throughout the time course of the experiment, as described in Example 36.

Results:

FIG. 45 graphically illustrates the percent survival of saline-treated control mice (n=5) and anti-MASP-2 antibody-treated mice (n=5) in the STX/LPS-induced model over time (hours). Notably, as shown in FIG. 45, all of the control mice died by 42 hours. In sharp contrast, 100% of the anti-MASP-2 antibody-treated mice survived throughout the time course of the experiment. Consistent with the results shown in FIG. 45, it was observed that all the untreated mice that either died or had to be culled with signs of severe disease had significant glomerular injuries, while the glomeruli of all anti-MASP-2-treated mice looked normal (data not shown). These results demonstrate that MASP-2 inhibitors, such as anti-MASP-2 antibodies, may be used to treat subjects suffering from, or at risk for developing a thrombotic microangiopathy (TMA), such as hemolytic uremic syndrome (HUS), atypical HUS (aHUS), or thrombotic thrombocytopenic purpura (TTP).

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of inhibiting MASP-2-dependent complement activation in a subject suffering from paroxysmal nocturnal hemoglobinuria (PNH), comprising administering to the subject a composition comprising an amount of a monoclonal MASP-2 inhibitory antibody, or antigen-binding fragment thereof, that specifically binds to a portion of SEQ ID NO:6 and selectively inhibits MASP-2-dependent complement activation without substantially inhibiting the C1q-dependent complement pathway.

2. The method of claim 1, wherein the composition increases the survival of red blood cells in the subject.

3. The method of claim 1, wherein the subject exhibits one or more symptoms selected from the group consisting of (i) below normal levels of hemoglobin, (ii) below normal levels of platelets; (iii) above normal levels of reticulocytes, and (iv) above normal levels of bilirubin.

4. The method of claim 1, wherein the subject has previously undergone, or is currently undergoing, treatment with an anti-C5 antibody or antigen binding fragment thereof that inhibits cleavage of complement protein C5.

5. The method of claim 1, wherein the method further comprises administering to the subject an anti-C5 antibody or antigen binding fragment thereof that inhibits cleavage of complement protein C5.

6. The method of claim 5, wherein the anti-C5 antibody or antigen binding fragment thereof is humanized.

7. The method of claim 6, wherein the anti-C5 antibody is eculizumab.

8. The method of claim 1, wherein the monoclonal antibody or antigen-binding fragment thereof is a recombinant antibody.

9. The method of claim 1, wherein the composition is administered subcutaneously, intra-muscularly, intra-arterially, intravenously, or as an inhalant.

10. The method of claim 1, wherein the composition is administered subcutaneously.

11. The method of claim 1, wherein the monoclonal antibody or antigen-binding fragment thereof is an antibody having reduced effector function.

12. The method of claim 1, wherein the monoclonal antibody or antigen-binding fragment thereof is a chimeric antibody.

13. The method of claim 1, wherein the monoclonal antibody or antigen-binding fragment thereof is a humanized antibody.

14. The method of claim 1, wherein the monoclonal antibody or antigen-binding fragment thereof is a human antibody.

* * * * *

UNITED STATES PATENT AND TRADEMARK OFFICE
CERTIFICATE OF CORRECTION

Page 1 of 4

PATENT NO. : 8,951,522 B2
APPLICATION NO. : 13/441827
DATED : February 10, 2015
INVENTOR(S) : Gregory A. Demopulos, Thomas Dudler and Hans-Wilhelm Schwaeble It is certified that error appears in the above-identified patent and that said Letters Patent is hereby corrected as shown below:

In the Specification

| COLUMN | LINE | ERROR |
|---|---|---|
| 8 | 49 | "aggultinin" should read --agglutinin-- |
| 11 | 9 | "WI" should read --WT-- |
| 11 | 61 | "FX1a" should read --FXIa-- |
| 11 | 66 | "Kaplain-Mcier" should read --Kaplan-Meier-- |
| 12 | 4 | "Kaplain-Meier" should read --Kaplan-Meier-- |
| 12 | 9 | "Kaplan-Meyer" should read --Kaplan-Meier-- |
| 12 | 12 | "A 22491" should read --A Z2491-- |
| 12 | 15 | "Kaplan-Meyer" should read --Kaplan-Meier-- |
| 12 | 29 | "WI" should read --WT-- |
| 12 | 34-35 | "Serogroup Serogroup B" should read --Serogroup B-- |
| 12 | 38 | "Kaplan-Meyer" should read --Kaplan-Meier-- |
| 15 | 50 | "MBL, M-ficolin," should read --MBL, H-ficolin, M-ficolin,-- |
| 15 | 59 | "only % or less" should read --only 10% or less-- |
| 19 | 4 | "Factor D)," should read --Factor D,-- |
| 21 | 7 | "of factor in" should read --of factor H in-- |
| 23 | 16 | "Shin, U. S." should read --Shin, H. S.-- |
| 23 | 58 | "Dickncite" should read --Dickneite-- |
| 27 | 39 | "scrum" should read --serum-- |
| 29 | 6 | "scrum" should read --serum-- |
| 30 | 21 | "factor 1" should read --factor I-- |
| 31 | 13-14 | "ofeculizumab" should read --of eculizumab-- |

Signed and Sealed this
Twenty-ninth Day of March, 2016

Michelle K. Lee
*Director of the United States Patent and Trademark Office*

| COLUMN | LINE | ERROR |
|---|---|---|
| 32 | 42 | "thrombodulin" should read --thrombomodulin-- |
| 33 | 65 | "plasmaphersis" should read --plasmapheresis-- |
| 33 | 66 | "plasmaphersis" should read --plasmapheresis-- |
| 34 | 26 | "eculizamab" should read --eculizumab-- |
| 34 | 51 | "blobotriaosyl ceramide" should read --globotriaosylceramide-- |
| 34 | 54 | "SIX induces" should read --STX induces-- |
| 35 | 32 | "prothombin" should read --prothrombin-- |
| 35 | 58 | "cycplatin" should read --cisplatin-- |
| 36 | 13-14 | "0157:1-17" should read --0157:H7-- |
| 36 | 62 | "MASA-2" should read --MASP-2-- |
| 37 | 26 | "plasmaphoresis" should read --plasmapheresis-- |
| 37 | 53 | "eculizamab" should read --eculizumab-- |
| 37 | 60 | "thomboses" should read --thromboses-- |
| 38 | 22 | "erythematosis" should read --erythematosus-- |
| 38 | 24 | "immunemediated" should read --immune mediated-- |
| 38 | 32 | "transplantion" should read --transplantation-- |
| 39 | 25 | "prothombin" should read --prothrombin-- |
| 39 | 55 | "less that or" should read --less than or-- |
| 40 | 26 | "plasmaphoresis" should read --plasmapheresis-- |
| 40 | 50 | "eculizamab" should read --eculizumab-- |
| 40 | 61 | "glomerulonepthritis" should read --glomerulonephritis-- |
| 44 | 7 | "atheroscelorsis" should read --atherosclerosis-- |
| 46 | 9 | "alter" should read --after-- |
| 46 | 58 | "chorodial" each occurrence, should read --choroidal-- |
| 48 | 24 | "Ophihalmol" should read --Ophthalmol-- |
| 56 | 29 | "(Fe)" should read --(Fc)-- |
| 58 | 1 | "Fey" should read --Fcγ-- |
| 60 | 39 | "MASA-2" should read --MASP-2-- |
| 67 | 26 | "Rychlik, 1." should read --Rychlik, I.-- |
| 69 | 19 | "339:585-591" should read --334:585-591-- |
| 71 | 53 | "neurokinin," should read --neurokinin$_1$-- |
| 75 | 48 | "Mori" should read --Hori-- |
| 80 | 20 | "thrombodulin" should read --thrombomodulin-- |
| 80 | 66 | "plasmaphersis" should read --plasmapheresis-- |

CERTIFICATE OF CORRECTION (continued)
U.S. Pat. No. 8,951,522 B2

| COLUMN | LINE | ERROR |
|---|---|---|
| 82 | 41 | "plasmaphersis" should read --plasmapheresis-- |
| 83 | 46-47 | "immunosupressant" should read --immunosuppressant-- |
| 84 | 6 | "plasmaphersis" should read --plasmapheresis-- |
| 85 | 2-38 | "aggultinin" each occurrence, should read --agglutinin-- |
| 86 | 19 | "aggultinin" should read --agglutinin-- |
| 90 | 1 | "MASA-2" should read --MASP-2-- |
| 90 | 7 | "scrum" should read --serum-- |
| 91 | 8 | "PstI and XbaI" should read --Pst1 and Xba1-- |
| 91 | 9 | "PstI-XbaI" should read --Pst1-Xba1-- |
| 91 | 26 | "XhoI and EcoRI" should read --Xho1 and EcoR1-- |
| 93 | 12 | "three 10 species" should read --three species-- |
| 94 | 12 | "tricthanolamine" should read --triethanolamine-- |
| 94 | 21 | "tricthanolamine" should read --triethanolamine-- |
| 95 | 8-9 | "dimethylsulfoxide" should read --dimethyl sulfoxide-- |
| 96 | 46 | "NotI-MAK1" should read --Not1-MAK1-- |
| 96 | 51 | "NotI" should read --Not1-- |
| 96 | 59 | "NotI-MAK1" should read --Not1-MAK1-- |
| 96 | 65 | "NotI" should read --Not1-- |
| 97 | 2 | "NotI" should read --Not1-- |
| 97 | 6 | "NotI-MAG1" should read --Not1-MAG1-- |
| 97 | 9 | "by" should read --bp-- |
| 99 | 12 | "20 mM 1 M NaCl," should read --20 mM Tris-HCl, 1 M NaCl,-- |
| 99 | 28 | "p-nitrophenyl" should read --ρ-nitrophenyl-- |
| 101 through 103 | 59 through 56 | "Tl" each occurrence, should read --μl--; "Tg" each occurrence, should read --μg-- |
| 101 | 59 | "ug" should read --μg-- |
| 102 | 65 | "Tl" should read --μl-- |
| 109 | 40 | "sec Ambati" should read --see Ambati-- |
| 110 | 19 | "serumalbumin" should read --serum albumin-- |
| 110 | 29 | "flatmounted" should read --flat-mounted-- |
| 110 | 32 | "Flatmounts" should read --Flat-mounts-- |
| 114 | 7 | "WT (+1+)" should read --WT (+/+)-- |
| 117 | 58 | "innoculated" should read --inoculated-- |

CERTIFICATE OF CORRECTION (continued)
U.S. Pat. No. 8,951,522 B2

| COLUMN | LINE | ERROR |
|---|---|---|
| 117 | 65 | "(log cfu/ml" should read --(log cfu/ml)-- |
| 119 | 7 | "type-I" should read --type-1-- |
| 119 | 52-53 | "sell-damage" should read --self-damage-- |
| 121 | 22 | "MASP-2$^{-/-}$ and MASP-2$^{-/-}$" should read --MASP-2$^{+/-}$ and MASP-2$^{-/-}$-- |
| 122 | 29 | "WI" should read --WT-- |
| 125 | 29 | "effect" should read --affect-- |
| 126 | 6 | "a chain" should read --a' chain-- |
| 126 | 24 | "7.4," should read --pH 7.4,-- |
| 129 | 16 | "opsoniation" should read --opsonization-- |
| 129 | 37-38 | "aggultinin-mediated" should read --agglutinin-mediated-- |
| 129 | 40 | "aggultinins" should read --agglutinins-- |
| 129 | 67 | "(CFI-1R3)" should read --(CFHR3)-- |
| 130 | 7 | "endogenouse" should read --endogenous-- |
| 130 | 9 | "Sec Pickering" should read --See Pickering-- |
| 130 | 48 | "retinal 1/R" should read --retinal I/R-- |
| 133 | 51 | "Control irraditation" should read --Control irradiation-- |
| 135 | 15 | "scrum" should read --serum-- |
| 135 | 65 | ""*"" should read --"**"-- |
| 138 | 33 | ""*"" should read --"**"-- |
| 140 | 5 | "CrCl$_3$.6H$_2$O" should read --CrCl$_3$ · 6H$_2$0-- |
| 141 | 40 | "Cryy" should read --Crry-- |
| 142 | 27 | "PNFI" should read --PNH-- |
| 143 | 3 | "(1: vehicle)" should read --(I: vehicle)-- |
| 143 | 39 | "WI" should read --WT-- |
| 143 | 44 | "microthromi" should read --microthrombi-- |
| 144 | 6 | "scrum" should read --serum-- |
| 144 | 28 | "ng/animal" should read --µg/animal-- |